(12) United States Patent
Barnes et al.

(10) Patent No.: US 8,394,858 B2
(45) Date of Patent: Mar. 12, 2013

(54) CYCLOHEXANE DERIVATIVES AND USES THEREOF

(75) Inventors: David Barnes, Waban, MA (US); Gregory Raymond Bebernitz, Stow, MA (US); Scott Louis Cohen, Peabody, MA (US); Robert Edson Damon, Hopkinton, MA (US); Robert Francis Day, Watertown, MA (US); Monish Jain, Belmont, MA (US); Rajeshri Ganesh Karki, Somerville, MA (US); Louise Clare Kirman, Swampscott, MA (US); Tajesh Jayprakash Patel, Medford, MA (US); Brian Kenneth Raymer, Holliston, MA (US); Herbert Franz Schuster, Ashland, MA (US); Wei Zhang, Somerville, MA (US)

(73) Assignee: Novartis AG, Basel (CH)

( * ) Notice: Subject to any disclaimer, the term of this patent is extended or adjusted under 35 U.S.C. 154(b) by 53 days.

(21) Appl. No.: 12/956,146

(22) Filed: Nov. 30, 2010

(65) Prior Publication Data

US 2011/0136735 A1 Jun. 9, 2011

Related U.S. Application Data

(60) Provisional application No. 61/266,288, filed on Dec. 3, 2009.

(51) Int. Cl.
*A01N 37/18* (2006.01)
*A61K 31/16* (2006.01)
*C07C 327/48* (2006.01)

(52) U.S. Cl. .................. 514/599; 564/74

(58) Field of Classification Search .............. 564/74; 514/599
See application file for complete search history.

(56) References Cited

U.S. PATENT DOCUMENTS

| | | | |
|---|---|---|---|
| 2005/0009906 A1 | 1/2005 | Ackermann et al. | |
| 2005/0065210 A1 | 3/2005 | Ackermann et al. | |
| 2005/0234033 A1 | 10/2005 | Anandan et al. | |
| 2005/0250784 A1 | 11/2005 | Anandan et al. | |
| 2011/0172189 A1* | 7/2011 | Greig et al. | 514/64 |

FOREIGN PATENT DOCUMENTS

| | | |
|---|---|---|
| DE | 4341666 A1 | 6/1995 |
| EP | 1655283 A1 | 5/2006 |
| JP | 8183759 A | 12/1994 |
| JP | 2005119987 A | 5/2005 |
| WO | 95/15944 A1 | 6/1995 |
| WO | 98/08822 A1 | 3/1998 |
| WO | 00/05214 A2 | 2/2000 |
| WO | 00/75107 A2 | 12/2000 |
| WO | 01/37826 A1 | 5/2001 |
| WO | 03/087098 A1 | 10/2003 |
| WO | 2004/002992 A1 | 1/2004 |
| WO | 2004/031145 A2 | 4/2004 |
| WO | 2005/044797 A1 | 5/2005 |
| WO | 2005/105777 A1 | 11/2005 |
| WO | 2006/106800 A1 | 10/2006 |
| WO | 2006/129199 A1 | 12/2006 |
| WO | 2007/003965 A1 | 1/2007 |
| WO | 2007/033002 A1 | 3/2007 |
| WO | 2007/070818 A1 | 6/2007 |
| WO | 2007/082840 A1 | 7/2007 |
| WO | 2007/119108 A2 | 10/2007 |
| WO | 2007/141318 A1 | 12/2007 |
| WO | 2008/016884 A2 | 2/2008 |
| WO | 2008/038640 A1 | 4/2008 |
| WO | 2009/035928 A1 | 3/2009 |
| WO | 2009/146539 A1 | 12/2009 |
| WO | 2010/032009 A1 | 3/2010 |

OTHER PUBLICATIONS

Johnston et al.; "cis -4-[ [ [ (2-Chloroethyl)nitrosoamino] carbonyl]methylamino]cyclohexanecarboxylic Acid, a Nitrosourea with Latent Activity against an Experimental Solid Tumor"; J. Med. Chem.; 27(1):97-99 (1984).

Schneider et al.; "Synthesis of DL-Slaframine"; J. Org. Chem.; 49(20):3681-3684 (1984).

\* cited by examiner

*Primary Examiner* — Rebecca Anderson
(74) *Attorney, Agent, or Firm* — Joshua Roth

(57) ABSTRACT

The present invention provides a compound of formula I;

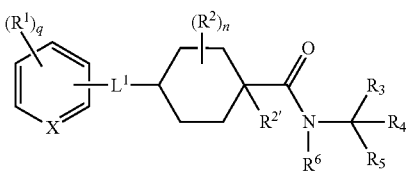

(I)

a method for manufacturing the compounds of the invention, and its therapeutic uses. The present invention further provides a combination of pharmacologically active agents and a pharmaceutical composition.

30 Claims, No Drawings

CYCLOHEXANE DERIVATIVES AND USES THEREOF

RELATED APPLICATIONS

This application claims the benefit of U.S. Provisional Application No. 61/266,288, filed Dec. 3, 2009, the entire teachings of which are incorporated herein by reference.

BACKGROUND OF THE INVENTION

In mammals, Acetyl-CoA carboxylase (ACC) exists as two isozymes. ACC1 is generally expressed in all tissues but its expression is higher in lipogenic tissues such as liver and adipose tissue. ACC2 is highly expressed in muscle tissue and to a lesser extent in liver tissue.

ACC has a central role in lipid metabolism. Malonyl-CoA, the product of the ACC-catalyzed reaction, inhibits mitochondrial fatty acid oxidation through direct inhibition of carnitine palmitoyltransferase 1 (CPT-1), and so controls the switch between carbohydrate and fatty acid oxidative utilization in liver and skeletal muscle. Malonyl-CoA is also a key intermediate in the de novo synthesis of lipids. When metabolic fuel is low, ACC is turned off by phosphorylation and the consequential reduction of levels of malonyl-CoA leads to generation of ATP by increasing fatty acid oxidation and decreasing consumption of ATP for fatty acid synthesis. Thus, in addition to inhibition of fatty acid synthesis, reduction in malonyl-CoA levels through ACC inhibition may provide a mechanism for increasing fatty acid utilization.

By decreasing de novo fatty acid synthesis and increasing fatty acid oxidation in liver, chronic administration of an ACC inhibitor may deplete liver triglyceride and other pathological lipid species, leading to improved liver function and hepatic insulin sensitivity. One might also expect a reduction in the secretion of triglyceride rich lipoprotein (VLDL), so reducing the risk of atherosclerosis.

Therefore, a well-tolerated agent that effectively and simultaneously treats the multiple risk factors associated with metabolic syndrome would have a significant impact on the prevention and treatment of the cardiovascular disease associated with obesity, hypertension, diabetes and atherosclerosis.

Metabolic syndrome (a.k.a. insulin resistance syndrome, syndrome X) is a common clinical disorder that is defined as the presence of increased insulin concentrations in association with other disorders including visceral obesity, hyperlipidemia and dyslipidemia, hyperglycemia, hypertension, and sometimes hyperuricemia and renal dysfunction.

Metabolic syndrome is considered by many as a common basic defect for type 2 diabetes, android obesity, dyslipidemia, and hypertension, leading to a clustering of these diseases. This syndrome has particular significance since it has been shown to be an antecedent of both type-2 diabetes and atherosclerosis, with cardiovascular events accounting for the majority of deaths in both populations.

It is estimated that more than 100 million people in the U.S. alone suffer from some form of metabolic syndrome.

Type 2 diabetes is a severe and prevalent disease in the Western world that affects roughly 13 million persons in the U.S., along with 5 million presumed to have undiagnosed type 2 diabetes and another 14 million with impaired glucose tolerance.

Projections indicate that the incidence of type 2 diabetes will increase to over 25 million by 2010 in the U.S., and to over 300 million worldwide by 2025. The annual direct medical cost associated with type 2 diabetes in the United States is significant, primarily due to the costs of hyperglycemia-related complications, such as retinopathy, nephropathy, peripheral neuropathy, and cardiovascular, peripheral vascular and cerebrovascular disease. Although the causes of type 2 diabetes have not yet been identified, it is well established that it is a polygenic disease characterized by multiple defects in insulin action in muscle, adipose, and liver, and defects in pancreatic insulin secretion. However, the relative importance of each of these defects to the etiology of type 2 diabetes is not clear.

In spite of the early discovery of insulin and its subsequent widespread use in the treatment of diabetes, and the later discovery of and use of sulfonylureas, biguanides and thiazolidenediones, such as troglitazone, rosiglitazone or pioglitazone, as oral hypoglycemic agents, the treatments for diabetes are currently believed to be inadequate. The use of insulin typically requires multiple daily doses. Determination of the proper dosage of insulin requires frequent estimations of the sugar in urine or blood. The administration of an excess dose of insulin causes hypoglycemia, with effects ranging from mild abnormalities in blood glucose to coma, or even death. Treatment of type 2 diabetes usually consists of a combination of diet, exercise, oral hypoglycemic agents, e.g., thiazolidenediones, and in more severe cases, insulin. However, the clinically available hypoglycemic agents can have side effects that limit their use. Moreover as few as 26% of patients with type 2 diabetes achieve target control using current therapies.

Obesity is a major health risk that leads to increased mortality and incidence of Type 2 diabetes mellitus, hypertension and dyslipidemia. It is the second leading cause of preventable death in the United States, and contributes to >300,000 deaths per year. In the U.S., more than 50% of the adult population is overweight, and almost ¼ of the population is considered to be obese (BMI greater than or equal to 30). Furthermore, the prevalence of obesity in the United States has increased by about 50% in the past 10 years. The prevalence of obesity in adults is 10%-25% in most countries of Western Europe. While the vast majority of obesity occurs in the industrialized world, particularly in US and Europe, the prevalence of obesity is also increasing in Japan. The rise in the incidence of obesity has prompted the WHO to recognize obesity as a significant disease. Two recently marketed anti-obesity agents, Xenical (Orlistat/Roche) and Meridia (Reductil/BASF) exhibit only modest efficacy (Orlistat) and have safety/side effect concerns (Orlistat-gastrointestinal and Meridia-hypertensive effects, respectively), that limit their use.

Thus, although there are a variety of anti-atherosclerosis, obesity and diabetes therapies, there is a continuing need and a continuing search in this field of art for alternative therapies.

Non-alcoholic fatty liver disease (NAFLD), and the more pathologic liver disorder, non-alcoholic steatohepatitis (NASH), develop from fat accumulation in the liver. Some degree of NAFLD affects up to one third of the general population. In particular insulin resistance, type 2 diabetes, obesity, hypertriglyceridemia, and female gender are independently associated with NAFLD. NAFLD is found in 30-100% of subjects with one or more metabolic abnormalities and is found in the majority of subject with type 2 diabetes. NAFLD is not only found in adults, but is also present in obese/diabetic children and adolescents. Patients with, or being treated for, human immunodeficiency virus are also at a much greater risk of developing NAFLD. Recent studies indicate that the progression of NAFLD to NASH can result in the development of fibrous tissue in the liver (fibrosis) in up to 40% of patients or cirrhosis in 5-10% of patients. Current treatments are limited, relying largely on exercise and weight loss.

Moreover, in patients with NAFLD and insulin resistance, de novo lipogenesis may contribute up to 25% of total liver lipid. It has been noted that patients with NAFLD have substantially increased mRNA levels of both ACC1 and ACC2, compared to control subjects.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth muscle cells and in macrophages of the intima layer of the arteries and aorta. Further, it is postulated that most of the cholesterol found within the fatty streaks, in turn, gives rise to development of the "fibrous plaque," which consists of accumulated intimal smooth muscle cells laden with lipid and surrounded by extra-cellular lipid, collagen, elastin and proteoglycans. These cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to a "complicated lesion," which accounts for arterial occlusion and a tendency toward mural thrombosis and arterial muscle spasm that characterize advanced atherosclerosis. Hyperlipidemia has been established as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particularly high risk. Additional independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

More than half a century ago it was first demonstrated that fatty acid synthesis in tumor tissues occurs at a very high rates. A number of studies have demonstrated that in tumor cells almost all fatty acids derive from de novo synthesis despite adequate nutritional supply. In addition, tumors overexpressing fatty acid synthase (FAS), the enzyme responsible for de novo synthesis of fatty acids, display aggressive biologic behavior compared to those tumors with normal FAS levels, suggesting that FAS overexpression confers a selective growth advantage.

SUMMARY OF THE INVENTION

This invention relates to compounds which are Acetyl-Coenzyme A Carboxylase (ACC) inhibitors, pharmaceutical compositions containing such inhibitors and the use of such inhibitors to treat, for example, metabolic syndrome, diabetes, obesity, fatty liver disease, atherosclerosis, cardiovascular disease and cancer in mammals, including humans.

For the purposes of this invention inhibition of ACC means inhibitions exclusively of ACC2, inhibitions exclusively of ACC1 or inhibition of both ACC1 and ACC2. Inhibition of either isozyme of ACC should beneficially affect the abnormalities associated with metabolic syndrome. Preferably an ACC inhibitor should inhibit both isoforms of the enzyme.

Accordingly, in one aspect, the invention provides compounds of formula (I):

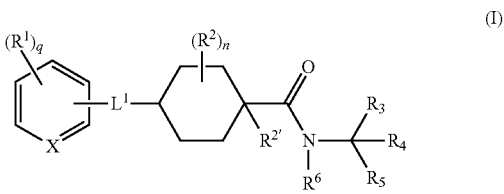

or a pharmaceutically acceptable salt thereof, wherein:

X is CH, CR$^1$, or N;

q and n are each, independently, 0, 1, 2, 3, or 4;

L$_1$ is —NHSO$_2$—, —SO$_2$NH—, —NHSO$_2$NH— or —NHC(O)NH—;

R$^1$, for each occurrence, is independently hydroxy, nitro, halo, carboxy, formyl, C$_{1-7}$alkyl, C$_{3-8}$cycloalkyl, C$_{2-7}$alkenyl, C$_{2-7}$alkynyl, C$_{1-7}$alkoxy, C$_{1-7}$alkylthio, C$_{3-8}$cycloalkoxy, heterocyclyloxy, C$_{6-10}$aryloxy, amino, C$_{1-7}$alkylamino, di-(C$_{1-7}$alkyl)amino, C$_{6-10}$aryl, 3- to 10-membered heterocyclyl, 5- to 10-membered heteroaryl, C$_{1-7}$alkanoyl, C$_{1-7}$alkoxycarbonyl, C$_{1-7}$alkanoyloxy, C$_{1-7}$alkylamido, C$_{6-10}$arylamido, heterocyclylamido, carbamoyl, N—C$_{1-7}$alkylcarbamoyl, N,N-di-(C$_{1-7}$ alkyl)carbamoyl, C$_{1-7}$alkoxyamido, C$_{1-7}$alkylureido, and C$_{6-10}$arylureido, wherein R$^1$ is optionally substituted on one or more carbon atom with one or more independently selected R$^{13}$; and wherein when R$^1$ comprises a heterocyclyl or a heteroaryl comprising —NH—, the hydrogen of the —NH— group may be optionally replaced with a C$_{1-7}$alkyl; and wherein when R$^1$ comprises a heterocyclyl or a heteroaryl comprising —N═, —S— or both, the —N═ may be substituted with —O$^-$ and the —S— group may be substituted with one or two ═O groups;

R$^2$, for each occurrence, is independently selected from the group consisting of hydroxy, cyano, C$_{1-7}$alkyl, C$_{1-7}$alkoxy, C$_{2-7}$alkenyl, amino, C$_{1-7}$alkylamino, di-(C$_{1-7}$alkyl)amino, C$_{1-7}$alkylamido, C$_{1-7}$alkoxycarbonylamino, or two or more R$^2$ groups on non-adjacent carbon atoms together form a C$_{1-4}$alkylene bridge; wherein R$^2$, for each occurrence, may be independently optionally substituted with one or more halo;

R$^{2'}$ is hydrogen or R$^2$; or

R$^{2'}$ and one or more R$^2$ groups form a C$_{1-4}$alkylene bridge; or

R$^{2'}$ and R$^6$, may be linked to form a 5-membered heterocyclyl spirocyclic ring which may be optionally substituted with one or more C$_{1-7}$alkyl;

R$^3$ is selected from the group consisting of a C$_{1-7}$alkyl, C$_{3-8}$cycloalkyl, C$_{6-10}$aryl, a 5- to 10-membered heteroaryl, or a 3- to 10-membered heterocyclyl, wherein R$^3$ is optionally substituted on one or more carbon atom with one or more independently selected R$^{14}$; and wherein when R$^3$ is a heteroaryl or heterocyclyl comprising —NH—, the hydrogen of the —NH— group may be optionally replaced with a C$_{1-7}$alkyl; and wherein when R$^3$ is a heteroaryl or a heterocyclyl comprising —N═, —S— or both, the —N═ may be substituted with —O$^-$ and the —S— group may be substituted with one or two ═O groups;

R$^4$ is hydrogen, a C$_{1-7}$alkyl, or carbamoyl, wherein the alkyl may be optionally substituted with one or more substituent which may be independently selected from the group consisting of duetero, hydroxy, amino, halo, carboxy, $C_{1-7}$alkoxy, $C_{1-7}$alkoxycarbonyl, phosphonooxy, a peptide having from 1 to 3 amino acids and $C_{1-7}$alkanoyloxy wherein the alkanoyloxy may be optionally substituted with one or more carboxy, amino, N—$C_{1-6}$alkylamino, N,N-di-($C_{1-6}$ alkyl)amino, or amino acid sidechain;

$R^5$ is hydrogen or a $C_{1-7}$ alkyl;

$R^6$ is hydrogen or $C_{1-7}$ alkyl; or $R^6$ and any one of $R^4$ or $R^5$ may be linked to form a 3- to 7-membered heterocyclyl, wherein the heterocyclyl may be optionally substituted on one or more carbon with one or more $R^{15}$; and wherein when the heterocyclyl comprises —NH—, the hydrogen of the —NH— group may be optionally replaced with $R^{16}$; and wherein when the heterocyclyl comprises —N═, —S— or both, the —N═ may be substituted with —O⁻ and the —S— group may be substituted with one or two ═O groups;

$R^{13}$, for each occurrence, is independently deutero, halo, hydroxy, oxo, carboxy, $C_{1-7}$alkyl, $C_{3-8}$cycloalkyl, $C_{1-7}$alkoxy, $C_{6-10}$aryl, 3- to 10-membered heterocyclyl, 5- to 10-membered heteroaryl, amino, $C_{1-7}$alkylamino, di-($C_{1-7}$ alkyl)amino, $C_{1-7}$alkoxycarbonyl, carbamoyl, wherein $R^{13}$ is optionally substituted on one or more carbon atom with one or more independently selected $R^{17}$; and wherein when $R^{13}$ is a heterocyclyl or a heteroaryl comprising —NH—, the hydrogen of the —NH— group may be optionally replaced with a $C_{1-7}$alkyl; and wherein when $R^{13}$ is a heterocyclyl or heteroaryl comprising —N═, —S— or both, the —N═ may be substituted with —O⁻ and the —S— group may be substituted with one or two ═O groups;

$R^{14}$, for each occurrence, is independently halo;

$R^{15}$, for each occurrence, is independently selected from the group consisting of hydroxy, oxo, carboxy, $C_{1-7}$alkyl, and $C_{1-7}$alkoxycarbonyl; or two $R^{15}$ on adjacent carbon atoms may form a fused phenyl;

$R^{16}$, for each occurrence, is independently selected from the group consisting of $C_{1-7}$alkanoyl, $C_{6-10}$arylcarbonyl, heteroarylcarbonyl, $C_{1-7}$alkoxycarbonyl, 5- to 10-membered heteroaryl, and $C_{1-7}$alkylsulfonyl, wherein $R^{16}$ may be optionally substituted with one or more substituent independently selected from the group consisting of carboxy, amino, $C_{1-7}$alkylamino, di-($C_{1-7}$alkyl)amino, and $C_{1-7}$alkoxycarbonyl; and $R^{17}$, for each occurrence, is independently selected from cyano, halo, hydroxy, carboxy, $C_{1-7}$alkyl, $C_{1-7}$alkoxy, amino, $C_{1-7}$alkylamino, di-($C_{1-7}$alkyl)amino, $C_{1-7}$alkoxycarbonyl, 3- to 10-membered heterocyclyl, wherein $R^{17}$ may be optionally substituted on one or more carbon atoms with one or more independently selected halo, trifluoromethyl, carboxy, or $C_{1-4}$alkyoxycarbonyl; and wherein when $R^{17}$ is a heterocyclyl comprising —NH—, the hydrogen of the —NH— group may be optionally replaced with a $C_{1-7}$alkyl; and wherein when $R^{17}$ is a heterocyclyl comprising —N═, —S— or both, the —N═ may be substituted with —O⁻ and the —S— group may be substituted with one or two ═O groups.

In another aspect, the invention relates to pharmaceutical compositions, comprising a compound according to formula (I), or a pharmaceutically acceptable salt thereof; and a pharmaceutically acceptable excipient or carrier. In another aspect, the invention relates to the use of this pharmaceutical composition as a medicament. In one embodiment, the medicament is used for the treatment of a disorder or disease in a subject mediated by the inhibition of acetyl CoA carboxylase.

In another aspect, the invention relates to pharmaceutical compositions, comprising a therapeutically effective amount of a compound according to formula (I), or a pharmaceutically acceptable salt thereof, in combination with a therapeutically effective amount of insulin, an insulin derivative or mimetic; an insulin secretagogue; an insulinotropic sulfonylurea receptor ligand; a PPAR ligand; an insulin sensitizer; a biguanide; an alpha-glucosidase inhibitors; a GLP-1, GLP-1 analog or mimetic; a DPPIV inhibitor; a HMG-CoA reductase inhibitor; a squalene synthase inhibitor; a FXR or a LXR ligand; a cholestyramine; a fibrates; a nicotinic acid; or aspirin. In another aspect, the invention relates to the use of this pharmaceutical composition as a medicament. In one embodiment, the medicament is used for the treatment of a disorder or disease in a subject mediated by the inhibition of acetyl CoA carboxylase.

In another aspect, the invention relates to a method of inhibiting Acetyl CoA carboxylase activity, comprising contacting a source of acetyl CoA carboxylase with a compound according to formula (I), or a pharmaceutically acceptable salt thereof.

In another aspect, the invention relates to a method of treating a disease or condition mediated by the inhibition of acetyl CoA carboxylase in a mammal, comprising administering to the mammal in need thereof a therapeutically effective amount of a compound according to formula (I), or a pharmaceutically acceptable salt thereof. In one embodiment, the disease or condition is metabolic syndrome, Syndrome X, diabetes, insulin resistance, decreased glucose tolerance, non-insulin-dependent diabetes mellitus, Type II diabetes, Type I diabetes, diabetic complications, body weight disorders, or leptin related diseases. In another embodiment, the disease or condition is insulin resistance, decreased glucose tolerance, non-insulin-dependent diabetes mellitus, Type II diabetes, or Type I diabetes. In another embodiment, the disease or condition is a metabolic syndrome wherein the metabolic syndrome is dyslipidemia, obesity, insulin resistance, hypertension, microalbuminemia, hyperuricaemia, or hypercoagulability. In another embodiment, the disease or condition is a bodyweight disorder and the bodyweight disorder is obesity, overweight, cachexia or anorexia.

In another aspect, the invention relates to the use of a compound of Formula (I), or a pharmaceutically acceptable salt thereof, for use as a medicament.

In another aspect, the invention relates to the use of a compound of Formula (I), or a pharmaceutically acceptable salt thereof, for the preparation of a pharmaceutical composition for the treatment of a disorder or disease in a subject mediated by the inhibition of acetyl CoA carboxylase.

DEFINITIONS

For purposes of interpreting this specification, the following definitions will apply unless specified otherwise and whenever appropriate, terms used in the singular will also include the plural and vice versa.

The requisite number of carbon atoms in a group is represented by using the prefix $C_{1-6}$, $C_{1-4}$, etc. For example, an alkyl group which may have from one to six carbons can be designated "$C_{1-6}$alkyl." Likewise, an aryl group having from six to ten carbon atom can be designated $C_{6-10}$aryl.

As used herein, the term "alkyl" refers to a fully saturated branched or unbranched hydrocarbon moiety having from 1 to 20 carbon atoms. In one embodiment, alkyl refers to hydrocarbon moieties having 1 to 16 carbon atoms, 1 to 10 carbon atoms, 1 to 7 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

As used herein, the term "alkylene" refers to divalent alkyl group as defined herein above having 1 to 20 carbon atoms. In one embodiment, an alkylene refers to moieties having 1 to 16 carbon atoms, 1 to 10 carbon atoms, 1 to 7 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

As used herein, the term "haloalkyl" refers to an alkyl as defined herein that is substituted by one or more halo groups as defined herein. The haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. The term "alkenyl" refers to a monovalent hydrocarbon which can be branched or unbranched and which has at least one carbon-carbon double bond. The term "$C_2$-$C_6$alkenyl" refers to a monovalent hydrocarbon having two to six carbon atoms and comprising at least one carbon-carbon double bond. Non-limiting examples of alkenyl groups include ethenyl, prop-2-en-1-yl, and 1-methyl-prop-1-en-1-yl.

The term "alkynyl" refers to a monovalent hydrocarbon which may be branched or unbranched and which has at least one carbon-carbon triple bond. The term "$C_2$-$C_6$-alkynyl" refers to a monovalent hydrocarbon having two to six carbon atoms and comprising at least one carbon-carbon triple bond. An example of an alkyne group is acetylenyl.

The term "aryl" refers to an aromatic hydrocarbon group having 6-20 carbon atoms in the ring portion. Typically, aryl is monocyclic, bicyclic or tricyclic. In one embodiment, an aryl group is mono- or bicyclic and contains 6 to 10 carbon atoms. Examples of aryl groups include phenyl, naphthyl, and anthracenyl. An aryl group also includes an aromatic hydrocarbon which is fused to another ring which is not aromatic if the point of attachment to another moiety is on the aromatic ring, such as 1,2,3,4-tetrahydronaphth-5-yl, 1H-inden-5-yl, and 1,2,3,4-tetrahydroquinolin-7-yl.

As used herein, the term "alkoxy" refers to alkyl-O—, wherein alkyl is defined herein above. Representative examples of alkoxy groups include, but are not limited to, methoxy, ethoxy, propoxy, 2-propoxy, n-butoxy, tert-butoxy, n-pentyloxy, n-hexyloxy, 2-methyl-propoxy, and the like. Typically, alkoxy groups have about 1-7, more preferably about 1-4 carbons.

As used herein, the term "alkylthio" refers to alkyl-S—, wherein alkyl is defined herein above. Representative examples of alkylthio groups include, but are not limited to, methylthio, ethylthio, propylthio, 2-propylthio, n-butylthio, tert-butylthio, n-pentylthio, n-hexylthio, 2-methyl-propylthio, and the like. Typically, alkylthio groups have about 1-7, more preferably about 1-4 carbons.

As used herein, the term "heterocyclyl" or "heterocyclo" refers to a saturated or unsaturated non-aromatic ring or ring system, e.g., which is a 3-, 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. In one embodiment, a heterocyclyl has 3- to 10-ring members. The heterocyclic group can be attached at a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like. A heterocyclyl also includes a non-aromatic heterocyclic ring system which is fused to another ring which is aromatic if the point of attachment to another moiety is on the non-aromatic ring, such as 1,2,3,4-tetrahydroquinoxalin-1-yl an 1,2,3,4-tetrahydropyrido[3,2-b]pyrazin-1-yl.

As used herein, the term "carbocyclyl" refers to saturated or unsaturated monocyclic, bicyclic or tricyclic non-aromatic hydrocarbon groups which have 3-12 carbon atoms. In one embodiment, carbocyclyl refers to cyclic hydrocarbon groups having between 3 and 9 ring carbon atoms or between 3 and 7 ring carbon atoms. In a preferred embodiment, a carbocyclyl is a monocyclic hydrocarbon having from 3 to 7 carbon atoms. Exemplary monocyclic carbocyclyl groups include, but are not limited to, cyclopropyl, cyclobutyl, cyclopentyl, cyclopentenyl, cyclohexyl and cyclohexenyl and the like. Exemplary bicyclic carbocyclic groups include bicyclo[2.2.1]heptanyl, decahydronaphthyl, bicyclo[2.1.1]hexanyl, bicyclo[2.2.1]heptanyl, bicyclo[2.2.1]heptenyl, bicyclo[2.2.2]octyl and the like. Exemplary tricyclic carbocyclic groups include adamantyl, dodecahydros-indacene, and the like. A carbocyclyl also includes a non-aromatic hydrocarbon ring which is fused to an aromatic ring if the point of attachment to another moiety is on the non-aromatic ring, such as 1,2,3,4-tetrahydronaphth-1-yl, 1H-inden-2-yl, and 5,6,7,8-tetrahydroquinolin-5-yl.

The term "carbocyclyl" encompasses cycloalkyl groups. The term "cycloalkyl" refers to a saturated monocyclic, bicyclic or tricyclic hydrocarbon groups which have 3-12 carbon atoms. In one embodiment, cycloalkyl refers to a saturated cyclic hydrocarbon groups having between 3 and 9 ring carbon atoms or between 3 and 7 ring carbon atoms. In a preferred embodiment, a cycloalkyl is a monocyclic hydrocarbon having from 3 to 7 carbon atoms. Exemplary monocyclic cycloalkyl groups include, but are not limited to, cyclopropyl, cyclobutyl, cyclopentyl, cyclohexyl, and the like. Exemplary bicyclic cycloalkyl groups include bicyclo[2.2.1]heptanyl, decahydronaphthyl, bicyclo[2.1.1]hexanyl, bicyclo[2.2.1]heptanyl, bicyclo[2.2.2]octyl and the like. Exemplary tricyclic cycloalkyl groups include adamantyl, dodecahydros-indacene, and the like.

As used herein, the term "heteroaryl" refers to a 5-14 membered monocyclic- or bicyclic- or tricyclic-aromatic ring system, having 1 to 8 heteroatoms selected from N, O or S. Typically, the heteroaryl is a 5-10 membered ring system (e.g., 5-7 membered monocycle or an 8-10 memberred bicycle). Typical heteroaryl groups include 2- or 3-thienyl, furanyl, pyrrolyl, imidazolyl, pyrazolyl, thiazolyl, isothiazolyl, oxazolyl, isoxazolyl, triazolyl, tetrazolyl, 2-, 3-, or pyridyl, pyridazinyl, pyrazinyl, pyrimidinyl, quinolinyl, isoquinolinyl, purinyl, indolinyl, benzo[b]thiophene, benzofuran, and the like. A heteroaryl group also includes an aromatic heteroaryl ring which is fused to another ring which is not aromatic if the point of attachment to another moiety is on the heteroaromatic ring, such as 5,6,7,8-tetrahydroquinolin-4-yl and 1,2,3,4-tetrahydropyrido[2,3-b]pyrazin-8-yl.

As used herein, the term "halogen" or "halo" refers to fluoro, chloro, bromo, and iodo.

As used herein, the term "aryloxy" refers to aryl-O—, wherein aryl is defined herein above. An example of an aryloxy is phenoxy.

As used herein, the term "cycloalkoxy" refers to cycloalkyl-O—, wherein cycloalkyl is defined herein above. Representative examples of cycloalkoxy groups include cyclopentyloxy and cyclohexyloxy.

As used herein, the term "heterocyclyloxy" refers to heterocyclyl-O—, wherein heterocyclyl is defined herein above. Representative examples of heterocyclcyloxy groups include piperadin-4-yloxy, piperazin-3-yloxy, and the like.

An "amino" group as used herein refers to —$NH_2$. The term "N-alkylamino" refers to an amino group in which one hydrogen is replaced by an alkyl group. For example, N—$C_{1-7}$alkylamino refers to an amino group in which one of the hydrogens has been replaced with an alkyl group having from 1 to 7 carbon atoms. Representative N—$C_{1-7}$alkylamino groups include N-methylamino, N-ethylamino, N-isopropylamino and the like. The term "N,N-di-(alkyl)amino" refers to an amino group in which both hydrogens have been replaced by an alkyl group which may be the same or different. For example, N,N-di-($C_{1-7}$alkyl)amino refers to an amino group in which both of the hydrogens have been replaced with an alkyl group which may be the same or different having from 1 to 7 carbon atoms. Representative N,N-di-($C_{1-7}$alkyl)amino groups include N,N-dimethylamino, N-methyl-N-ethyl-amino, N-isopropyl-N-ethyl-amino, and the like.

A "carbamoyl" group as used herein refers to —$C(O)NH_2$. The term "N-(alkyl)-carbamoyl" refers to a carbamoyl group in which one hydrogen is replaced by an alkyl group. For example, N—($C_{1-7}$alkyl)-carbamoyl refers to a carbamoyl group in which one of the hydrogens has been replaced with an alkyl group having from 1 to 7 carbon atoms. Representative N—($C_{1-7}$alkyl)-carbamoyl include N-methylcarbamoyl, N-isopropyl-carbamoyl, and the like. The term "N,N-di-(alkyl)-carbamoyl" refers to a carbamoyl group in which both hydrogens have been replaced by an alkyl group which may be the same or different. For example, N,N-di-($C_{1-7}$alkyl)-carbamoyl refers to a carbamoyl group in which both of the hydrogens have been replaced with an alkyl group which may be the same or different having from 1 to 7 carbon atoms. Representative N,N-di-($C_{1-7}$alkyl)-carbamoyl include N,N-dimethylcarbamoyl, N-methyl-N-isopropyl-carbamoyl, and the like.

The term "alkylamido" refers to a group having the formula —NHC(O)—$R^i$, wherein $R^i$ is an alkyl group. For example, $C_{1-7}$alkylamido refers to an alkylamido group which has from one to seven carbon atoms, such as butyramido, and the like.

The term "arylamido" refers to a group having the formula —NHC(O)—$R^{ii}$, wherein $R^{ii}$ is an aryl group. For example, $C_{6-10}$arylamido refers to an arylamido group which has from six to ten carbon atoms, such as benzamido, and the like.

The term "heterocyclylamido" refers to a group having the formula —NHC(O)—$R^{iii}$, wherein $R^{iii}$ is an heterocycyl group. Example of heterocyclylamido groups include piperidine-1-carboxamido, piperidine-3-carboxamido, and the like.

The term "alkanoyl" refers to a group having the formula —C(O)—$R^i$, wherein $R^i$ is an alkyl group. For example, $C_{1-7}$alkanoyl refers to an alkanoyl group which has from one to seven carbon atoms, such as acetyl, isopropyl-carbonyl, and the like.

The term "alkanoyloxy" refers to a group having the formula —OC(O)—$R^i$, wherein $R^i$ is an alkyl group. For example, $C_{1-7}$alkanoyl refers to an alkanoyloxy group which has from one to seven carbon atoms, such as ethoxycarbonyloxy, isopropoxycarbonyloxy, and the like.

The term "alkoxycarbonyl" refers to a group having the formula —C(O)—$OR^i$, wherein $R^i$ is an alkyl group. For example, $C_{1-7}$alkoxycarbonyl refers to an alkoxycarbonyl group which has from one to seven carbon atoms, such as methoxycarbonyl, tert-butoxycarbonyl, and the like.

The term "alkoxyamido" refers to a group having the formula —NHC(O)—$OR^i$, wherein $R^i$ is an alkyl group. For example, $C_{1-7}$alkoxamido refers to an alkoxyamido group which has from one to seven carbon atoms, such as methoxycarbonylamino, tert-butoxycarbonylamino, and the like.

The term "alkylureido" refers to a group having the formula —NHC(O)—$NHR^i$, wherein $R^i$ is an alkyl group. For example, $C_{1-7}$alkylureido refers to an alkylureido group which has from one to seven carbon atoms, such as N'-methylureido, N'-(tert-butyl)-ureido, and the like.

The term "arylureido" refers to a group having the formula —NHC(O)—$NHR^{ii}$, wherein $R^{ii}$ is an aryl group. For example, $C_{6-10}$arylureido refers to an arylureido group which has from six to ten carbon atoms, such as N'-phenylureido, N'-(naphth-3-yl)-ureido, and the like.

The term "alkylsulfonyl" refers to a group having the formula —$S(O)_2R^i$, wherein $R^i$ is an alkyl group. For example, $C_{1-7}$alkylsulfonyl refers to an alkylsulfonyl group which has from one to seven carbon atoms, such as mesyl, tert-butylsulfonyl, and the like.

The term "oxo" refers to a double bonded oxygen substituent (i.e. =O).

The term "phosphonooxy" refers to a group having the following formula:

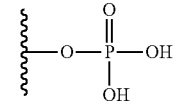

which may be neutral (as shown) or a mono- or di-anion depending on the pH of the media in which it is formed or in which it is dissolved in.

The term "amino acid" includes natural and synthetic α- or β-amino acids, such as alanine, cysteine, 3,5-dibromotyrosine, 3,5-diiodotyrosine, glutamine, glycine, gem-dimethylglycine, histidine, hydroxylysine, isoleucine, leucine, methionine, phenylalanine, proline, serine, threonine, thyroxine, tryptophane, tyrosine, valine, α-aminobutyric acid, β-alanine. In addition, wherein the amino acid has a chiral center, the side-chain may be from either the D or L isomer of the amino acid. The term "amino acid sidechain" to a sidechain of a naturally occurring amino acid.

Formula (I) encompasses Formulas (II) through (V) and (IA) through (IVA). Thus, the phrase "a compound of Formula (I)" includes compounds of Formulas (II) through (V) and (IA) through (IVA).

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood or conversion in the gut or liver. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)).

A discussion of prodrugs is provided in Higuchi, T., et al., "Pro-drugs as Novel Delivery Systems," A. C. S. Symposium Series, Vol. 14, and in Bioreversible Carriers in Drug Design, ed. Edward B. Roche, Anglican Pharmaceutical Association arid Pergamon Press, 1987.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

Compounds of the present invention are either obtained in the free form, as a salt thereof, or as prodrug derivatives thereof. When both a basic group and an acid group are present in the same molecule, the compounds of the present invention may also form internal salts, e.g., zwitterionic molecules.

Furthermore, the compounds of the present invention, including their salts, can also be obtained in the form of their hydrates, or include other solvents used for their crystallization.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients thereof.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques. Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O, O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

When the compounds described herein contain olefinic double bonds or other centers of geometric asymmetry, and unless specified otherwise, it is intended that the compounds include both E and Z geometric isomers. Likewise, all tautomeric forms are also intended to be included.

The present invention includes all pharmaceutically acceptable isotopically-labeled compounds of Formula (I) wherein one or more atoms are labeled with an atom having the same atomic number, but an atomic mass or mass number different from the atomic mass or mass number usually found in nature.

Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Enrichment with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Isotopically-labeled compounds of Formula (I) can generally be prepared by conventional techniques known to those skilled in the art or by processes analogous to those described in the accompanying Examples and Preparations Sections using an appropriate isotopically-labeled reagent in place of the non-labeled reagent previously employed.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by ACC2, or (ii) associated with ACC2 activity, or (iii) characterized by abnormal activity of ACC2; or (2) reducing or inhibiting the activity of ACC2 (3) reducing or inhibiting the expression of ACC2. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of ACC2; or at least partially reducing or inhibiting the expression of ACC2.

As used herein, the term "patient" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

EMBODIMENTS OF THE INVENTION

Throughout this specification and in the claims that follow, unless the context requires otherwise, the word "comprise", or variations such as "comprises" or "comprising", will be understood to imply the inclusion of a stated integer or step or group of integers or steps but not the exclusion of any other integer or step or group of integers or steps.

In one aspect, the invention provides compounds of formula (I):

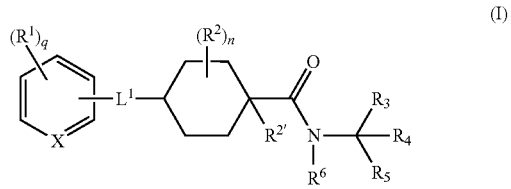

or a pharmaceutically acceptable salt thereof, wherein:
X is CH, CR$^1$, or N;
q and n are each, independently, 0, 1, 2, 3, or 4;
L$_1$ is —NHSO$_2$—, —SO$_2$NH—, —NHSO$_2$NH— or —NHC(O)NH—;
R$^1$, for each occurrence, is independently hydroxy, nitro, halo, carboxy, formyl, C$_{1-7}$alkyl, C$_{3-8}$cycloalkyl, C$_{2-7}$alkenyl, C$_{2-7}$alkynyl, C$_{1-7}$alkoxy, C$_{1-7}$alkylthio, C$_{3-8}$cycloalkoxy, heterocyclyloxy, C$_{6-10}$aryloxy, amino, C$_{1-7}$alkylamino, di-(C$_{1-7}$ alkyl)amino, C$_{6-10}$aryl, 3- to 10-membered heterocyclyl, 5- to 10-membered heteroaryl, C$_{1-7}$alkanoyl, C$_{1-7}$alkoxycarbonyl, C$_{1-7}$alkanoyloxy, C$_{1-7}$alkylamido, C$_{6-10}$arylamido, heterocyclylamido, carbamoyl, N—C$_{1-7}$alkylcarbamoyl, N,N-di-(C$_{1-7}$ alkyl)carbamoyl, C$_{1-7}$alkoxyamido, C$_{1-7}$alkylureido, and C$_{6-10}$arylureido, wherein R$^1$ is optionally substituted on one or more carbon atom with one or more independently selected R$^{13}$; and wherein when R$^1$ comprises a heterocyclyl or a heteroaryl comprising —NH—, the hydrogen of the —NH—group may be optionally replaced with a $C_{1-7}$alkyl; and wherein when $R^1$ comprises a heterocyclyl or a heteroaryl comprising —N═, —S— or both, the —N═ may be substituted with —O⁻ and the —S— group may be substituted with one or two ═O groups;

$R^2$, for each occurrence, is independently selected from the group consisting of hydroxy, cyano, $C_{1-7}$alkyl, $C_{1-7}$alkoxy, $C_{2-7}$alkenyl, amino, $C_{1-7}$alkylamino, di-($C_{1-7}$alkyl)amino, $C_{1-7}$alkylamido, $C_{1-7}$alkoxycarbonylamino, or two or more $R^2$ groups on non-adjacent carbon atoms together form a $C_{1-4}$alkylene bridge; wherein $R^2$, for each occurrence, may be independently optionally substituted with one or more halo;

$R^{2'}$ is hydrogen or $R^2$; or $R^{2'}$ and one or more $R^2$ groups form a $C_{1-4}$alkylene bridge; or $R^{2'}$ and $R^6$, may be linked to form a 5-membered heterocyclyl spirocyclic ring which may be optionally substituted with one or more $C_{1-7}$alkyl;

$R^3$ is selected from the group consisting of a $C_{1-7}$alkyl, $C_{3-8}$cycloalkyl, $C_{8-10}$aryl, a 5- to 10-membered heteroaryl, or a 3- to 10-membered heterocyclyl, wherein $R^3$ is optionally substituted on one or more carbon atom with one or more independently selected $R^{14}$; and wherein when $R^3$ is a heteroaryl or heterocyclyl comprising —NH—, the hydrogen of the —NH— group may be optionally replaced with a $C_{1-7}$alkyl; and wherein when $R^3$ is a heteroaryl or a heterocyclyl comprising —N═, —S— or both, the —N═ may be substituted with —O⁻ and the —S— group may be substituted with one or two ═O groups;

$R^4$ is hydrogen, a $C_{1-7}$alkyl, or carbamoyl, wherein the alkyl may be optionally substituted with one or more substituent which may be independently selected from the group consisting of duetero, hydroxy, amino, halo, carboxy, $C_{1-7}$alkoxy, $C_{1-7}$alkoxycarbonyl, phosphonooxy, a peptide having from 1 to 3 amino acids and $C_{1-7}$alkanoyloxy wherein the alkanoyloxy may be optionally substituted with one or more carboxy, amino, N—$C_{1-6}$alkylamino, N,N-di-($C_{1-6}$ alkyl)amino, or amino acid sidechain;

$R^5$ is hydrogen or a $C_{1-7}$ alkyl;

$R^6$ is hydrogen or $C_{1-7}$ alkyl; or $R^6$ and any one of $R^4$ or $R^5$ may be linked to form a 3- to 7-membered heterocyclyl, wherein the heterocyclyl may be optionally substituted on one or more carbon with one or more $R^{15}$; and wherein when the heterocyclyl comprises —NH—, the hydrogen of the —NH— group may be optionally replaced with $R^{16}$; and wherein when the heterocyclyl comprises —N═, —S— or both, the —N═ may be substituted with —O⁻ and the —S— group may be substituted with one or two ═O groups;

$R^{13}$, for each occurrence, is independently deutero, halo, hydroxy, oxo, carboxy, $C_{1-7}$alkyl, $C_{3-8}$cycloalkyl, $C_{1-7}$alkoxy, $C_{6-10}$aryl, 3- to 10-membered heterocyclyl, 5- to 10-membered heteroaryl, amino, $C_{1-7}$alkylamino, di-($C_{1-7}$alkyl)amino, $C_{1-7}$alkoxycarbonyl, carbamoyl, wherein $R^{13}$ is optionally substituted on one or more carbon atom with one or more independently selected $R^{17}$; and wherein when $R^{13}$ is a heterocyclyl or a heteroaryl comprising —NH—, the hydrogen of the —NH— group may be optionally replaced with a $C_{1-7}$alkyl; and wherein when $R^{13}$ is a heterocyclyl or heteroaryl comprising —N═, —S— or both, the —N═ may be substituted with —O⁻ and the —S— group may be substituted with one or two ═O groups;

$R^{14}$, for each occurrence, is independently halo;

$R^{15}$, for each occurrence, is independently selected from the group consisting of hydroxy, oxo, carboxy, $C_{1-7}$alkyl, and $C_{1-7}$alkoxycarbonyl; or two $R^{15}$ on adjacent carbon atoms may form a fused phenyl;

$R^{16}$, for each occurrence, is independently selected from the group consisting of $C_{1-7}$alkanoyl, $C_{6-10}$arylcarbonyl, heteroarylcarbonyl, $C_{1-7}$alkoxycarbonyl, 5- to 10-membered heteroaryl, and $C_{1-7}$alkylsulfonyl, wherein $R^{16}$ may be optionally substituted with one or more substituent independently selected from the group consisting of carboxy, amino, $C_{1-7}$alkylamino, di-($C_{1-7}$alkyl)amino, and $C_{1-7}$alkoxycarbonyl; and $R^{17}$, for each occurrence, is independently selected from cyano, halo, hydroxy, carboxy, $C_{1-7}$alkoxy, amino, $C_{1-7}$alkylamino, di-($C_{1-7}$alkyl)amino, $C_{1-7}$alkoxycarbonyl, 3- to 10-membered heterocyclyl, wherein $R^{17}$ may be optionally substituted on one or more carbon atoms with one or more independently selected halo, trifluoromethyl, carboxy, or $C_{1-4}$alkyoxycarbonyl; and wherein when $R^{17}$ is a heterocyclyl comprising —NH—, the hydrogen of the —NH— group may be optionally replaced with a $C_{1-7}$alkyl; and wherein when $R^{17}$ is a heterocyclyl comprising —N═, —S— or both, the —N═ may be substituted with —O⁻ and the —S— group may be substituted with one or two ═O groups.

In one embodiment, the compounds of Formula (I) are represented by Formula (II):

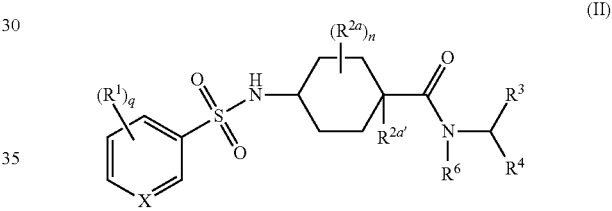

wherein $R^1$, for each occurrence, is independently selected from halo, hydroxy, nitro, $C_{1-7}$alkyl, $C_{1-7}$alkoxy, —NH—C(O)$R^9$, $C_{2-7}$alkynyl, $C_{3-7}$cycloalkyl, $C_{3-7}$cycloalkoxy, $C_{1-7}$alkoxycarbonyl, $C_{1-7}$alkanoyl, $C_{1-7}$alkylamido, amino, N—$C_{1-7}$alkylamino, N,N-di-($C_{1-7}$alkyl)amino, $C_{1-7}$alkoxycarbonylamino, phenoxy, 3- to 7-membered heterocyclyl, 3- to 7-membered heterocyclyloxy, 3- to 7-membered heterocyclylamido, —NH—C(O)NHR$^{19}$, and $C_{1-7}$alkylthio; wherein $R^1$ may be optionally substituted on one or more carbon atoms with from one to three independently selected $R^{13}$;

$R^{2a}$, for each occurrence, is independently selected from cyano, amino, hydroxy, $C_{1-4}$alkyl, and $C_{2-4}$alkenyl;

n is 0 or 1;

$R^{2a'}$ is hydrogen, cyano, amino, hydroxy, $C_{1-4}$alkyl, or $C_{2-4}$alkenyl;

$R^9$, for each occurrence, is independently selected from $C_{1-7}$alkyl, phenyl, and benzyl, wherein $R^9$ may be optionally substituted on one or more carbon atoms with from one to three independently selected $R^{13}$;

$R^{10}$, for each occurrence, is independently selected from hydrogen, $C_{1-7}$alkyl, phenyl, and benzyl, wherein $R^{10}$ may be optionally substituted on one or more carbon atoms with from one to three independently selected $R^{13}$;

$R^{13}$, for each occurrence, is independently selected from the group consisting of halo, duetero, hydroxy, oxo, amino, $C_{1-7}$alkyl, $C_{1-7}$alkoxy, $C_{1-7}$alkoxycarbonyl, $C_{3-7}$cycloalkyl, $C_{1-7}$alkoxy$C_{1-7}$alkyl, $C_{1-7}$alkylsulfonyl, and phenyl which is optionally substituted with halo, cyano; and the remaining variables are defined as for formula (I);
or a pharmaceutically acceptable salt thereof.

In one embodiment, the compounds of Formula (I) are represented by Formula (III):

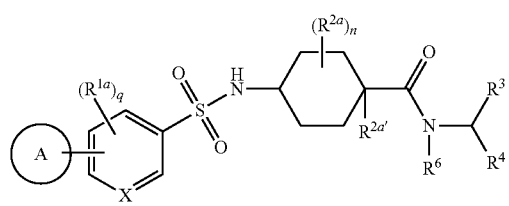

(III)

wherein
ring A is a $C_{6-10}$ aryl or a $C_{1-10}$ heteroaryl, wherein ring A may be optionally substituted with one to three independently selected $R^{17}$; and when ring A is a heterocyclyl comprising —NH—, the hydrogen of the —NH— group may be optionally replaced with a $C_{1-7}$alkyl; and wherein when ring A is a heterocyclyl comprising —N═, —S— or both, the —N═ may be substituted with —O⁻ and the —S— group may be substituted with one or two ═O groups;

q is 0 or 1;
$R^{1a}$ is halo, $C_{1-4}$alkyl, or $C_{1-4}$alkoxy;
$R^{2a}$, for each occurrence, is independently selected from cyano, amino, hydroxy, $C_{1-4}$alkyl, and $C_{2-4}$alkenyl;
n is 0 or 1;
$R^{2a'}$ is hydrogen, cyano, amino, hydroxy, $C_{1-4}$alkyl, or $C_{2-4}$alkenyl; and
the remaining variables are defined as for formula (I);
or a pharmaceutically acceptable salt thereof.

In one embodiment, the compounds of Formula (I) are represented by Formula (IV):

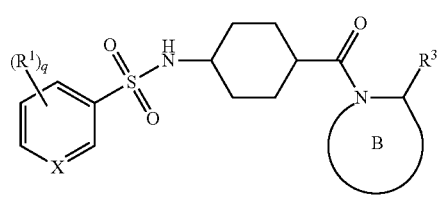

(IV)

wherein
ring B is a $C_{2-10}$ heterocyclyl ring which is optionally substituted on one or more carbon atoms with one to three independently selected $R^{15}$; and wherein when the heterocyclyl comprises —NH—, the hydrogen of the —NH— group may be optionally replaced with $R^{16}$; and wherein when the heterocyclyl comprises —N═, —S— or both, the —N═ may be substituted with —O⁻ and the —S— group may be substituted with one or two ═O groups;
$R^{2a}$, for each occurrence, is independently selected from cyano, amino, hydroxy, $C_{1-4}$alkyl, and $C_{2-4}$alkenyl;
n is 0 or 1; and
the remaining variables are defined as for formula (I);
or a pharmaceutically acceptable salt thereof.

In one embodiment, the compounds of Formula (I) are represented by Formula (V):

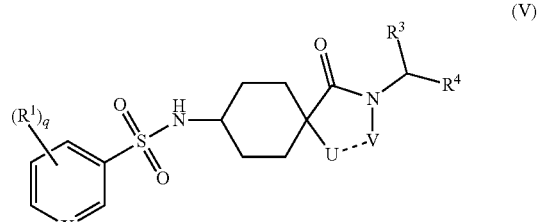

(V)

wherein:
the dashed line is a single or double bond;
U and V are each, independently N, $CR^{11}R^{12}$ or $CR^{11}$;
$R^{11}$ and $R^{12}$, for each occurrence, are independently hydrogen or a $C_{1-7}$alkyl; and
the remaining variables are defined as for formula (I);
or a pharmaceutically acceptable salt thereof.

In one embodiment, the compounds of Formula (I) have the stereochemcal configuration of formula (IA):

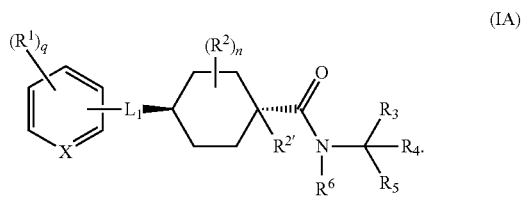

(IA)

In one embodiment, the compounds of Formula (II) have the stereochemcal configuration of formula (IIA):

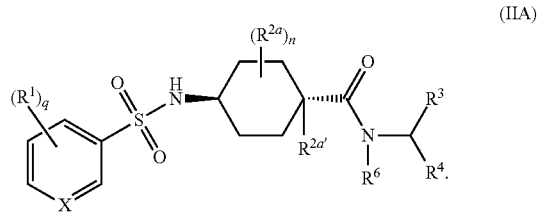

(IIA)

In one embodiment, the compounds of Formula (III) have the stereochemcal configuration of formula (IIIA):

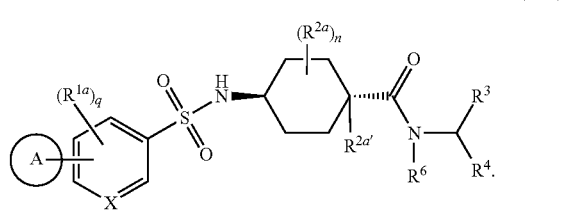

(IIIA)

In one embodiment, the compounds of Formula (I) have the stereochemcal configuration of formula (IVA):

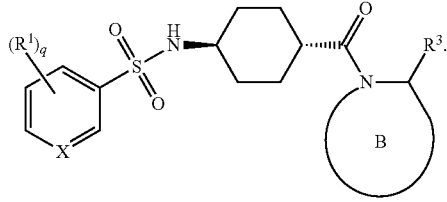

(IVA)

In one embodiment, of the compounds of Formula (I), (II), (IV), (V), (IA), (IIA), or (IVA), $R^1$, for each occurrence, is independently selected from fluoro, chloro, bromo, methyl, ethyl, isopropyl, tert-butyl, methoxy, ethoxy, isopropoxy, phenoxy, methoxymethyl, cyclopentoxy, trifluoromethyl, trifluoromethoxy, 1-hydroxy-1-methyl-ethyl, nitro, amino, N-methylamino, N,N-dimethylamino, N-(trideuteromethyl)-N-(2-hydroxyethyl)-amino, N-ethylamino, N-propylamino, n-propylamino, 2-aminoethylthio, phenylamido, 2-cyanophenyl-ethynyl, 3-hydroxy-but-1-yn-1-yl, 4-hydroxy-pent-1-yn-1-yl, 5-hydroxy-pent-1-yn-1-yl, acetyl, acetamido, carbamoyl, ethoxycarbonyl, methoxycarbonylamino, (t-butoxycarbonyl)-methoxy, 3-methyl-oxetan-3-yl, oxetan-3-yloxy, N'-methyl-ureido, N'-ethyl-ureido, N'-phenyl-ureido, N'-(1-phenyl-ethyl)-ureido, piperidine-1-carboxamido, cyclopropyl-ethynyl, 2-oxopyrrolidino, 2-methoxymethyl-pyrrolidino, 2-(methoxycarbonyl)-ethyl, 2-methoxy-ethoxy, methoxycarbonyl-methoxy, and cyclopropyl.

In another embodiment, of the compounds of Formula (I), (II), (IV), (V), (IA), (IIA), or (IVA), q is 1 and $R^1$ is trifluoromethyl.

In one embodiment, of the compounds of Formula (III) or (IIIA), ring A is phenyl, pyrazolyl, pyridinyl, oxazolyl, pyrimidinyl, thiazolyl, pyrrolyl, tetrazolyl, imidazolyl, pyridazinyl, pyrazinyl, or 1,2,4-oxadiazolyl, each of which may be optionally substituted with one to three independently selected $R^{17}$; and when ring A is a heterocyclyl comprising —NH—, the hydrogen of the —NH— group may be optionally replaced with a $C_{1-7}$alkyl; and wherein when ring A is a heterocyclyl comprising —N=, —S— or both, the —N= may be substituted with —O⁻ and the —S— group may be substituted with one or two =O groups.

In another embodiment, of the compounds of Formula (III) or (IIIA), ring A is selected from:

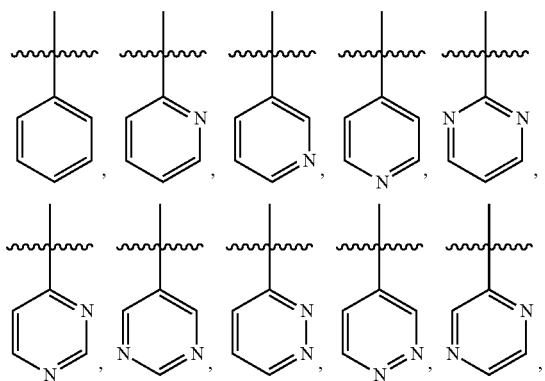

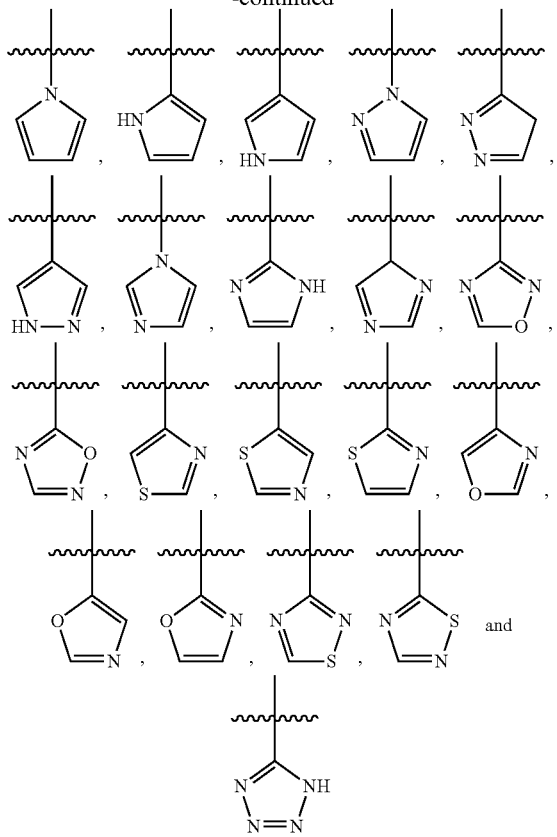

each of which may be optionally substituted with from one to three independently selected $R^{17}$.

In one embodiment, of the compounds of Formula (I), (II), (III), (IV), (V), (IA), (IIA), (IIIA), or (IVA), $R^{17}$, for each occurrence, is independently selected from halo, $C_{1-4}$alkyl, $C_{1-4}$alkoxy, halo$C_{1-4}$alkyl, carboxy-$(CR'R'')_a$—, $C_{1-4}$alkoxy-carbony-$(CR'R'')_a$—, hydroxy-$(CR'R'')_a$—, cyano-$(CR'R'')_a$—, —$(CR'R'')_a$—$NR^{18}R^{18}$, carboxy-$(CR'R'')_a$—O—, $C_{1-4}$alkoxycarbony-$(CR'R'')_a$—O—, hydroxy-$(CR'R'')_a$—O—, —O—$(CR'R'')_a$—$NR^{18}R^{19}$, carbamoyl, N—$(C_{1-4}$alkyl)carbamoyl, N,N-di-$(C_{1-4}$alkyl)carbamoyl, oxetanyl, cyclopropyl, pyrrolidino-$C_{1-4}$alkyl, pyrrolidino-$C_{1-4}$alkoxy, morpholino-$C_{1-4}$alkyl, morpholino-$C_{1-4}$alkoxy, S,S-dioxothiomorpholino-$C_{1-4}$alkyl, piperazino-$C_{1-4}$alkyl, wherein oxetanyl, cyclopropyl, pyrrolidino, morpholino, thiomorpholino, and piperazino, for each occurrence may be optionally substituted with one to three substituents that are independently selected from amino, halo, $C_{1-4}$alkyl, trifluoromethyl, carboxy, ethoxycarbonyl, and methoxycarbonyl;

R' and R'', for each occurrence, is independently hydrogen, a halo, a $C_{1-4}$alkyl or amino;

$R^{18}$ and $R^{19}$, for each occurrence, are independently selected from hydrogen, $C_{1-4}$alkyl, $C_{1-4}$alkoxycarbonyl$C_{1-4}$alkyl, and carboxy$C_{1-4}$alkyl;

a is 0, 1, 2, or 3.

In another embodiment, of the compounds of Formula (I), (II), (III), (IV), (V), (IA), (IIA), (IIIA), or (IVA), $R^{17}$, for each occurrence is independently selected from fluoro, chloro, methyl, methoxy, hydroxymethyl, carboxy, ethoxycarbonyl, carboxymethyl, 2-carboxyethyl, 2-(ethoxycarbonyl)-ethyl, 2-carboxy-2-methylpropyl, carboxymethoxy, 2-carboxy-2-amino-ethyl, amino-(methoxycarbonyl)-methyl, N,N-dimethylamino, carbamoyl, trifluoromethyl, 3-methyl-oxetan-3- yl, 1-hydroxy-1-methyl-ethyl, 1-aminocyclopropyl, cyano-difluoro-methyl, aminomethyl, 2-aminoethyl, 2-amino-1,1-difluoro-ethyl, 3,3-difluoropyrrolidinomethyl, morpholinomethyl, 2-morpholino-ethyl, 2-morpholino-ethoxy, 2-(3,3-difluoropyrrolidino)-ethyl, 2-(3,3-difluoropyrrolidino)-ethoxy, 2-(2-carboxy-pyrrolidino)-ethoxy, 2-[2-(ethoxycarbonyl)-pyrrolidino]-ethoxy, N-(ethoxycarbonylmethyl)-N-methyl-amino-methyl, 2-[N-(ethoxycarbonylmethyl)-N-methyl-amino]-ethyl, N-(carboxymethyl)-amino-methyl, N-(carboxymethyl)-N-methyl-amino-methyl, 2-[N-(carboxymethyl)-N-methyl-amino]-ethyl, 2-[N-(carboxymethyl)-amino]-ethyl, 2-(N,N-dimethylamino)-ethoxy, S,S-dioxo-thiomorpholino-methyl, 2-(S,S-dioxo-thiomorpholino)-ethyl, 2-(S,S-dioxo-thiomorpholino)-ethoxy, 2-(3-trifluoromethyl-piperazino)-ethyl, and 2-(3-trifluoromethyl-piperazino)-ethoxy.

In one embodiment, of the compounds of Formula (I), (II), (III), (V), (IA), (IIA), or (IIIA), $R^6$ is hydrogen and $R^4$ is an unsubstituted $C_{1-7}$alkyl.

In another embodiment, of the compounds of Formula (I), (II), (III), (V), (IA), (IIA), or (IIIA), $R^6$ is hydrogen and $R^4$ is a $C_{1-7}$alkyl which is substituted with a hydroxy.

In another embodiment, of the compounds of Formula (I), (II), (III), (V), (IA), (IIA), or (IIIA), $R^6$ is hydrogen and $R^4$ is 1-hydroxy-ethyl or 1-hydroxy-1-methyl-ethyl.

In another embodiment, of the compounds of Formula (I), (II), (III), (V), (IA), (IIA), or (IIIA), $R^6$ is hydrogen and $R^4$ is a $C_{1-7}$alkyl which is substituted with from one to three substituents which are independently selected from deutero, halo, amino, carboxy, methoxycarbonyl, tert-butoxycarbonyl, and $C_{1-4}$alkoxy.

In one embodiment, of the compounds of Formula (IV) or (IVA), ring B is

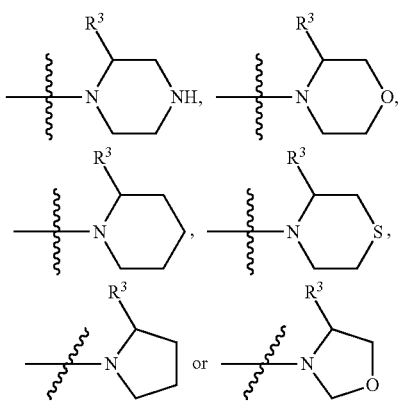

each of which is optionally substituted on one or more carbon atoms with one to three independently selected $R^{15}$; and wherein when the heterocyclyl comprises —NH—, the hydrogen of the —NH— group may be optionally replaced with $R^{16}$; and wherein when the heterocyclyl comprises —S—, it may be substituted with one or two =O groups.

In one embodiment, of the compounds of Formula (IV) or (IVA), $R^{15}$, for each occurrence, is independently selected from hydroxy, oxo, methyl, carboxy, and methoxycarbonyl.

In one embodiment, of the compounds of Formula (IV) or (IVA), $R^{16}$, for each occurrence, is independently selected from pyridin-2-yl, acetyl, benzoyl, pyridin-2-ylcarbonyl, pyridin-3-ylcarbonyl, pyridin-4-ylcarbonyl, 1-oxo-4-carboxy-butan-1-yl, 1-oxo-3,3-dimethyl-4-carboxy-butan-1-yl, N,N-dimethylamino-acetyl, ethoxycarbonyl, tert-butoxycarbonyl, and methylsulfonyl.

In one embodiment, of the compounds of Formula (I), (II), (III), (IV), (V), (IA), (IIA), (IIIA), or (IVA), $R^3$ is phenyl or pyridinyl, wherein $R^3$ is optionally substituted on one or more carbon atom with one to three independently selected $R^{14}$; and wherein when $R^3$ is pyridinyl, the —N= may be substituted with —O$^-$.

In one embodiment, of the compounds of Formula (I), (II), (III), (IV), (V), (IA), (IIA), (IIIA), or (IVA), $R^3$ is unsubstituted. For example, $R^3$ is selected from:

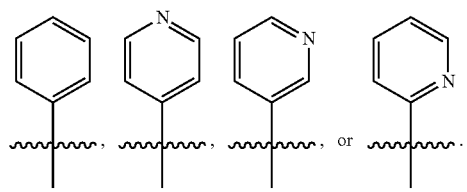

In another embodiment, of the compounds of Formula (I), (II), (III), (IV), (V), (IA), (IIA), (IIIA), or (IVA), $R^3$ is substituted with one $R^{14}$; and $R^{14}$ is selected from the group consisting of fluoro, chloro, and bromo.

In another embodiment, of the compounds of Formula (I), (II), (III), (IV), (V), (IA), (IIA), (IIIA), or (IVA), $R^3$ is 4-fluorophenyl.

In one embodiment, of the compounds of Formula (I), (II), (III), (IV), (V), (IA), (IIA), (IIIA), or (IVA), X is CH.

In another embodiment, of the compounds of Formula (I), (II), (III), (IV), (V), (IA), (IIA), (IIIA), or (IVA), X is $CR^1$.

In another embodiment, of the compounds of Formula (I), (II), (III), (IV), (V), (IA), (IIA), (IIIA), or (IVA), X is N.

In one embodiment, of the compounds of Formula (I), the compounds have the stereochemcal configuration of formula (IA):

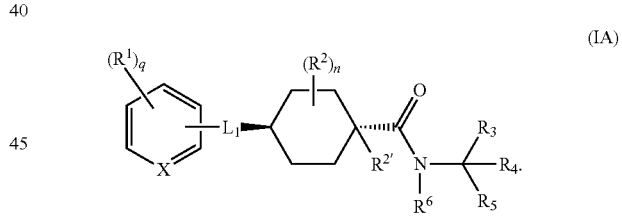

In another embodiment, of the compounds of Formula (I), the compounds have the stereochemcal configuration of formula (IIA):

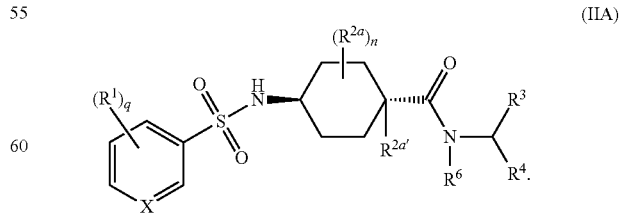

In another embodiment, of the compounds of Formula (I), the compounds have the stereochemcal configuration of formula (IIIA):

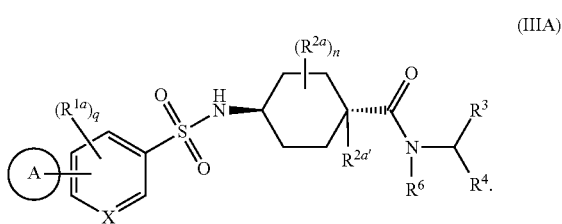

(IIIA)

In another embodiment, of the compounds of Formula (I), the compounds have the stereochemcal configuration of formula (IVA):

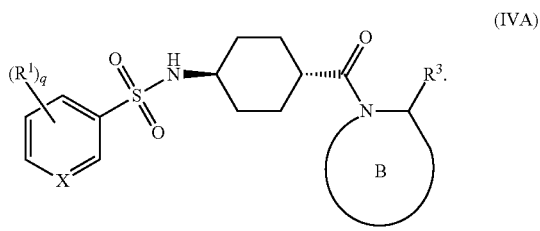

(IVA)

In another embodiment, of a compound of Formula (I) is selected from the examples, or a pharmaceutically acceptable salt thereof.

The compounds of the present invention are useful as both prophylactic and therapeutic treatments for diseases or conditions related to the inhibition of ACC2.

Thus, as a further aspect, the invention relates to a method for treating a disease or condition related to the inhibition of ACC2, comprising administration of an effective therapeutic amount of a compound of formula (I), (II), (III), (IV), (V), (IA), (IIA), (IIIA) or (IVA), or a pharmaceutically acceptable salt thereof.

Compounds of formula (I), (II), (III), (IV), (V), (IA), (IIA), (IIIA) or (IVA), or a pharmaceutically acceptable salt thereof, may be useful in the treatment of metabolic disorders, or conditions, metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, edema and hyperuricaemia.

Compounds of formula (I), (II), (III), (IV), (V), (IA), (IIA), (IIIA) or (IVA), or a pharmaceutically acceptable salt thereof, may, for example, be used to treat various diseases or disorders such as type 1 diabetes, type 2 diabetes mellitus, hyperlipidemia, idiopathic type 1 diabetes, latent autoimmune diabetes in adults, early-onset type 2 diabetes, youth-onset atypical diabetes, maturity onset diabetes of the young, malnutrition-related diabetes and gestational diabetes, coronary heart disease, ischemic stroke, restenosis after angioplasty, peripheral vascular disease, arterial occlusive disease, intermittent claudication, myocardial infarction, dyslipidemia, mixed dyslipidemia, post-prandial lipemia, conditions of impaired glucose tolerance, conditions of impaired fasting plasma glucose, metabolic acidosis, ketosis, arthritis, osteoporosis, diabetic hypertension, familial chylomicromia syndrome, congestive heart failure, left ventricular hypertrophy, peripheral arterial disease, diabetic retinopathy, other ophthalmic complications of diabetes, macular degeneration, cataract, diabetic nephropathy, diabetic foot ulcer, glomerulosclerosis, chronic renal failure, diabetic neuropathy, peripheral angiopathy, peripheral angiopathy gangrene, microangiopathic changes that result in amputation, cancer, cancer deaths, metabolic syndrome, syndrome X, Reaven syndrome, coronary heart disease, other acute and subacute forms of coronary ischemia, angina pectoris, thrombosis, atherosclerosis, myocardial infarction, transient ischemic attacks, stroke, vascular restenosis, hypoglycemia, hyperglycemia, hyperuricemia, hyperinsulinemia, hyperlipidemia, hypertryglyceridemia, hypercholesterolemia, high blood pressure, excessive cardiovascular morbidity, and cardiosvascular mortality in diabetics, elevated non-HDL cholesterol, decreased HDL cholesterol, elevated triglycerides, low high density lipoprotein, high low density lipoprotein, pancreatitis, insulin resistance, impaired glucose metabolism, conditions of impaired glucose tolerance, obesity, central obesity, nonalcoholic fatty liver disease, erectile dysfunction, skin and connective tissue disorders, foot ulcerations and ulcerative colitis, endothelial dysfunction and impaired vascular compliance, conditions characterized by low bone mass (e.g. osteopenia, osteoporosis, rheumatoid arthritis, osteoarthritis, periodontal disease, alveolar bone loss, osteotomy loss, childhood idiopathic bone loss, Paget's disease, bone loss due to metastatic cancer, osteolytic lesions, curvature of the spine, and loss of height), neurodegenerative disease, neurological disorders, seizure, peripheral sensory neuropathy, lipid disorders, cognitive impairment (learning and memory conditions) and dementia.

It is also well-established that metabolic diseases exert a negative influence on other physiological systems. Thus, there is often the codevelopment of multiple disease states (e.g. type I diabetes, type II diabetes, inadequate glucose tolerance, insulin resistance, hyperglycemia, hyperlipidemia, hypertriglyceridemia, hypercholesterolemia, dyslipidemia, obesity or cardiovascular disease in "Syndrome X") or secondary diseases which clearly occur secondary to diabetes (e.g. kidney disease, peripheral neuropathy). Thus, it is expected that effective treatment of the diabetic condition will in turn be of benefit to such interconnected disease states.

In one embodiment, compounds of formula (I), (II), (III), (IV), (V), (IA), (IIA), (IIIA) or (IVA), or a pharmaceutically acceptable salt thereof, may be useful for treating a disorder selected from type 1 and type 2 diabetes mellitus, or complications of diabetes.

In another embodiment, the invention provides a method for treating a metabolic syndrome, such as Syndrome X, diabetes, insulin resistance, decreased glucose tolerance, non-insulin-dependent diabetes mellitus, Type II diabetes, Type I diabetes, diabetic complications, body weight disorders, or leptin related diseases, comprising administering to a mammal in need thereof a therapeutically effective amount of a compound according to formula (I), (II), OD, (IV), (V), (IA), (IIA), (IIIA) or (IVA), or a pharmaceutically acceptable salt thereof. In another embodiment, the metabolic syndrome is dyslipidemia, obesity, insulin resistance, hypertension, microalbuminemia, hyperuricaemia, or hypercoagulability.

In another embodiment, the invention provides a method for treating insulin resistance, decreased glucose tolerance, non-insulin-dependent diabetes mellitus, Type II diabetes, or Type I diabetes, comprising administering to a mammal in need thereof a therapeutically effective amount of a compound according to formula (I), (II), (III), (IV), (V), (IA), (IIA), (IIIA) or (IVA), or a pharmaceutically acceptable salt thereof.

In another embodiment, the invention provides a method for treating a bodyweight disorder such as obesity, overweight, cachexia or anorexia, comprising administering to a mammal in need thereof a therapeutically effective amount of a compound according to formula (I), (II), (III), (IV), (V), (IA), (IIA), (IIIA) or (IVA), or a pharmaceutically acceptable salt thereof.

Compounds of formula (I), (II), (III), (IV), (V), (IA), (IIA), (IIIA) or (IVA), or a pharmaceutically acceptable salt thereof, may be also suitable for preventing beta-cell degeneration such as apoptosis or necrosis of pancreatic beta cells, for improving or restoring the functionality of pancreatic cells, increasing the number and size of pancreatic beta cells, for use as diuretics or antihypertensives and for the prevention and treatment of acute renal failure.

As the product of the ACC reaction, malonyl CoA, is a substrate for FAS, and it is expected that inhibition of ACC will result in either, the selective destruction of, or a reduction in proliferation of, cancerous cells, particularly tumors containing cells overexpressing FAS or ACC, including prostate and breast cancers.

A compound of formula (I), (II), (III), (IV), (V), (IA), (IIA), (IIIA) or (IVA), or a pharmaceutically acceptable salt thereof, may be usefully combined with another pharmacologically active compound, or with two or more other pharmacologically active compounds, for use in therapy. For example, a compound of the formula (I), (II), (III), (IV), (V), (IA), (IIA), (IIIA) or (IVA), or a pharmaceutically acceptable salt thereof, may be administered simultaneously, sequentially or separately in combination with one or more agents for the treatment of disorders previously listed.

In one embodiment, the other therapeutic agent is another anti-obesity agents, anorectic agents, appetite suppressant and related agents. Diet and/or exercise can also have synergistic effects. Anti-obesity agents include, but are not limited to, apolipoprotein-B secretion/microsomal triglyceride transfer protein (apo-B/MTP) inhibitors, MCR-4 agonists, cholescystokinin-A (CCK-A) agonists, serotonin and norepinephrine reuptake inhibitors (for example, sibutramine), sympathomimetic agents, adrenergic receptor agonists, dopamine agonists (for example, bromocriptine), melanocyte-stimulating hormone receptor analogs, cannabinoid 1 receptor antagonists [for example, compounds described in WO2006/047516), melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion).

Where compounds of the invention are administered in conjunction with other therapies, dosages of the co-administered compounds will of course vary depending on the type of co-drug employed, on the specific drug employed, on the condition being treated and so forth. A combined preparation or pharmaceutical composition can comprise a compound of the invention as defined above or a pharmaceutical acceptable salt thereof and at least one additional active ingredient selected from:

a) anti-diabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; insulin sensitizer such as protein tyrosine phosphatase-1B (PTP-1B) inhibitors such as PTP-112; GSK3 (glycogen synthase kinase-3) inhibitors such as SB-517955, SB-4195052, SB-216763, NN-57-05441 and NN-57-05445; cholesterylester transfer protein inhibitors (CETP inhibitors); RXR ligands such as GW-0791 and AGN-194204; sodium-dependent glucose co-transporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; DPPIV (dipeptidyl peptidase IV) inhibitors such as DPP728, LAF237 (vildagliptin—Example 1 of WO 00/34241), MK-0431, saxagliptin, GSK23A; an AGE breaker; a thiazolidone derivative (glitazone) such as pioglitazone, rosiglitazone, or (R)-1-{-4-[5-methyl-2-(4-trifluoromethyl-phenyl)-oxazol-4-ylmethoxy]-benzenesulfonyl}-2,3-dihydro-1H-indole-2-carboxylic acid described in the patent application WO 03/043985, as compound 19 of Example 4, a non-glitazone type PPAR gamma agonist e.g. GI-262570; Monoacylglycerol O-acyltransferase 2 inhibitots (MGAT-2) inhibitors; Diacylglycerol acetyltransferase (DGAT) inhibitors such as those disclosed in WO 2005044250, WO 2005013907, WO 2004094618 and WO 2004047755;

b) hypolipidemic agents such as 3-hydroxy-3-methyl-glutaryl coenzyme A (HMG-CoA) reductase inhibitors, e.g., lovastatin and related compounds such as those disclosed in U.S. Pat. No. 4,231,938, pitavastatin, simvastatin and related compounds such as those disclosed in U.S. Pat. Nos. 4,448,784 and 4,450,171, pravastatin and related compounds such as those disclosed in U.S. Pat. No. 4,346,227, cerivastatin, mevastatin and related compounds such as those disclosed in U.S. Pat. No. 3,983,140, velostatin, fluvastatin, dalvastatin, atorvastatin, rosuvastatin and related statin compounds disclosed in U.S. Pat. No. 5,753,675, rivastatin, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propanephosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837; squalene synthase inhibitors; FXR (farnesoid X receptor) and LXR (liver X receptor) ligands; cholestyramine; fibrates; nicotinic acid and aspirin;

c) an anti-obesity agent or appetite regulating agent such as a CB1 activity modulator, melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonsist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inihibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and GB98/284425 (KaroBio), a SCD-1 inhibitor as disclosed in WO2005011655, a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, phentermine, leptin, bromocriptine, dexamphetamine, amphetamine, fenfluramine, dexfenfluramine, sibutramine, orlistat, dexfenfluramine, mazindol, phentermine, phendimetrazine, diethylpropion, fluoxetine, bupropion, topiramate, diethylpropion, benzphetamine, phenylpropanolamine or ecopipam, ephedrine, pseudoephedrine;

d) anti-hypertensive agents such as loop diuretics such as ethacrynic acid, furosemide and torsemide; diuretics such as thiazide derivatives, chlorithiazide, hydrochlorothiazide, amiloride; angiotensin converting enzyme (ACE) inhibitors such as benazepril, captopril, enalapril, fosinopril, lisinopril, moexipril, perinodopril, quinapril, ramipril and trandolapril; inhibitors of the Na-K-ATPase membrane pump such as digoxin; neutralendopeptidase (NEP) inhibitors e.g. thiorphan, terteo-thiorphan, SQ29072; ECE inhibitors e.g. SLV306; ACE/NEP inhibitors such as omapatrilat, sampatrilat and fasidotril; angiotensin II antagonists such as candesartan, eprosartan, irbesartan, losartan, telmisartan and valsartan, in particular valsartan; renin inhibitors such as aliskiren, terlakiren, ditekiren, RO 66-1132, RO-66-1168; beta-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; aldosterone synthase inhibitors; and dual ET/AII antagonist such as those disclosed in WO 00/01389;

e) a HDL increasing compound, such as niacin, fibrates (e.g., Lopid, others) and statins;

f) Cholesterol absorption modulator such as Zetia® and KT6-971;

g) Apo-A1 analogues and mimetics;

h) thrombin inhibitors such as Ximelagatran;

i) aldosterone inhibitors such as anastrazole, fadrazole, eplerenone;

j) Inhibitors of platelet aggregation such as aspirin, clopidogrel bisulfate;

k) estrogen, testosterone, a selective estrogen receptor modulator, a selective androgen receptor modulator;

l) a chemotherapeutic agent such as aromatase inhibitors e.g. femara, anti-estrogens, topoisomerase I inhibitors, topoisomerase II inhibitors, microtubule active agents, alkylating agents, antineoplastic antimetabolites, platin compounds, compounds decreasing the protein kinase activity such as a PDGF receptor tyrosine kinase inhibitor preferably Imatinib ({N-{5-[4-(4-methyl-piperazino-methyl)-benzoylamido]-2-methylphenyl}-4-(3-pyridyl)-2-pyrimidine-amine}) described in the European patent application EP-A-0 564 409 as example 21 or 4-Methyl-N-[3-(4-methyl-imidazol-1-yl)-5-trifluoromethyl-phenyl]-3-(4-pyridin-3-yl-pyrimidin-2-ylamino)-benzamide described in the patent application WO 04/005281 as example 92;

m) an agent interacting with a 5-HT$_3$ receptor and/or an agent interacting with 5-HT$_4$ receptor such as tegaserod described in the U.S. Pat. No. 5,510,353 as example 13, tegaserod hydrogen maleate, cisapride, cilansetron;

n) an agent for treating tobacco abuse, e.g., nicotine receptor partial agonists, bupropion hypochloride (also known under the tradename Zyban®) and nicotine replacement therapies;

o) an agent for treating erectile dysfunction, e.g., dopaminergic agents, such as apomorphine), ADD/ADHD agents (e.g., Ritalin®, Strattera®, Concerta® and Adderall®);

p) an agent for treating alcoholism, such as opioid antagonists (e.g., naltrexone (also known under the tradename ReVia®) and nalmefene), disulfuram (also known under the tradename Antabuse®), and acamprosate (also known under the tradename Campral®)). In addition, agents for reducing alcohol withdrawal symptoms may also be co-administered, such as benzodiazepines, beta-blockers, clonidine, carbamazepine, pregabalin, and gabapentin (Neurontin®);

q) other agents that are useful including anti-inflammatory agents (e.g., COX-2 inhibitors); antidepressants (e.g., fluoxetine hydrochloride (Prozac®)); cognitive improvement agents (e.g., donepezil hydrochloride (Aircept®) and other acetylcholinesterase inhibitors); neuroprotective agents (e.g., memantine); antipsychotic medications (e.g., ziprasidone (Geodon®), risperidone (Risperdal®), and olanzapine (Zyprexa®));

or, in each case a pharmaceutically acceptable salt thereof; and optionally a pharmaceutically acceptable carrier.

In one embodiment, the other therapeutic agent is selected from DPP4 inhibitors, renin inhibitors, angiotensin 2 receptor blockers, HMG-co-A reductase inhibitors, GLP mimetics, PPAR-agonists, beta-2 angiotensin receptor blockers, ACE inhibitors, niacin, glyburide, exendin, metformin and diuretics.

Such combinations may offer significant advantages, including synergistic activity, in therapy.

The present invention is also in relation to a pharmaceutical composition comprising a compound of formulas (I), (II), (III), (IV), (V), (IA), (IIA), (IIIA) or (IVA), or a pharmaceutically acceptable salt thereof, and pharmaceutically acceptable excipients.

In another aspect, the present invention provides a pharmaceutical composition comprising a compound of formulas (I), (II), (III), (IV), (V), (IA), (IIA), (IIIA) or (IVA), or a pharmaceutically acceptable salt thereof, and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

Typically, the pharmaceutical compositions are tablets and gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

General Synthetic Aspects

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973.

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

In general, starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

Typically, the compounds of formula (I), (II), (III), (IV), (V), (IA), (IIA), (IIIA) or (IVA) can be prepared according to the Schemes provided infra.

Method of Preparation

The invention provides, in another aspect, a process for preparing a compound of formula (I). The schemes detailed below show general schemes for synthesizing compounds of formula (I). In the reactions described in the schemes herein below, any reactive group present, such as hydroxyl, amino, carbonyl or imino groups may be protected during the reaction by conventional protecting groups such as trimethylsilyl, tert-butyldimethylsilyl, benzyl, acetal, ketal etc., which are cleaved again after the reaction.

The following schemes represent general procedures used to synthesize compounds in this application.

Scheme 1

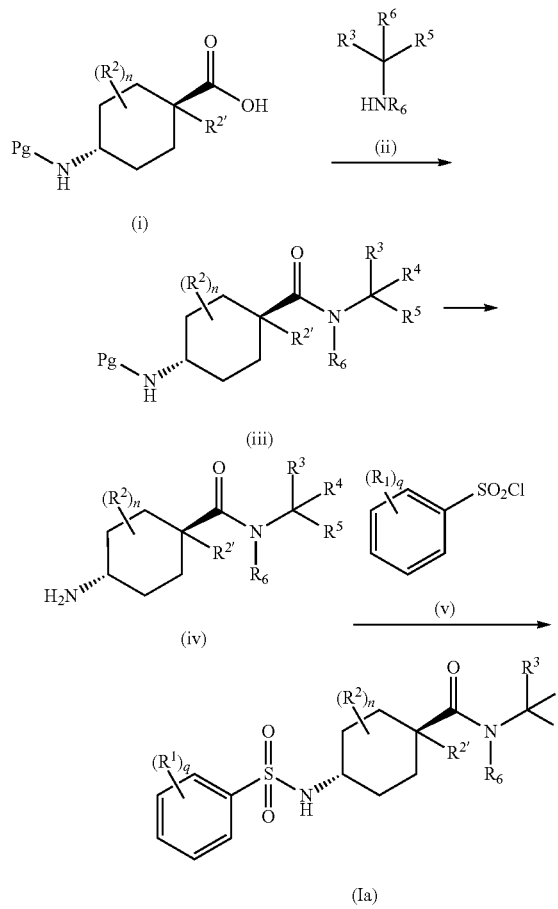

Wherein $R^{2'}$ is hydrogen or $R^2$; or
$R^{2'}$ and one or more $R^2$ groups form a $C_{1-4}$alkylene bridge; and
Pg is a protecting group.

Scheme I provides a method of preparing compounds of the invention in which $L^1$ is —$SO_2NH$— and $R^{2'}$ is a hydrogen or $R^2$ or $R^{2'}$ and one or more $R^2$ groups form a $C_{1-4}$alkylene bridge. In Scheme I, a trans-aminocyclohexane carboxylic acid (i) in which the amino group is protected with an amine protecting group such as a Boc protecting group, is condensed with an amine (ii) using standard amide forming conditions to produce an amino-protected trans-aminocyclohexane carboxamide (iii). The amine protecting group is removed to provide a trans-aminocyclohexane carboxamide (iv) which is then condensed with an appropriate benzene sulfonyl chloride (v) in the presense of a base to yield a compound of the invention (Ia). The sulfonyl chloride in this scheme is either commercially available or is prepared from a commercially available sulfonic acid or aniline as shown in Scheme 3.

Examples in which $R^1$ or $R^3$-$R^5$ in the final product contain a free basic $NH_2$ may be prepared via an amine protected (e.g., Boc) followed by deprotection as a final step or may be present as a nitro group which can be reduced to an amine in the final step. Examples in which $R^1$ or $R^3$-$R^5$ in the final product contain a carboxylic acid may be prepared from the corresponding ester followed by ester hydrolysis as a final step. This variation may apply for any of the following general synthetic schemes.

Scheme 2

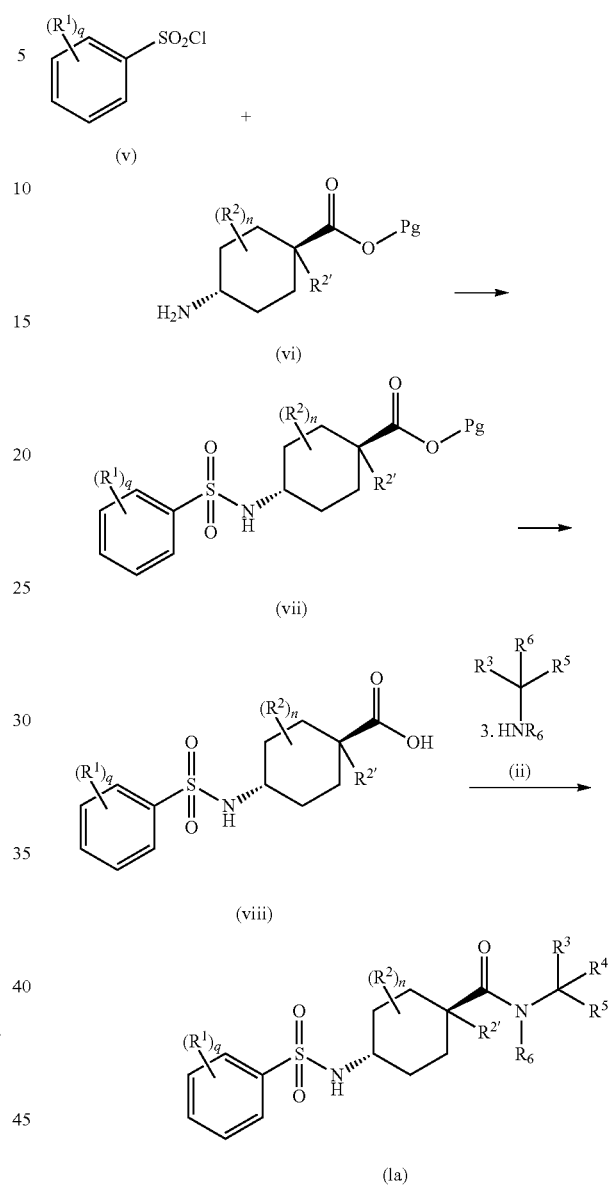

Wherein $R^{2'}$ is hydrogen or $R^2$; or
$R^{2'}$ and one or more $R^2$ groups form a $C_{1-4}$alkylene bridge; and
Pg is a protecting group.

Scheme II provides an alternative method of preparing compounds of the invention in which $L^1$ is —$SO_2NH$— and $R^{2'}$ is a hydrogen or $R^2$ or $R^{2'}$ and one or more $R^2$ groups form a $C_{1-4}$alkylene bridge. In Scheme II, a benzene sulfonyl chloride (v) is condensed with a trans-aminocyclohexane carboxylic acid in which the carboxylic acid group is protected (vi) (e.g., as an ester, such as a methyl ester) to form a sulfonamide (vii). The sulfonamide (vii) is treated to remove the carboxylic acid protecting group (for example an ester can be treated with a base to form a carboxylic acid) to form a carboxylic acid (viii). The carboxylic acid (viii) is then condensed with an amine (ii) using standard amide forming conditions to form a compound of the invention (Ia).

Scheme 3

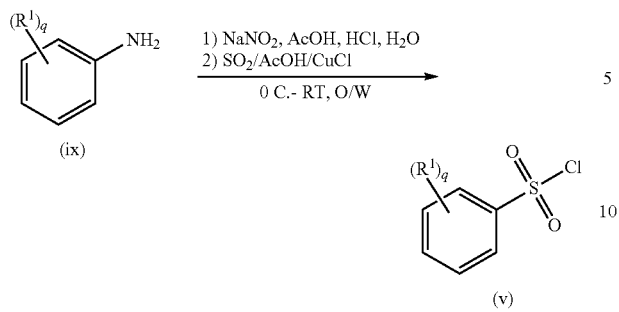

Anilines (ix) may be converted into benzenesulfonyl chlorides (v) by treating the aniline with sodium nitrate in acetic acid/HCl/H$_2$O followed by treatment sulfur dioxide/acetic acid and CuCl at 0° C.

Scheme 4

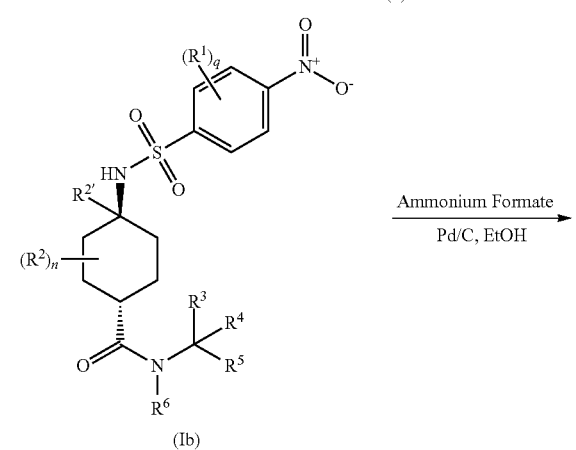

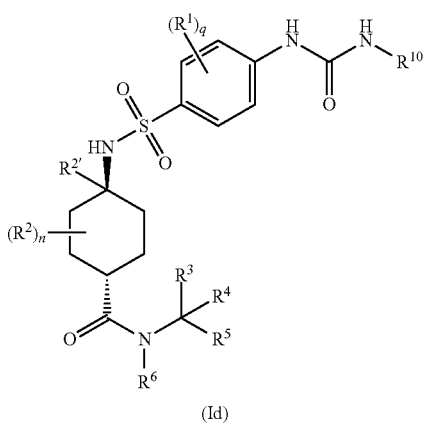

Wherein R$^{2'}$ is hydrogen or R$^2$; or
R$^{2'}$ and one or more R$^2$ groups form a C$_{1-4}$alkylene bridge.

Ureas may be formed according to Scheme 4 by reacting a nitrobenzenesulfonyl chloride (x) with trans-aminocyclohexane carboxamide (iv). In one embodiment a salt, such as the hydrochloride salt of the aminocyclohexane carboxamide (iv) can be used to form a compound of formula (Ib) in which one of R$^1$ is a nitro group. The nitro group can be converted to an amino group by treating the compound of formula (Ib) with ammonium formate in ethanol in the presence of a palladium on carbon catalyst to form a compound of formula (Ic) in which one of R$^1$ is an amine. The amine compound (1c) is then treated with an isocyanate to form a compound of formula (Id) in which one of R$^1$ is a urea.

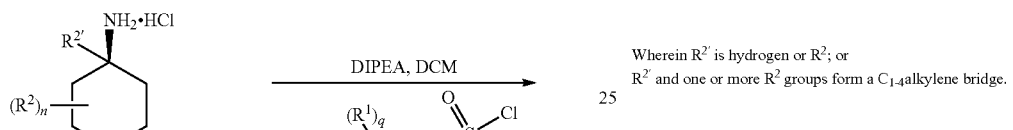

Scheme 5

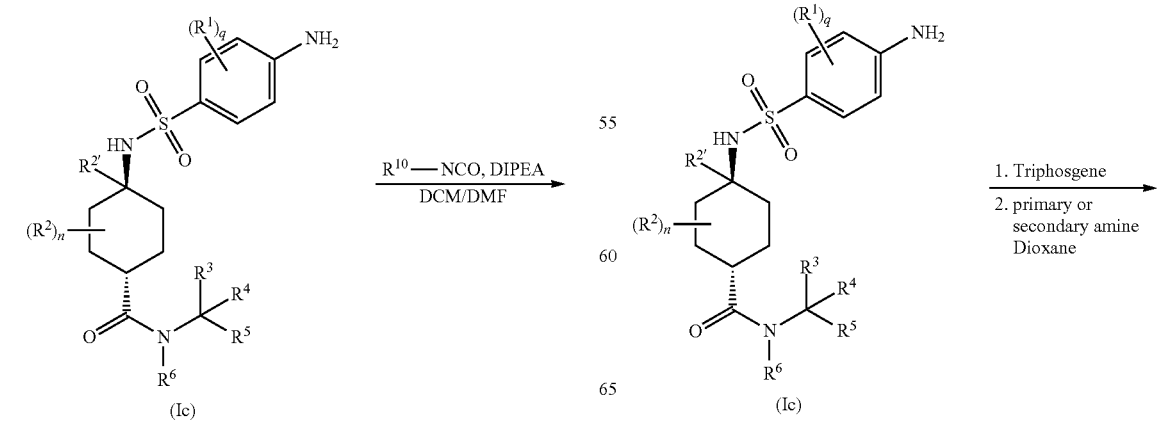

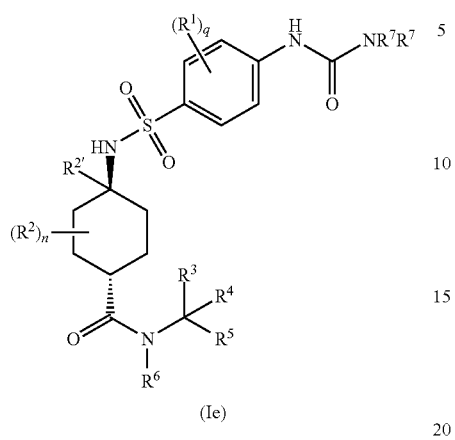

(Ie)

Wherein:
$R^{2'}$ is hydrogen or $R^2$; or
$R^{2'}$ and one or more $R^2$ groups form a $C_{1-4}$alkylene bridge; and
$R^7$ for each occurrence is independently hydrogen, $C_{1-7}$alkyl, $C_{3-7}$cycloalkyl, $C_{6-10}$aryl, heterocyclyl, or heteroaryl; or
two $R^7$ taken together with the nitrogen to which they are attached form a heterocycly.

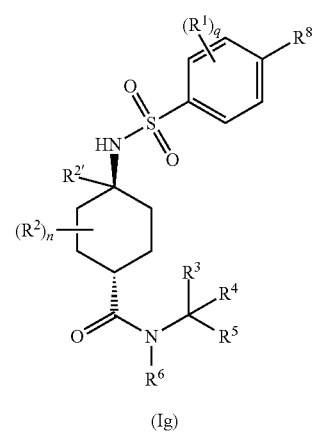

(Ig)

Wherein:
$X^1$ is a halo or triflate;
$R^{2'}$ is hydrogen or $R^2$; or
$R^{2'}$ and one or more $R^2$ groups form a $C_{1-4}$alkylene bridge;
$R^8$ is $C_{2-7}$alkenyl, $C_{6-10}$aryl, or heteroaryl; and
$R^{20}$ for each occurrence is independently hydrogen or alkyl; or
two $R^{20}$ taken together with the oxygen an boron atoms to which they are attached form a cyclic group.

As shown in Scheme 5, a compound of the invention in which one $R^1$ is an amine group (Ic) can be converted to a compound of the invention in which one $R^1$ is a urea (Ie) by treating the amine (Ic) with triphosgene (i.e., bis(trichloromethyl) carbonate) followed by treatment with a primary or secondary amine to form the urea (Ie).

A halo or triflate $R^1$ substituent of a compound of the invention (If) can be converted to an alkenyl, aryl or heteroaryl using a Suzuki coupling reaction. In one method shown in Scheme 6, the compound of the invention having the halo or triflate group (If) is treated with an boronic acid or boronic ester having an aryl, heteroaryl or alkenyl substituent (xi) in the presence of a palladium catalyst and a base to form a compound of the invention which has an aryl, heteroaryl or alkenyl substituent (Ig).

Scheme 6

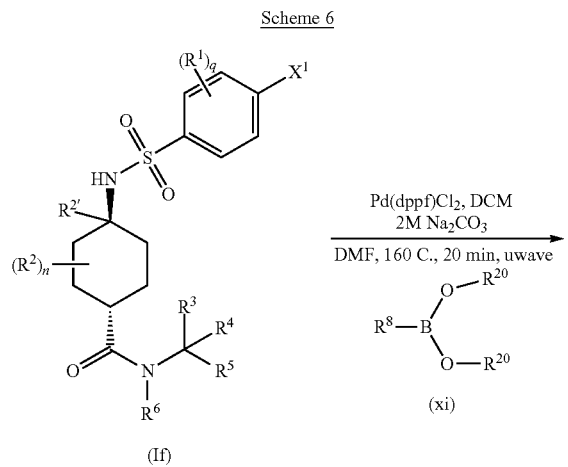

Scheme 7

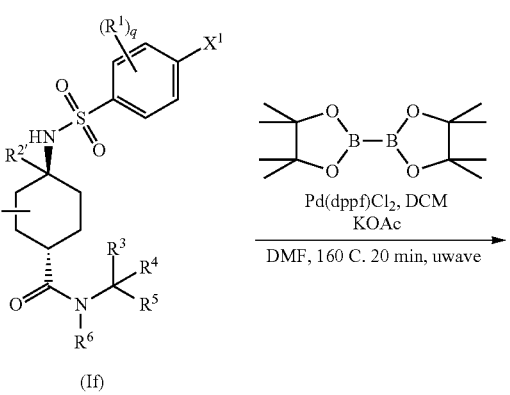

-continued

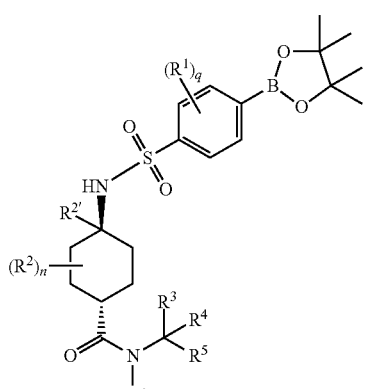

(xii)

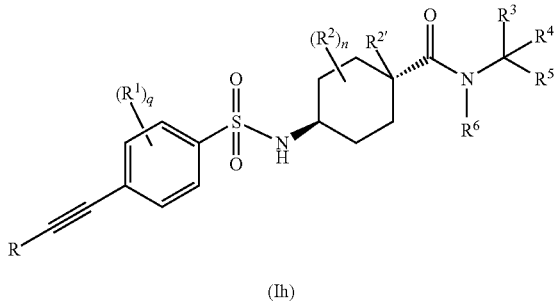

(Ih)

Wherein:
X¹ is a halo or triflate;
R²' is hydrogen or R²; or
R²' and one or more R² groups form a $C_{1-4}$alkylene bridge; and
R is $C_{1-7}$alkyl, $C_{6-10}$aryl, or heteroaryl.

As shown in Scheme 8, a halo or triflate R¹ substituent of a compound of the invention (If) can also be converted a compound of the invention having an alkynyl substituent (Ih) by treating the halide with a 1-alkyne in the presence of a palladium catalyst and a base.

Scheme 9

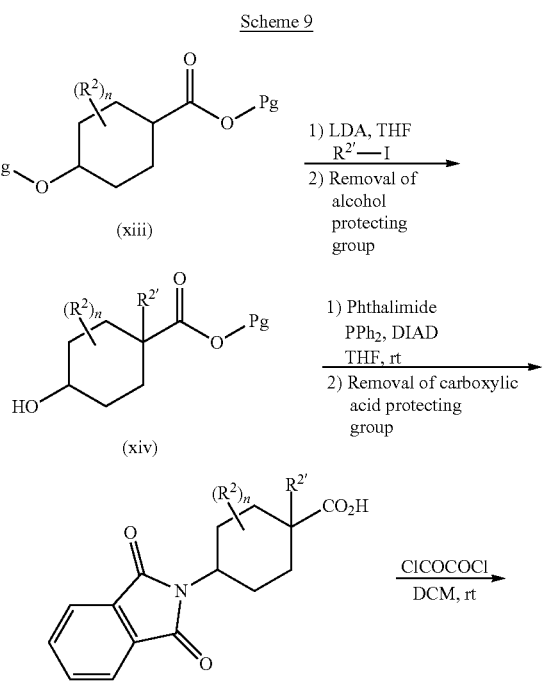

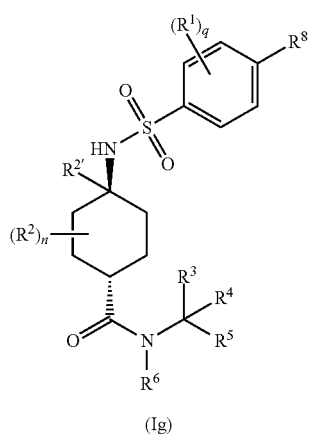

(Ig)

Wherein:
X¹ and X² are each independently a halo or triflate;
R²' is hydrogen or R²; or
R²' and one or more R² groups form a $C_{1-4}$alkylene bridge; and
R⁸ is $C_{2-7}$alkenyl, $C_{6-10}$aryl, or heteroaryl.

As shown in Scheme 7, a halo or triflate R¹ substituent of a compound of the invention (If) can also be converted to a boronic ester by treating it with a bis(boronic ester) in the presence of a palladium catalyst and a base. The boronic ester can then be treated with an aryl halide, heteroaryl halide or a vinyl halide to form a compound of the invention which has an aryl, heteroaryl or alkenyl substituent (Ig).

Scheme 8

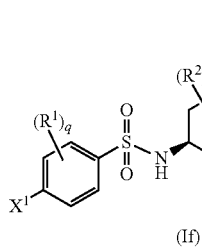

(If)

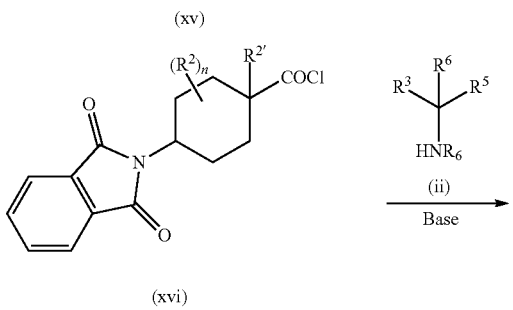

-continued

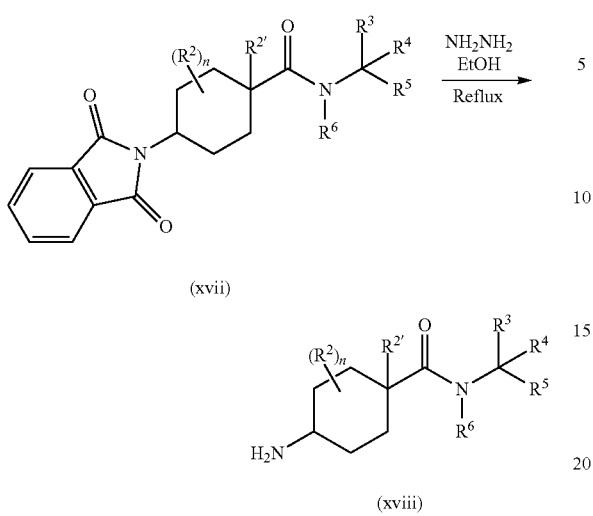

Wherein:
R$^{2'}$ is an alkyl or alkenyl;
R$^{2'}$ and one or more R$^2$ groups form a C$_{1-4}$alkylene bridge.

Compounds of the invention which have an R$^{2'}$ substituent that is an alkyl or an alkenyl can be prepared using the sulfonyl chloride coupling reaction described above from the intermediate prepared in Scheme 9. A 4-hydroxycyclohexanecarboxylic acid in which the alcohol and the carboxylic acid group are protected (xiii) is deprotonated with a strong base (e.g., LDA) and the resulting ester enolate is alkylated with an alkyl or allyl halide. The alcohol is then deprotected to form compound (xiv). Compound (xiv) is converted to an amine via Mitsunobu reaction with phthalimide, followed by deprotection of the carboxylic acid to form compound (xv). The carboxylic acid of compound (xv) is converted to an acid chloride by treatment with oxalyl chloride. The acid chloride (xvi) is coupled with an amine (ii) to form an amide (xvii) which is treated hydrazine to remove the phthalimide group and for the free amine (xviii). Condensation of the resulting amine with an aryl sulfonyl chloride as described for previous schemes provides compounds of the invention.

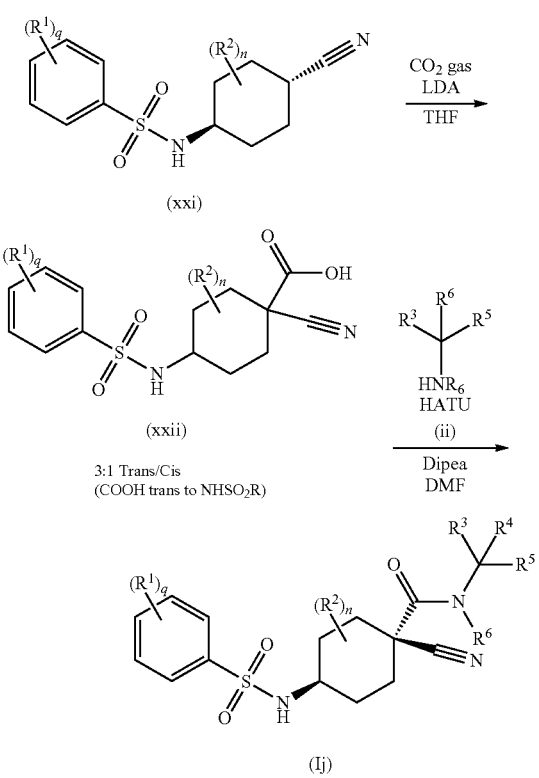

As seen in Scheme 10, compounds of the invention in which R$^{2'}$ is a cyano group can be prepared by converting a carboxylic acid of formula (xix) to an amide (xx) with HATU and ammonium chloride. The amide (xx) can be converted to a cyano group by treating it with trifluoroacetic anhydride to for compound (xxi). A carboxylic acid group can be added to compound (xxi) by treating it with CO$_2$ in the presence of a strong base to form compound (xxii). Compound (xxii) can be coupled with an amine (ii) using a standard amide couple reaction to form a compound of the invention in which R$^{2'}$ is a cyano (Ij).

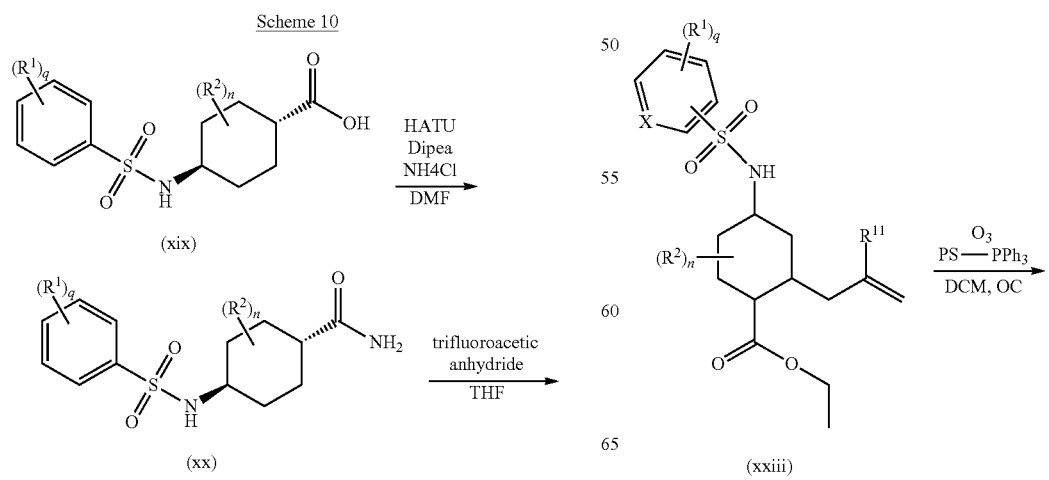

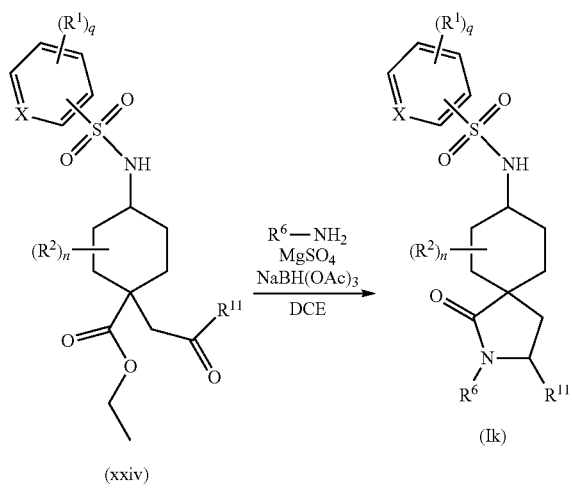

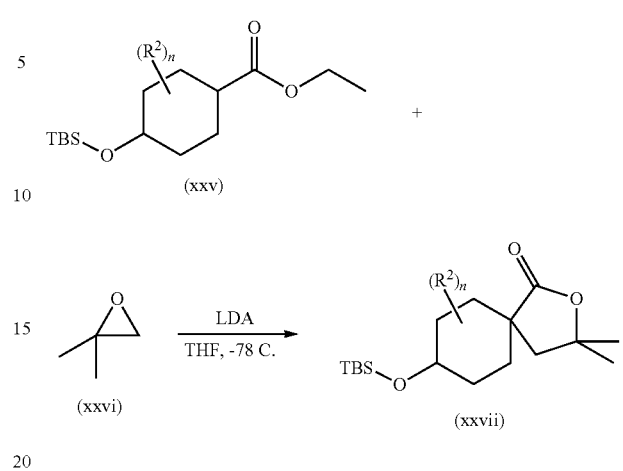

Scheme 12

As shown in Scheme 11, compounds of the invention which are spirolactam analogues may be constructed by conversion of an allyl intermediate (xxiii) to an appropriate aldehyde or ketone (xxiv) using ozone and polystyrene-triphenylphosphine. Reductive amination and cyclization of compound (xxiv) then can be used to form the spirolactam of the invention (Ik).

Spirolactone analogues may be constructed by treating a cyclohexanecarboxylate ester (xxv) with a strong base such as LDA to form an enolate which can add to an epoxide (xxvi) then cyclize to form compound (xvii) as shown in Scheme 12. The resulting protected alcohol can be deprotected and converted to an amine as shown in Scheme 9. The amine can be coupled with a sulfonyl chloride compound as shown in Scheme 1 to form a compound of the invention.

Scheme 13

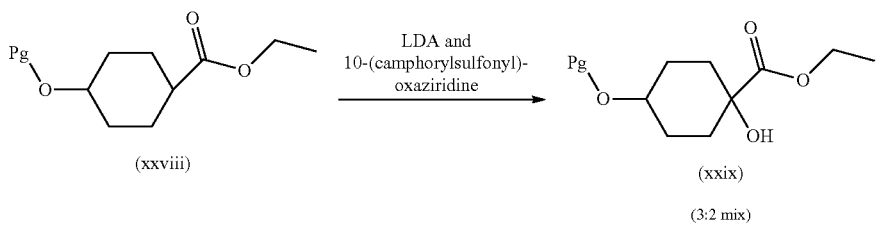

1. Hydrolysis of ester
2. Amide formation
3. Removal of alcohol protecting group

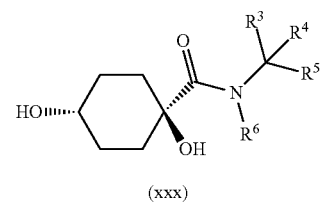

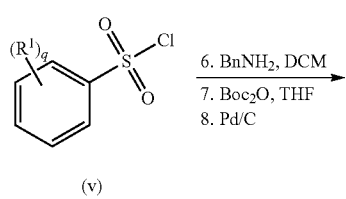

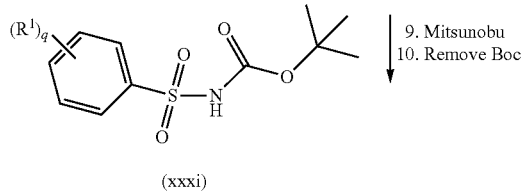

9. Mitsunobu
10. Remove Boc

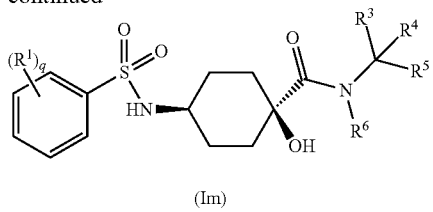

(Im)

Compounds of the invention in which $R^{2'}$ is a hydroxy can be prepared as shown in Scheme 13. A 4-hydroxycyclohexanecarboxylate ester in which the alcohol is protected (xxviii) is treated with a strong base such as LDA and 10-(camphorylsulfonyl)oxaziridine to add the hydroxy group and form compound (xxix). The ester of compound (xxix) is hydrolyzed to an acid and an amide is for using methods described above, followed by removal of the alcohol protecting group to form compound (xxx). A benzene sulfonyl chloride (v) is reacted with benzyl amine, followed by reaction with Boc anhydride then removal of the benzyl group to form compound (xxxi). Compound (xxx) is then coupled with compound (xxxi) via Mitsunobu reaction, followed by removal of the Boc group to form a compound of the invention in which $R^{2'}$ is a hydroxy group.

The following specific examples are intended to illustrate the invention without limiting the scope thereof.

EXEMPLIFICATION

Compounds prepared by these methods were analyzed by a variety of methods to determine identity and purity. These methods included NMR, mass spectroscopy, and HPLC. A variety of HPLC methods were used, and these are described in the following table.

TABLE 1

HPLC Methods

| Method | | Description |
|---|---|---|
| A | Column | SunFire C18 20 × 4.6 mm, 3.5 m |
| | Column Temperature | 40° C. |
| | Eluents | A: H$_2$O, B: acetonitrile, both containing 0.1% TFA |
| | Flow Rate | 3.0 mL/min |
| | Gradient | 5-100% B in 4.0 min (A1) or 15-90% B in 4.0 min (A2) |
| B | Column | SunFire C18 20 × 4.6 mm, 3.5 m |
| | Column Temperature | RT |
| | Eluents | A: H$_2$O, B: acetonitrile, both containing 0.1% TFA |
| | Flow Rate | 3.0 mL/min |
| | Gradient | 5-50% B in 4.0 min (B1) or 10-70% B in 4.0 min (B2) |
| C | Column | Waters X Terra C18 30 × 3 mm, 2.5 m |
| | Column Temperature | RT |
| | Eluents | A: H$_2$O (containing 5% acetonitrile and 0.05% TFA), B: acetonitrile (containing 0.05% TFA) |
| | Flow Rate | 0.7 mL/min |
| | Gradient | 10-95% B in 1.5 min, then 95% B for 1 min |
| D | Column | Phenomenex Luna C8 50 × 5 mm, 4.6 m |
| | Column Temperature | RT |
| | Eluents | A: H$_2$O, B: acetonitrile, both containing 0.1% TFA |
| | Flow Rate | 3 mL/min |
| | Gradient | 10-100% B in 15 min |
| E | Column | Waters Atlantis C18 150 × 4.6 mm, 5.0 m |
| | Column Temperature | RT |
| | Eluents | A: H$_2$O, B: acetonitrile, both containing 0.1% TFA |
| | Flow Rate | 1.4 mL/min |
| | Gradient | 0-95% B in 19 min |

TABLE 2

Commonly Used Abbreviations

| Abbreviation | Description |
|---|---|
| AcCN | acetonitrile |
| Bn | Benzyl |
| Boc | Tert-butoxycarbonyl |
| CAN | Ceric ammonium nitrate |
| DCC | 1,3-Dicyclohexylcarbodiimide |
| DCE | Dichloroethane |
| DCM | Dichloromethane |
| Pd(dppf)Cl$_2$ | 1,1'-bis(diphenylphosphino)ferrocene paladium dichloride |
| DIAD | Diisopropylazodicarboxylate |
| DIPEA | Diisopropylethylamine |
| DMAP | N,N-dimethylpyridin-4-amine |
| DMF | N,N-dimethylformamide |
| DMSO | Dimethyl sulfoxide |
| EDCI | 1-Ethyl-3-(3-dimethylaminopropyl)carbodiimide |
| Et$_2$O | Diethyl ether |
| EtOAc | Ethyl acetate |
| Ex. | Example |
| h | Hour(s) |
| HATU | 2-(1H-7-azabenzotriazol-1-yl)-1,1,3,3,-tetramethyluronium hexafluorophosphate |
| HOBt | N-Hydroxybenzotriazole |
| HPLC | High performance liquid chromatography |
| HV | High vacuum |

TABLE 2-continued

Commonly Used Abbreviations

| Abbreviation | Description |
|---|---|
| Intermed. | Intermediate |
| LC-MS or LCMS | Liquid chromatography - mass spectrometry |
| LDA | Lithium diisopropylamide |
| MeOH | methanol |
| min | Minute(s) |
| mL | Milliliter(s) |
| MS-Es | Electrospray mass spectrometry |
| NMM | N-methylmorpholine |
| O/N | Overnight |
| $Pd_2(dba)_3$ | Tris(dibenzylideneacetone)dipalladium(0) |
| Phos X | 2-Dicyclohexylphosphino-2',4',6'-triisopropylbiphenyl |
| rt | Room temperature |
| sat'd | saturated |
| S.M. | Starting Material |
| TBAF | Tetrabutylammonium fluoride |
| TFA | Trifluoroacetic acid |
| TFAA | Trifluoroacetic anhydride |
| THF | Tetrahydrofuran |
| $t_R$ | Retention time |
| Xphos | 2-Dicyclohexylphosphino-2',4',6'-triisopropylbiphenyl |
| Xantphos | 4,5-Bis(diphenylphosphino)-9,9-dimethylxanthene |

Intermediates

Intermediate 1: Methyl trans-4-(4-chloro-3-nitrophenylsulfonamido)cyclohexane-carboxylate

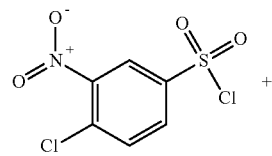

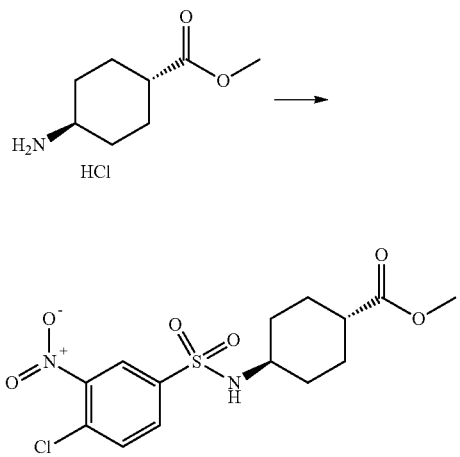

Sodium bicarbonate (521 mg, 6.20 mmol) in the minimum amount of water to dissolve it was added to a THF slurry of trans-amino-methylester cyclohexane HCl salt (600 mg, 3.10 mmol). The mixture was stirred for a couple minutes then 4-chloro-3-nitrobenzenesulfonyl chloride (793 mg, 3.10 mmol) was added, and the reaction was stirred over the weekend. The reaction was diluted with EtOAc and adjust pH to 9 with 1N NaOH. The layers were separated and the organic layer was washed 1× brine then dried over magnesium sulfate, filter, and concentrate to yield the title compound as a tan solid (1042 mg, 2.77 mmol, 89% yield). [M−H]=375.1

The Intermediates listed in the Table below were prepared by a method analogous to the method used to prepare Intermediate 1 using trans-amino-methylester cyclohexane HCl salt and the starting benzenesulfonyl chloride indicated.

| Intermed. | Structure | S.M. | MS |
|---|---|---|---|
| 2 | (structure shown) | 4-Bromo-benzenesulfonyl chloride | M − H = 376.2 |
| 3 | (structure shown) | 4-trifluoromethyl-benzenesulfonyl chloride | M + H = 366.0<br>M − H = 364.3 |

-continued

| Intermed. | Structure | S.M. | MS |
|---|---|---|---|
| 4 | 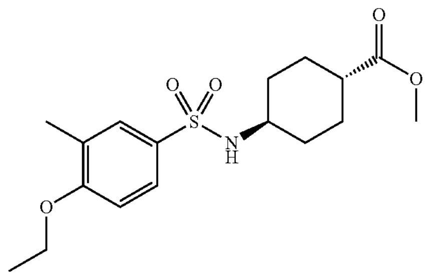 [SMILES: CCOc1ccc(S(=O)(=O)N[C@H]2CC[C@H](C(=O)OC)CC2)cc1C] | 4-ethoxy-3-methyl-benzenesulfonyl chloride | M + H = 356.1 |
| 5 | 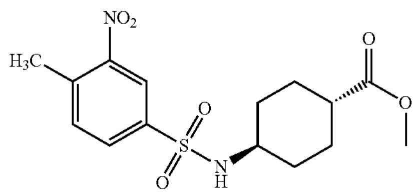 | 4-methyl-3-nitro-benzenesulfonyl chloride | M − H = 355.2 |
| 6 | 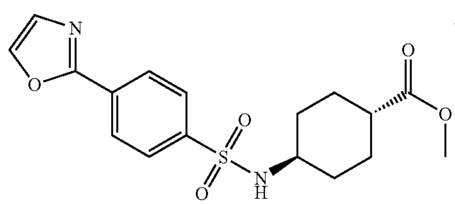 [SMILES: COC(=O)[C@H]1CC[C@H](NS(=O)(=O)c2ccc(-c3ncco3)cc2)CC1] | 4-(oxazol-2-yl)-benzenesulfonyl chloride (Intermediate 26) | M + H = 365.0 |
| 7 | 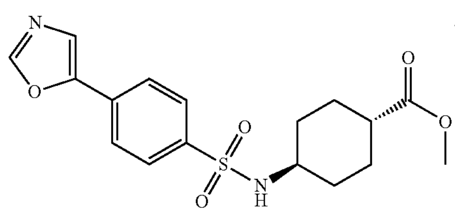 | 4-(oxazol-5-yl)-benzenesulfonyl chloride | M + H = 365.2 |
| 8 | 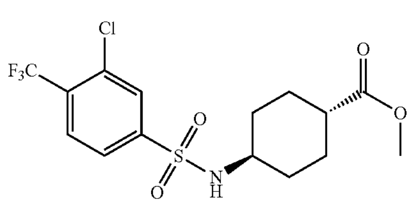 [SMILES: COC(=O)[C@H]1CC[C@H](NS(=O)(=O)c2ccc(C(F)(F)F)c(Cl)c2)CC1] | 4-(trifluoromethyl)-3-chloro-benzenesulfonyl chloride | — |
| 9 | 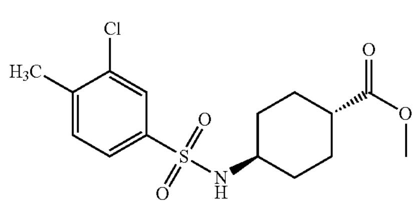 | 4-methyl-3-chloro-benzenesulfonyl chloride | — |

Intermediate 10: Methyl trans-4-(3-amino-4-chloro-phenylsulfonamido)cyclohexane-carboxylate

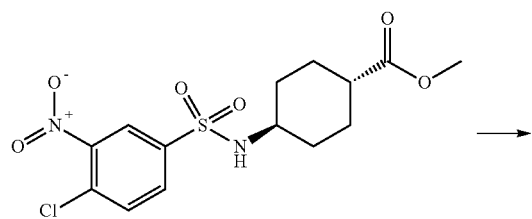

Zinc dust (1345 mg, 20.57 mmol) was added to a room temperature solution of methyl trans-4-(4-chloro-3-nitrophenylsulfonamido)cyclohexanecarboxylate (Intermediate 1, 775 mg, 2.057 mmol) in acetic acid (15.200 ml). The reaction was heated to 50° C. overnight, the filtered over celite and rinsed with acetic acid. The acetic acid was removed in vacuo at 60° C., and the residue was partitioned between EtOAc/sat'd NaHCO$_3$. The aqueous layer was extracted with a second portion EtOAc, and the organic layers were combined then rinsed 1× brine, dry over MgSO$_4$, filter, and concentrated to give the title compound as a solid (670 mg, 1.932 mmol, 94% yield). MS MH+ 347.1

Intermediate 11: Methyl trans-4-(3-amino-4-methyl-phenylsulfonamido)cyclohexane-carboxylate

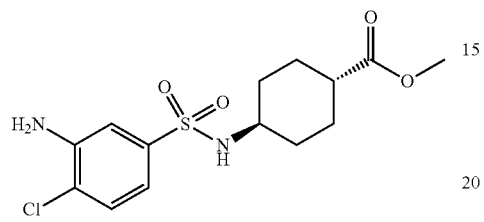

Methyl trans-4-(3-amino-4-methyl-phenylsulfonamido)cyclohexane-carboxylate was prepared by a method analogous to the method used to prepare Intermediate 10 using methyl trans-4-(3-nitro-4-methyl-phenylsulfonamido)cyclohexane-carboxylate (Intermediate 5) as the starting material. MS MH+ 327.2

Intermediate 12: Methyl trans-4-(4-chloro-3-(ethylamino)phenylsulfonamido)cyclo-hexanecarboxylate

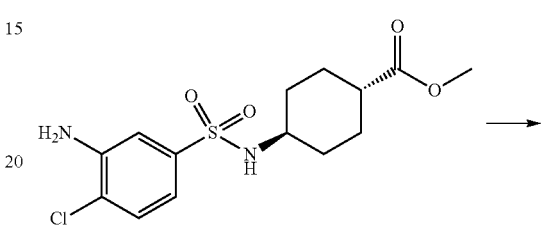

A round bottom flask was charged with methyl trans-4-(3-amino-4-chlorophenylsulfonamido)cyclohexamecarboxylate (Intermediate 10, 333 mg, 0.922 mmol) and acetaldehyde (52.1 µl, 0.922 mmol) followed by sodium triacetoxyborohydride (293 mg, 1.383 mmol) in DCE (9217 µl) and the reaction was stirred overnight. The reaction was diluted with DCM/sat'd NaHCO$_3$, and the organic layer was separated and dried over MgSO$_4$, then filtered and chromatographed on a Biotage 25S column to yield the title compound (224 mg, 0.598 mmol, 64.8% yield). Rf (50% EtOAc/heptane): sm=0.43; product=0.58. MS MH+=375.2

The intermediates in the following Table were prepared by a method analogous to the method used to prepare Intermediate 12 using the starting materials indicated.

| Intermed. | Structure | S.M. | MS MH+ |
|---|---|---|---|
| 13 | 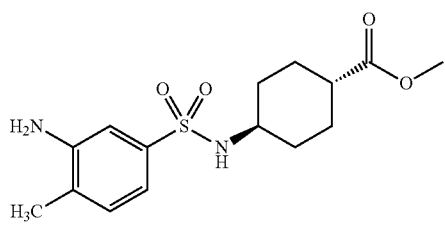 [SMILES: COC(=O)[C@H]1CC[C@H](NS(=O)(=O)c2ccc(C)c(N)c2)CC1] | Propionaldehyde & Intermediate 10 | 389.2 |

| Intermed. | Structure | S.M. | MS MH+ |
|---|---|---|---|
| 14 | 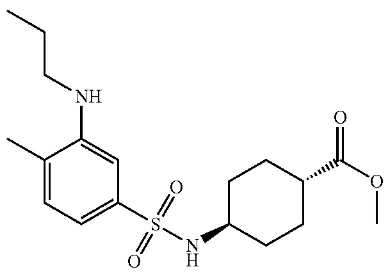 | Propionaldehyde & Intermediate 11 | 369.3 |

Intermediate 15: Trans-4-(4-Chloro-3-(ethylamino)phenylsulfonamido)cyclohexane-carboxylic acid

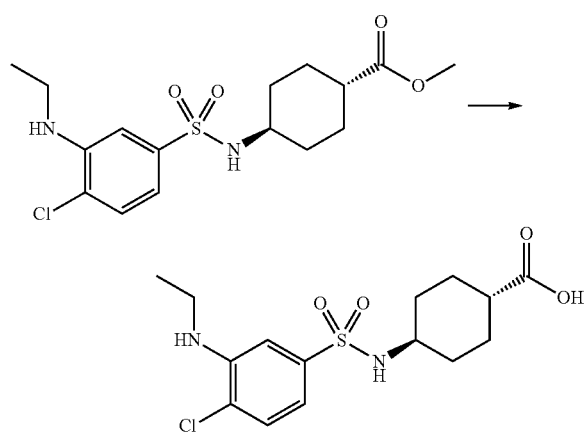

Methyl trans-4-(4-chloro-3-(ethylamino)phenylsulfonamido)cyclohexane-carboxylate (Intermediate 12, 220 mg, 0.552 mmol) in 1/1/1 THF/MeOH/1N LiOH was warmed to 45° C. overnight. The reaction was cooled to room temperature, then acidified to pH 3 with 1N HCl and extracted with multiple volumes EtOAc. The combined organic layers were dried over sodium sulfate, filtered and concentrated to give the title compound as colorless solid (169 mg, 0.468 mmol, 85% yield). MS MH+ 361.2

The Intermediates listed in the Table below were prepared by a method analogous to the method used to prepare Intermediate 15 using the ester indicated.

| Intermed. | Structure | S.M. | MS |
|---|---|---|---|
| 16 | 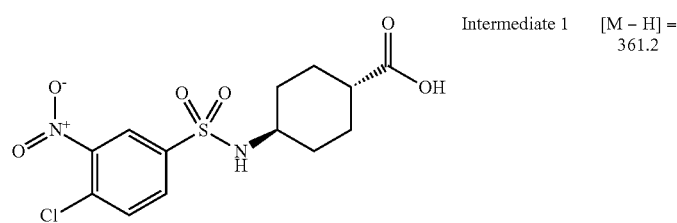 | Intermediate 1 | [M − H] = 361.2 |
| 17 | 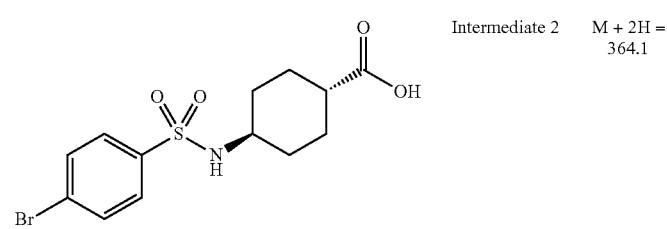 | Intermediate 2 | M + 2H = 364.1 |

-continued

| Intermed. | Structure | S.M. | MS |
|---|---|---|---|
| 18 | (4-(trifluoromethyl)phenylsulfonylamino)cyclohexanecarboxylic acid | Intermediate 3 | M + H = 362.0 |
| 19 | (4-ethoxy-3-methylphenylsulfonylamino)cyclohexanecarboxylic acid | Intermediate 4 | [M + H] = 342.1 |
| 20 | (4-(oxazol-2-yl)phenylsulfonylamino)cyclohexanecarboxylic acid | Intermediate 6 | 351.0 |
| 21 | (4-methyl-3-(propylamino)phenylsulfonylamino)cyclohexanecarboxylic acid | Intermediate 15 | 355.2 |
| 22 | (4-(oxazol-5-yl)phenylsulfonylamino)cyclohexanecarboxylic acid | Intermediate 9 | 351.2 |
| 23 | (4-chloro-3-(propylamino)phenylsulfonylamino)cyclohexanecarboxylic acid | Intermediate 13 | 375.2 |

| Intermed. | Structure | S.M. | MS |
|---|---|---|---|
| 24 | 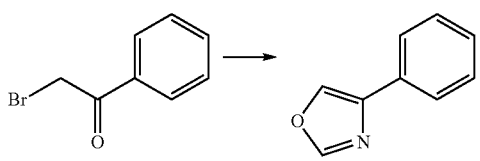 [SMILES: O=C(CBr)c1ccccc1 ; c1ccc(-c2cocn2)cc1] | Intermediate 12 | 361.2 |

Intermediate 25: 4-Phenyl-oxazole

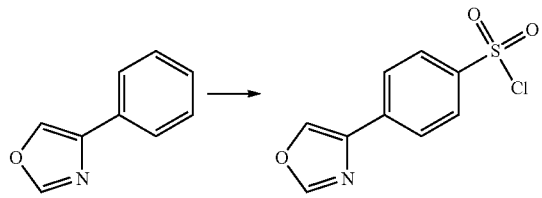 [SMILES: c1ccc(-c2cocn2)cc1 ; O=S(=O)(Cl)c1ccc(-c2cocn2)cc1]

Bromoacetophenone (595 mg, 2.99 mmol) and formamide (1781 μl, 44.8 mmol) were combined and heated at 130° C. for 90 min. The reaction was cooled then dilute with ethyl acetate and water and extracted with ethyl acetate. The organic layer was dried over sodium sulfate, filtered, and concentrated. The concentrate was purified by chromatography on a Biotage 25M column using a 5-8% ethyl acetate in heptane gradiant to yield 4-phenyl-oxazole (170 mg, 1.17 mmol). TLC (5% ethyl acetate in heptane) of product: Rf=0.28.

Intermediate 26: 4-Oxazol-4-yl-benzenesulfonyl chloride

4-Phenyl-oxazole (Intermediate 25, 550 mg, 3.79 mmol) was dissolved in a minimum of dichloromethane and was added slowly to chlorosulfonic acid (2.537 mL, 37.9 mmol) at 0° C. The reaction mixture was stirred for 20 min 0-5° C. then warmed to room temperature then to 45° C. and stirred for 2 h. The reaction mixture was cooled to room temperature and cautiously poured on ice water. The aqueous layer was extracted with ethyl acetate, dried over sodium sulfate, and concentrated to crude 4-oxazol-4-yl-benzenesulfonyl chloride. The starting material and product have Rf values in 20% EtOAc/heptane of Rf=0.47 and Rf=0.23, respectively. The crude product was purifed by chromatography on a Biotage 25M column eluting ethyl acetate/heptane to yield 4-oxazol-4-yl-benzenesulfonyl chloride (212 mg, 0.870 mmol). MH+=244.2.

Intermediate 27: Preparation of Internal Oxazole Compounds

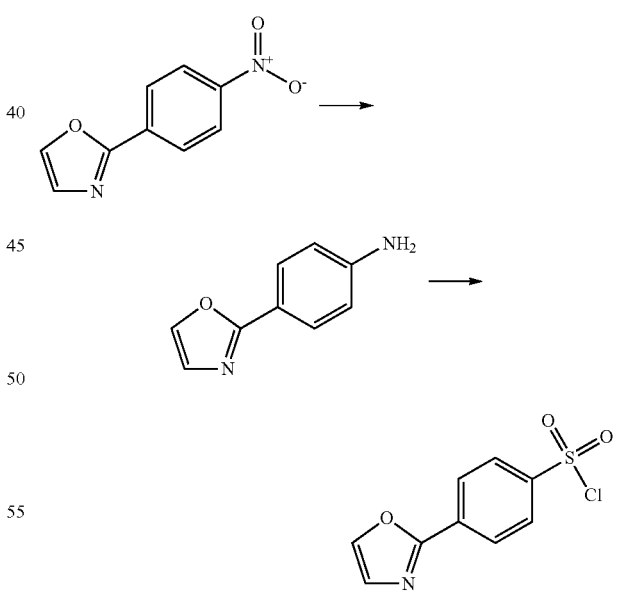

4-(Oxazol-2-yl)-analine was prepared from 1-nitro-4-(oxazol-2-yl)-benzene by the method described for Intermediate 10. 4-Oxazol-2-yl-benzenesulfonyl chloride was prepared from 4-(oxazol-2-yl)-analine using the method described for Intermediate 39. MS MH+ 244.2.

Intermediate 28: Trans-4-((4-Oxazol-4-yl)-phenyl-sulfonamido)-cyclohexanecarboxylic acid

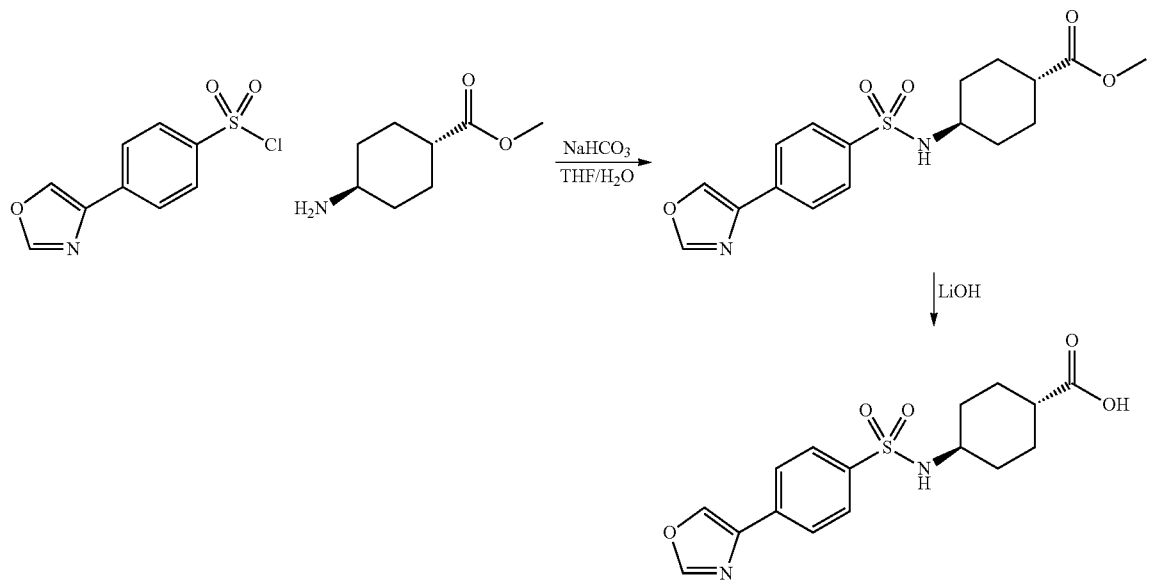

4-Oxazol-4-yl-benzenesulfonyl chloride (Intermediate 26, 203 mg, 0.833 mmol) in 1.0 ml THF was added to a slurry of trans-4-amino-cyclohexanecarboxylic acid methyl ester (161 mg, 0.833 mmol) and sodium bicarbonate (140 mg, 1.666 mmol) in ca 2.5 mL 3:1 THF:H$_2$O. The reaction was stirred at room temperature for 16 h then LCMS indicated that the reaction was complete and yielded a single compound having a mass ion of MH+ 365.2 indicating that it was the desired methyl-ester. 1M LiOH (4166 µl, 4.17 mmol) was added, and the reaction heated 50° C. overnight. LCMS indicates the methyl ester was hydrolyzed to a single compound having a mass ion of MH+ 351.2 consistent with the desired carboxylic acid. The pH was adjusted to 3 with 1N HCl and the reaction was extracted with ethyl acetate. The organic layers were dried over sodium sulfate, filtered and concentrated to trans-4-((4-Oxazol-4-yl)-phenylsulfonamido)-cyclohexanecarboxylic acid (245 mg, 0.699 mmol). LCMS [M+H]=351.0

Intermediate 29: (S)-5-Isopropylmorpholin-3-one

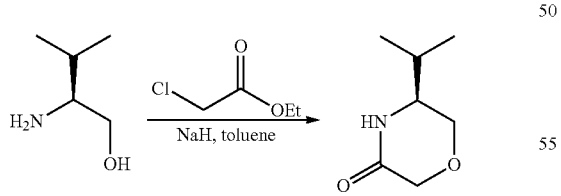

To an ice-cold, stirred suspension of sodium hydride (2.59 g, 64.8 mmol) in toluene (90 mL) was added dropwise a solution of (S)-2-amino-3-methylbutan-1-ol (3 g, 29.1 mmol) in toluene (60 mL). The reaction was then warmed to room temperature and a solution of ethyl chloroacetate (3.56 g, 29.1 mmol) in toluene (16 mL) was added dropwise. The resulting mixture was heated to reflux for 20 h under nitrogen and then concentrated under vacuum. The residue was purified by flash chromatography to afford 2.8 g of product. MS MH+=144.20

The intermediates in the following Table were prepared by a method analogous to the method for preparing Intermediate 33 using ethyl chloroacetate and the starting material indicated.

| Intermed. | Structure | S.M. | MS MH+ |
|---|---|---|---|
| 30 | 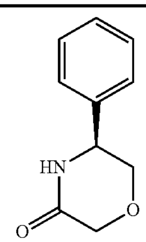 | (S)-2-amino-2-phenylethanol | — |
| 31 | 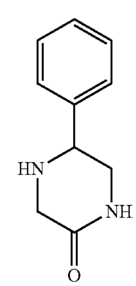 | 1-phenylethane-1,2-diamine | 177.1 |
| 32 | 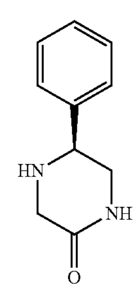 | (S)-1-phenylethane-1,2-diamine | 177.1 |

-continued

| Intermed. | Structure | S.M. | MS MH+ |
|---|---|---|---|
| 33 | ![structure] | 1-(4-chloro-phenyl)ethane-1,2-diamine | — |
| 34 | ![structure] | (S)-3,3,3-trifluoro-propane-1,2-diamine | 191.1 |
| 35 | ![structure] | 1-phenylpropane-1,2-diamine | — |
| 36 | ![structure] | (R)-2-amino-2-phenylethanol | — |

Intermediate 37: (S)-3-Isopropylmorpholine

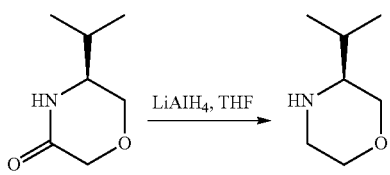

(S)-5-Isopropylmorpholin-3-one (Intermediate 29, 2.8 g, 19.56 mmol) in THF (12 mL) was added dropwise over 20 min. to a solution of lithium aluminum hydride (2M in THF, 19.5 mL, 39.1 mmol) in THF (30 mL) at 0° C. Following the addition, the ice bath was removed, and the reaction was heated to reflux for 18 h. The reaction was cooled in an ice bath and quenched with water (1.5 mL) and 2M aq. sodium hydroxide (3 mL). The resulting mixture was stirred at room temperature for 1 h and filtered. The solid was washed with ethyl acetate, and the organic solution was concentrated under vacuum to give product (2.13 g) as an oil. MS MH+=130.30

The intermediates in the following Table were prepared by a method analogous to the method for preparing Intermediate 37 using the starting material indicated.

| Intermed. | Structure | S.M. |
|---|---|---|
| 38 | ![structure] | Intermediate 39 |

Intermediate 39:
3-Chloro-4-(trifluoromethyl)benzene-1-sulfonyl chloride

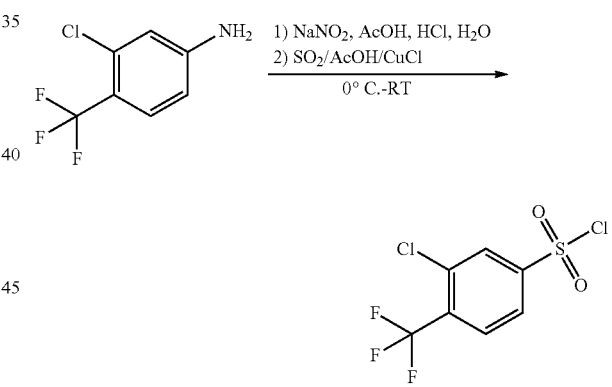

3-Chloro-4-(trifluoromethyl)aniline (1 g, 5.11 mmol) was dissolved in AcOH (72 ml) and concentrated HCl (12M) (19.6 ml). The reaction was cooled to 0° C. then sodium nitrite (0.353 g, 5.11 mmol) in $H_2O$ (5.2 ml) was added and the reaction mixture was stirred for 10 min at 0° C. then added slowly to a cold solution of AcOH/$SO_2$/CuCl (175 ml). The reaction mixture turned bright green after the addition, then faded to a lighter colour after 1 h. The reaction was left to stir over the weekend then concentrated in vacuo to a yellow crude oil which was taken up in EtOAc (300 ml) and washed with $H_2O$ (2×300 ml). The EtOAc layer was concentrated in vacuo and purified via normal phase chromatography on a biotage SP1 column 40+M with a gradient 5-20% EtOAc in heptane to yield the title compound as a light yellow oil (680 mg, 43.8%). LCMS (R—$SO_3^-$)=259.1

Intermediate 40: 6-(Trifluoromethyl)pyridine-3-sulfonyl chloride

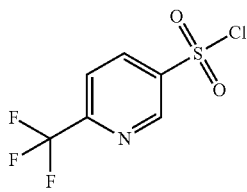 [SMILES: O=S(=O)(Cl)c1ccc(C(F)(F)F)nc1]

The title compound was prepared by a method analogous to the method used to prepare Intermediate 39 using 6-(trifluoromethyl)pyridin-3-amine as the starting material. LCMS (R—SO3⁻)=226.2.

Intermediate 41: tert-Butyl Trans-4-((R)-1-phenylethylcarbamoyl)cyclohexyl-carbamate

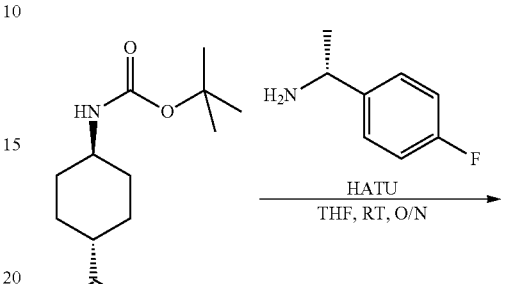

Trans-4-tert-butoxycarbonylamino-cyclohexanecarboxylic acid (5 g, 20.5 mmol) was dissolved in THF, to which triethylamine (3 mL) was added. The reaction mixture was cooled to 0° C. and a solution of isobutyl chloroformate (2.8 g, 20.7 mmol) in THF was added dropwise. The resulting white suspension was stirred at room temperature for 30 min, after which a solution of (R)-1-phenylethanamine (2.9 g, 20.5 mmol) in THF was added dropwise. The reaction mixture was then stirred at room temperature for 4 h, after which LC-MS showed one major peak corresponding to desired product. The reaction mixture was concentrated, and the residue was diluted with water (250 mL). The resulting white precipitate was filtered, washing with ether, to afford a dry white solid tert-butyl trans-4-((R)-1-phenylethylcarbamoyl)cyclohexylcarbamate (5.2 g).

Intermediate 42: tert-Butyl trans-4-((R)-1-(4-fluorophenyl)ethylcarbamoyl)cyclo-hexylcarbamate

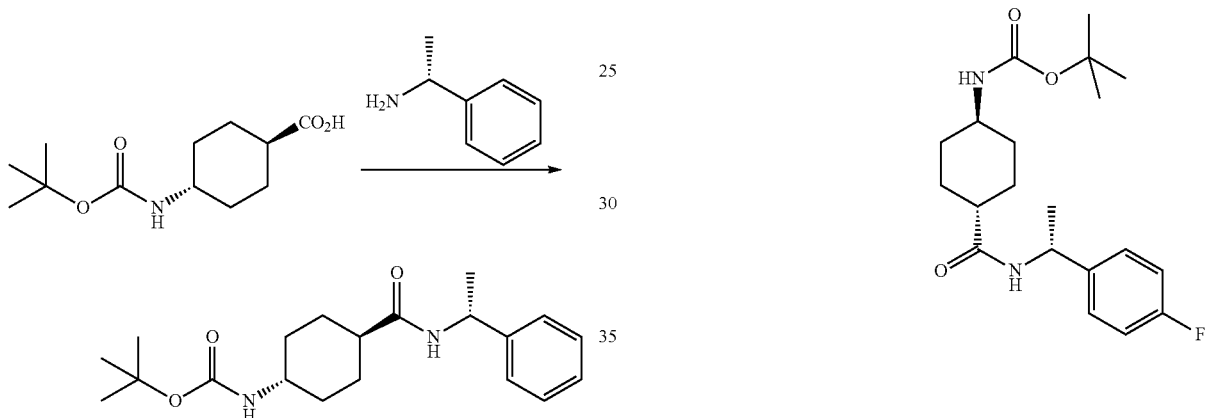

Trans-4-(tert-Butoxycabonylamino)cyclohexanecarboxylic acid (10.2 g, 42 mmol), HATU (24 g, 63 mmol) and N,N-diisopropylethylamine (22 ml, 126 mmol) were dissolved in THF (350 ml). The reaction mixture was stirred for 30 min at room temperature, then (R)-1-(4-Fluoro-phenyl)-ethylamine 6.3 ml, 46 mmol) was added. The reaction was stirred overnight at room temperature. LCMS indicated that the reaction was complete, and it was concentrated in vacuo. The concentrate was taken up in 1M NaOH (500 ml) and EtOAc (100 ml) and was stirred for 1 hr. The precipitate that formed was collected by filtration and washed with 1M NaOH:EtOAc (4:1) and dried to give the title compound as a white solid (14.8 g, 97%). LCMS [M+H]=365.3

Intermediate 43 was prepared by a method analogous to the method of preparing Intermediate 42.

| Intermed | Structure | S.M. | MS MH+ |
|---|---|---|---|
| 43 | (structure shown) | (R)-1-(pyridin-3-yl)-ethanamine | 348.2 |

Intermediate 44: Trans-4-Amino-N—((R)-1-phenyl-ethyl)cyclohexanecarboxamide hydrochloride

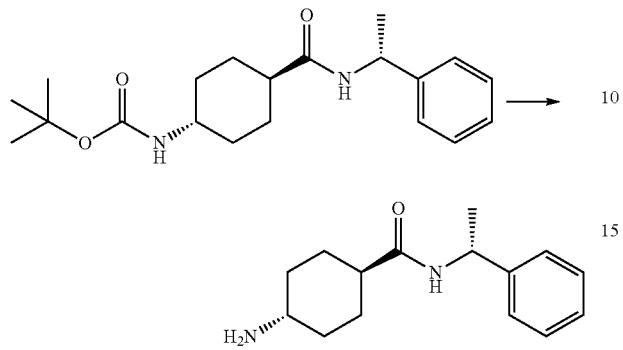

tert-Butyl trans-4-((R)-1-phenylethylcarbamoyl)cyclohexylcarbamate (Intermediate 41, 5.2 g) was dissolved in DCM (50 mL) to which TFA was added. The resulting mixture was stirred for 45 min at room temperature. LC-MS of material showed one major peak which corresponded to desired product. The reaction mixture was then concentrated to give a clear oil. The oil was then dissolved in diethyl ether (200 mL) to which HCl (2M solution in ether) (20 mL) was added. The resulting mixture was stirred at room temperature for 2 h, resulting in a white precipitate that was collected by filtration and washed with diethyl ether (4.1 g).

Intermediate 45: Trans-4-Amino-N—((R)-1-(4-fluorophenyl)ethyl)cyclo-hexanecarboxaminde hydrochloride

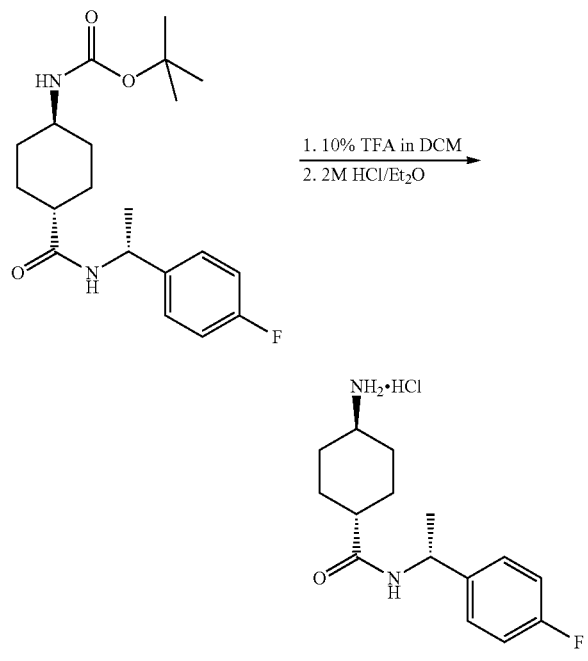

tert-Butyl trans-4-((R)-1-(4-fluorophenyl)ethylcarbamoyl)cyclohexylcarbamate (Intermediate 42, 1.74 g, 4.77 mmol) was dissolved in DCM (45 ml) and TFA (5 ml) was added. The reaction mixture was stirred overnight at room temperature. LCMS indicated that the reaction was complete and it was in vacuo. Crude material was dissolved in ether (200 ml), then 2M HCl (in ether, 20 ml) were added, and the mixture was stirred at room temperature for 2 hr. The precipitate that formed was collected by filtration and washed with ether to afford the title compound as a white powder (1.24 g, 87%). LCMS [M+H]=265.3

Intermediate 46: Trans-4-Amino-N—((R)-1-(pyridin-3-yl)ethyl)cyclo-hexanecarboxaminde hydrochloride

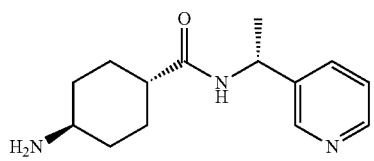 [SMILES: C[C@@H](NC(=O)[C@H]1CC[C@H](N)CC1)c1cccnc1]

Intermediate 46 was prepared using a method analogous to the method used to prepare Intermediates 44 and 45 using Intermediate 43 as the starting material.

Intermediate 47: (S)-Methyl 2-(tert-butoxycarbonylamino)-2-phenylacetate

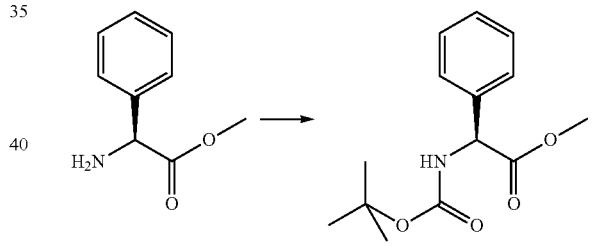

A stirred suspension of (S)-phenylglycine methyl ester hydrochloride (30.0 g, 149.0 mmol) in anhydrous methylene chloride (300 mL) was cooled to 5° C. in an ice-water bath. Ammonia was bubbled through the suspension for ca. 10 minutes. The reaction mixture was stirred at room temperature for 20 minutes following which the suspension was filtered through a celite pad. The celite pad was washed with methylene chloride (2×100 mL). The combined filtrate was concentrated to afford a slightly cloudy oil. The oil was dissolved in anhydrous acetonitrile (250 mL) and to this was added Boc$_2$O (35.7 g, 164 mmol). The reaction mixture warmed up slightly and some gas evolution was observed. The reaction mixture was stirred at room temperature for 30 minutes following which it was diluted with toluene (250 ml). The solvent was removed on the rotary evaporator to afford a sticky white crystalline solid. This was triturated with 10% EtOAc/Heptane (200 mL) and stirred overnight. The suspension was the filtered through a glass frit. The solid was washed with cold 10% EtOAc/heptane (2×50 mL) and then dried under house vacuum to afford a white solid (34.5 g, 87%).

Intermediate 48: (S)-tert-Butyl 2-hydroxy-2-methyl-1-phenylpropylcarbamate

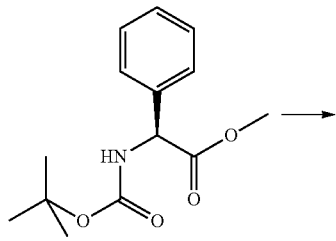

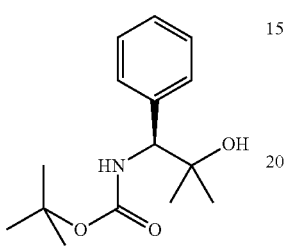

A solution of (S)-methyl 2-(tert-butoxycarbonylamino)-2-phenylacetate (Intermediate 47, 25.0 g, 94.0 mmol) in anhydrous THF (300 mL) was cooled to 0° C. in an ice bath under a nitrogen atmosphere. To this stirred, slightly cloudy solution was added dropwise via an addition funnel, MeMgBr (377.0 mL, 377.0 mmol). The reaction mixture was stirred at 0° C. for 10 minutes following which the cooling bath was removed, and the reaction mixture was stirred at room temperature. After 3 h, the reaction mixture was quenched with sat. aqueous NH$_4$Cl solution (25 mL), and the resulting suspension was stirred at room temperature. The suspension was filtered through a celite pad which was subsequently washed with THF (3×50 mL). The combined filtrate was concentrated to afford a pale yellow solid. This solid was taken up in EtOAc (25 mL) and warmed to ca. 50° C. Most of the solid dissolved. With vigorous agitation, heptane (250 mL) was added in a slow, steady stream via an addition funnel over 30 minutes. The resulting suspension was slowly cooled to room temperature and then further diluted with heptane (250 mL). The suspension was stirred at 0° C. for 3 h, then filtered through a glass frit. The filtercake was broken and washed with cold 5% EtOAc/Heptane (2×100 mL). The solid was dried under vacuum to afford a white solid (18.0 g, 72%).

Intermediate 49: Hydrochloride salt of (S)-1-Amino-2-methyl-1-phenylpropan-2-ol

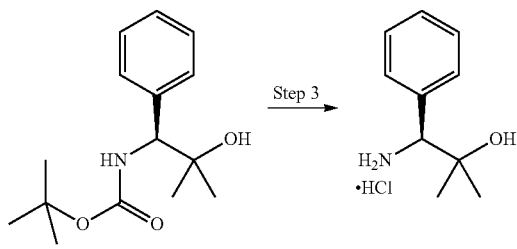 [SMILES: CC(C)(C)OC(=O)N[C@@H](c1ccccc1)C(C)(C)O ; Cl ; CC(C)(O)[C@@H](N)c1ccccc1]

To a stirred suspension (S)-tert-butyl 2-hydroxy-2-methyl-1-phenylpropylcarbamate (Intermediate 48, 17.0 g, 64.1 mmol) in toluene (85 mL) was added, conc. HCl (26.3 mL, 320.0 mmol). The reaction mixture was warmed to ca. 55° C. Within minutes, the reaction mixture turned brown and the solid slowly went into solution. The biphasic solution was stirred at 55° C. for 2 h following which the reaction mixture was concentrated to afford a brown solid. This was triturated with 5% isopropyl alcohol in ether (200 mL) and the suspension was stirred at room temperature overnight. The resulting suspension was filtered through a glass frit. The filtercake was broken and washed with ether (2×25 mL) and then dried under house vacuum to afford the product as an off-white solid (12.2 g, 94%).

Intermediate 50: (S)-1-Amino-2-methyl-1-phenylpropan-2-ol

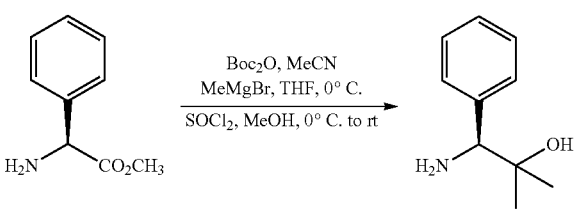

The preparation of (S)-1-amino-2-methyl-1-phenylpropan-2-ol from (S)-methyl 2-amino-2-phenylacetate was carried out according to the procedure for the preparation of this compound in Rikimaru, K., et al., *Synthesis*, 2004 (6), 909-917. MS MH+ 166.2

Intermediate 51: (1R,2R)-1-Phenylpropane-1,2-diol

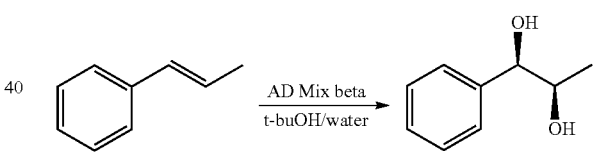

AD Mix beta (Aldrich cat. No. 392766) (6.44 g, 4.60 mmol) was suspended in water (50 ml) and t-buOH (50 ml) and resulting slurry was cooled to 0° C. Trans-methyl beta styrene (Aldrich) (0.6 ml, 4.60 mmol) was then added directly and the reaction mixture was stirred at 0° C. for 6 hours with carefully monitoring of the temperature. TLC at this point showed 2 spots, one of which corresponded to the starting material (visible by UV, Rf 0.8 in 1:1 EtOAc/Hept). The other, more polar spot (visible by KMnO$_4$, Rf 0.35 in 1:1 EtOAc/Hept) was weaker. Therefore, the reaction mixture was left to warm to room temperature overnight. TLC at this point showed only the more polar spot. The reaction mixture was quenched via addition of solid sodium sulfite (6 g). Water was then added to dilute the solids at bottom of mixture. The pH of this solution was 14. The aqueous solution was extracted with EtOAc (×3). Combined organic layers were washed with brine, dried over MgSO$_4$, filtered and concentrated to afford a clear mobile oil. This material was purified via Biotage automated flash column chromatography 40M, eluting with 10-100% EtOAc/Hept. Relevant fractions were pooled and concentrated to afford a clear, sticky oil, which was dried under high vacuum. Mass of dry material=1.67 g (quantitative yield plus solvent).

¹H NMR (400 MHz, DMSO-d₆) δ ppm 0.82 (d, J=6.32 Hz, 3H) 3.57-3.70 (m, J=6.28, 6.28, 6.28, 6.28, 4.42 Hz, 1H) 4.28 (dd, J=6.19, 4.17 Hz, 1H) 4.60 (d, J=4.29 Hz, 1H) 5.17 (d, J=4.04 Hz, 1H) 7.17-7.27 (m, 2H) 7.27-7.38 (m, 3H)

Intermediate 52: Sulfinate ester of (1R,2R)-1-Phenylpropane-1,2-diol

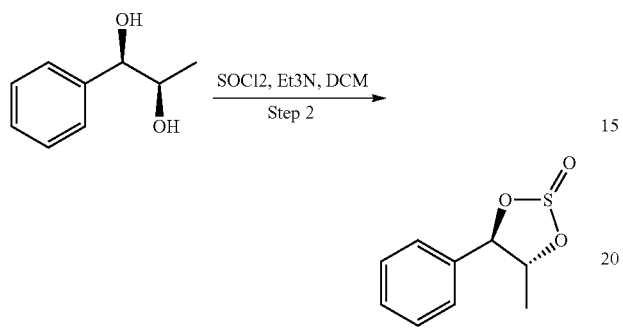

(1R,2R)-1-Phenylpropane-1,2-diol (Intermediate 51, 5.46 g, 35.9 mmol) was dissolved in triethylamine (15 ml, 108 mmol) and DCM (75 ml). This mixture was cooled to 0° C. Thionyl chloride (3.93 ml, 53.8 mmol) in DCM (25 ml) was then added dropwise, upon which addition the reaction mixture became a brown colour and there was vigorous with gas evolution. The mixture was stirred at 0° C. for 45 mins. TLC in 1:1 heptane/EtOAc at this point showed another more non-polar spot than the starting material, therefore the reaction mixture was concentrated to remove majority of DCM, and the residue was partitioned between cold water and Et₂O. The organic layer was washed with 1M HCl, saturated NaHCO₃ solution and brine, then dried over MgSO₄, filtered and concentrated to afford a brown oil. This material was purified via Biotage automated flash column chromatography (330 g column), eluting with 2-50% EtOAc/Heptane. Relevant fractions were pooled and concentrated to afford a brown mobile oil, which was dried under high vacuum. Mass of dry material was 6.98 g (98% yield). Material was a 1:1 mix of diastereoisomers around the sulfoxide.

¹H NMR (400 MHz, DMSO-d₆) δ ppm 1.44 (dd, J=12.00, 6.19 Hz, 3H) 4.63 (dq, J=8.97, 6.19 Hz, 0.5H) 4.76-4.88 (m, 0.5H) 5.23 (d, J=9.60 Hz, 0.5H) 5.60 (d, J=9.09 Hz, 0.5H) 7.42-7.51 (m, 3H) 7.53-7.57 (m, 2H)

Intermediate 53: (1S,2R)-1-Azido-1-phenylpropan-2-ol

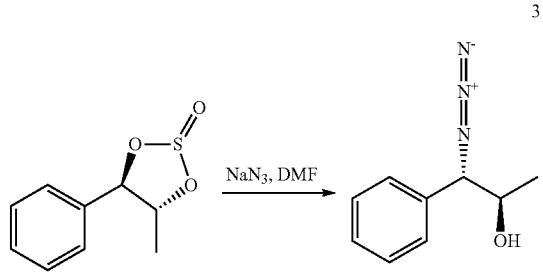

Intermediate 52 (1.57 g, 7.92 mmol) was dissolved in DMF and solid sodium azide (2.059 g, 31.7 mmol) was added. The reaction mixture was heated at 80° C. for 6 h. TLC showed 2 spots, one of which corresponded to the starting material and another more polar spot. The reaction mixture was poured into water and extracted with Et₂O (×3). The combined organic layers were washed with brine, dried over MgSO₄, filtered and concentrated to afford a yellow oil, which was stored in the fridge overnight. The oil was purified via Biotage automated flash column chromatography 40M, eluting with 10-100% EtOAc/Heptane. Relevant fractions were pooled and concentrated to afford a clear oil, which was dried under high vacuum. Mass of dry material was 1.26 g (90% yield).

¹H NMR (400 MHz, CHLOROFORM-d) δ ppm 1.21 (d, J=6.32 Hz, 3H) 1.71 (s, 1H) 3.96-4.04 (m, 1H) 4.50 (d, J=5.81 Hz, 1H) 7.35-7.46 (m, 5H)

Intermediate 54: tert-Butyl (1S,2R)-2-hydroxy-1-phenylpropylcarbamate

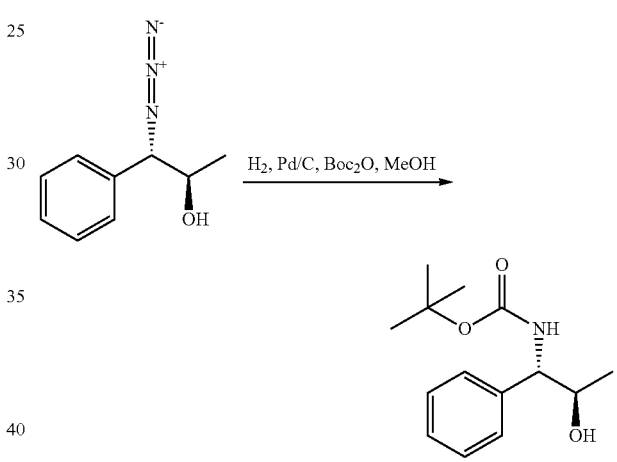

(1S,2R)-1-Azido-1-phenylpropan-2-ol (Intermediate 53, 132 mg, 0.745 mmol) was dissolved in MeOH (5 ml), to which Boc₂O (0.346 ml, 1.490 mmol) was added. The reaction mixture was stirred at room temperature for 5 mins, after it was flushed with N₂. Pd/C (50 mg, 0.470 mmol) was then added and reaction mixture was flushed with N₂ once more, then placed under a balloon of H₂ and stirred vigorously overnight. LC-MS at this point showed one major peak corresponding to desired product. Therefore, the reaction mixture was filtered through a syringe filter and filtrate was concentrated to afford a clear oil, which started to solidify. This material was purified via Biotage automated flash column chromatography 12M, eluting with 10-100% EtOAc/Heptane. Relevant fractions were pooled and concentrated to afford a fluffy white solid, which was dried under high vacuum. Mass of dry material=134 mg (71% yield).

1H NMR (400 MHz, DMSO-d₆) δ ppm 1.44 (dd, J=12.00, 6.19 Hz, 3H) 4.63 (dq, J=8.97, 6.19 Hz, 0.5H) 4.76-4.88 (m, 0.5H) 5.23 (d, J=9.60 Hz, 0.5H) 5.60 (d, J=9.09 Hz, 0.5H) 7.42-7.51 (m, 3H) 7.53-7.57 (m, 2H) t-butyl group is in a rotameric relationship with peak at 4.32 which has proportional peak to its right as weak multiplet at 4.15 but is integrated as 1 with 4.32 multiplet.

Intermediate 55: Hydrochloride salt of (1S,2R)-1-Amino-1-phenylpropan-2-ol

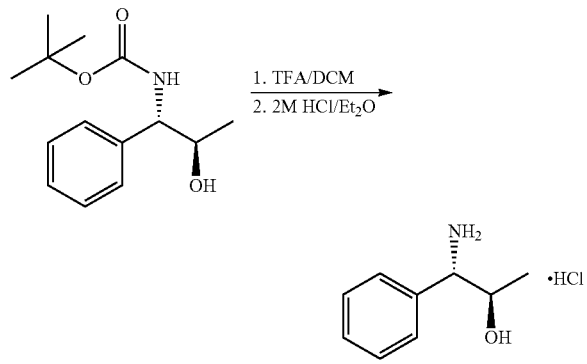

tert-Butyl (1S,2R)-2-hydroxy-1-phenylpropylcarbamate (Intermediate 54, 134 mg, 0.533 mmol) was dissolved in DCM (5 ml), to which TFA (1 ml, 12.98 mmol) was added. The reaction mixture was stirred at room temperature for 30 mins, after which LC-MS showed one major peak corresponding to desired product. The reaction mixture was therefore concentrated and the residue was dried under high vacuum to remove majority of TFA. The resulting oil was dissolved in THF (5 ml), to which an HCl solution (2M in ether) (1 ml, 32.9 mmol) was added. No precipitation occurred, therefore the mixture was concentrated to afford a white solid. This material was dried under high vacuum and then dissolved in water and lypholized. Mass of dry material was 63 mg (63% yield).

$^1$H NMR (400 MHz, DMSO-$d_6$) δ ppm 0.93 (d, J=6.06 Hz, 3H) 4.16 (d, J=4.80 Hz, 2H) 5.38 (br. s., 1H) 7.34-7.52 (m, 5H) 8.65 (br. s., 2H)

Intermediate 56: (1r,4r)-Methyl 4-aminocyclohexanecarboxylate

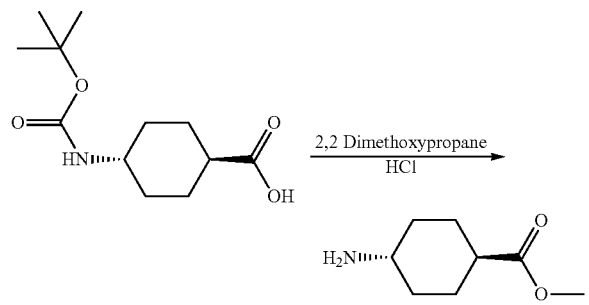

(1r,4r)-4-(tert-Butoxycarbonylamino)cyclohexanecarboxylic acid (25 g, 103 mmol) was dissolved in MeOH (250 ml), to which 2,2-dimethoxypropane (10.70 g, 12.63 ml, 103 mmol) and then 2M HCl in ether (51 ml, 103 mmol) were added. The reaction mixture was stirred at room temperature overnight, then concentrated and the residue was treated with ether (100 ml). The resulting white suspension was filtered then dried to afford a white powder (16.8 g, 84% yield).

$^1$H NMR (400 MHz, DMSO-$d_6$) δ ppm 1.31-1.42 (m, 4H) 1.89-2.01 (m, 4H) 2.20-2.31 (m, 1H) 2.95 (br. s., 1H) 3.59 (s, 3H) 8.13 (br. s., 2H)

Intermediate 57: (1r,4r)-Methyl 4-(4-(trifluoromethyl)phenylsulfonamido)-cyclohexanecarboxylate

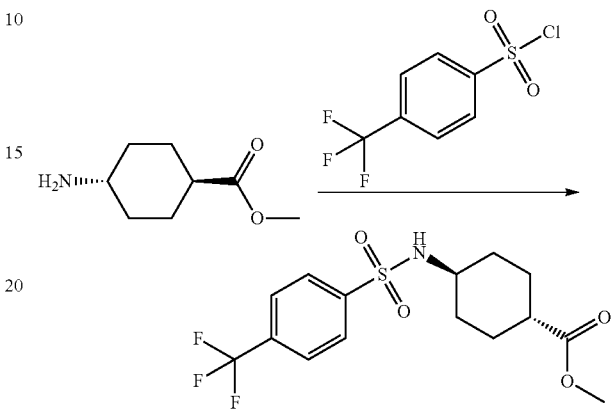

(1r,4r)-Methyl 4-aminocyclohexanecarboxylate (Intermediate 56, 9.5 g, 49 mmol) was dissolved in DCM (100 ml), to which, DIPEA (21.42 ml, 15.85 g, 123 mmol) was added. The reaction mixture was stirred for five minutes then 4-(trifluoromethyl)benzene-1-sulfonyl chloride (12 g, 49 mmol) was then added, and the mixture was stirred at room temperature for 2 hrs, then concentrated to remove the DCM. 1M HCl was then added and the reaction mixture was extracted with EtOAc. The organic layer was washed with saturated NaHCO$_3$, brine, dried over MgSO$_4$, filtered and concentrated to afford a light yellow solid (15.4 g-86% yield).

$^1$H NMR (400 MHz, DMSO-$d_6$) δ ppm 1.14 (d, J=3.28 Hz, 1H) 1.16-1.24 (m, 2H) 1.25-1.35 (m, 1H) 1.65 (dd, J=12.88, 2.78 Hz, 1H) 1.79 (d, J=2.53 Hz, 1H) 1.82 (br. s., 1H) 2.18-2.33 (tt, J=11.62, 3.54 Hz, 1H) 2.92-3.05 (m, J=11.01, 11.01, 7.36, 3.88, 3.88 Hz, 1H) 3.49-3.60 (m, 3H) 7.94-8.06 (m, 5H)

Intermediate 58: (1r,4r)-4-(4-(trifluoromethyl)phenylsulfonamido)-cyclohexancarboxylic acid

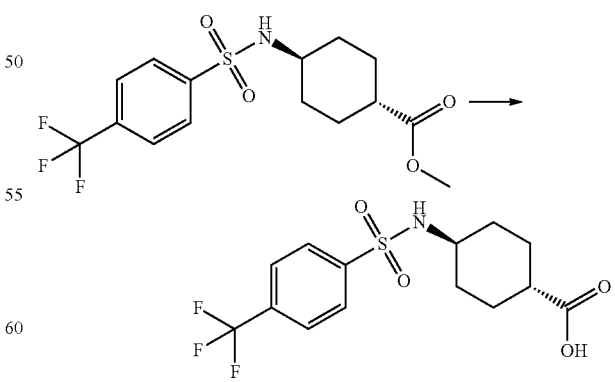

(1r,4r)-Methyl 4-(4-(trifluoromethyl)phenylsulfonamido)-cyclohexanecarboxylate (Intermediate 57, 10 g, 27 mmol) was dissolved in EtOH (150 ml), to which a sodium hydroxide solution (20.45 ml, 2.5M, 41.1 mmol) was added.

The reaction mixture was stirred at 45° C. overnight, then concentrated and water was added. The mixture was acidified with 1M HCl and then extracted with EtOAc. The organic layer was dried over MgSO$_4$, filtered, and concentrated to yield an orange oil. Ether and heptane were added and the resulting off white solid was filtered and dried to afford a beige powder (8.8 g, 92% yield).

$^1$H NMR (400 MHz, DMSO-d$_6$) δ ppm 1.14-1.24 (m, 2H) 1.26 (d, J=2.78 Hz, 1H) 1.30 (d, J=2.78 Hz, 1H) 1.55-1.66 (m, 2H) 1.73-1.85 (m, 2H) 2.00-2.11 (m, 1H) 2.91-3.03 (m, J=10.91, 10.91, 7.23, 3.79, 3.79 Hz, 1H) 7.93-8.06 (m, 5H) 12.04 (br. s., 1H)

Intermediate 59: Isotopically labelled (S)-1-Amino-2-methyl-1-phenylpropan-2-ol

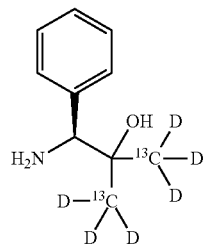

Isotopically labelled (S)-1-Amino-2-methyl-1-phenylpropan-2-ol was prepared by a method analogous to the method used to prepare Intermediate 50 using the corresponding isotopically labelled starting material. MS MH+ 174.3

Intermediate 60: (R)-tert-Butyl 3-hydroxy-1-phenylpropylcabamate (Typical Boc Protection Method)

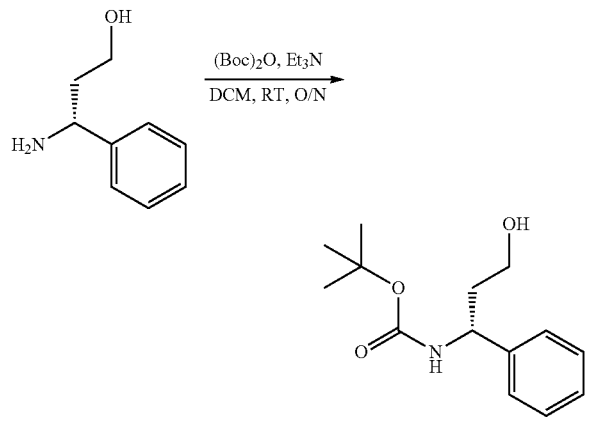

(R)-3-amino-3-phenylpropan-1-ol (500 mg, 2.66 mmol) and Et$_3$N (741 ul, 5.32 mmol) was dissolved in DCM (15 ml). Di-tert-butyl dicarbonate was added and the reaction mixture was stirred overnight at RT. When the reaction was complete, as indicated by LCMS, it was concentrated in vacuo, and purified via column chromatography using a biotage SP1 25+S column with a gradient 50% EtOAc in heptane calculated from TLC. Product fractions were combined and concentrated to give the title compound as a clear oil (578 mg, 87%). LCMS=[M+H]=252.29

Intermediate 61: (R)-tert-Butyl 3-methoxy-1-phenylpropylcarbamate (Typical O-Alkylation Method)

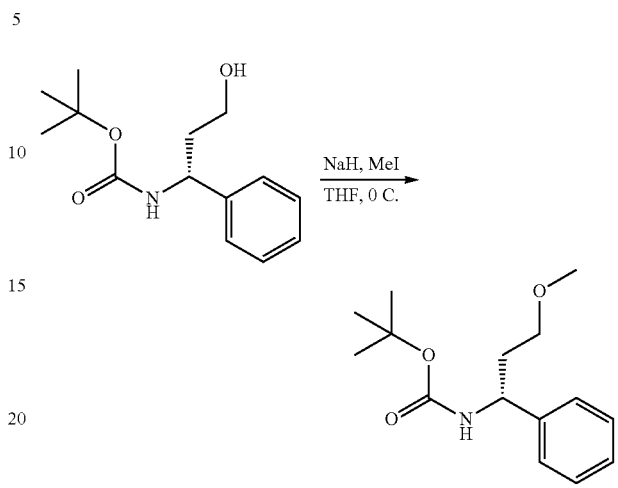

(R)-tert-Butyl 3-hydroxy-1-phenylpropylcarbamate (Intermediate 60, 258 mg, 1.03 mmol) was dissolved in THF under nitrogen at 0° C. NaH was added and the reaction mixture was stirred at 0° C. for 10 min. MeI was added and the reaction mixture was stirred at room temperature for 30 min. then quenched with sat. aq. Na$_2$SO$_4$ and extracted with Et$_2$O. The organic layer was dried over MgSO$_4$, filtered and concentrated in vacuo. The crude material was purified via column chromatography using a biotage SP1 25+M column with a gradient 50% EtOAc in heptane calculated from TLC. Product fractions were combined and concentrated to give the title compound as a white solid (78 mg, 29%). LCMS=[M+H]=266

Intermediate 62: (R)-3-Methoxy-1-phenylpropan-1-amine (Typical Boc Deprotection Method)

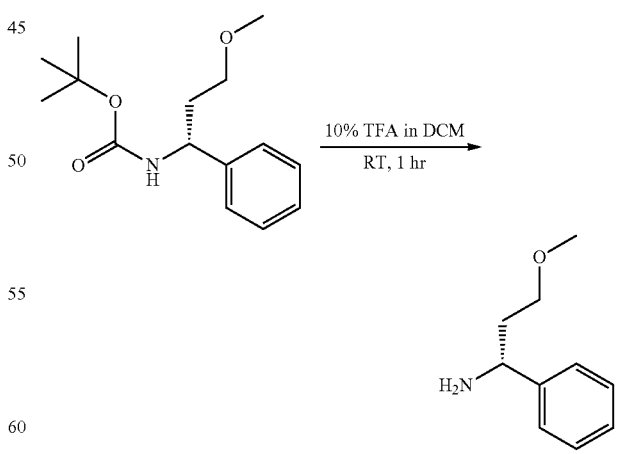

(R)-tert-Butyl 3-methoxy-1-phenylpropylcarbamate (Intermediate 61, 78 mg, 0.294 mmol) was dissolved in DCM (4.5 ml) and TFA (0.5 ml) was added. The reaction mixture was stirred for 1 h at room temperature when LCMS indicated that the reaction was complete. The reaction mixture was concentrated in vacuo, and the crude product was taken onto next step without further purification (0.294 mmol). LCMS [M+H]=166

Intermediate 63: Methyl 3-(4-bromophenyl)propanoate

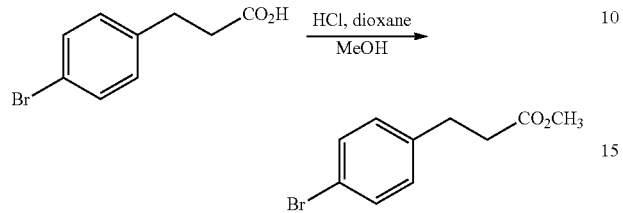

HCl in dioxane (4M, 61.1 mL) was added to a solution of 3-(4-bromophenyl)propanoic acid in methanol (60 mL) at room temperature. The reaction was stirred 18 h and then concentrated under vacuum. The crude product was purified by flash chromatography on silica gel using a 0-50% ethyl acetate-n-heptane gradient to afford 5.1 g of product as a colorless oil.

Intermediate 64: Trans-N—((R)-1-(4-fluorophenyl)ethyl)-4-(4,4,5,5-tetramethyl-1,3,2-dioxaborolan-2-yl)phenylsulfonamido)cyclohexanecaboxamide

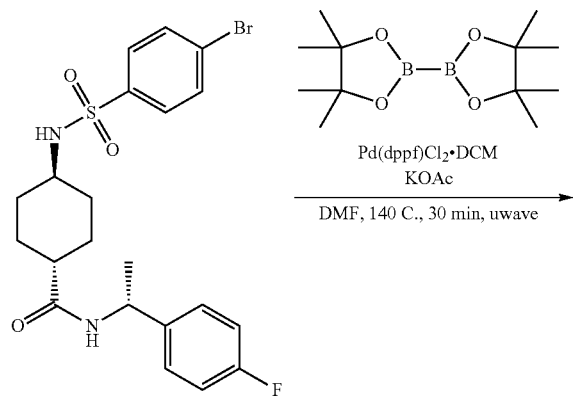

Trans-4-(4-Bromo-benzenesulfonylamino)-cyclohexanecarboxylic acid [(R)-1-(4-fluoro-phenyl)-ethyl]-amide (Example 115, 100 mg, 0.206 mmol), Pd(dppf)Cl$_2$.DCM (8.5 mg, 0.01 mmol), potassium acetate (61 mg, 0.618 mmol) and 4,4,5,5,4',4',5',5'-octamethyl-[2,2']bi[[1,3,2]dioxaborolanyl] (54 mg, 0.207 mmol) were dissolved in DMF (2-3 ml) under N$_2$ and the mixture was microwaved at 140° C. for 30 min., after which LCMS indicated that the reaction was complete. The crude reaction mixture was taken onto next step with assumption of 100% conversion to desired product (0.206 mmol).

Intermediate 65: (1r,4r)-Ethyl 4-(2,3,3-trimethylbutan-2-yloxy)cyclohexanecarboxylate

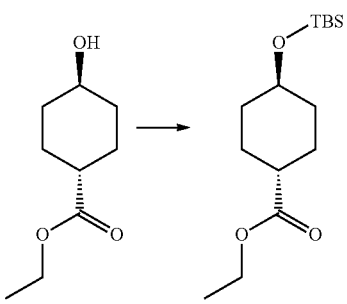

4-Hydroxy cyclohexane carboxylic acid ethyl ester (Aldrich) (10 g, 58.1 mmol) was dissolved in DMF (75 ml) to which t-butyldimethylsilyl chloride (TBSCl, 9.63 g, 63.9 mmol) and then imidazole (4.74 g, 69.7 mmol) were added as solids in portions. The reaction mixture was stirred at room temperature overnight, then poured into water and extracted with EtOAc (×2). The combined organics were washed with brine and then dried over MgSO$_4$, filtered and concentrated to afford a clear oil. This material was purified via flash column chromatography 65i, eluting with 2-20% EtOAc/Hept. Relevant fractions were pooled and concentrated to afford a clear oil, which was dried under high vacuum overnight.

Mass of dry material=2.34 g (14% yield).

$^1$H NMR (400 MHz, DMSO-d$_6$) δ ppm −0.04-0.05 (m, 9H) 0.77-0.89 (m, 13H) 1.07-1.17 (m, 5H) 1.18-1.28 (m, 1H) 1.29-1.41 (m, 1H) 1.43-1.56 (m, 6H) 1.68-1.85 (m, 4H) 2.19 (tt, J=11.37, 3.60 Hz, 0.5H) 2.30 (tt, J=9.92, 3.66 Hz, 1H) 3.48-3.60 (m, 0.5H) 3.80-3.90 (m, 1H) 3.96-4.06 (m, 3H) (unknown mixture of cis and trans isomers)

Intermediate 66: Ethyl 4-(tert-butyldimethylsilyloxy)-1-methylcyclohexanecarboxylate

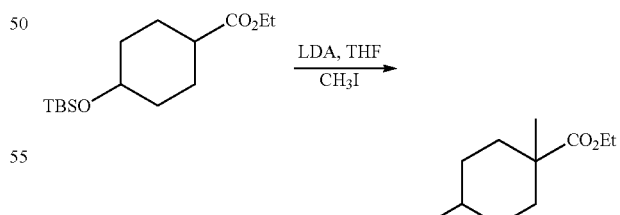

Diisopropylamine (2.91 ml, 20.42 mmol) was dissolved in THF (20 ml) and cooled to −78° C. under N$_2$. An nBuLi (2.7M in Hexane) (7.56 ml, 20.42 mmol) solution was then added slowly and the resulting LDA solution was stirred at −78° C. for 10 mins. A solution of (1r,4r)-ethyl 4-(2,3,3-trimethylbutan-2-yloxy)cyclohexanecarboxylate (Intermediate 65, 2.34 g, 8.17 mmol) in THF (30 ml) was then added fast dropwise and the reaction mixture was stirred at −78° C. for 1 hour. MeI (1.788 ml, 28.6 mmol) was then added directly via syringe and the reaction mixture was allowed to warm to room temperature overnight, then quenched by adding it to a saturated ammonium chloride solution. The resulting mixture was extracted with EtOAc (×2). The combined organics were washed with brine, dried over MgSO$_4$, filtered and concentrated to afford a pink oil, which was dried under high vacuum for 1 h. Mass of dry material was 1.32 g (53% yield).

1H NMR (400 MHz, DMSO-d$_6$) δ ppm −0.06-0.05 (m, 8H) 0.77-0.89 (m, 11H) 1.03-1.10 (m, 4H) 1.13-1.23 (m, 8H) 1.39-1.56 (m, 1H) 1.65 (t, J=3.92 Hz, 1H) 1.96 (br. s., 0.5H) 2.00 (t, J=3.92 Hz, 2H) 3.62 (br. s., 1H) 3.75-3.81 (m, 0.5H) 4.07 (q, J=7.16 Hz, 3H) (unknown mixture of cis and trans isomers)

LCMS [M+H]=301.3

Intermediate 67: Ethyl 4-hydroxy-1-methylcyclohexanecarboxylate

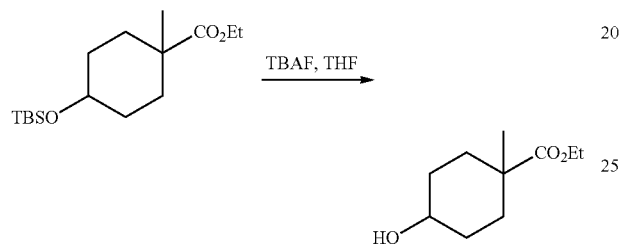

Ethyl 4-(tert-butyldimethylsilyloxy)-1-methylcyclohexanecarboxylate (Intermediate 66, 1.32 g, 4.39 mmol) was dissolved in THF (25 ml), to which tetrabutylammonium fluoride (TBAF, 1M solution in THF) (7.34 ml, 7.34 mmol) was added. The reaction mixture was stirred at room temperature overnight, then concentrated and the residue was partitioned between EtOAc/water. The aqueous layer was back extracted and combined organics were dried over MgSO$_4$, filtered and concentrated to afford a brown oil. This material was purified via flash column chromatography, eluting with 2-50% EtOAc/Hept. Relevant fractions were pooled and concentrated to afford a clear oil—797 mg (97% yield).

1H NMR (400 MHz, DMSO-d$_6$) δ ppm 1.06 (s, 3H) 1.18 (t, J=7.07 Hz, 3H) 1.12-1.20 (m, 2H) 1.21-1.32 (m, 2H) 1.61-1.73 (m, 2H) 1.96-2.06 (m, 2H) 3.36 (dt, J=9.47, 4.74 Hz, 1H) 4.08 (q, J=7.07 Hz, 2H) 4.45 (br. s., 1H)

LCMS [M+H]=187.4

Intermediate 68: (1r,4r)-Ethyl 4-azido-1-methylcyclohexanecarboxylate

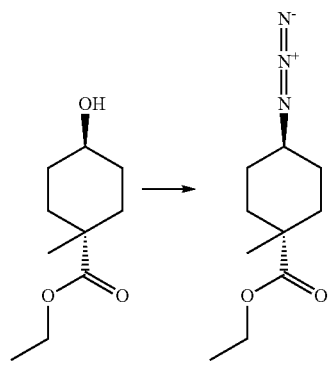

Ethyl 4-hydroxy-1-methylcyclohexanecarboxylate (Intermediate 67, 272 mg, 1.460 mmol) was dissolved in THF (10 ml), to which triphenylphosphine (804 mg, 3.07 mmol), DIAD (0.596 ml, 3.07 mmol) and a solution of diphenylphosphoryl azide (DPPA, 844 mg, 3.07 mmol) in THF (10 ml) were added. The reaction mixture was heated at 40° C. overnight, then concentrated and purified directly via flash column chromatography, eluting with 10-50% EtOAc/Hept. Relevant fractions were pooled and concentrated to afford a yellow/orange oil=153 mg (50% yield).

$^1$H NMR (400 MHz, CHLOROFORM-d) δ ppm 1.21 (s, 3H) 1.27 (t, J=7.07 Hz, 3H) 1.54-1.63 (m, 2H) 1.64-1.78 (m, 4H) 1.89 (d, J=4.04 Hz, 1H) 1.93 (dd, J=11.87, 5.31 Hz, 1H) 3.63 (d, J=3.54 Hz, 1H) 4.16 (q, J=7.07 Hz, 2H)

Intermediate 69: (1r,4r)-Ethyl 4-amino-1-methylcyclohexanecarboxylate

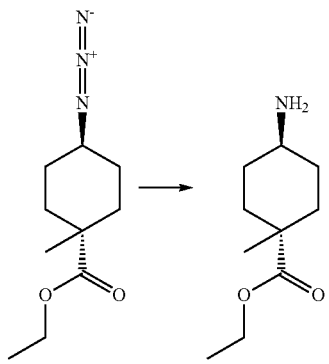

(1r,40-Ethyl 4-azido-1-methylcyclohexanecarboxylate (Intermediate 68, 1 g, 4.73 mmol) was suspended in MeOH (50 ml) and 1M HCl (15 ml), to which Pd/C (500 mg, 4.70 mmol) was then added. The reaction mixture was flushed with N$_2$ and then stirred vigourously under a balloon of H$_2$ for 2 h. After 2 h, the reaction mixture was filtered through a syringe filter and the filtrate was concentrated to remove majority of the MeOH. Remaining water was frozen and lypholized to a sticky pink solid having a mass of 949 mg (90% yield).

$^1$H NMR (400 MHz, DMSO-d$_6$) δ ppm 1.12-1.15 (m, 3H) 1.17 (t, J=7.07 Hz, 3H) 1.56-1.71 (m, 2H) 1.65 (d, J=7.71 Hz, 4H) 1.75-1.79 (m, 2H) 3.02 (br. s., 1H) 4.07 (q, J=7.16 Hz, 2H) 8.20 (br. s., 2H)

Intermediate 70: (1r,40-Ethyl 1-methyl-4-(4-(trifluoromethyl)phenylsulfonamido)cyclohexancarboxylate

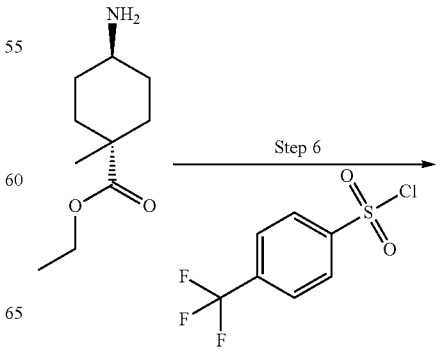

-continued

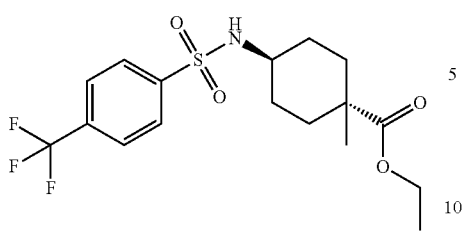

(1r,4r)-Ethyl 4-amino-1-methylcyclohexanecarboxylate (Intermediate 69, 949 mg, 4.28 mmol) was suspended in DCM (50 ml), to which DIPEA (2.243 ml, 12.84 mmol) was added. A solution of p-trifluoromethylbenzene sulfonyl chloride (Oakwood) (1047 mg, 4.28 mmol) in DCM (50 ml) was added. The reaction mixture was stirred at room temperature overnight, then concentrated and residue was adsorbed onto silica and purified via flash column chromatography, eluting with 10-100% EtOAc/Hept. Relevant fractions were pooled and concentrated to afford a clear oily sticky solid, which was dried under high vacuum. Mass of dry material was 738 mg (44% yield).

$^1$H NMR (400 MHz, DMSO-$d_6$) δ ppm 1.07 (s, 3H) 1.13 (t, J=7.07 Hz, 3H) 1.31-1.53 (m, 6H) 1.58-1.68 (m, 2H) 3.11 (d, J=7.58 Hz, 1H) 4.02 (q, J=7.16 Hz, 2H) 7.94-8.07 (m, 5H)

Intermediate 71: (1r,4r)-1-Methyl-4-(4-(trifluoromethyl)phenylsulfonamido)cyclohexancarboxylic acid

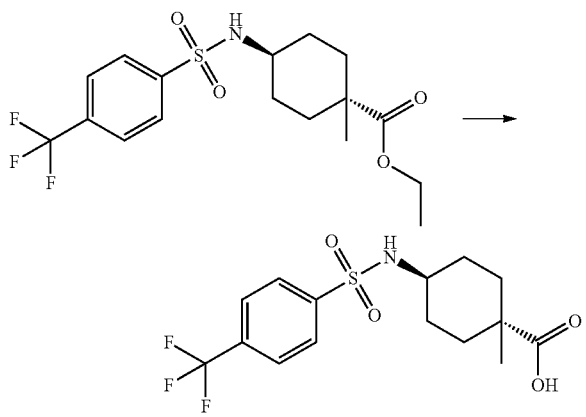

(1r,4r)-Ethyl 1-methyl-4-(4-(trifluoromethyl)phenylsulfonamido)cyclohexancarboxylate (Intermediate 70, 738 mg, 1.876 mmol) was dissolved in EtOH (5 ml), to which NaOH (1M solution) (9.38 ml, 9.38 mmol) was added. The reaction mixture was heated at 50° C. overnight, then concentrated, and the residue was acidified to pH 1 via addition of 1M HCl. The aqueous mixture was extracted with EtOAc (×2), and the combined organics were dried over MgSO$_4$, filtered and concentrated to afford a white solid (603 mg-88% yield).

$^1$H NMR (400 MHz, DMSO-$d_6$) δ ppm 1.06 (s, 3H) 1.36 (t, J=8.53 Hz, 1H) 1.30-1.39 (m, 1H) 1.40 (br. s., 1H) 1.40-1.50 (m, 4H) 1.55-1.66 (m, 1H) 3.11 (dt, J=7.36, 3.58 Hz, 1H) 7.90-8.05 (m, 5H) 12.13 (br. s., 1H)

Intermediate 72: Ethyl 4-(1,3-dioxoisoindolin-2-yl)-1-methylcyclohexanecarboxylate

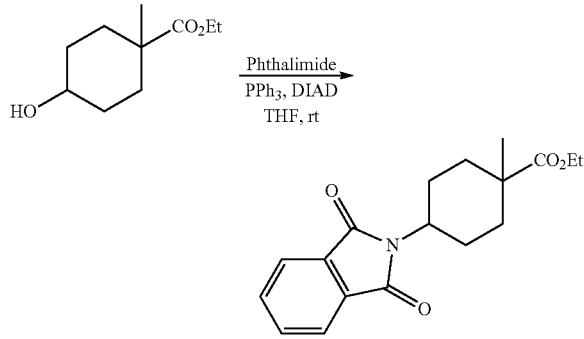

Ethyl 4-hydroxy-1-methylcyclohexanecarboxylate (Intermediate 67, 930 mg, 4.99 mmol), triphenylphosphine (3.143 g, 11.98 mmol), and phthalimide (882 mg, 5.99 mmol) were dissolved in 60 mL of THF. DIAD (2.33 mL, 11.98 mmol) was then added and the reaction mixture was stirred overnight at room temperature. The mixture was concentrated under vacuum, and the residue was chromatographed on silica gel using an ethyl acetate/heptane gradient. The title compound (1 g) was obtained as a clear oil.

LCMS [M+H]=316.3

Intermediate 73: 1-Allyl-4-(1,3-dioxo-1,3-dihydroisoindol-2-yl)-cyclohexanecarboxylic acid ethyl ester

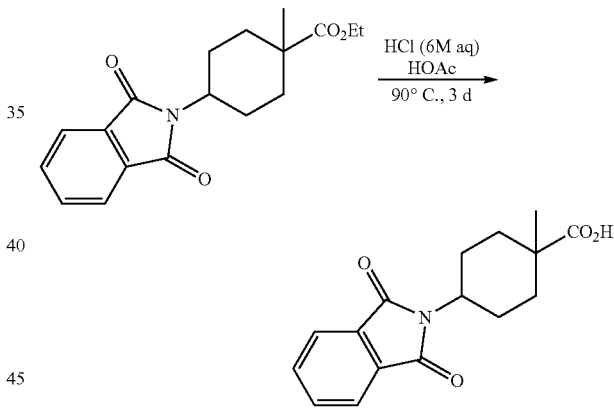

The title compound was prepared by a method analogous to the method used to prepare Intermediate 72 using ethyl 1-allyl-4-hydroxycyclohexanecarboxylate (Intermediate 99) as the starting material.

Intermediate 74: 4-(1,3-Dioxoisoindolin-2-yl)-1-methylcyclohexanecarboxylic acid

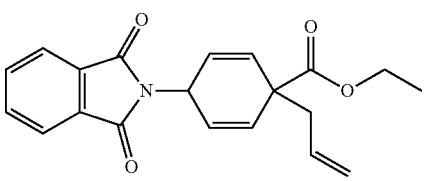 [SMILES: C=CCC1(C(=O)OCC)C=CC(N2C(=O)c3ccccc3C2=O)C=C1]

Ethyl 4-(1,3-dioxoisoindolin-2-yl)-1-methylcyclohexanecarboxylate (Intermediate 72, 900 mg, 2.85 mmol) was added to 6M aq. hydrochloric acid (0.951 mL, 5.71 mmol) in acetic acid (5 mL). The reaction mixture was heated to 90° C. for 48 h and then concentrated under vacuum. The residue was taken up in a minimal volume of ethyl acetate and a white solid precipitated. The solid was collected by filtration, washed with acetonitrile and dried to provide the product acid (475 mg) as a white solid. LCMS [M−H]=286.3

Intermediate 75: 4-(1,3-Dioxoisoindolin-2-yl)-1-methylcyclohexanecarbonyl chloride

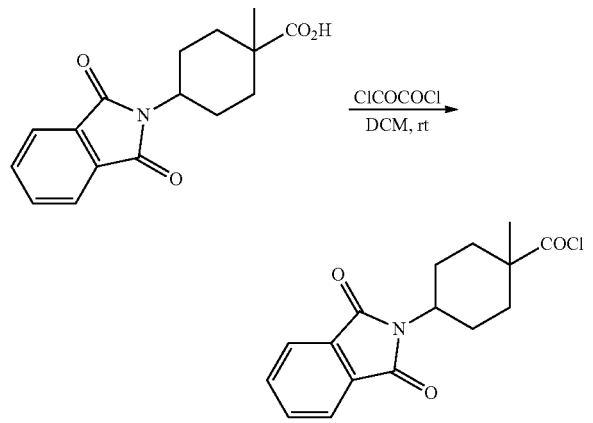

4-(1,3-Dioxoisoindolin-2-yl)-1-methylcyclohexanecarboxylic acid (Intermediate 74, 220 mg, 0.786 mmol) was dissolved in DCM (5 mL), and oxalyl chloride (146 mg, 0.1 mL, 1.149 mmol) was added slowly, followed by addition of a drop of DMF. The mixture was stirred at room temperature for 20 min, then concentrated under vacuum to provide the product as a yellow solid that was used as is in the next step.

Intermediate 76: (R)-4-(1,2-Dioxoisoindolin-2-yl)-N-(1-(4-fluorophenyl)ethyl)-methylcyclohexancarboxamide

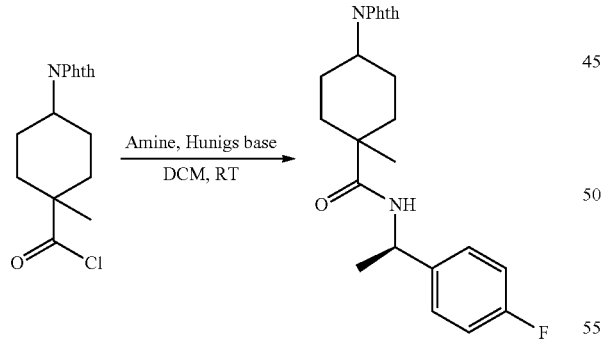

(R)-1-(4-Fluorophenyl)ethylamine (0.335 ml, 2.477 mmol) and Hunig's Base (1.442 ml, 8.26 mmol) were dissolved in DCM (10 ml). The mixture was stirred for 10 min, then 4-(1,3-dioxoisoindolin-2-yl)-1-methylcyclohexanecarbonyl chloride (Intermediate 69, 505 mg, 1.652 mmol) in DCM was added. The reaction mixture was stirred at room temperature for 24 hr. LCMS indicated that the reaction was complete. Therefore, the mixture was washed with H₂O, brine and DCM concentrated in vacuo. Crude material purified via normal phase chromatography on SP1 Biotage, column 40+S, with calculated TLC conditions of 40% EtOAc in heptane to yield the product as a white solid (345 mg, 51%). LCMS [M+H]=409.2

Intermediate 77: (R)-4-Amino-N-(1-(4-fluorophenyl)ethyl)-1-methylcyclohexanecarboxamide

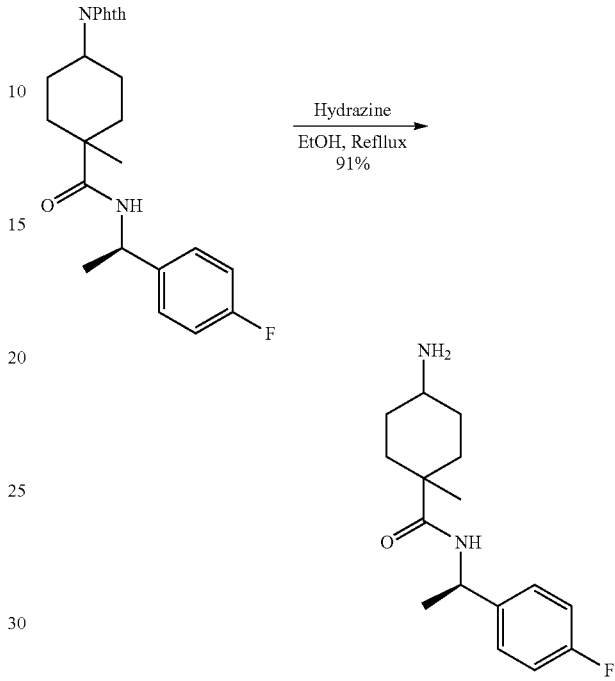

Hydrazine (0.207 ml, 4.22 mmol) was added to a solution of (R)-4-(1,2-dioxoisoindolin-2-yl)-N-(1-(4-fluorophenyl)ethyl)-methylcyclohexancarboxamide (Intermediate 76, 345 mg, 0.845 mmol) in EtOH (50 ml) and the reaction mixture was refluxed 80° C. under N₂ for 24 hr. LCMS indicated that the reaction was complete and the mixture was cooled to room temperature. A white solid crashed out on cooling. The mixture was concentrated in vacuo to a white solid, and the crude material was taken up in DCM and filtered through sinter funnel. The white solid was washed with DCM multiple times to yield the product as a creamy white solid (213 mg, 91%). LCMS [M−H]=277.4

Intermediate 78: 4-(tert-Butyl-dimethyl-silanyloxy)-1-hydroxy-cyclohexanecarboxylic acid ethyl ester

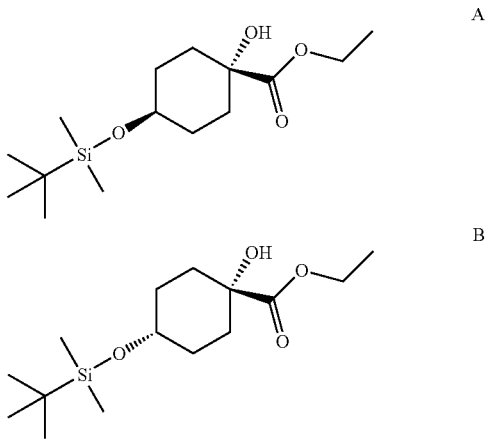

An enolate of ethyl 4-(tert-butyldimethylsilyloxy)cyclohexanecarboxylate (2.5 g) was prepared as described in the procedure for preparing Intermediate 66, followed by treatment with (1R)-(−)-(10)-(camphorylsulfonyl)oxaziridine (3.0 g) per conditions described in Franklin Davis, et al. *J. Am. Chem. Soc.* 1990, 112, 6679; *Tet. Lett* 1990, 31(47), 6823. Chromatography using gradient elution 0-10% ethyl acetate in heptane yielded a 3:2 mixture (A:B) of diastereomers (58%). MS MH+ 303.4

Intermediate 79: 4-(tert-Butyl-dimethyl-silanyloxy)-1-hydroxy-cyclohexanecarboxylic acid

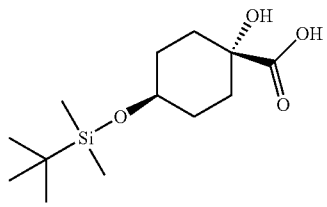

4-(tert-Butyl-dimethyl-silanyloxy)-1-hydroxy-cyclohexanecarboxylic acid ethyl ester (Intermediate 78, 1.35 g) was hydrolyzed to an acid by adding it to 45 ml of a solution of 1M LiOH in 1:1 THF:MeOH at room temperature. The pH was adjusted to 3 and the mixture was extracted with ethyl acetate. The organic layer was dried over sodium sulfate, filtered, and concentrated to give the title compound. MS MH+ 275.4

Intermediate 80: 4-(tert-Butyl-dimethyl-silanyloxy)-1-hydroxy-cyclohexanecarboxylic acid [(R)-1-(4-fluoro-phenyl)-ethyl]-amide

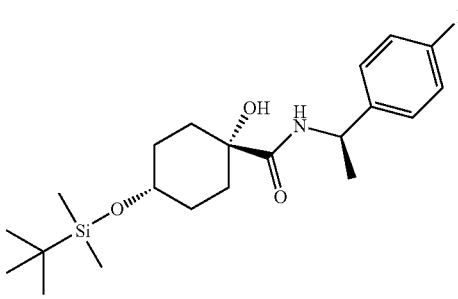

4-(tert-Butyl-dimethyl-silanyloxy)-1-hydroxy-cyclohexanecarboxylic acid (Intermediate 79, 1.15 g) and with (R)-1-(4-Fluoro-phenyl)-ethylamine (640 mg) were coupled using the standard HATU coupling procedure as described in Example 1 to yield a 3:2 mixture (A:B) of diastereomers the title compound (44%).

Intermediate 81: 4-(tert-butyldimethylsiyloxy)-1-hydroxy-N-(1-phenylethyl)cyclohexanecarboxamide

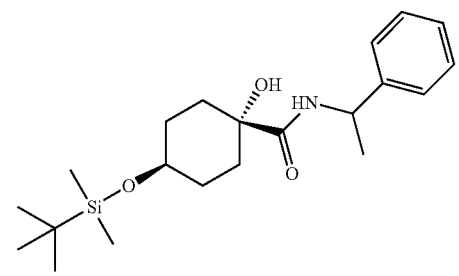

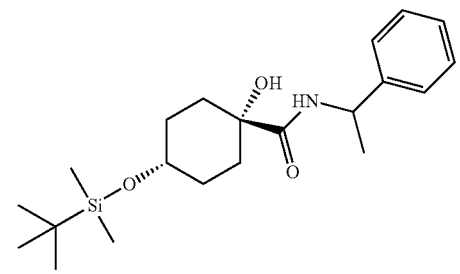

Intermediate 81 can be prepared by a method analogous to the method used to prepare intermediate 80 from Intermediate 79 using 1-phenyl-ethylamine as the starting material.

Intermediate 82: 1,4-Dihydroxy-cyclohexanecarboxylic acid [(R)-1-(4-fluoro-phenyl)-ethyl]-amide

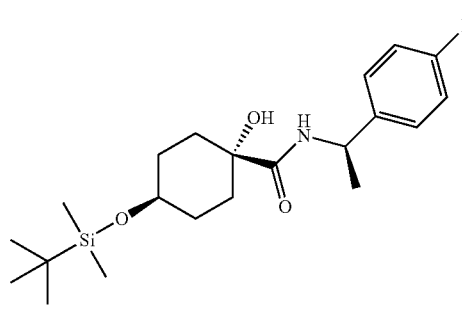

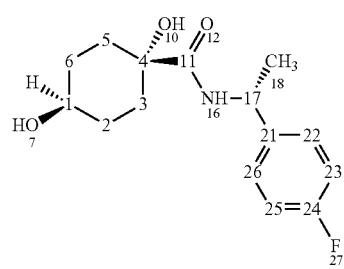

4-(tert-Butyl-dimethyl-silanyloxy)-1-hydroxy-cyclohexanecarboxylic acid [(R)-1-(4-fluoro-phenyl)-ethyl]-amide (Intermediate 80, 700 mg) was treated with 1.0M TBAF in THF (3.0 ml) for 16 hours. The reaction was concentrated to reduce the volume of THF, then diluted with ethyl acetate. The organic layer was washed once with water followed by brine, then filtered and dried over sodium sulfate. The resulting residue was suspended in a minimum of dichloromethane and the resulting precipitate was isolated by filtration to yield a single diastereomer of 1,4-dihydroxy-cyclohexanecarboxylic acid [(R)-1-(4-fluoro-phenyl)-ethyl]-amide (132 mg). MS MH+ 282.4

Stereochemistry was assigned based on NMR. H-1 did not demonstrate axial J-coupling therefore, it must be in the equatorial position. ROESY demonstrated a through space correlation from H-10 to axial H-21H-6 indicating that the hydroxyl group is axial.

Intermediate 83: (1,4-Dihydroxy-N-(1-phenylethyl)cyclohexanecarboxamide

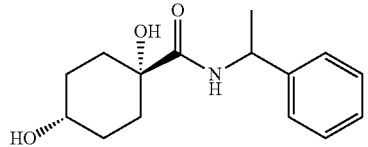 [SMILES: CC(NC(=O)[C@]1(O)CC[C@@H](O)CC1)c1ccccc1]

(1,4-Dihydroxy-N-(1-phenylethyl)cyclohexanecarboxamide can be prepared by a method analogous to the method used to prepare Intermediate 82 using Intermediate 81 instead of Intermediate 72 as the starting material.

Intermediate 84: N-Benzyl-4-(trifluoromethyl)benzenesulfonamide

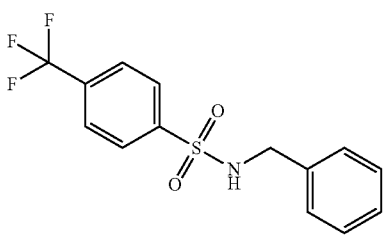 [SMILES: O=S(=O)(NCc1ccccc1)c1ccc(C(F)(F)F)cc1]

4-(Trifluoromethyl)benzene-1-sulfonyl chloride (1 gm) was coupled to benzylamine using conditions analogous to those used to prepare intermediate 1. Purification by chromatography yielded N-benzyl-4-(trifluoromethyl)benzenesulfonamide (770 mg). Rf=0.38 by TLC eluting with 30% ethyl acetate in heptane. MS MH+ 316.2

Intermediate 85: N-Benzyl-4-(oxazol-4-yl)benzenesulfonamide

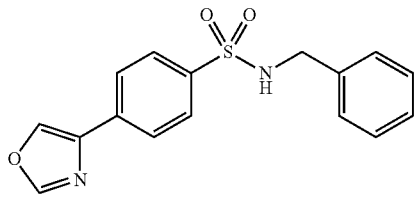 [SMILES: O=S(=O)(NCc1ccccc1)c1ccc(-c2cocn2)cc1]

N-Benzyl-4-(oxazol-4-yl)benzenesulfonamide can be prepared by a method analogous to the method used to prepare Intermediate 84 using Intermediate 26 as the starting material.

Intermediate 86: tert-Butyl benzyl(4-(trifluoromethyl)phenylsulfonyl)carbamate

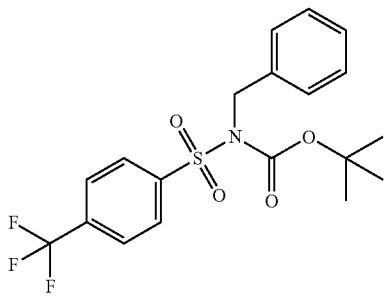 [SMILES: CC(C)(C)OC(=O)N(Cc1ccccc1)S(=O)(=O)c1ccc(C(F)(F)F)cc1]

A solution on N-benzyl-4-(trifluoromethyl)benzenesulfonamide (Intermediate 84, 768 mg) in THF (8 ml) at 0° C. was treated with di-tert-butyl dicarbonate (877 mg) followed by 4-dimethylaminopyridine (45 mg). The ice/water bath was removed and solution stirred 18 hours. The volatiles were removed and crude chromatographed in 20-100% ethyl acetate in heptane to afford the title compound (990 mg). MS MH+ 360.2 (minus Boc fragment).

Intermediate 87: tert-Butyl benzyl(4-(oxazol-4-yl)phenylsulfonyl)carbamate

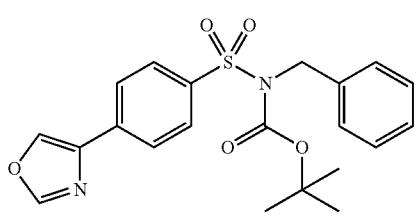 [SMILES: CC(C)(C)OC(=O)N(Cc1ccccc1)S(=O)(=O)c1ccc(-c2cocn2)cc1]

tert-Butyl benzyl(4-(oxazol-4-yl)phenylsulfonyl)carbamate can be prepared by a method analogous to the method used to prepare Intermediate 86 using Intermediate 85 as the starting material.

Intermediate 88: tert-Butyl 4-(trifluoromethyl)phenylsulfonylcarbamate

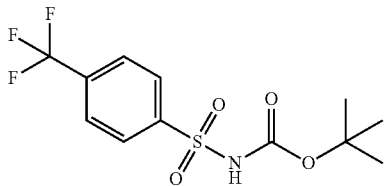 [SMILES: CC(C)(C)OC(=O)NS(=O)(=O)c1ccc(C(F)(F)F)cc1]

tert-Butyl 4-(trifluoromethyl)phenylsulfonylcarbamate was prepared by a method analogous to the method disclosed in Tet. Lett. 2004, 45, 8483-8487. tert-Butyl benzyl(4-(trifluoromethyl)phenylsulfonyl)carbamate (Intermediate 86, 520 mg) was hydrogenated (1 atm $H_2$) over 20 wt % Pd(OH)$_2$ (52 mg) in 1:1:1 methanol:ethanol:ethyl acetate (8 ml) for 16 hours. The reaction was filtered over celite and concentrated to yield the title compound (407 mg). MS M−H 324.3

Intermediate 89: tert-Butyl 4-(oxazol-4-yl)phenylsulfonylcarbamate

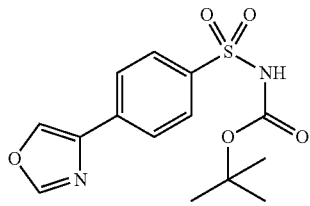 [SMILES: CC(C)(C)OC(=O)NS(=O)(=O)c1ccc(-c2cocn2)cc1]

tert-Butyl 4-(oxazol-4-yl)phenylsulfonylcarbamate can be prepared by a method analogous to the method used to prepare Intermediate 88 using Intermediate 87 as the starting material.

Intermediate 90: tert-Butyl (1S,4s)-4-((R)-1-(−4-fluorophenyl)ethylcarbamoyl)-4-hydroxycyclohexyl (4-(trifluoromethyl)phenylsulfonyl)cabamate

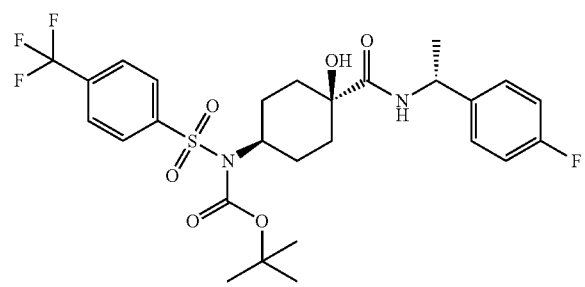 [SMILES: C[C@@H](NC(=O)[C@]1(O)CC[C@@H](N(C(=O)OC(C)(C)C)S(=O)(=O)c2ccc(C(F)(F)F)cc2)CC1)c1ccc(F)cc1]

Triphenylphosphine (79 mg) then diethyl azodicarboxylate (DEAD), 40 wt % in toluene (131 mg) were added to room slurry of tert-butyl 4-(trifluoromethyl)phenylsulfonylcarbamate (Intermediate 88, 75 mg) and 1,4-dihydroxy-cyclohexanecarboxylic acid [(R)-1-(4-fluoro-phenyl)-ethyl]-amide (Intermediate 82, 65 mg), and the reaction was stirred 16 hours. The reaction was concentrated and chromatographed with gradient elution 20-100% ethyl acetate in heptane to yield mixed fractions containing the desired product (55 mg). The crude was suspended in 2.0 mL 10% water in acetonitrile and subject to reverse-phase 25-100% AcCN in water on Phenomenx Gemini Axia C18 30×100 mm over a 12 minute run. Desired fractions were lyophilized to yield the title compound (4 mg). MS M−H 586.96

Intermediate 91: 4-(tert-Butoxycarbonylamino)-1-(phenylethylcarbamoyl)cyclo-hexyl acetate

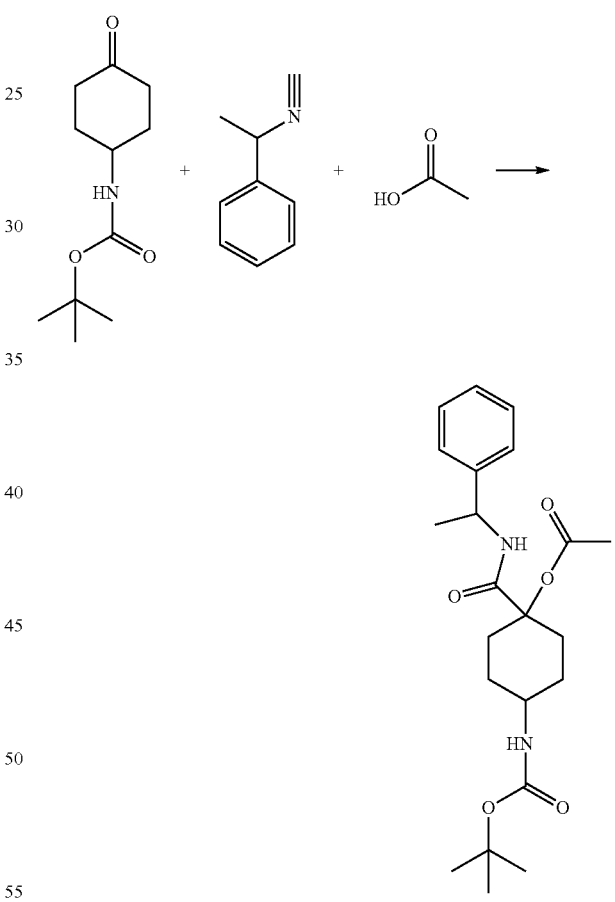

Acetic acid (0.107 ml, 1.87 mmol) then alpha-methyl benzyl isocyanide (0.248 g, 1.87 mmol) were added to a solution of (4-oxo-cyclohexyl)-carbamic acid tert-butyl ester (0.400 g, 1.87 mmol) in dichloromethane (18.7 ml) and the mixture was stirred 3 days at ambient temperature. [per Osipova, et al, Synthesis (2007) 131, compound 15j] Volatiles removed and the residue was chromatographed on normal phase Biotage using 20% ethyl acetate in heptane to yield acetic acid 4-tert-butoxycarbonylamino-1-(1-phenyl-ethylcarbamoyl)-cyclohexyl ester (390 mg) LCMS M+H=405.3.

89

Intermediate 92: 4-Amino-1-hydroxy-N-(1-phenyl-ethyl)cyclohexanecarboxamide

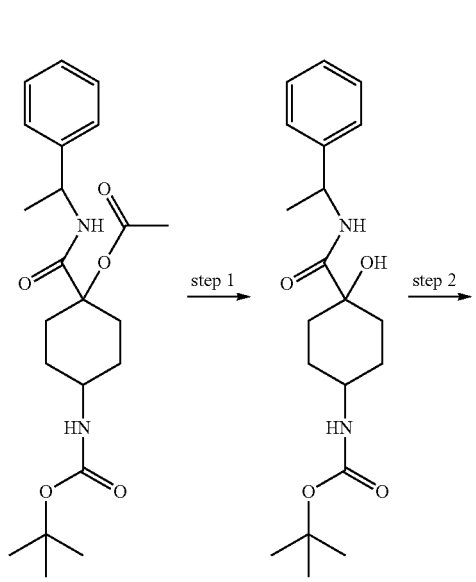

Intermediate 92

Step 1: 5N Sodium hydroxide (2.86 ml) was added to a solution of 4-(tert-Butoxycarbonylamino)-1-(phenylethylcarbamoyl)cyclo-hexyl acetate (Intermediate 91, 390 mg) in methanol (5 ml). When the reaction was judged to be complete by LCMS, it was quenched to pH 7 with 1N HCl then extracted with ethyl acetate. The organics were dried over sodium sulfate, filtered and concentrated to 328 mg of a crude solid. The major spot had an Rf=0.36 by TLC using 50% ethyl acetate in heptane. The crude product was used in the next step without further purification. LCMS M+H=363.1.

Step 2: Trifluoroacetic acid (1.5 ml) was added to a solution of crude [4-hydroxy-4-(1-phenyl-ethylcarbamoyl)-cyclohexyl]-carbamic acid tert-butyl ester (320 mg) in dichloromethane (6.0 ml). The reaction was judged to be complete by LCMS in less than 90 minutes. The reaction was diluted with dichloromethane and quenched to pH 12 using 5N sodium hydroxide. The crude product was extracted with two volumes of dichloromethane, dried over sodium sulfate, filtered and concentrated to 4-amino-1-hydroxy-cyclohexanecarboxylic acid (1-phenyl-ethyl)-amide (210 mg). LCMS M+H=263.2.

90

Intermediate 93: (R)-tert-butyl 1-(1-(4-fluorophenyl)ethylcarbamoyl)-4-oxocyclohexylcarbamate

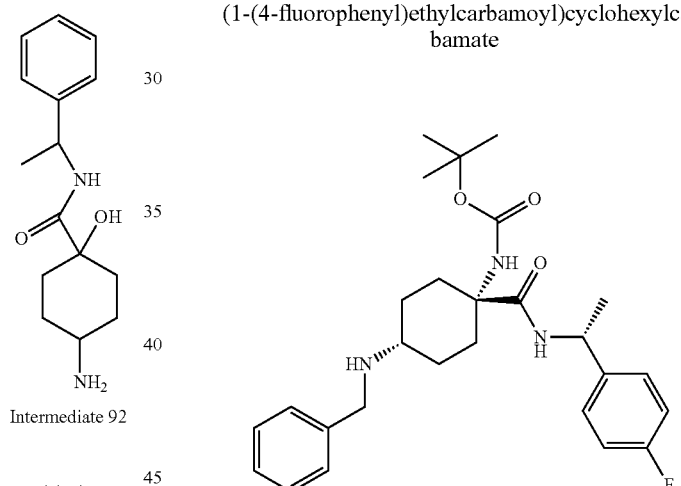

1-(tert-Butoxycarbonylamino)-4-oxocyclohexanecarboxylic acid (750 mg) was coupled with (R)-1-(4-fluorophenyl)ethanamine using the HATU procedure as described in Example 1. The crude was chromatographed with gradient elution 15-80% ethyl acetate in heptane to yield the title compound (900 mg). MS MH+ 379.3

Intermediate 94: (R)-tert-Butyl 4-(benzylamino)-1-(1-(4-fluorophenyl)ethylcarbamoyl)cyclohexylcarbamate

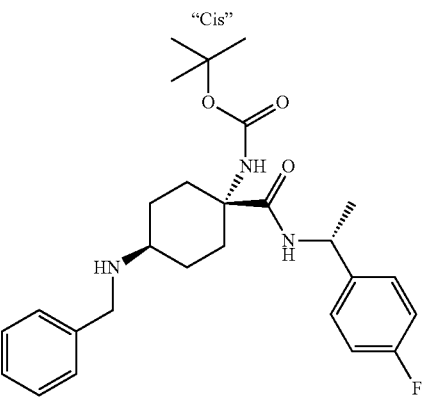

(R)-tert-butyl 1-(1-(4-fluorophenyl)ethylcarbamoyl)-4-oxocyclohexylcarbamate (Intermediate 93, 400 mg) was subjected to reductive amination using benzylamine, acetic acid, and sodium triacetoxyborohydride by know methods (J. Org.

Chem. 1996, 61, 3849). The crude product was chromatographed using a gradient elution of 0 to 8% methanol in dichloromethane containng 0.5% ammonium hydroxide as modifier. The desired fractions were concentrated to a 2:1 mixture of cis: trans isomers of (R)-tert-butyl 4-(benzylamino)-1-(1-(4-fluorophenyl)ethylcarbamoyl)cyclohexylcarbamate (395 mg).

The cis/trans isomers (390 mg) were separated by reverse-phase preparative chromatography over several injections using Phenomenex Gemini Axia C18 30×100 mm 30-100% acetonitrile in water containing 5 mM ammonium hydroxide at 40 ml/min. The first isomer ("cis") eluted at approximately 7.00 minutes and the second isomer at 7.65 minutes. The desired fractions were lyophilized to dryness and stereochemistry assigned based on NMR studies. For example, in the "cis" isomer shown below: H-15 display through space coupling to axial protons H-2/H-6 indicating it is axial. H-2/H-6 exhibit quartet line shape with large J-coupling, indicating H-1 is also axial. Yielded 92 mg "cis" isomer and 178 mg "trans" isomer. MS M+: 470.4 for both the "cis" and "trans" isomers)

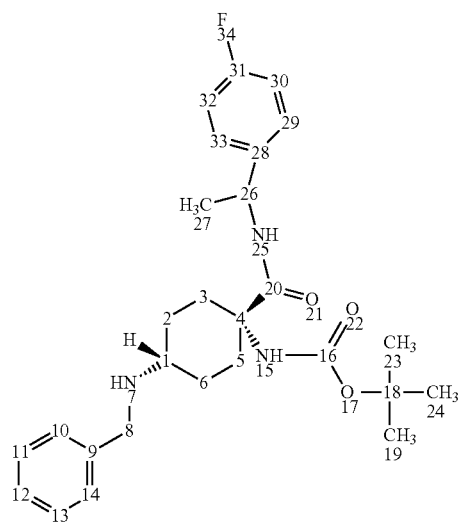

Intermediate 95: {4-Amino-1-[(R)-1-(4-fluoro-phenyl)-ethylcarbamoyl]-cyclohexyl}-carbamic acid tert-butyl ester

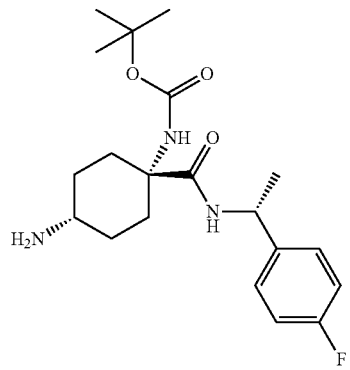 [SMILES: C[C@@H](NC(=O)[C@]1(NC(=O)OC(C)(C)C)CC[C@@H](N)CC1)c1ccc(F)cc1]

(R)-tert-butyl 4-(benzylamino)-1-(1-(4-fluorophenyl)ethylcarbamoyl)cyclohexylcarbamate (Intermediate 94, the "cis" isomer, 87 mg) was hydrogenated at 1 atm hydrogen gas using 10% Pd/C (26 mg, Degussa type E101 NE/W 50% wet) for 16 hours. The reaction was filtered over celite to yield {4-Amino-1-[(R)-1-(4-fluoro-phenyl)-ethylcarbamoyl]-cyclohexyl}-carbamic acid tert-butyl ester (70 mg). MS MH+ 380.4

Intermediate 96: tert-Butyl (1s,4s)-1-((R)-1-(4-fluorophenyl)ethylcarbamoyl)-4-(4-(trifluoromethyl)phenylsulfonamido)cyclohexylcarbamate

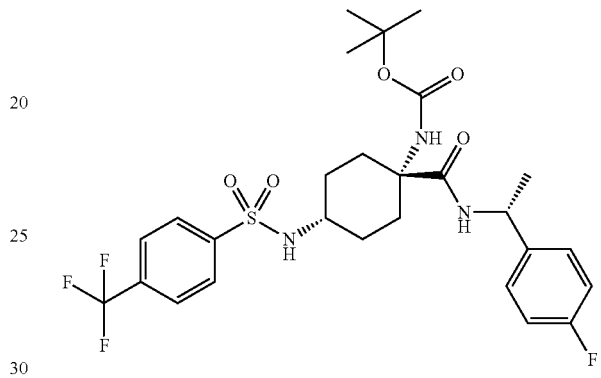

tert-Butyl (1s,4S)-1-((R)-1-(4-fluorophenyl)ethylcarbamoyl)-4-(4-(trifluoromethyl)phenylsulfonamido)cyclohexylcarbamate was prepared from Intermediate 95 and 4-trifluoromethyl benzene sulfonyl chloride using the sulfonyl chloride coupling procedure described for Intermediate 1. MS MH+ 588.3

Intermediate 97: tert-Butyl (1s,4S)-1-((R)-1-(4-fluorophenyl)ethylcarbamoyl)-4-(4-(oxazol-4-yl)phenylsulfonamido)cyclohexylcarbamate

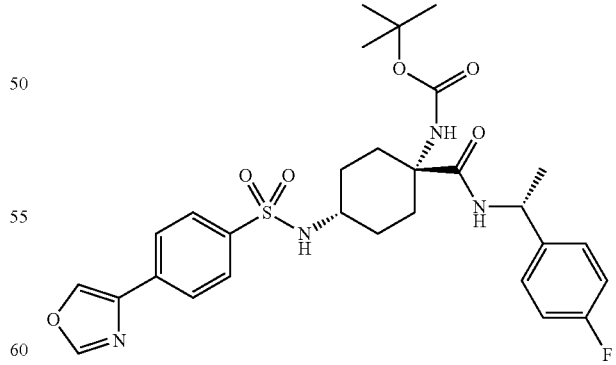

tert-Butyl (1s,4S)-1-((R)-1-(4-fluorophenyl)ethylcarbamoyl)-4-(4-(oxazol-4-yl)phenylsulfonamido)cyclohexylcarbamate was prepared using a method analogous to the method used to prepare Intermediate 96 using Intermediate 95 and Intermediate 26 as the starting materials. MS MH+ 587.4

Intermediate 98: 1-Allyl-4-(tert-butyl-dimethyl-silanyloxy)-cyclohexanecarboxylic acid ethyl ester

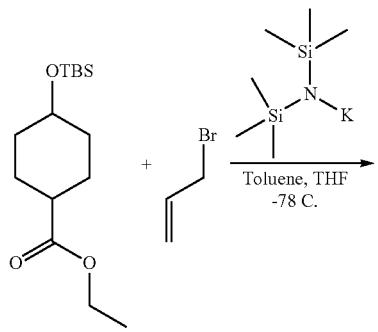

4-(tert-Butyl-dimethyl-silanyloxy)-cyclohexanecarboxylic acid ethyl ester (5.3 g, 18.50 mmol) in THF (56 ml) was cooled to −78° C. and then potassium hexamethyldisilazide (KHMDS) (74.0 ml, 37.0 mmol) (0.5M in toluene) was added slowly and reaction mixture was stirred at −78° C. for 10 min., then warmed to 0° C. for 5 mins and cooled back down to −78° C. 3-Bromo-propene (2.401 ml, 27.8 mmol) was added via syringe, and the reaction mixture was kept at −78° C. for another 10 mins before it was allowed to warm to room temperature overnight. The reaction mixture was quenched with aqueous ammonium chloride, and volatile solvents were removed under reduced pressure. The product was extracted from water with ether and concentrated. The crude oil was purified on biotage SP1, on column 65i, using gradient 5-35% EtOAc in heptane, with 25×150 tubes. Since the product as not UV active, it was detected by iodine staining. The product was a clear oil (4.88 g, 71%). LCMS [M+H]=327.2

Intermediate 99: 1-Allyl-4-hydroxy-cyclohexanecarboxylic acid ethyl ester

1-Allyl-4-hydroxy-cyclohexanecarboxylic acid ethyl ester was prepared by deprotecting Intermediate 98 using a method analogous to the method used to prepare Intermediate 67.

The intermediates in the following Table can be prepared by a method analogous to the method used to prepare Intermediate 84 using benzyl amine and the starting materials indicated.

| Intermed. | Structure | S.M. |
|---|---|---|
| 100 | 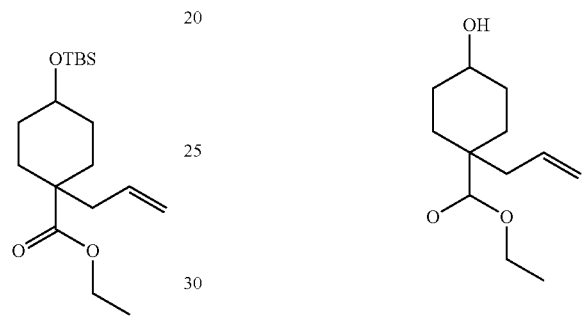 | 4-pyrazolo-benzene sulfonyl chloride |
| 101 | 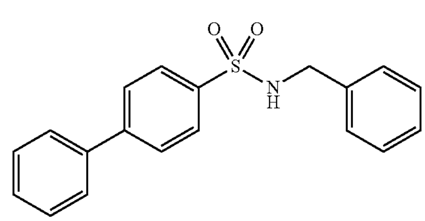 [SMILES: O=S(=O)(NCc1ccccc1)c1ccc(-c2ccccc2)cc1] | 4-phenyl-benzene sulfonyl chloride |

The intermediates in the following Table can be prepared by a method analogous to the method used to prepare Intermediate 86 using the starting materials indicated.

| Intermed. | Structure | S.M. |
|---|---|---|
| 102 | 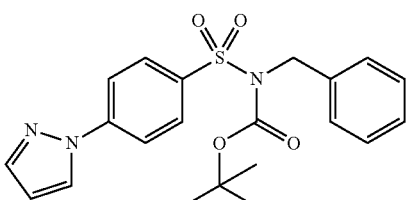 | Intermediate 100 |
| 103 | 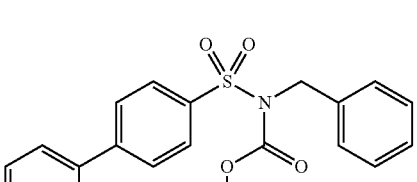 | Intermediate 101 |

The intermediates in the following Table can be prepared by a method analogous to the method used to prepare Intermediate 88 using the starting materials indicated.

| Intermed. | Structure | S.M. |
|---|---|---|
| 104 | 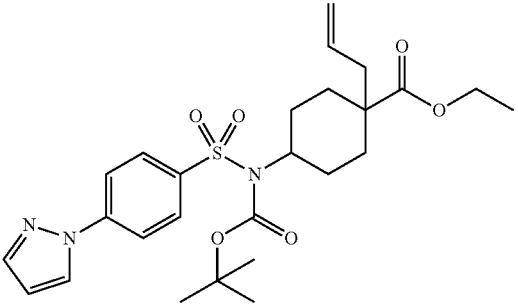 | Intermediate 102 |
| 105 | 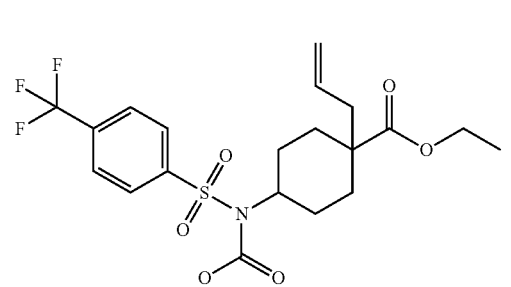 | Intermediate 103 |

The intermediates in the following Table can be prepared by a method analogous to the method used to prepare Intermediate 90 using the starting materials indicated.

| Intermed. | Structure | S.M. |
|---|---|---|
| 106 | 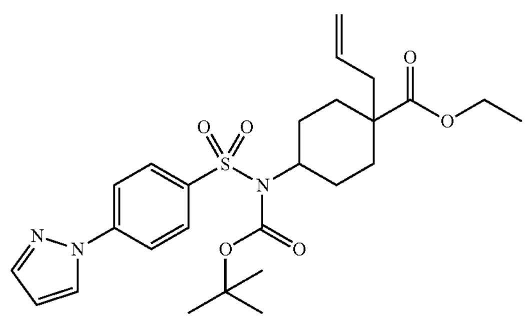 [SMILES: C=CCC1(C(=O)OCC)CCC(N(C(=O)OC(C)(C)C)S(=O)(=O)c2ccc(-n3cccn3)cc2)CC1] | Intermediate 99 and Intermediate 104 |
| 107 | 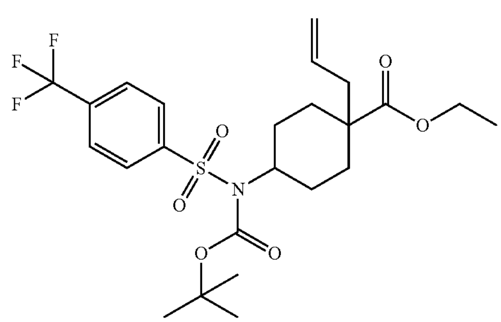 [SMILES: C=CCC1(C(=O)OCC)CCC(N(C(=O)OC(C)(C)C)S(=O)(=O)c2ccc(C(F)(F)F)cc2)CC1] | Intermediate 99 and Intermediate 88 |

Intermediate 108: Ethyl 4-(4-(1H-pyrazol-1-yl)phenylsulfonamido)-1-allycyclohexanecarboxylate

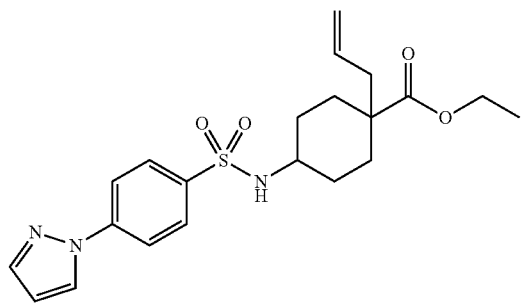 [SMILES: C=CCC1(C(=O)OCC)CCC(NS(=O)(=O)c2ccc(-n3cccn3)cc2)CC1]

Intermediate 106 was deprotected using standard TFA in dichloromethane conditions (see Example 177) to afford the title compound. LCMS [M+H]=418.0

The intermediates in the following Table was prepared by a method analogous to the method used to prepare Intermediate 108 using the starting materials indicated.

in DMF (16 ml) was added and the mixture was stirred at room temperature for 66 hr under $O_2$. LCMS shows 100% conversion to product and the reaction mixture was diluted with water and 1M HCl, then extracted with ethyl acetate (×3). The organic layers were washed with water, brine, dried (MgSO$_4$), filtered and concentrated in vacuo to give the title compound as a yellow oil (410 mg, >100%) which was taken to the next step without further purification. LCMS [M+H]= 358.3

Intermediate 112: Ethyl 4-amino-1-(2-oxopropyl)cyclohexanecarboxylate

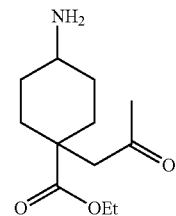

Intermediate 112 can be prepared from Intermediate 111 using a method analogous to the method used to prepare Intermediate 77.

| Intermed. | Structure | S.M. | MS |
|---|---|---|---|
| 109 | (4-trifluoromethylphenyl sulfonamide allyl cyclohexanecarboxylate) | Intermediate 99 and Intermediate 88 | M − H = 418.0 |
| 110 | (4-(oxazol-4-yl)phenyl sulfonamide allyl cyclohexanecarboxylate) | Intermediate 99 and Intermediate 89 | M + H = 419.2 |

Intermediate 111: Ethyl 4-(1,3-dioxoisoindolin-2-yl)-1-(2-oxopropyl)cyclo-hexanecarboxylate

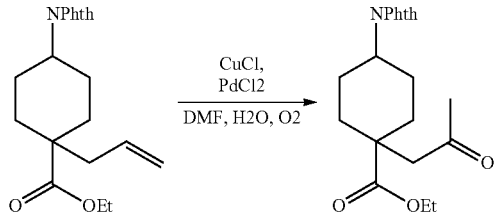

A mixture of CuCl (147 mg, 1.484 mmol) and PdCl$_2$ (46.1 mg, 0.26 mmol) in DMF (24 ml) and water (4 ml) was stirred under an oxygen (balloon) for 3 hours. A solution of 1-Allyl-4-(1,3-dioxo-1,3-dihydro-isoindol-2-yl)-cyclohexanecarboxylic acid ethyl ester (Intermediate 73, 362 mg, 1.06 mmol)

Intermediate 113: Ethyl 4-(4-(oxazol-4-yl)phenylsulfonamido)-1-(2-oxopropyl)cyclohexanecarboxylate

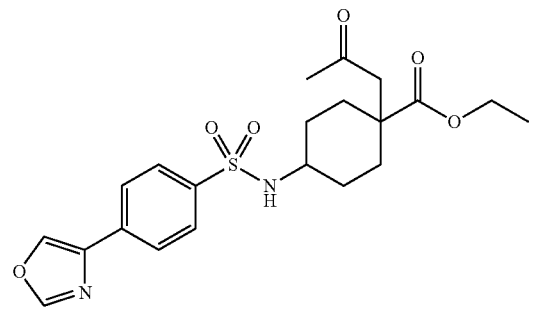 [SMILES: CCOC(=O)C1(CC(C)=O)CCC(NS(=O)(=O)c2ccc(-c3cocn3)cc2)CC1]

Intermediate 113 can be prepared by a method analogous to the method used to prepare Intermediate 1 using Intermediate 112 and Intermediate 26 as the starting materials.

Intermediate 114: 1-(2-oxo-ethyl)-4-(4-pyrazol-1-yl-benzenesulfonylamino)-cyclohexanecarboxylic acid ethyl ester

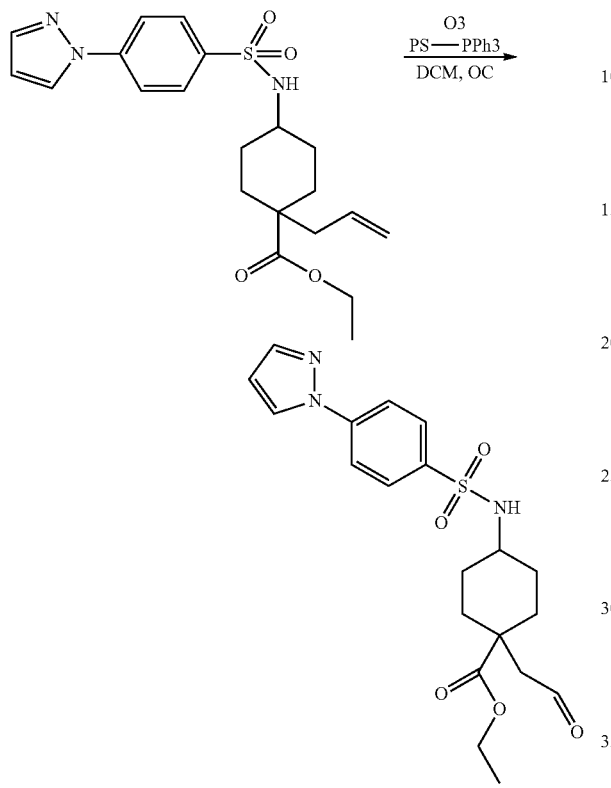

$O_3$ was passed through a solution of ethyl 4-(4-(1H-pyrazol-1-yl)phenylsulfonamido)-1-allylcyclohexanecarboxylate (Intermediate 108, 285 mg, 0.683 mmol) in DCM (5.988 ml) at −78° C. until a blue colour appeared. The solution was kept at −78° C. and $O_2$ gas was passed through until the colour faded to colourless (about 20 min.) The reaction mixture was left to warm for 15 mins. and TLC (20% EtOAc in Heptane, Iodine stain) indicated that the reaction was complete. The ozonide was then quenched/reduced by adding polystyrene triphenyl phosphine (PS-PPh$_3$, 4982 mg, 6.83 mmol) and the reaction mixture was left to shake overnight, then filtered through a fritt and beads washed with DCM. The DCM filtrate and wash was collected and concentrated in vacuo to yield the title compound as a white solid (286 mg, 100%). LCMS [M+H]=420.1

Intermediate 115: 1-(2-oxo-ethyl)-4-(4-trifluoromethyl-benzenesulfonylamino)-cyclohexanecarboxylic acid ethyl ester

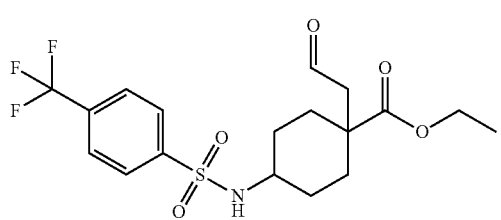 [SMILES: CCOC(=O)C1(CC=O)CCC(NS(=O)(=O)c2ccc(C(F)(F)F)cc2)CC1]

1-(2-oxo-ethyl)-4-(4-trifluoromethyl-benzenesulfonylamino)-cyclohexanecarboxylic acid ethyl ester was prepared by a method analogous to the method used to prepare Intermediate 114 using Intermediate 109 as the starting material. LCMS [M−H]=420.0

Intermediate 116: 4-(1,3-Dioxo-1,3-dihydro-isoindol-2-yl)-1-((E)-propenyl)-cyclohexanecarboxylic acid ethyl ester

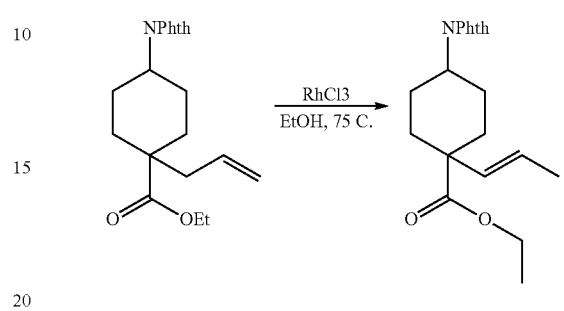

1-Allyl-4-(1,3-dioxo-1,3-dihydro-isoindol-2-yl)-cyclohexanecarboxylic acid ethyl ester (Intermediate 73, 975 mg, 2.86 mmol) was dissolved in ethanol (13.900 mL) in a round-bottom flask with reflux condensor. The flask was charged with rhodium(III) chloride (32.5 mg, 0.143 mmol), and the reaction mixture was heated to 75° C. and stirred for 18 hr, then filtered and concentrated in vacuo to yield the title compound as a brown oil (965 mg, 99%) which was taken to the next step without further purification.

Intermediate 117: (E)-Ethyl 4-amino-1-(prop-1-enyl)cyclohexane carboxylate

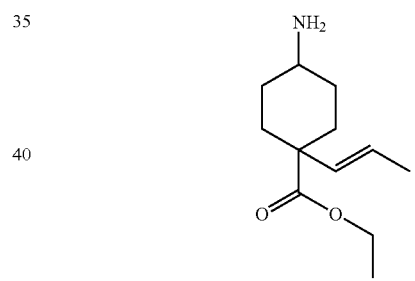

Intermediate 117 was prepared from Intermediate 116 using standard phthalamide deprotection conditions analogous to the conditions used to prepare Intermediate 77.

Intermediate 118: 1-((E)-Propenyl)-4-(4-trifluoromethyl-benzenesulfonylamino)-cyclohexanecarboxylic acid ethyl ester

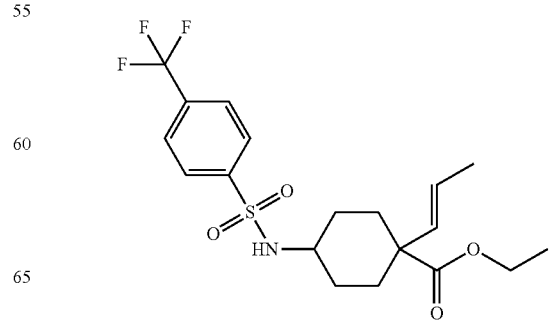

Intermediate 118 was prepared by a method analogous to the method used to prepare Intermediate 1 using Intermediate 117 and 4-trifluoromethyl benzene sulfonyl chloride as the starting materials. LCMS [M+H]=420.2

Intermediate 119: 1-((E)-Propenyl)-4-(4-pyrazin-1-yl-benzenesulfonylamino)-cyclohexanecarboxylic acid ethyl ester

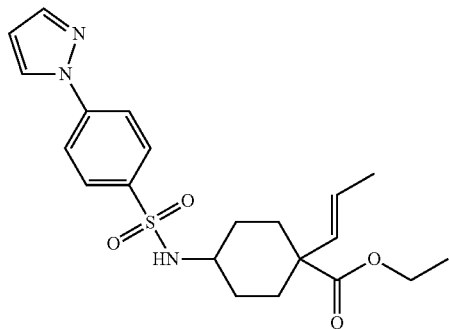 [SMILES: C/C=C/C1(C(=O)OCC)CCC(NS(=O)(=O)c2ccc(-n3cccn3)cc2)CC1]

1-((E)-Propenyl)-4-(4-pyrazin-1-yl-benzenesulfonylamino)-cyclohexanecarboxylic acid ethyl ester was prepared by a method analogous to the method used to prepare Intermediate 118 using Intermediate 117 and 4-pyrazol-1-yl-benzene sulfonyl chloride as the starting materials. LCMS [M−H]=418.3

Intermediate 120: 1-Formyl-4-(4-trifluoromethyl-benzenesulfonylamino)-cyclohexanecarboxylic acid ethyl ester

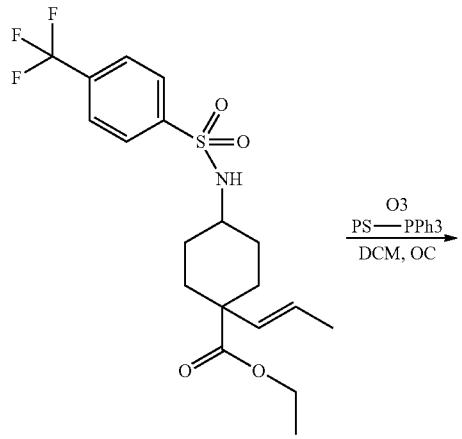

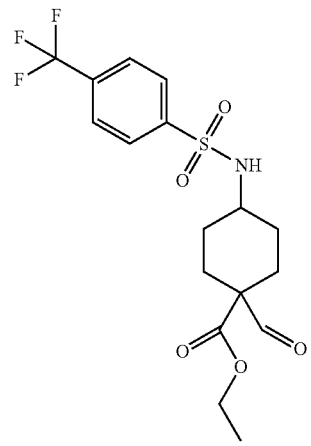

O₃ was passed through a solution of 1-((E)-Propenyl)-4-(4-trifluoromethyl-benzenesulfonylamino)-cyclohexanecarboxylic acid ethyl ester (Intermediate 118, 965 mg, 2.83 mmol) in DCM (30 ml) at −78° C. for 12 min. The solution was kept at −78° C. and O₂ gas was passed through it for 10 min. The reaction was monitored by LCMS. When no starting material was present, the reaction mixture was left to warm for 15 mins. The ozonide was then quenched/reduced by adding PS-PPh₃ (loading=2.34 mmol/g) (6040 mg, 14.13 mmol) and the solution was left to shake overnight. The reaction was filtered through a fritt and beads and washed with DCM. The DCM filtrate and wash were concentrated in vacuo to yield the title compound as a tan solid (850 mg, 91%). LCMS [M−H]=406.2

Intermediate 121: 1-Formyl-4-(4-pyrazol-1-yl-benzenesulfonylamino)-cyclohexanecarboxylic acid ethyl ester

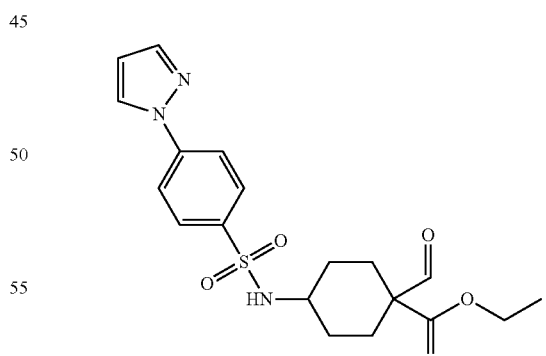

1-Formyl-4-(4-pyrazol-1-yl-benzenesulfonylamino)-cyclohexanecarboxylic acid ethyl ester was prepared by a method analogous to the method used to prepare Intermediate 120 using Intermediate 119 as the starting material. LCMS [M−H]=404.2

Intermediate 122: 4-Ethoxy-3-methyl-N-(4-oxocyclohexyl)benzenesulfonamide

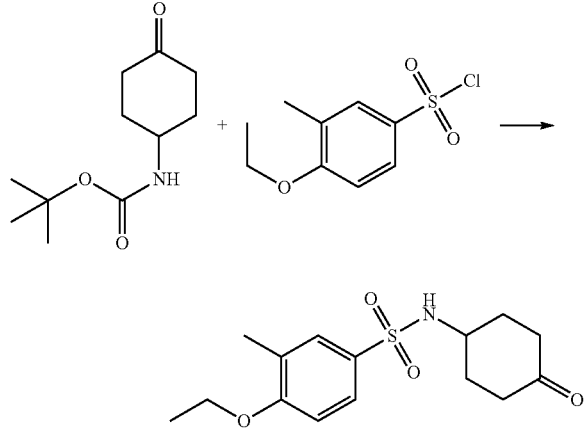

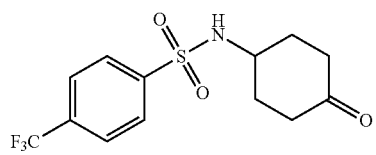 [SMILES: O=C1CCC(NS(=O)(=O)c2ccc(C(F)(F)F)cc2)CC1]

Trifluoroacetic acid (13.13 ml, 170 mmol) was added via addition funnel to solution of tert-butyl 4-oxocyclohexylcarbamate (1.817 g, 8.52 mmol) in DCM (34.1 ml) at room temperature. The reaction was stirred 3.5 hours then concentrated and the residue was placed under vacuum for 30 minutes. The residue was suspended in DCM (34.1 ml) and cooled in ice/water bath. N-methylmorpholine (20.61 ml, 187 mmol) was added followed by solid 4-ethoxy-3-methylbenzenesulfonyl chloride (2.0 g, 8.52 mmol) and the ice/water bath was removed. After stirring for 70 hours, LCMS indicated some product mass. The reaction was placed in water bath and pH adjust to 3 using 3N hydrochloric acid (aq). The resulting layers were separated, and the aqueous extracted second time with dichloromethane. The combined organics were dried over sodium sulfate to yield 2.9 g of a crude oil. TLC (50% ethyl acetate in heptane): indicated a major product at Rf=0.40, with minor spots at Rf=0.58 and Rf=0.12. The crude was chromatograph on Biotage 40M by TLC generated gradient to yield 4-ethoxy-3-methyl-N-(4-oxocyclohexyl) benzenesulfonamide (650 mg, 2.087 mmol). LCMS [M+H]= 312.3.

Intermediate 123: 4-(Trifluoromethyl)-N-(4-oxocyclohexyl)benzenesulfonamide

Intermediate 123 was prepared by a method analogous to the method of preparing Intermediate 122 using 4-trifluoromethyl benzenesulfonyl chloride instead of 4-ethoxy-3-methylbenzenesulfonyl chloride.

Intermediate 124: N-(4-Amino-4-cyanocyclohexyl)-4-ethoxy-3-methylbenzenesulfonamide

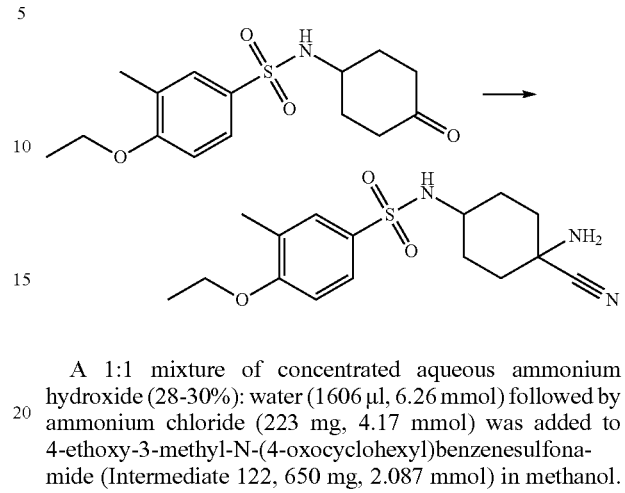

A 1:1 mixture of concentrated aqueous ammonium hydroxide (28-30%): water (1606 µl, 6.26 mmol) followed by ammonium chloride (223 mg, 4.17 mmol) was added to 4-ethoxy-3-methyl-N-(4-oxocyclohexyl)benzenesulfonamide (Intermediate 122, 650 mg, 2.087 mmol) in methanol. The reaction was stirred for a few minutes then potassium cyanide (272 mg, 4.17 mmol) was added in one portion. After 18 hours the reaction was diluted with dichloromethane and 5N sodium hydroxide followed by water was added to make the aqueous layer pH 12. The aqueous layer was extracted fives times with dichloromethane. TLC (50% ethyl acetate in heptane) suggested a small amount starting material was present, but a major UV spot was just off baseline. Combined organic layers were dried over sodium sulfate, filtered, and concentrated, to yield crude N-(4-amino-4-cyanocyclohexyl)-4-ethoxy-3-methylbenzenesulfonamide (770 mg, 2.282 mmol) which was used without further purification. LCMS [M+H]=338.3.

Intermediate 125: N-(4-Amino-4-cyanocyclohexyl)-4-trifluoromethyl benzenesulfonamide

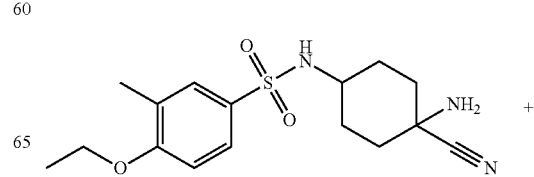

Intermediate 125 was prepared by a method analogous to the method of preparing Intermediate 124 using 4-(trifluoromethyl)-N-(4-oxocyclohexyl)benzenesulfonamide (Intermediate 123) as the starting material.

Intermediate 126: N-(1-Cyano-4-(4-ethoxy-3-methylphenylsulfonamido)-cyclohexyl)acetamide -continued

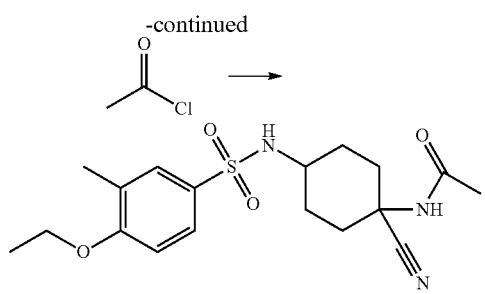

Acetyl chloride (0.106 g, 1.356 mmol) in dichloromethane (1 ml) was added to room temperature solution of N-(4-amino-4-cyanocyclohexyl)-4-ethoxy-3-methylbenzenesulfonamide (Intermediate 124, 0.366 g, 1.085 mmol) in dichloromethane (9 ml) and the reaction was stirred 18 hours. The reaction was diluted with dichloromethane and rinsed with two volumes of saturated sodium bicarbonate. The organics were dried over magnesium sulfate, filtered, and concentrated to yield 464 mg of a crude film. TLC (50% ethyl acetate in heptane) indicated a major spot Rf=0.07 by UV. The crude product was chromatographed on Biotage 25S by TLC generated gradient to yield N-(1-cyano-4-(4-ethoxy-3-methylphenylsulfonamido)cyclohexyl)-acetamide (320 mg, 0.843 mmol) as a colorless solid. Carbon-13 NMR displayed a characteristic signature for nitrile at 119.1 ppm along with a signal at 110.7 ppm for the aromatic carbon ortho to aryl ether; in addition the peaks at 169.7 ppm and 160.97 ppm represent the amide and ipso-carbon of the aryl ether (no assignment implied). LCMS [M+H]=380.2.

Intermediate 127: N-(1-Cyano-4-(4-trifluormethylphenylsulfonamido)-cyclohexyl)acetamide

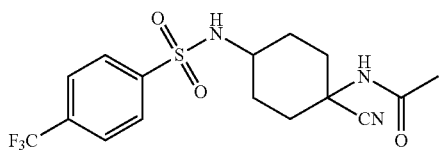 [SMILES: CC(=O)NC1(C#N)CCC(NS(=O)(=O)c2ccc(C(F)(F)F)cc2)CC1]

Intermediate 127 was prepared by a method analogous to the method of preparing Intermediate 126 using N-(4-amino-4-cyanocyclohexyl)-4-trifluoromethyl benzenesulfonamide (Intermediate 125) as the starting material.

Intermediate 128: N-(1-Cyano-4-(4-ethoxy-3-methylphenylsulfonamido)-cyclohexyl)formamide

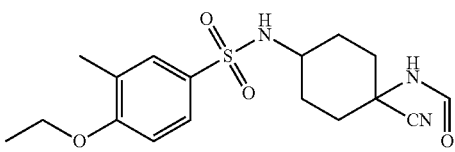 [SMILES: CCOc1ccc(S(=O)(=O)NC2CCC(C#N)(NC=O)CC2)cc1C]

Intermediate 128 was prepared from Intermediate 124 by a method analogous to the method of preparing Intermediate 126 using formyl chloride instead of acetyl chloride as the starting material.

The Intermediates in the table below were prepared by a method analogous to the method used to prepare Intermediate 1 using Intermediate 69 and the starting materials indicated.

| Intermed. | Structure | S.M. |
| --- | --- | --- |
| 129 | 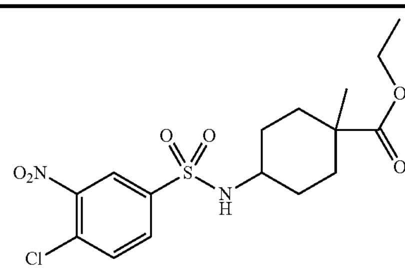 | 4-chloro-3-nitro-benzene sulfonyl chloride |
| 130 | 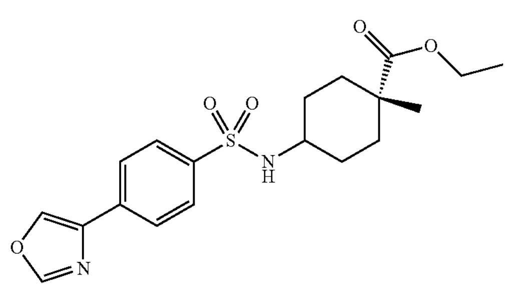 | Intermediate 26 |

The Intermediates in the table below can be prepared by a method analogous to the method used to prepare Intermediate 1 using Intermediate 69 and the starting materials indicated.

| Intermed. | Structure | S.M. |
|---|---|---|
| 131 | 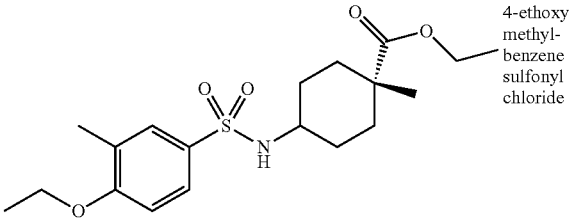 | 4-ethoxy-3-methyl-benzene sulfonyl chloride |
| 132 | 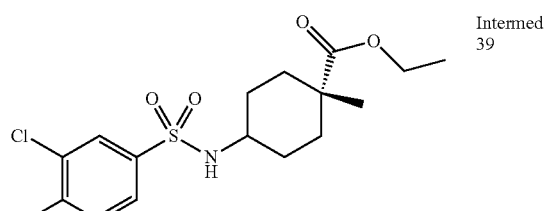 | Intermediate 39 |
| 133 | 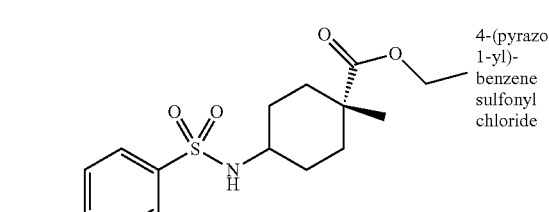 | 4-(pyrazol-1-yl)-benzene sulfonyl chloride |

The Intermediates in the table below were prepared by a method analogous to the method used to prepare Intermediate 58 using the starting materials indicated.

| Intermed. | Structure | S.M. | MS |
|---|---|---|---|
| 134 | 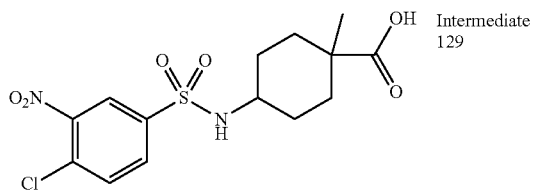 | Intermediate 129 | |
| 135 | 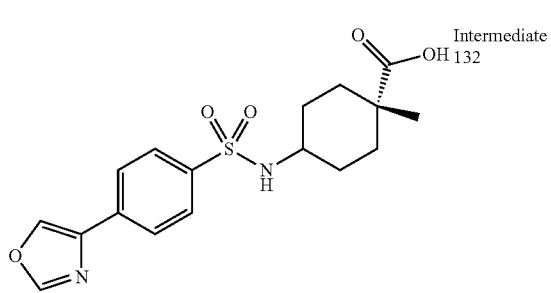 | Intermediate 132 | |

-continued
| Intermed. | Structure | S.M. | MS |
|---|---|---|---|
| 136 | (structure) | Intermediate 118 | [M + H] = 392.2 |
| 137 | (structure) | Intermediate 130 | |
| 138 | (structure) | Intermediate 131 | |
| 139 | (structure) | Intermediate 133 | |
Intermediate 140: (1r,4r)-4-(4-(trifluoromethyl)phe-nylsulfonamido)cyclo-hexanecarboxamide
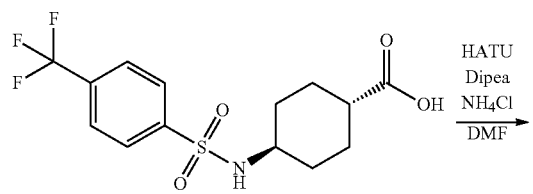
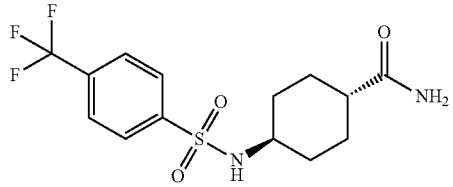
4-(4-Trifluoromethyl-benzenesulfonylamino)-cyclohex-anecarboxylic acid amide was prepared according to the method in Example 1. MS MH+ 351.2

Intermediate 141: N-((1r,4r)-4-Cyanocyclohexyl)-4-(trifluoromethyl)benzene-sulfonamide

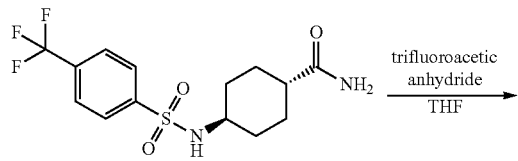

To 4-(4-Trifluoromethyl-benzenesulfonylamino)-cyclohexanecarboxylic acid (Intermediate 140, 80 mg, 0.228 mmol) in 1 mL THF was added trifluoroacetic anhydride (0.097 ml, 0.685 mmol) and the reaction was stirred at room temperature for 30 min. Water was added and the mixture was extracted with ether. The organic layer was dried over sodium sulfate, filtered and concentrated to afford 76 mg (100%) N-(4-Cyano-cyclohexyl)-4-trifluoromethyl-benzenesulfonamide MS MH– 331.2

Intermediate 142: (1s,4s)-1-Cyano-4-(4-(trifluoromethyl)phenylsulfonamido)cyclo-hexanecarboxylic acid

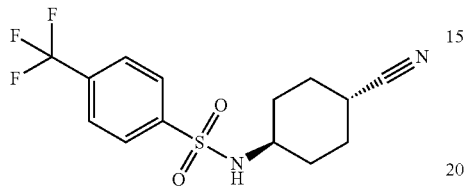

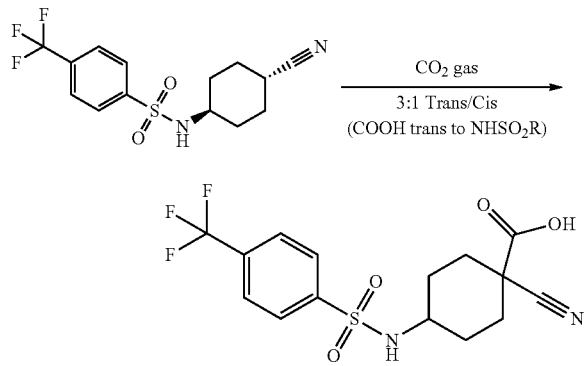

To diisopropylamine (71.7 µl, 0.503 mmol) in 1 mL THF under $N_2$ at −78° C. was added n-butyllithium (1.6M THF) (314 µl, 0.503 mmol). The mixture was stirred at −78° C. for 30 min. A solution of N-(4-cyano-cyclohexyl)-4-trifluoromethyl-benzenesulfonamide (Intermediate 141, 76 mg, 0.229 mmol) in 1 mL THF was added to the mixture at −78° C. and allowed to warm to 0° C., then stirred for 30 min at 0° C. The mixture was cooled to −78° C. and $CO_2$ gas was bubbled at −78° C. for 30 min (needle outgas from septa).

LCMS was consistent with 1:1 ratio of starting material to target products in a 3:1 ratio. The solvent was removed under vacuum and 5 mL ether was added followed by 10 mL 1N HCl. The mixture was extracted with EtOAc and washed with brine. The organic layers were dried over sodium sulfate, filtered and concentrated on vacuum, the taken up in 2 mL acetonitrile with 0.5 mL water and filtered with 0.45µ PTFE filter and purified by HPLC on a C8 column eluting with 5-100% ACN/$H_2O$ (0.1% $NH_4OH$) to yield 2 isomers (30 mg of the first eluting peak and 4 mg the second eluting peak) of 1-Cyano-4-(4-trifluoromethyl-benzenesulfonylamino)-cyclohexanecarboxylic acid MS MH– 374.9

Intermediate 143: Methyl 4-(4-(trifluoromethyl)phenylsulfonamido)bicyclo[2.2.2]octane-1-carboxylate

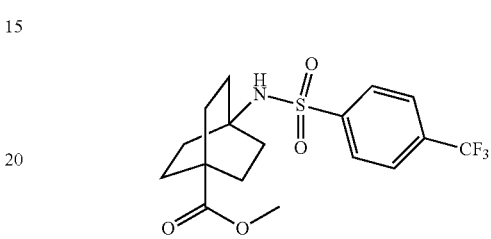

Methyl 4-(4-(trifluoromethyl)phenylsulfonamido)bicyclo[2.2.2]octane-1-carboxylate was prepared from 4-aminobicyclo[2.2.2]octane-1-carboxylic acid methyl ester and 4-trifluoromethylbenzene sulfonamide using a method analogous to the method used to prepare Intermediate 1.

Intermediate 144: 4-(4-(Trifluoromethyl)phenylsulfonamido)bicyclo[2.2.2]octane-1-carboxylic acid

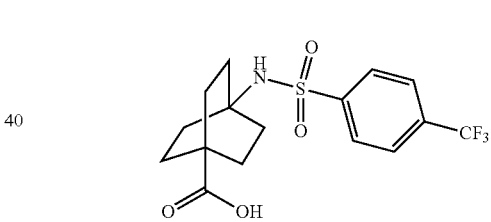

Intermediate 144 was prepared using the method described for the preparation of intermediate 15 using Intermediate 143 as the starting material.

Intermediate 145: Methyl 4-(4-(trifluoromethyl)phenylsulfonamido)-adamantane-1-carboxylate

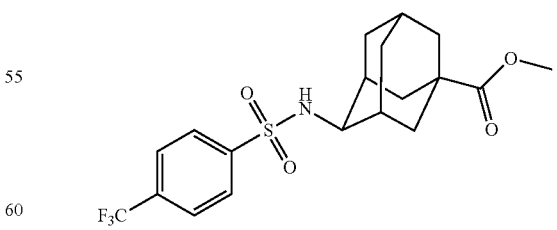

Methyl 4-(4-(trifluoromethyl)phenylsulfonamido)-adamantane-1-carboxylate was prepared from 4-amino-adamantane-1-carboxylic acid methyl ester and 4-trifluoromethylbenzene sulfonamide using a method analogous to the method used to prepare Intermediate 1.

Intermediate 146: 4-(4-(Trifluoromethyl)phenylsulfonamido)-adamantane-1-carboxylic acid

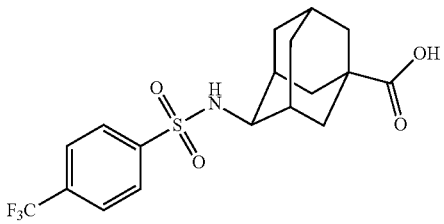 [SMILES: O=C(O)C12CC3CC(C1)C(NS(=O)(=O)c1ccc(C(F)(F)F)cc1)C(C3)C2]

Intermediate 146 was prepared using the method described for the preparation of Intermediate 15 using Intermediate 145 as the starting material.

EXAMPLES

Particular compounds of the invention can be prepared via an amide coupling reaction by coupling a trans-4-(phenylsulfonamido)cyclohexane-carboxylic acid or trans-4-(pyridinylsulfonamido)cyclohexane-carboxylic acid with a primary or secondary amine, as shown in Example 1.

Alternatively, particular compounds of the invention can be prepared by coupling trans-4-amino-cyclohexanecarboxamide with a benzene sulfonyl chloride or pyridinyl sulfonyl chloride, as shown in Example 2 (Method A) or Example 2 (Method B).

Example 1

(1r,4S)—N—((S)-2-Hydroxy-2-methyl-1-phenylpropyl)-4-(4-(trifluoromethyl)phenylsulfonamido)cyclohexanecarboxamide

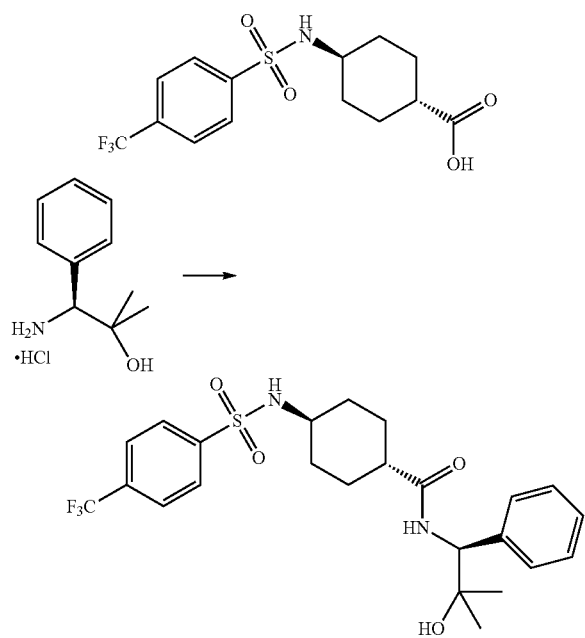

(1r,4r)-4-(4-(Trifluoromethyl)phenylsulfonamido)-cyclohexancarboxylic acid (Intermediate 58, 4 g, 11.38 mmol), the hydrochloride salt of (S)-1-amino-2-methyl-1-phenylpropan-2-ol (Intermediate 49, 2.342 g, 11.61 mmol) and DIPEA (3.24 g, 4.37 ml, 25.05 mmol) were dissolved in DMF (20 ml) and cooled to 0° C. HATU (5.19 g, 13.66 mmol) was then added as a solid and the reaction mixture was allowed to warm to room temperature for over 3 hours. The reaction mixture was then slowly poured into 0.5M HCl (250 ml) and extracted twice with EtOAc. Combined organics were washed with water and brine, then dried over MgSO$_4$. Resulting material was purified via flash column chromatography eluting with acetone/heptane. Relevant fractions were pooled and concentrated to afford a white solid (3.5 g-61% yield).

$^1$H NMR (400 MHz, DMSO-d$_6$) δ ppm 0.95 (s, 3H) 1.04 (s, 3H) 1.10-1.32 (m, 4H) 1.34 (br. s., 1H) 1.53 (d, J=12.38 Hz, 1H) 1.71 (d, J=6.06 Hz, 1H) 1.66 (d, J=16.67 Hz, 2H) 2.18 (t, J=11.49 Hz, 1H) 2.96 (dd, J=11.12, 3.79 Hz, 1H) 4.43 (br. s., 1H) 4.66 (d, J=9.60 Hz, 1H) 7.15-7.31 (m, 5H) 7.88-8.04 (m, 6H)

M+H=499.3

Example 2

Trans-4-(4-Hydroxy-3-methoxy-benzenesulfonylamino)-cyclohexanecarboxylic acid [(R)-1-(4-fluoro-phenyl)-ethyl]-amide Method A:

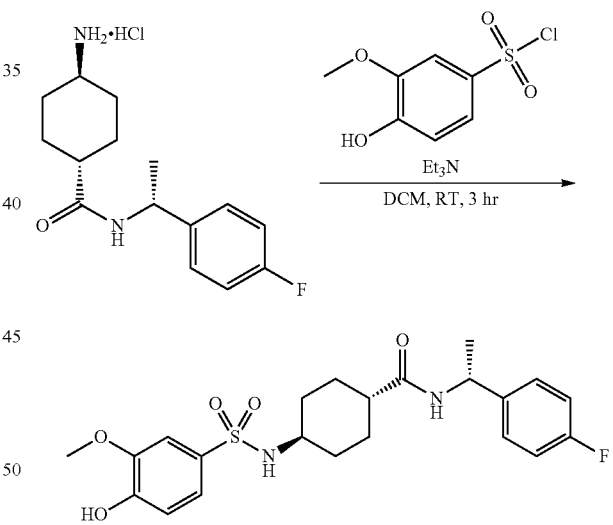

Trans-4-Amino-N—((R)-1-(4-fluorophenyl)ethyl)cyclohexanecarboxamide hydrochloride (Intermediate 45, 200 mg, 0.66 mmol) and Et$_3$N (371 ul, 2.66 mmol) were dissolved in DCM (10 ml). 4-Hydroxy-3-methoxy-benzenesulphonyl chloride (178 mg, 0.798 mmol) was added, and the reaction mixture was stirred for 3 hr at room temperature, after which LCMS indicated that the reaction was complete. The mixture was concentrated in vacuo, and the crude material was purified via reverse phase chromatography on prep-HPLC (150 mm, C8 luna, 15-20 min run, 10%-100% MeCN in water containing 0.1% TFA). Fractions containing the product were lyophilized to yield the title compound as a white solid (14 mg, 0.031 mmol). MS MH$^+$ 451.1

Example 2

Trans-4-(4-Hydroxy-3-methoxy-benzenesulfonylamino)-cyclohexanecarboxylic acid [(R)-1-(4-fluoro-phenyl)-ethyl]-amide Method B:

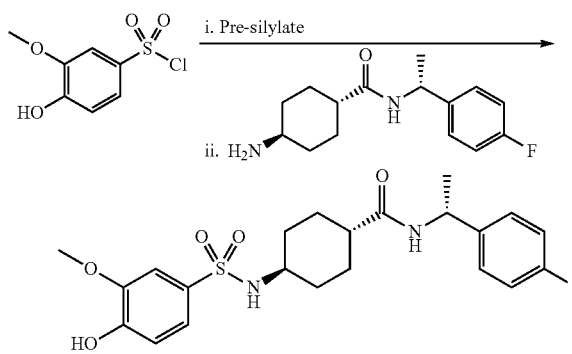

N,N'-Bis-trimethylsilylurea (209 mg, 1.02 mmol) was added to solution of 4-hydroxy-3-methxoybenzenesulfonyl chloride (445 mg, 2.0 mmol) in dichloromethane (6 ml). The reaction was stirred 30 minutes at room temperature, then diluted with dichloromethane (6 ml) and filtered. To the filtrate was added N,N-diisopropylethylamine followed by trans-4-amino-cyclohexanecarboxylic acid [(R)-1-(4-fluoro-phenyl)-ethyl]-amide (Intermediate 45, 529 mg, 2.0 mmol). The reaction was allowed to stir at room temperature overnight, then saturated sodium bicarbonate solution was added and the mixture was stirred for 10 minutes. The reaction was diluted with additional dichloromethane and the layers were separated. The organic layer was dried over MgSO$_4$, filter and concentrated to yield a crude residue. The crude was chromatographed on a Biotage 40S column using a stepwise gradient (0%, 1.5%, 3%) to yield the title compound. MS MH$^+$ 451.1

The compounds in the Table below were prepared by a method analogous to the method described in Example 1, Example 2 (method A) or Example 2 (method B) as indicated in the Table below using the appropriate starting materials. In the tables below, mass ions are given in the protonated form (MH$^+$) unless otherwise noted.

| Example | Structure | Method of | MS |
|---|---|---|---|
| 3 | 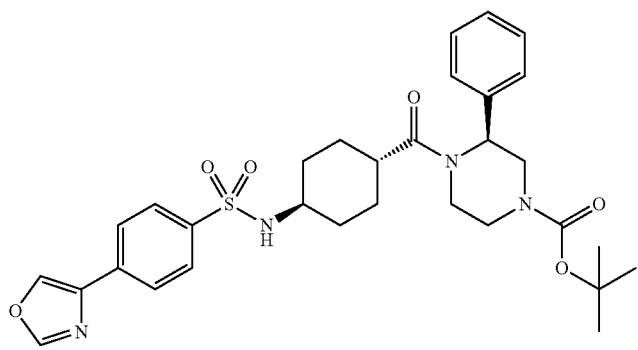 [SMILES: CC(C)(C)OC(=O)N1CCN(C(=O)[C@H]2CC[C@H](NS(=O)(=O)c3ccc(-c4cocn4)cc3)CC2)[C@@H](c2ccccc2)C1] | Example 1 | 595.3 |
| 4 | 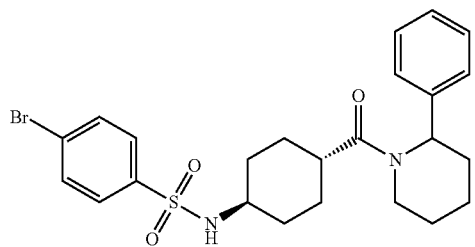 [SMILES: O=C([C@H]1CC[C@H](NS(=O)(=O)c2ccc(Br)cc2)CC1)N1CCCCC1c1ccccc1] | Example 1 | 507.0 |
| 5 | 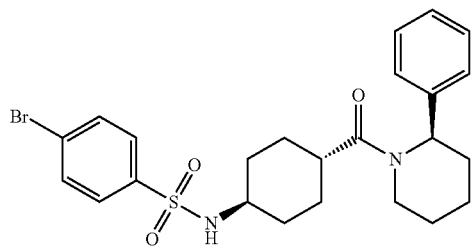 [SMILES: O=C([C@H]1CC[C@H](NS(=O)(=O)c2ccc(Br)cc2)CC1)N1CCCC[C@@H]1c1ccccc1] | Example 1 | 507.0 |

-continued
| Example | Structure | Method of | MS |
|---|---|---|---|
| 6 | 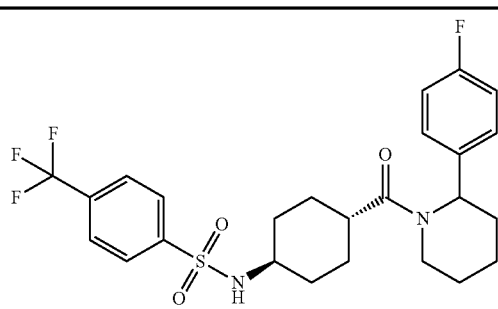 | Example 1 | 513.0 |
| 7 | 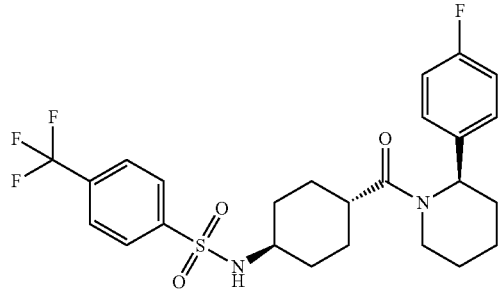 [SMILES: O=C([C@H]1CC[C@H](NS(=O)(=O)c2ccc(C(F)(F)F)cc2)CC1)N1CCCC[C@@H]1c1ccc(F)cc1] | Example 1 | 513.0 |
| 8 | 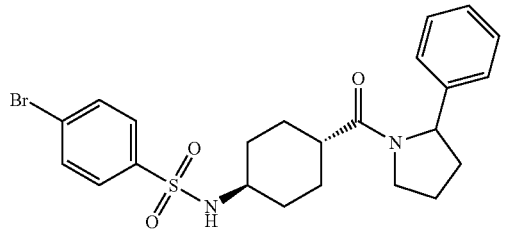 [SMILES: O=C([C@H]1CC[C@H](NS(=O)(=O)c2ccc(Br)cc2)CC1)N1CCCC1c1ccccc1] | Example 1 | 493.0 |
| 9 | 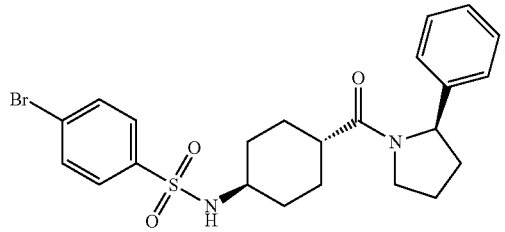 [SMILES: O=C([C@H]1CC[C@H](NS(=O)(=O)c2ccc(Br)cc2)CC1)N1CCC[C@@H]1c1ccccc1] | Example 1 | 493.0 |
| 10 | 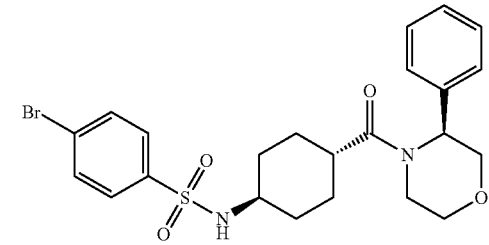 | Example 1 | 509.0 |
| 11 | 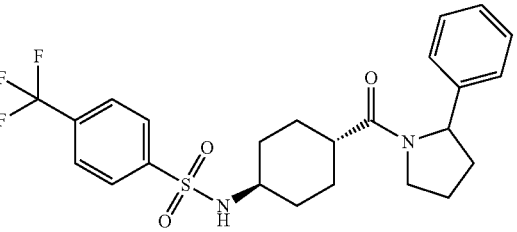 | Example 1 | 481.0 |

-continued

| Example | Structure | Method of | MS |
|---------|-----------|-----------|------|
| 12 | 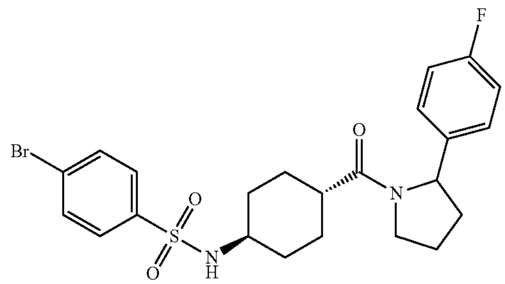 [SMILES: O=C([C@H]1CC[C@H](NS(=O)(=O)c2ccc(Br)cc2)CC1)N1CCCC1c1ccc(F)cc1] | Example 1 | 511.0 |
| 13 | 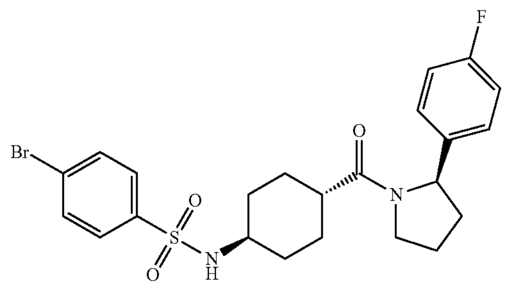 [SMILES: O=C([C@H]1CC[C@H](NS(=O)(=O)c2ccc(Br)cc2)CC1)N1CCC[C@@H]1c1ccc(F)cc1] | Example 1 | 511.0 |
| 14 | 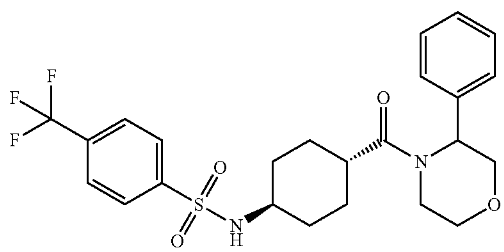 | Example 1 | 497.0 |
| 15 | 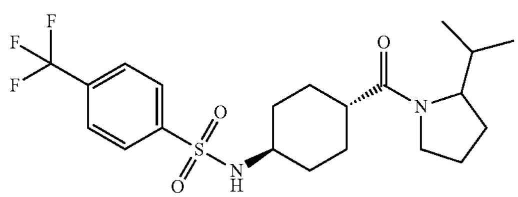 [SMILES: CC(C)C1CCCN1C(=O)[C@H]1CC[C@H](NS(=O)(=O)c2ccc(C(F)(F)F)cc2)CC1] | Example 1 | 447.0 |
| 16 | 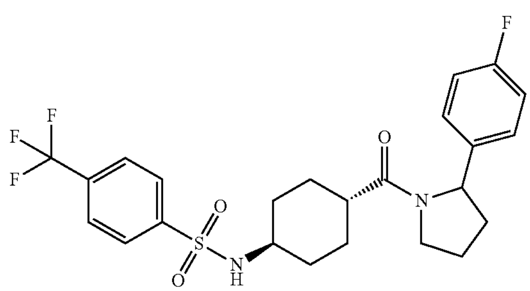 [SMILES: O=C([C@H]1CC[C@H](NS(=O)(=O)c2ccc(C(F)(F)F)cc2)CC1)N1CCCC1c1ccc(F)cc1] | Example 1 | 499.0 |
| 17 | 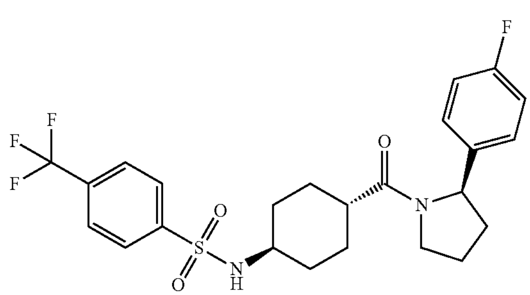 [SMILES: O=C([C@H]1CC[C@H](NS(=O)(=O)c2ccc(C(F)(F)F)cc2)CC1)N1CCC[C@@H]1c1ccc(F)cc1] | Example 1 | 499.0 |

-continued

| Example | Structure | Method of | MS |
|---------|-----------|-----------|-----|
| 18 | 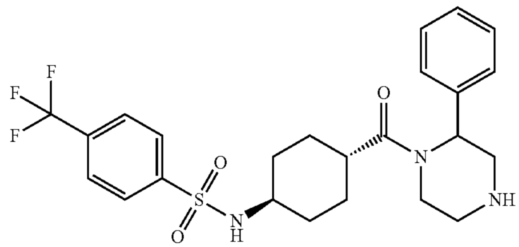 [SMILES: O=C([C@H]1CC[C@H](NS(=O)(=O)c2ccc(C(F)(F)F)cc2)CC1)N1CCNCC1c1ccccc1] | Example 1 | 496.0 |
| 19 | 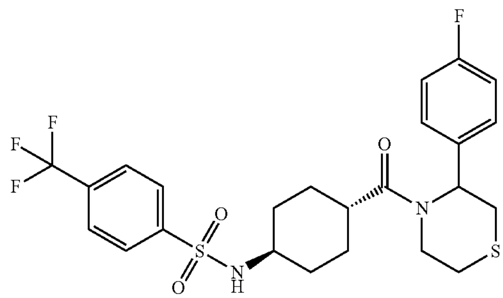 [SMILES: O=C([C@H]1CC[C@H](NS(=O)(=O)c2ccc(C(F)(F)F)cc2)CC1)N1CCSCC1c1ccc(F)cc1] | Example 1 | 531.0 |
| 20 | 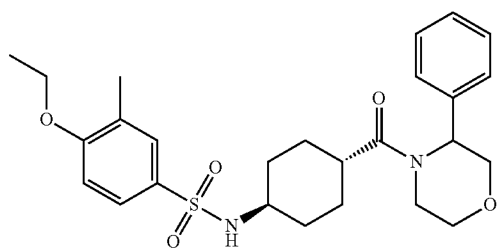 [SMILES: CCOc1ccc(S(=O)(=O)N[C@H]2CC[C@H](C(=O)N3CCOCC3c3ccccc3)CC2)cc1C] | Example 1 | 487.0 |
| 21 | 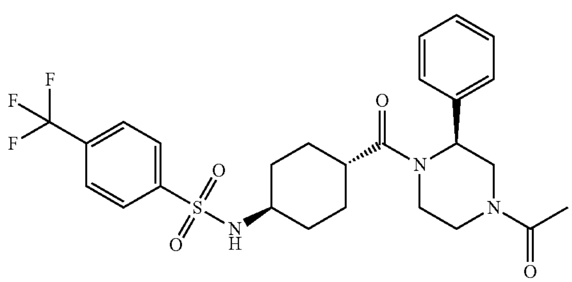 [SMILES: CC(=O)N1CCN(C(=O)[C@H]2CC[C@H](NS(=O)(=O)c3ccc(C(F)(F)F)cc3)CC2)[C@@H](c2ccccc2)C1] | Example 1 | 538.0 |
| 22 | 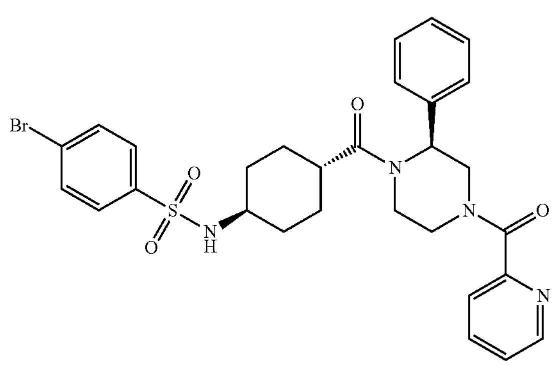 [SMILES: O=C(c1ccccn1)N1CCN(C(=O)[C@H]2CC[C@H](NS(=O)(=O)c3ccc(Br)cc3)CC2)[C@@H](c2ccccc2)C1] | Example 1 | 613.0 |

-continued

| Example | Structure | Method of | MS |
|---|---|---|---|
| 23 | 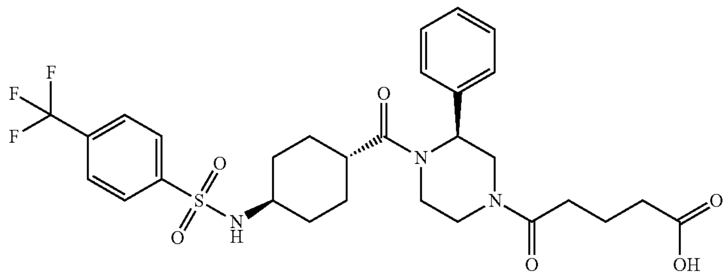 [SMILES: O=C(O)CCCC(=O)N1CCN(C(=O)[C@H]2CC[C@H](NS(=O)(=O)c3ccc(C(F)(F)F)cc3)CC2)[C@@H](c2ccccc2)C1] | Example 1 | 610.0 |
| 24 | 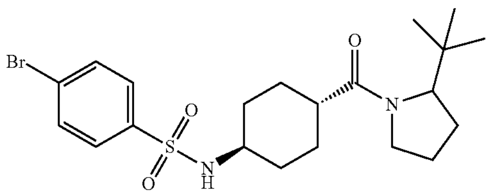 [SMILES: CC(C)(C)C1CCCN1C(=O)[C@H]1CC[C@H](NS(=O)(=O)c2ccc(Br)cc2)CC1] | Example 1 | 473.0 |
| 25 | 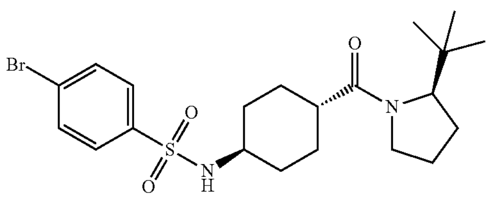 [SMILES: CC(C)(C)[C@H]1CCCN1C(=O)[C@H]1CC[C@H](NS(=O)(=O)c2ccc(Br)cc2)CC1] | Example 1 | 471.1 |
| 26 | 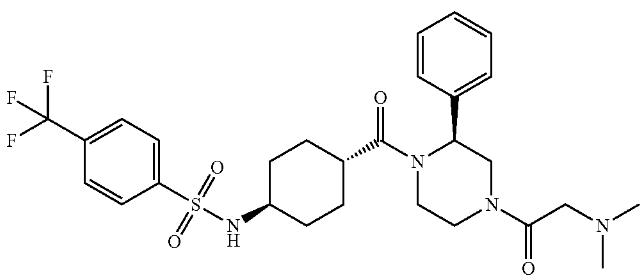 [SMILES: CN(C)CC(=O)N1CCN(C(=O)[C@H]2CC[C@H](NS(=O)(=O)c3ccc(C(F)(F)F)cc3)CC2)[C@@H](c2ccccc2)C1] | Example 1 | 581.0 |
| 27 | 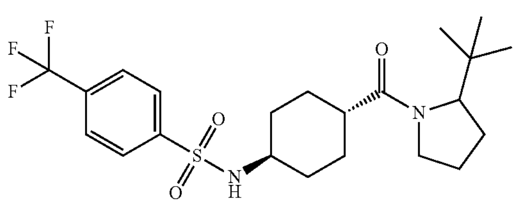 [SMILES: CC(C)(C)C1CCCN1C(=O)[C@H]1CC[C@H](NS(=O)(=O)c2ccc(C(F)(F)F)cc2)CC1] | Example 1 | 461.0 |
| 28 | 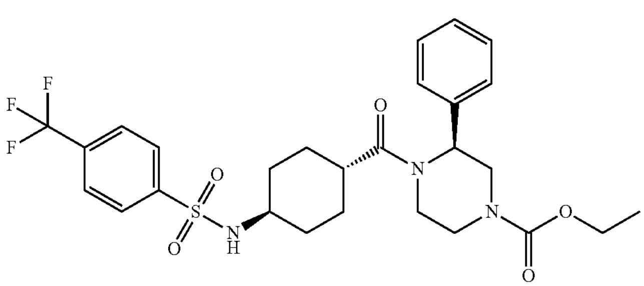 [SMILES: CCOC(=O)N1CCN(C(=O)[C@H]2CC[C@H](NS(=O)(=O)c3ccc(C(F)(F)F)cc3)CC2)[C@@H](c2ccccc2)C1] | Example 1 | 568.0 |

| Example | Structure | Method of | MS |
|---|---|---|---|
| 29 | 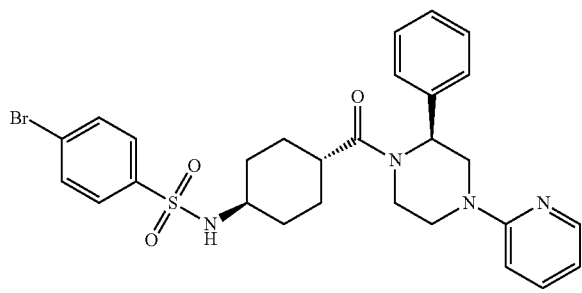 [SMILES: O=C([C@H]1CC[C@H](NS(=O)(=O)c2ccc(Br)cc2)CC1)N1CCN(c2ccccn2)C[C@@H]1c1ccccc1] | Example 1 | 585.0 |
| 30 | 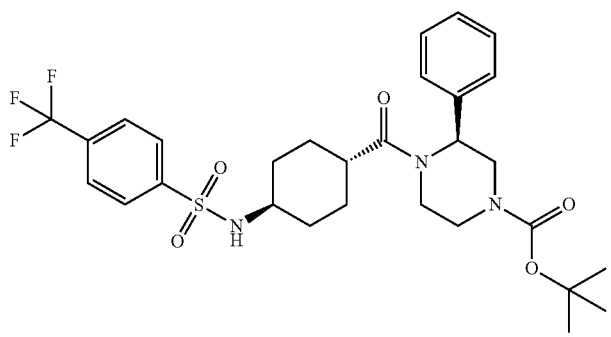 [SMILES: CC(C)(C)OC(=O)N1CCN(C(=O)[C@H]2CC[C@H](NS(=O)(=O)c3ccc(C(F)(F)F)cc3)CC2)[C@@H](c2ccccc2)C1] | Example 1 | |
| 31 | 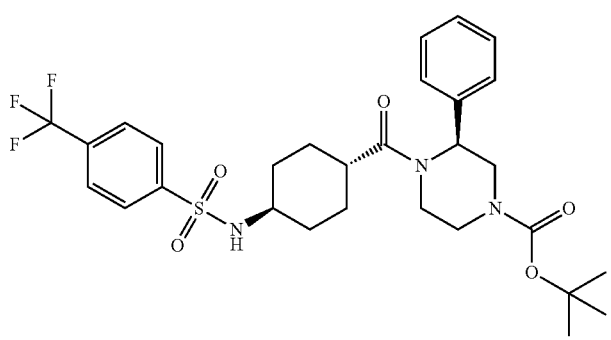 [SMILES: CC(C)(C)OC(=O)N1CCN(C(=O)[C@H]2CC[C@H](NS(=O)(=O)c3ccc(C(F)(F)F)cc3)CC2)[C@@H](c2ccccc2)C1] | Example 1 | 596.0 |
| 32 | 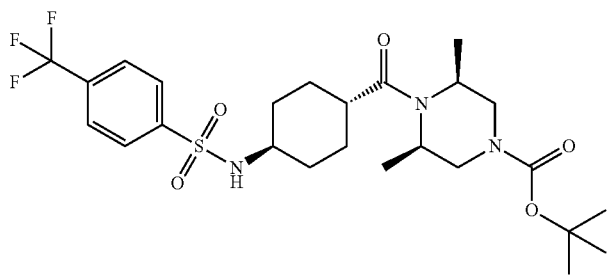 [SMILES: C[C@@H]1CN(C(=O)OC(C)(C)C)C[C@H](C)N1C(=O)[C@H]1CC[C@H](NS(=O)(=O)c2ccc(C(F)(F)F)cc2)CC1] | Example 1 | 548.0 |

-continued

| Example | Structure | Method of | MS |
|---|---|---|---|
| 33 | 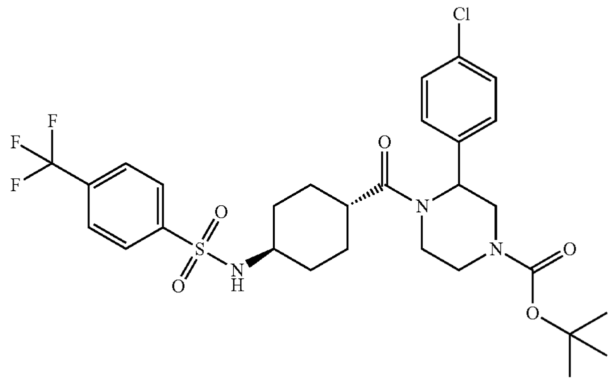 [SMILES: CC(C)(C)OC(=O)N1CCN(C(=O)[C@H]2CC[C@H](NS(=O)(=O)c3ccc(C(F)(F)F)cc3)CC2)C(c2ccc(Cl)cc2)C1] | Example 1 | 630.0 |
| 34 | 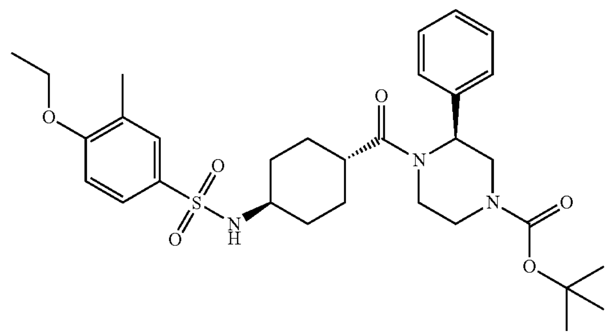 [SMILES: CCOc1ccc(S(=O)(=O)N[C@H]2CC[C@H](C(=O)N3CCN(C(=O)OC(C)(C)C)C[C@@H]3c3ccccc3)CC2)cc1C] | Example 1 | 586.0 |
| 35 | 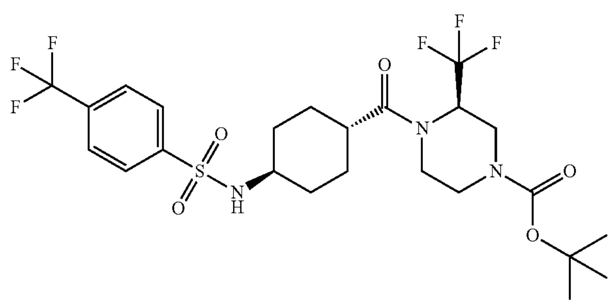 [SMILES: CC(C)(C)OC(=O)N1CCN(C(=O)[C@H]2CC[C@H](NS(=O)(=O)c3ccc(C(F)(F)F)cc3)CC2)[C@@H](C(F)(F)F)C1] | Example 1 | 605.0 |
| 36 | 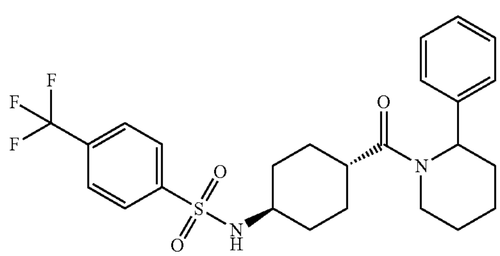 [SMILES: O=C([C@H]1CC[C@H](NS(=O)(=O)c2ccc(C(F)(F)F)cc2)CC1)N1CCCCC1c1ccccc1] | Example 1 | 495.0 |
| 37 | 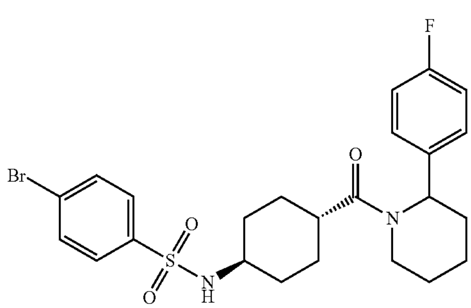 [SMILES: O=C([C@H]1CC[C@H](NS(=O)(=O)c2ccc(Br)cc2)CC1)N1CCCCC1c1ccc(F)cc1] | Example 1 | 525.0 |

-continued

| Example | Structure | Method of | MS |
|---|---|---|---|
| 38 | 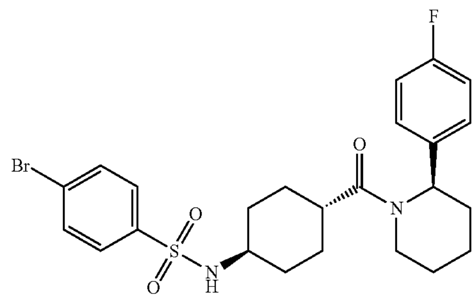 [SMILES: O=C([C@H]1CC[C@H](NS(=O)(=O)c2ccc(Br)cc2)CC1)N1CCCC[C@@H]1c1ccc(F)cc1] | Example 1 | 525.0 |
| 39 | 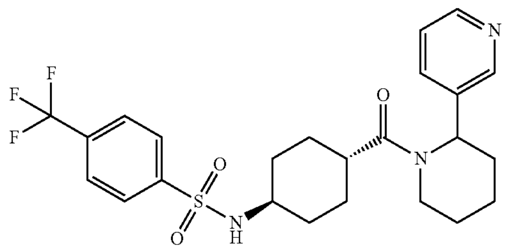 [SMILES: O=C([C@H]1CC[C@H](NS(=O)(=O)c2ccc(C(F)(F)F)cc2)CC1)N1CCCCC1c1cccnc1] | Example 1 | 496.0 |
| 40 | 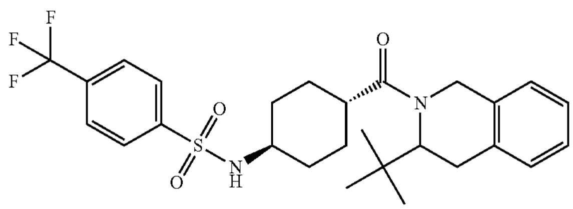 [SMILES: CC(C)(C)C1Cc2ccccc2CN1C(=O)[C@H]1CC[C@H](NS(=O)(=O)c2ccc(C(F)(F)F)cc2)CC1] | Example 1 | 523.0 |
| 41 | 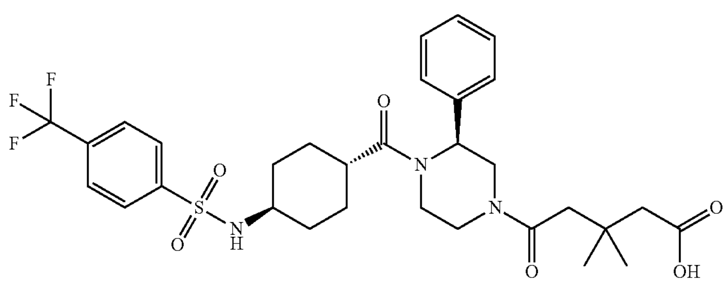 [SMILES: CC(C)(CC(=O)O)CC(=O)N1CCN(C(=O)[C@H]2CC[C@H](NS(=O)(=O)c3ccc(C(F)(F)F)cc3)CC2)[C@@H](c2ccccc2)C1] | Example 1 | 638.0 |
| 42 | 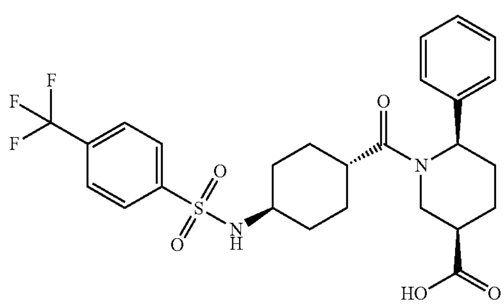 [SMILES: O=C(O)[C@@H]1CC[C@H](c2ccccc2)N(C(=O)[C@H]2CC[C@H](NS(=O)(=O)c3ccc(C(F)(F)F)cc3)CC2)C1] | Example 1 | 539.0 |
| 43 | 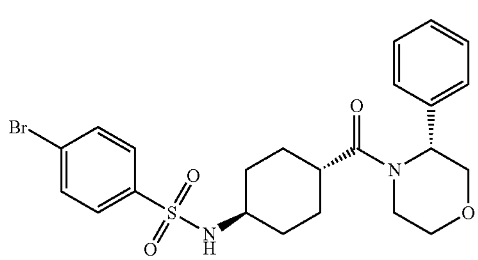 [SMILES: O=C([C@H]1CC[C@H](NS(=O)(=O)c2ccc(Br)cc2)CC1)N1CCOC[C@H]1c1ccccc1] | Example 1 | 507.1 |

| Example | Structure | Method of | MS |
|---|---|---|---|
| 44 | 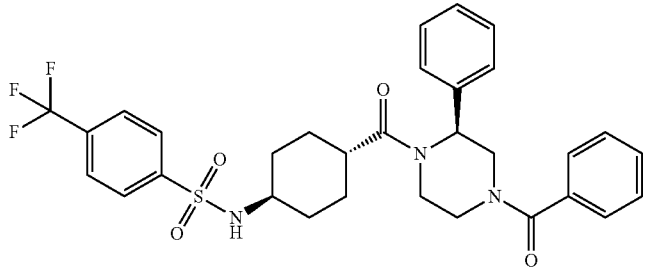 [SMILES: O=C(c1ccccc1)N1CCN(C(=O)[C@H]2CC[C@H](NS(=O)(=O)c3ccc(C(F)(F)F)cc3)CC2)[C@@H](c2ccccc2)C1] | Example 1 | 600.0 |
| 45 | 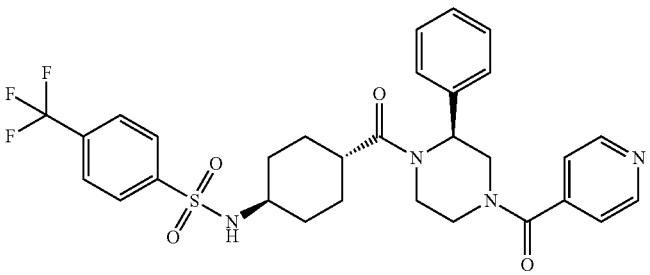 [SMILES: O=C(c1ccncc1)N1CCN(C(=O)[C@H]2CC[C@H](NS(=O)(=O)c3ccc(C(F)(F)F)cc3)CC2)[C@@H](c2ccccc2)C1] | Example 1 | 601.0 |
| 46 | 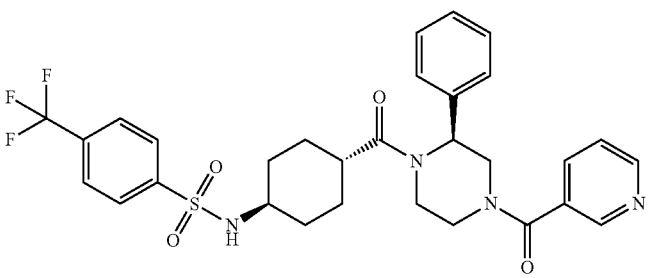 [SMILES: O=C(c1cccnc1)N1CCN(C(=O)[C@H]2CC[C@H](NS(=O)(=O)c3ccc(C(F)(F)F)cc3)CC2)[C@@H](c2ccccc2)C1] | Example 1 | 601.0 |
| 47 | 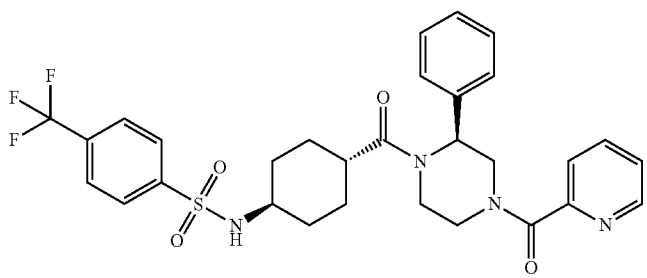 [SMILES: O=C(c1ccccn1)N1CCN(C(=O)[C@H]2CC[C@H](NS(=O)(=O)c3ccc(C(F)(F)F)cc3)CC2)[C@@H](c2ccccc2)C1] | Example 1 | 601.0 |
| 48 | 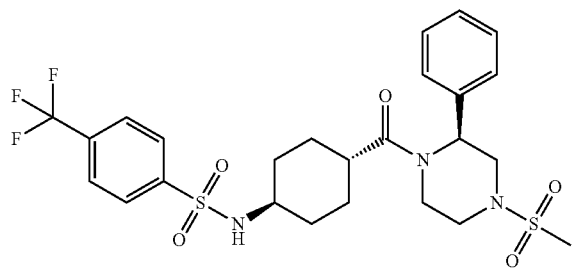 [SMILES: CS(=O)(=O)N1CCN(C(=O)[C@H]2CC[C@H](NS(=O)(=O)c3ccc(C(F)(F)F)cc3)CC2)[C@@H](c2ccccc2)C1] | Example 1 | 574.0 |

-continued

| Example | Structure | Method of | MS |
|---|---|---|---|
| 49 | 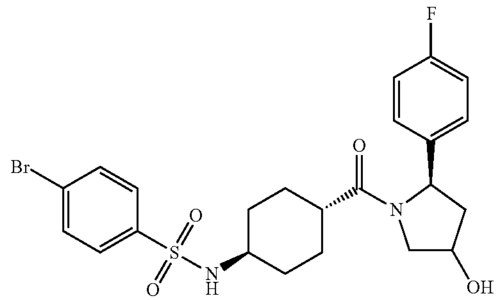 [SMILES: O=C([C@H]1CC[C@H](NS(=O)(=O)c2ccc(Br)cc2)CC1)N1CC(O)C[C@@H]1c1ccc(F)cc1] | Example 1 | 527.0 |
| 50 | 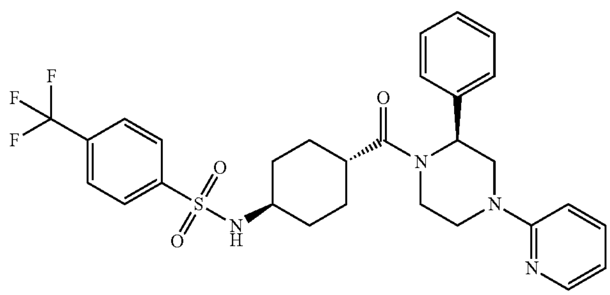 [SMILES: O=C([C@H]1CC[C@H](NS(=O)(=O)c2ccc(C(F)(F)F)cc2)CC1)N1CCN(c2ccccn2)C[C@@H]1c1ccccc1] | Example 1 | 573.0 |
| 51 | 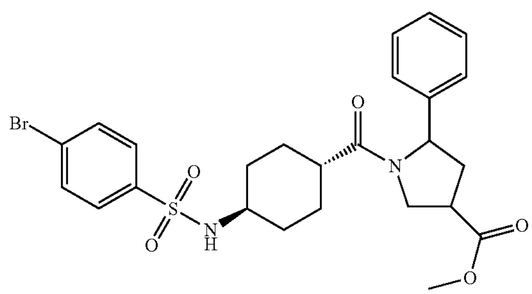 [SMILES: COC(=O)C1CC(c2ccccc2)N(C(=O)[C@H]2CC[C@H](NS(=O)(=O)c3ccc(Br)cc3)CC2)C1] | Example 1 | 537.0 |
| 52 | 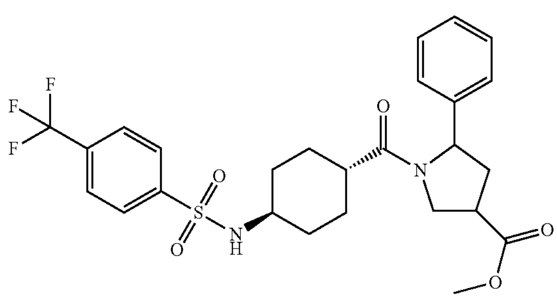 [SMILES: COC(=O)C1CC(c2ccccc2)N(C(=O)[C@H]2CC[C@H](NS(=O)(=O)c3ccc(C(F)(F)F)cc3)CC2)C1] | Example 1 | 539.0 |
| 53 | 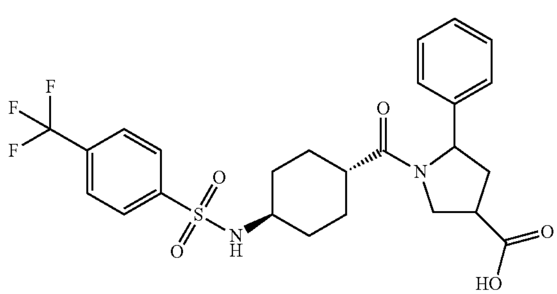 [SMILES: O=C(O)C1CC(c2ccccc2)N(C(=O)[C@H]2CC[C@H](NS(=O)(=O)c3ccc(C(F)(F)F)cc3)CC2)C1] | Example 1 | 525.0 |

| Example | Structure | Method of | MS |
|---------|-----------|-----------|-----|
| 54 | 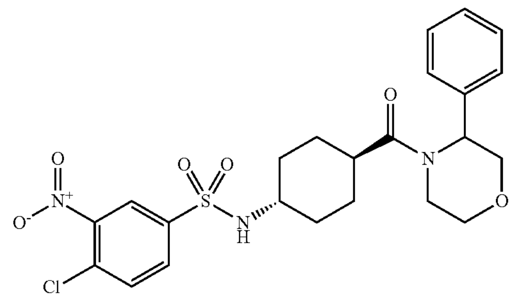 [SMILES: O=C([C@H]1CC[C@H](NS(=O)(=O)c2ccc(Cl)c([N+](=O)[O-])c2)CC1)N1CCOCC1c1ccccc1] | Example 1 | — |
| 55 | 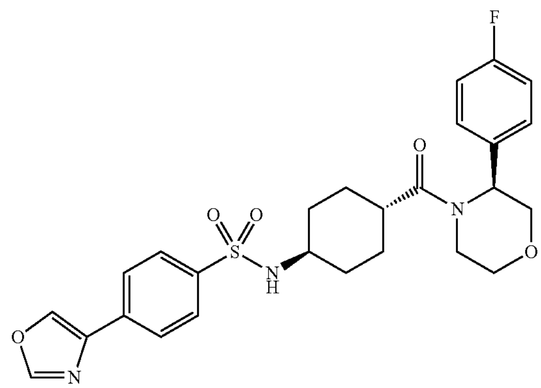 [SMILES: O=C([C@H]1CC[C@H](NS(=O)(=O)c2ccc(-c3cocn3)cc2)CC1)N1CCOC[C@@H]1c1ccc(F)cc1] | Example 1 | 514.0 |
| 56 | 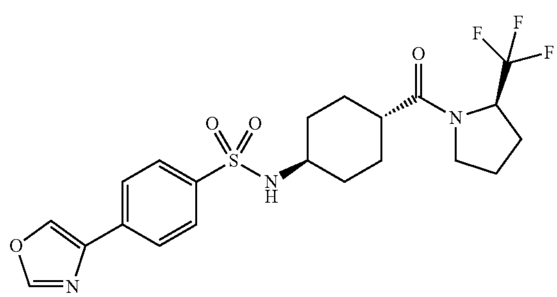 [SMILES: O=C([C@H]1CC[C@H](NS(=O)(=O)c2ccc(-c3cocn3)cc2)CC1)N1CCC[C@@H]1C(F)(F)F] | Example 1 | 472.2 |
| 57 | 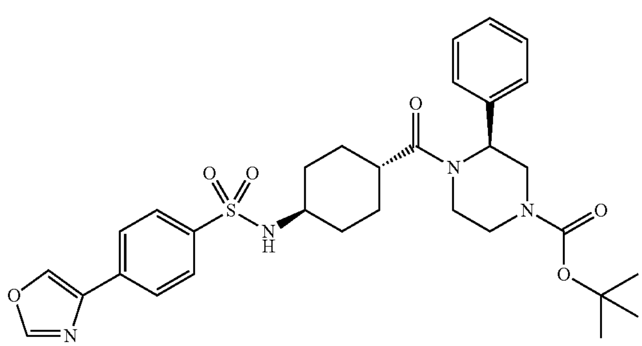 [SMILES: CC(C)(C)OC(=O)N1CCN(C(=O)[C@H]2CC[C@H](NS(=O)(=O)c3ccc(-c4cocn4)cc3)CC2)[C@@H](c2ccccc2)C1] | Example 1 | 595.3 |

-continued

| Example | Structure | Method of | MS |
|---|---|---|---|
| 58 | 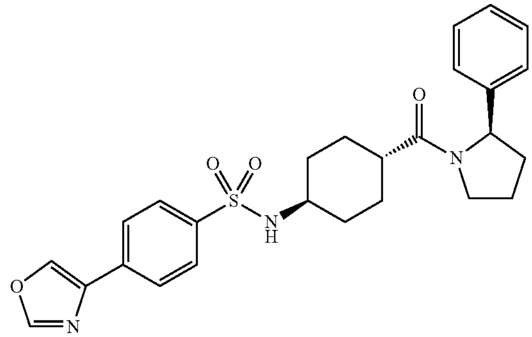 [SMILES: O=C([C@H]1CC[C@H](NS(=O)(=O)c2ccc(-c3cocn3)cc2)CC1)N1CCC[C@@H]1c1ccccc1] | Example 1 | 480.3 |
| 59 | 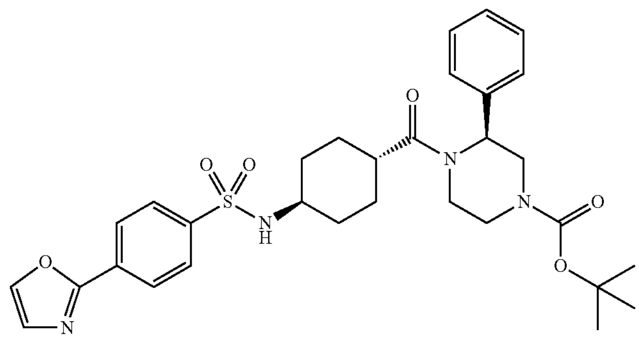 [SMILES: CC(C)(C)OC(=O)N1CCN(C(=O)[C@H]2CC[C@H](NS(=O)(=O)c3ccc(-c4ncco4)cc3)CC2)[C@@H](c2ccccc2)C1] | Example 1 | 595.0 |
| 60 | 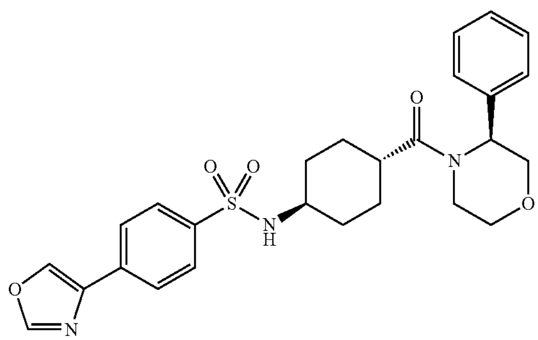 [SMILES: O=C([C@H]1CC[C@H](NS(=O)(=O)c2ccc(-c3cocn3)cc2)CC1)N1CCOC[C@@H]1c1ccccc1] | Example 1 | 496.2 |
| 61 | 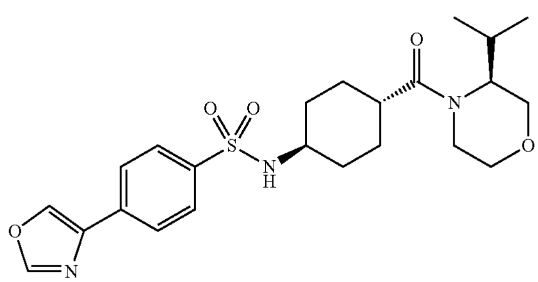 [SMILES: CC(C)[C@H]1COCCN1C(=O)[C@H]1CC[C@H](NS(=O)(=O)c2ccc(-c3cocn3)cc2)CC1] | Example 1 | 462.1 |
| 62 | 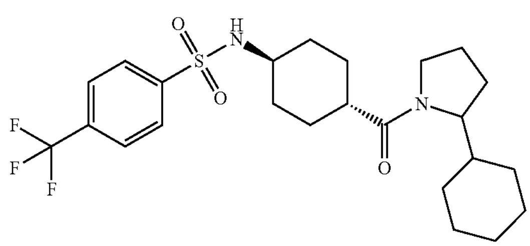 [SMILES: O=C([C@H]1CC[C@H](NS(=O)(=O)c2ccc(C(F)(F)F)cc2)CC1)N1CCCC1C1CCCCC1] | Example 1 | 487.0 |

-continued

| Example | Structure | Method of | MS |
|---------|-----------|-----------|------|
| 63 | 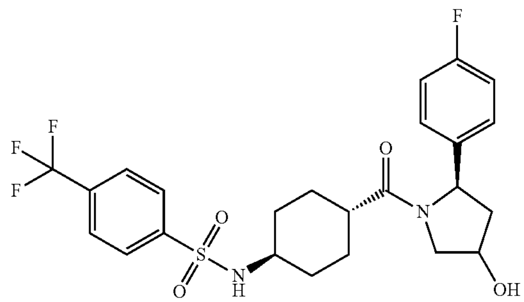 [SMILES: O=C([C@H]1CC[C@H](NS(=O)(=O)c2ccc(C(F)(F)F)cc2)CC1)N1CC(O)C[C@@H]1c1ccc(F)cc1] | Example 1 | 515.0 |
| 64 | 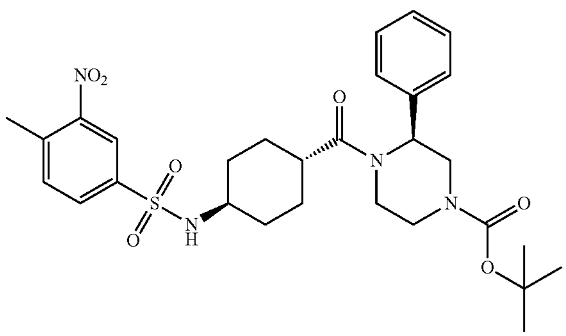 [SMILES: Cc1ccc(S(=O)(=O)N[C@H]2CC[C@H](C(=O)N3CCN(C(=O)OC(C)(C)C)C[C@@H]3c3ccccc3)CC2)cc1[N+](=O)[O-]] | Example 1 | — |
| 65 | 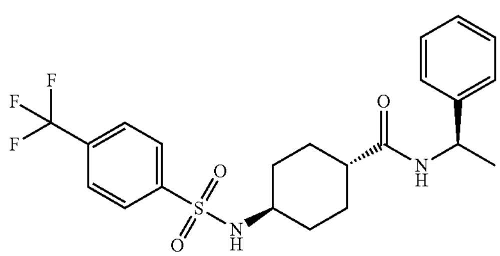 [SMILES: C[C@@H](NC(=O)[C@H]1CC[C@H](NS(=O)(=O)c2ccc(C(F)(F)F)cc2)CC1)c1ccccc1] | Example 1 | — |
| 66 | 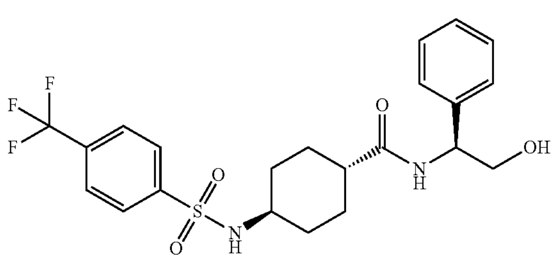 [SMILES: O=C(N[C@H](CO)c1ccccc1)[C@H]1CC[C@H](NS(=O)(=O)c2ccc(C(F)(F)F)cc2)CC1] | Example 1 | 471.2 |
| 67 | 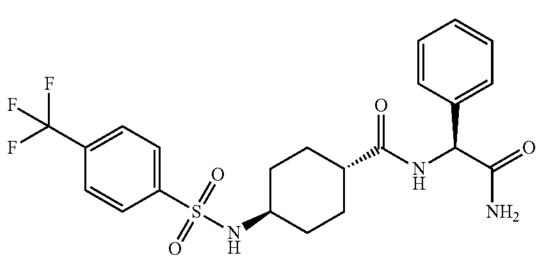 [SMILES: NC(=O)[C@@H](NC(=O)[C@H]1CC[C@H](NS(=O)(=O)c2ccc(C(F)(F)F)cc2)CC1)c1ccccc1] | Example 1 | 484.0 |

-continued

| Example | Structure | Method of | MS |
|---|---|---|---|
| 68 | 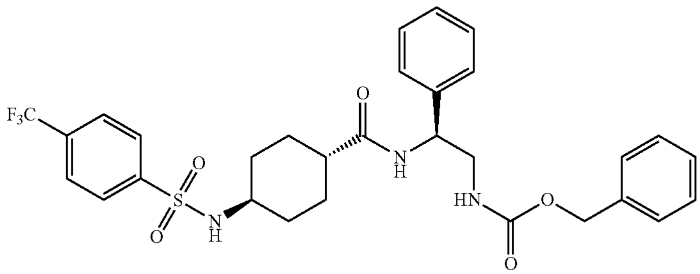 [SMILES: O=C(NC[C@@H](NC(=O)[C@H]1CC[C@H](NS(=O)(=O)c2ccc(C(F)(F)F)cc2)CC1)c1ccccc1)OCc1ccccc1] | Example 1 | — |
| 69 | 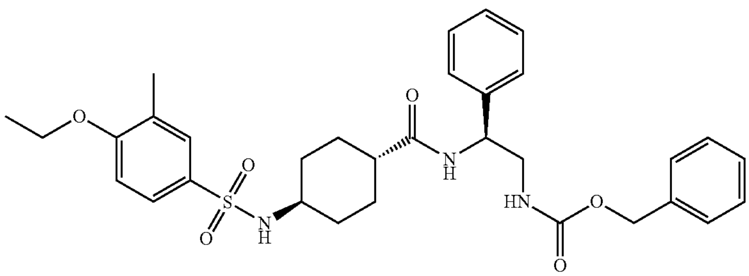 [SMILES: CCOc1ccc(S(=O)(=O)N[C@H]2CC[C@H](C(=O)N[C@H](CNC(=O)OCc3ccccc3)c3ccccc3)CC2)cc1C] | Example 1 | — |
| 70 | 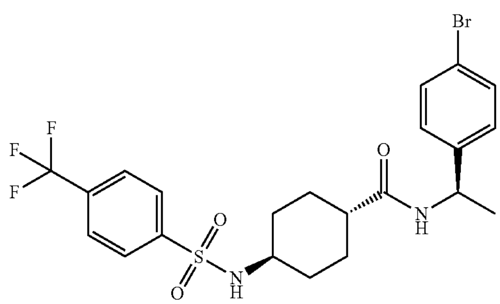 | Example 1 | 535.0 |
| 71 | 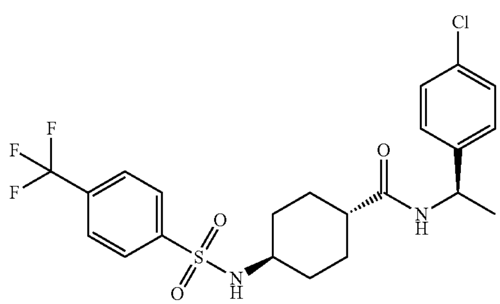 [SMILES: C[C@@H](NC(=O)[C@H]1CC[C@H](NS(=O)(=O)c2ccc(C(F)(F)F)cc2)CC1)c1ccc(Br)cc1] | Example 1 | 489.0 |
| 72 | 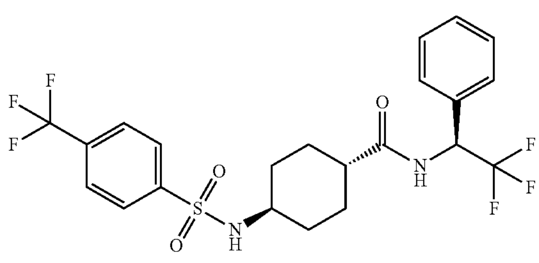 [SMILES: O=C(N[C@@H](c1ccccc1)C(F)(F)F)[C@H]1CC[C@H](NS(=O)(=O)c2ccc(C(F)(F)F)cc2)CC1] | Example 1 | 509.0 |

-continued
| Example | Structure | Method of | MS |
|---|---|---|---|
| 73 | 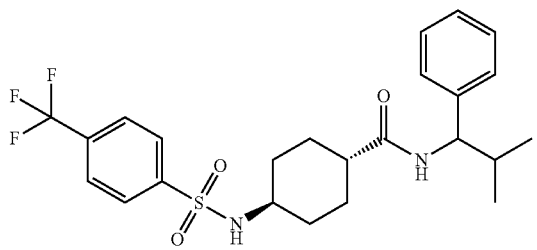 [SMILES: CC(C)C(NC(=O)[C@H]1CC[C@H](NS(=O)(=O)c2ccc(C(F)(F)F)cc2)CC1)c1ccccc1] | Example 1 | 483.0 |
| 74 | 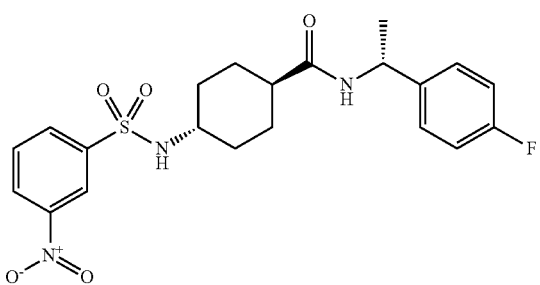 [SMILES: C[C@@H](NC(=O)[C@H]1CC[C@H](NS(=O)(=O)c2cccc([N+](=O)[O-])c2)CC1)c1ccc(F)cc1] | Example 2A | 450.0 |
| 75 | 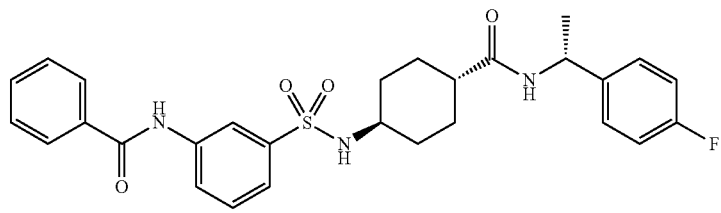 [SMILES: C[C@@H](NC(=O)[C@H]1CC[C@H](NS(=O)(=O)c2cccc(NC(=O)c3ccccc3)c2)CC1)c1ccc(F)cc1] | Example 2A | 524.0 |
| 76 | 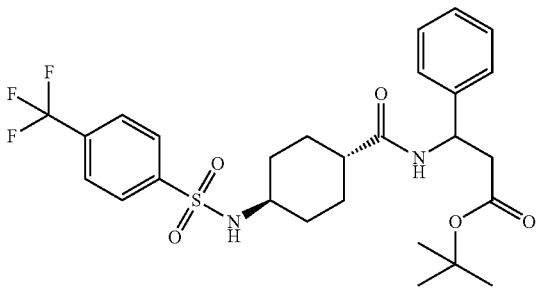 [SMILES: CC(C)(C)OC(=O)CC(NC(=O)[C@H]1CC[C@H](NS(=O)(=O)c2ccc(C(F)(F)F)cc2)CC1)c1ccccc1] | Example 1 | 555.0 |
| 77 | 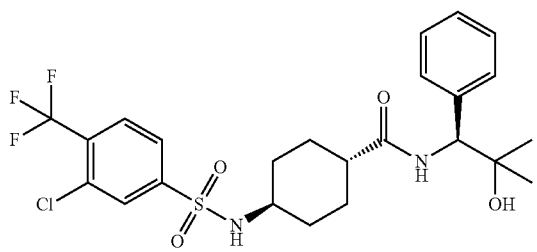 [SMILES: CC(C)(O)[C@@H](NC(=O)[C@H]1CC[C@H](NS(=O)(=O)c2ccc(C(F)(F)F)c(Cl)c2)CC1)c1ccccc1] | Example 1 | 533.0 |

| Example | Structure | Method of | MS |
|---|---|---|---|
| 78 | 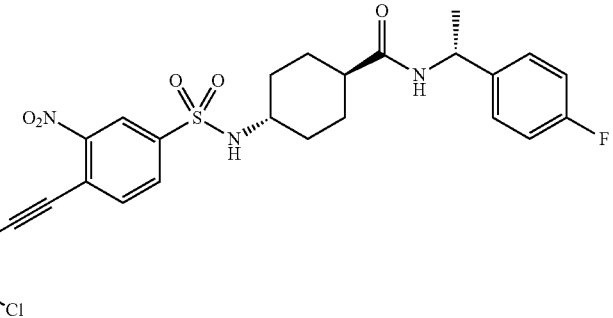 | Example 2A | — |
| 79 | 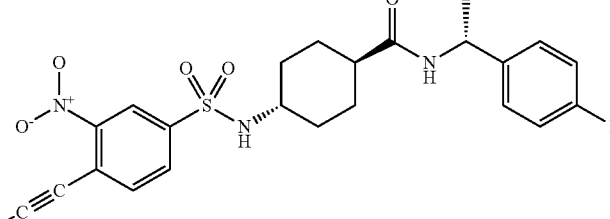 | Example 2A | — |
| 81 | 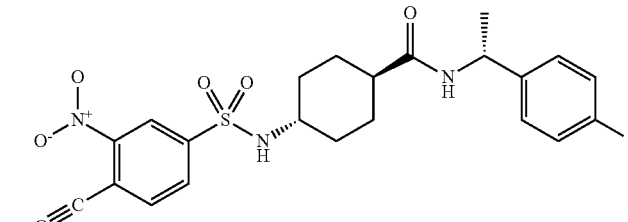 | Example 2A | — |
| 83 | 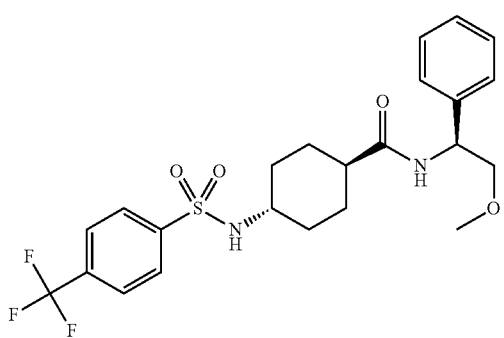 [SMILES: COC[C@@H](NC(=O)[C@H]1CC[C@H](NS(=O)(=O)c2ccc(C(F)(F)F)cc2)CC1)c1ccccc1] | Example 1 | — |
| 84 | 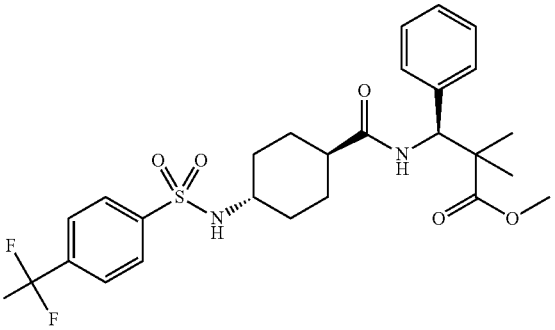 | Example 1 | 541.2 |

| Example | Structure | Method of | MS |
|---|---|---|---|
| 85 | 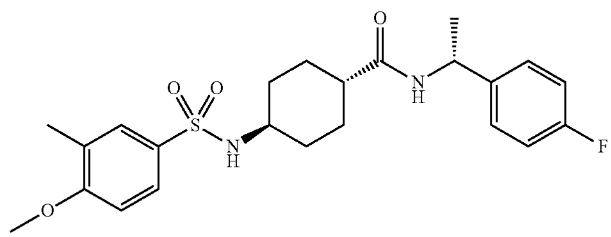 [SMILES: COc1ccc(S(=O)(=O)N[C@H]2CC[C@H](C(=O)N[C@H](C)c3ccc(F)cc3)CC2)cc1C] | Example 2A | 449.2 |
| 86 | 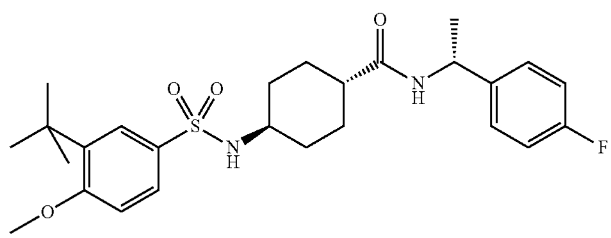 [SMILES: COc1ccc(S(=O)(=O)N[C@H]2CC[C@H](C(=O)N[C@H](C)c3ccc(F)cc3)CC2)cc1C(C)(C)C] | Example 2A | 491.4 |
| 87 | 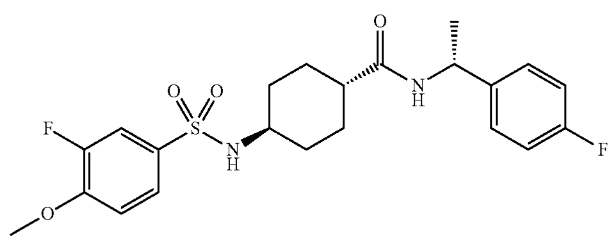 [SMILES: COc1ccc(S(=O)(=O)N[C@H]2CC[C@H](C(=O)N[C@H](C)c3ccc(F)cc3)CC2)cc1F] | Example 2A | 453.1 |
| 88 | 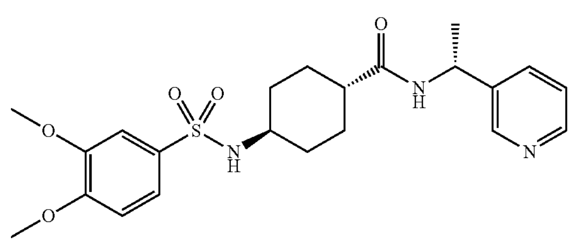 [SMILES: COc1ccc(S(=O)(=O)N[C@H]2CC[C@H](C(=O)N[C@H](C)c3cccnc3)CC2)cc1OC] | Example 2A | 448.1 |
| 89 | 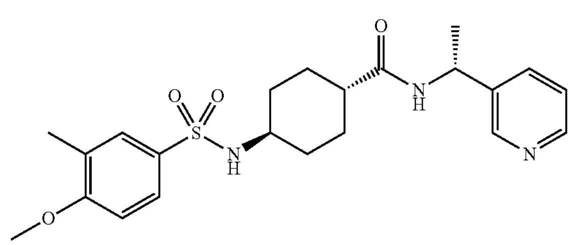 [SMILES: COc1ccc(S(=O)(=O)N[C@H]2CC[C@H](C(=O)N[C@H](C)c3cccnc3)CC2)cc1C] | Example 2A | 432.1 |
| 90 | 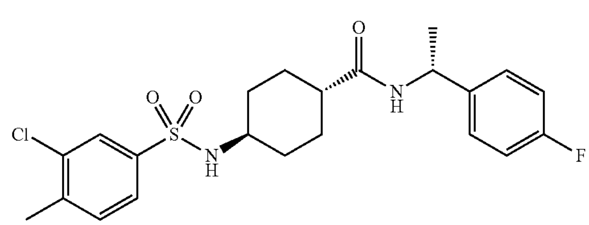 [SMILES: Cc1ccc(S(=O)(=O)N[C@H]2CC[C@H](C(=O)N[C@H](C)c3ccc(F)cc3)CC2)cc1Cl] | Example 2A | 453.0 |

-continued

| Example | Structure | Method of | MS |
|---|---|---|---|
| 91 | 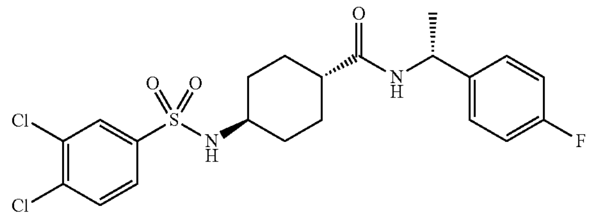 [SMILES: C[C@@H](NC(=O)[C@H]1CC[C@H](NS(=O)(=O)c2ccc(Cl)c(Cl)c2)CC1)c1ccc(F)cc1] | Example 2A | 472.9 |
| 92 | 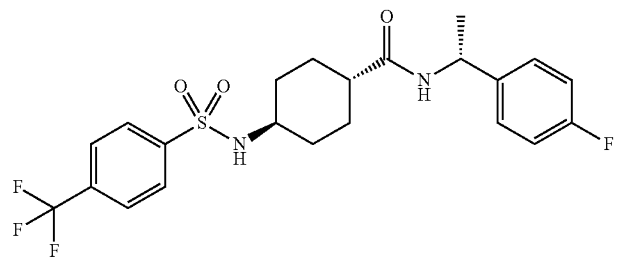 [SMILES: C[C@@H](NC(=O)[C@H]1CC[C@H](NS(=O)(=O)c2ccc(C(F)(F)F)cc2)CC1)c1ccc(F)cc1] | Example 2A | 473.1 |
| 93 | 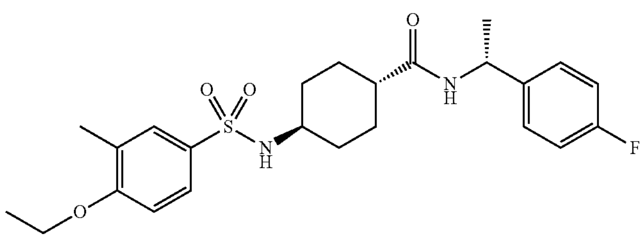 [SMILES: CCOc1ccc(S(=O)(=O)N[C@H]2CC[C@H](C(=O)N[C@H](C)c3ccc(F)cc3)CC2)cc1C] | Example 2A | 463.1 |
| 94 | 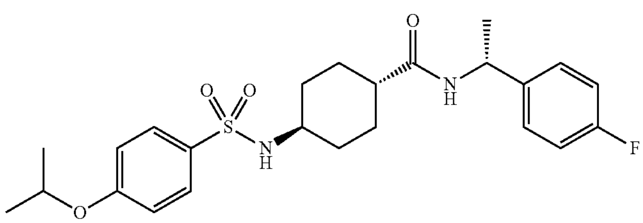 [SMILES: CC(C)Oc1ccc(S(=O)(=O)N[C@H]2CC[C@H](C(=O)N[C@H](C)c3ccc(F)cc3)CC2)cc1] | Example 2A | 463.1 |
| 95 | 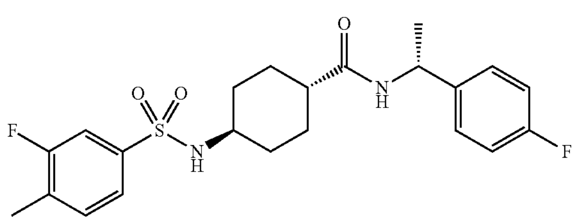 [SMILES: Cc1ccc(S(=O)(=O)N[C@H]2CC[C@H](C(=O)N[C@H](C)c3ccc(F)cc3)CC2)cc1F] | Example 2A | 437.1 |
| 96 | 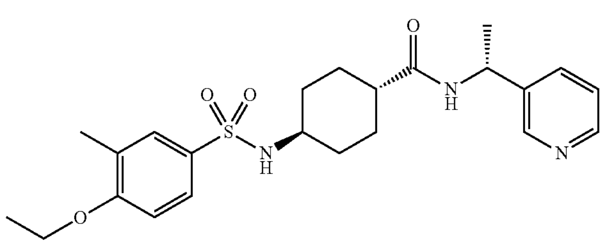 [SMILES: CCOc1ccc(S(=O)(=O)N[C@H]2CC[C@H](C(=O)N[C@H](C)c3cccnc3)CC2)cc1C] | Example 2A | 446.1 |

-continued

| Example | Structure | Method of | MS |
|---|---|---|---|
| 97 | 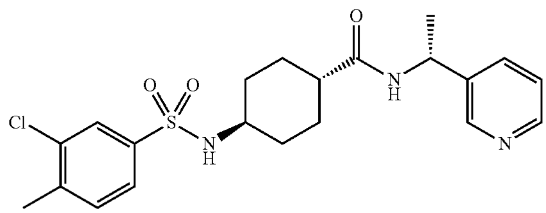 [SMILES: Cc1ccc(S(=O)(=O)N[C@H]2CC[C@H](C(=O)N[C@H](C)c3cccnc3)CC2)cc1Cl] | Example 2A | 436.1 |
| 98 | 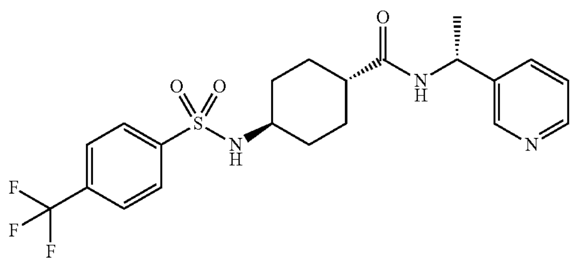 [SMILES: C[C@@H](NC(=O)[C@H]1CC[C@H](NS(=O)(=O)c2ccc(C(F)(F)F)cc2)CC1)c1cccnc1] | Example 2A | 456.0 |
| 99 | 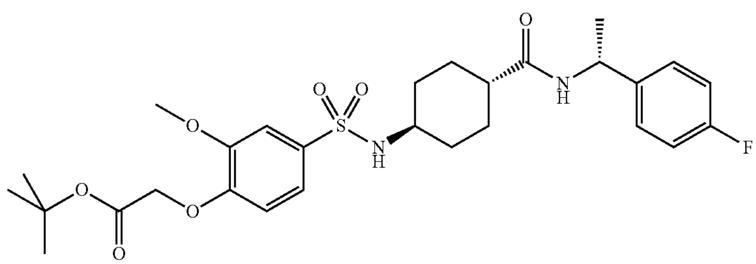 [SMILES: COc1cc(S(=O)(=O)N[C@H]2CC[C@H](C(=O)N[C@H](C)c3ccc(F)cc3)CC2)ccc1OCC(=O)OC(C)(C)C] | Example 2A | 564.2 (M+ ion) |
| 100 | 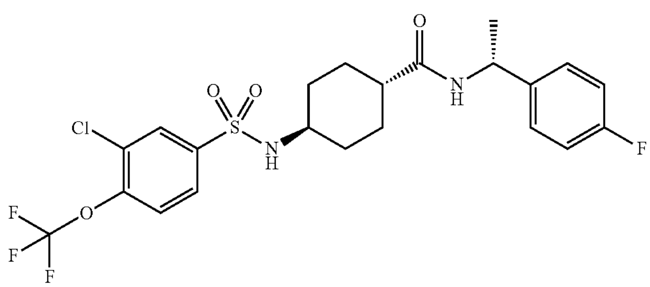 [SMILES: C[C@@H](NC(=O)[C@H]1CC[C@H](NS(=O)(=O)c2ccc(OC(F)(F)F)c(Cl)c2)CC1)c1ccc(F)cc1] | Example 2A | 523.0 |
| 101 | 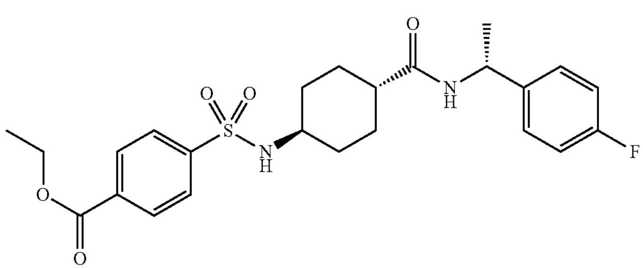 [SMILES: CCOC(=O)c1ccc(S(=O)(=O)N[C@H]2CC[C@H](C(=O)N[C@H](C)c3ccc(F)cc3)CC2)cc1] | Example 2A | 477.2 |
| 102 | 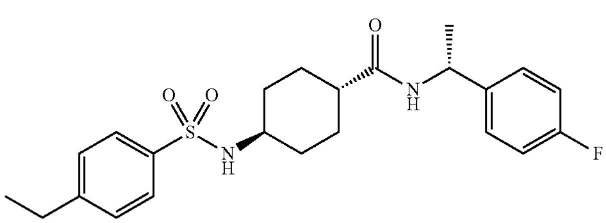 [SMILES: CCc1ccc(S(=O)(=O)N[C@H]2CC[C@H](C(=O)N[C@H](C)c3ccc(F)cc3)CC2)cc1] | Example 2A | 433.1 |

-continued

| Example | Structure | Method of | MS |
|---|---|---|---|
| 103 | 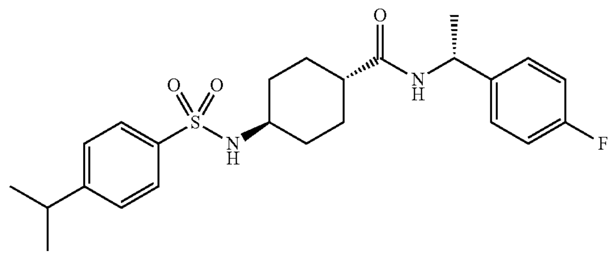 | Example 2A | 447.1 |
| 104 | 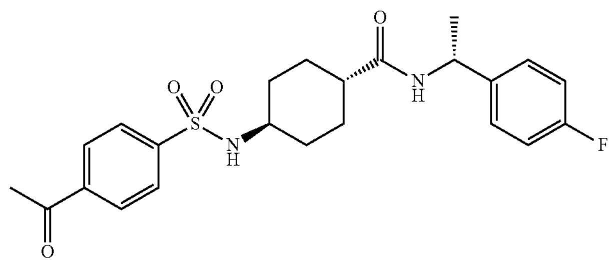 [SMILES: CC(=O)c1ccc(S(=O)(=O)N[C@H]2CC[C@H](C(=O)N[C@H](C)c3ccc(F)cc3)CC2)cc1] | Example 2A | 447.1 |
| 105 | 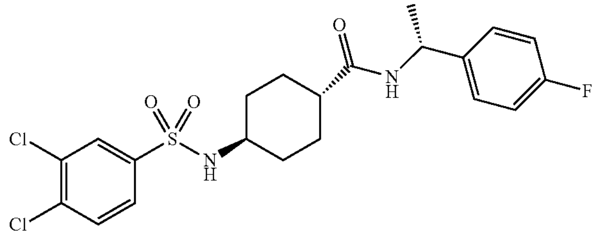 [SMILES: C[C@@H](NC(=O)[C@H]1CC[C@H](NS(=O)(=O)c2ccc(Cl)c(Cl)c2)CC1)c1ccc(F)cc1] | Example 2A | — |
| 106 | 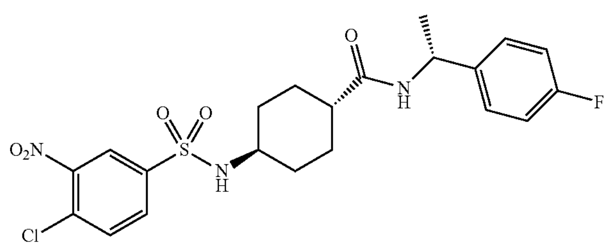 [SMILES: C[C@@H](NC(=O)[C@H]1CC[C@H](NS(=O)(=O)c2ccc(Cl)c([N+](=O)[O-])c2)CC1)c1ccc(F)cc1] | Example 2A | — |
| 107 | 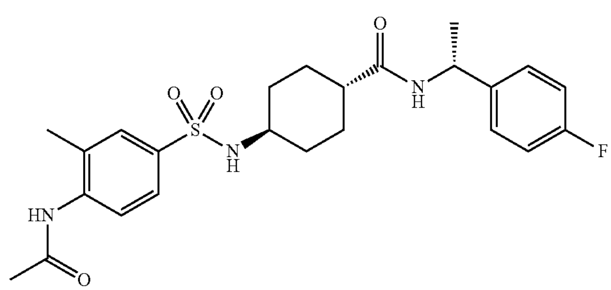 [SMILES: CC(=O)Nc1ccc(S(=O)(=O)N[C@H]2CC[C@H](C(=O)N[C@H](C)c3ccc(F)cc3)CC2)cc1C] | Example 2A | 476.1 |
| 108 | 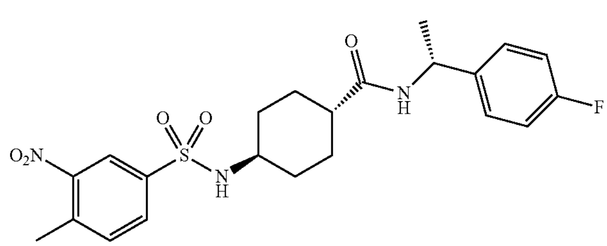 [SMILES: Cc1ccc(S(=O)(=O)N[C@H]2CC[C@H](C(=O)N[C@H](C)c3ccc(F)cc3)CC2)cc1[N+](=O)[O-]] | Example 2A | — |

-continued

| Example | Structure | Method of | MS |
|---|---|---|---|
| 109 | 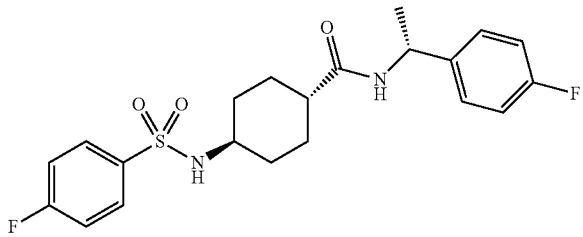 [SMILES: C[C@@H](NC(=O)[C@H]1CC[C@H](NS(=O)(=O)c2ccc(F)cc2)CC1)c1ccc(F)cc1] | Example 2A | — |
| 110 | 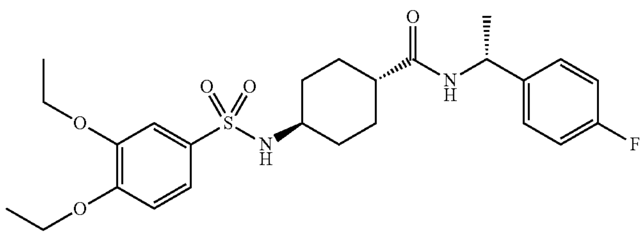 [SMILES: CCOc1ccc(S(=O)(=O)N[C@H]2CC[C@H](C(=O)N[C@H](C)c3ccc(F)cc3)CC2)cc1OCC] | Example 2A | 493.1 |
| 111 | 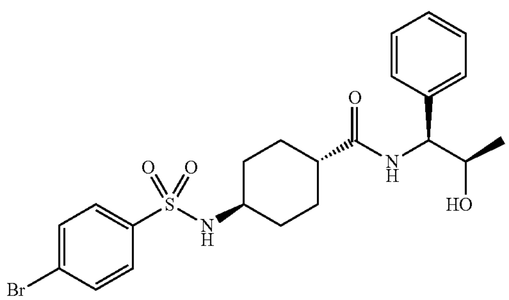 [SMILES: C[C@@H](O)[C@@H](NC(=O)[C@H]1CC[C@H](NS(=O)(=O)c2ccc(Br)cc2)CC1)c1ccccc1] | Example 1 | 497.1 |
| 112 | 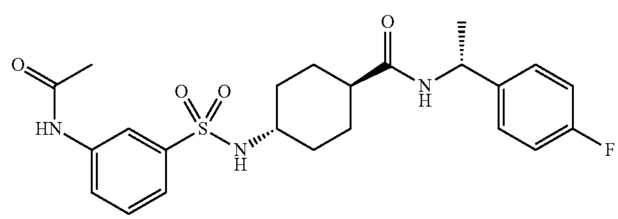 [SMILES: CC(=O)Nc1cccc(S(=O)(=O)N[C@H]2CC[C@H](C(=O)N[C@H](C)c3ccc(F)cc3)CC2)c1] | Example 2A | 462.3 |
| 113 | 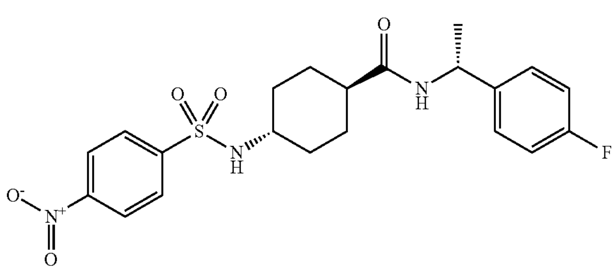 [SMILES: C[C@@H](NC(=O)[C@H]1CC[C@H](NS(=O)(=O)c2ccc([N+](=O)[O-])cc2)CC1)c1ccc(F)cc1] | Example 2A | 450.2 |
| 114 | 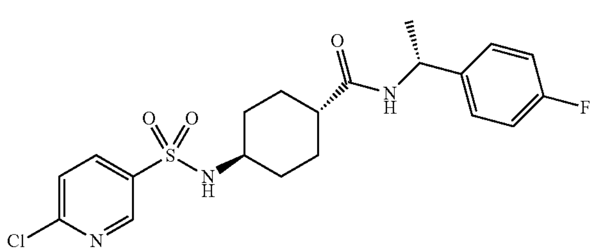 [SMILES: C[C@@H](NC(=O)[C@H]1CC[C@H](NS(=O)(=O)c2ccc(Cl)nc2)CC1)c1ccc(F)cc1] | Example 2A | [M + H] = 440.02 |

-continued

| Example | Structure | Method of | MS |
|---|---|---|---|
| 115 | 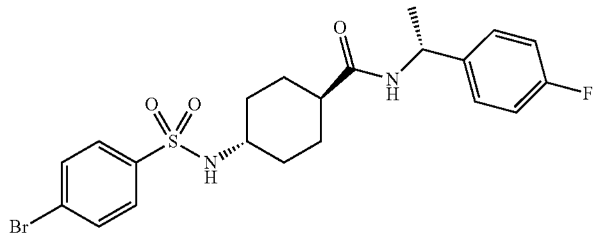 [SMILES: C[C@@H](NC(=O)[C@H]1CC[C@H](NS(=O)(=O)c2ccc(Br)cc2)CC1)c1ccc(F)cc1] | Example 2A | [M + H] = 484.90 |
| 116 | 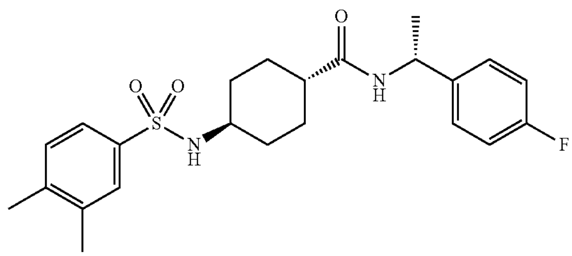 [SMILES: Cc1ccc(S(=O)(=O)N[C@H]2CC[C@H](C(=O)N[C@H](C)c3ccc(F)cc3)CC2)cc1C] | Example 2A | 433.2 |
| 117 | 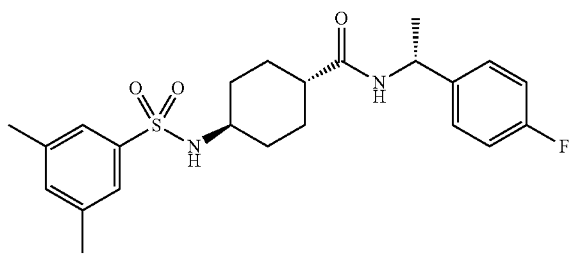 [SMILES: Cc1cc(C)cc(S(=O)(=O)N[C@H]2CC[C@H](C(=O)N[C@H](C)c3ccc(F)cc3)CC2)c1] | Example 2A | 433.2 |
| 118 | 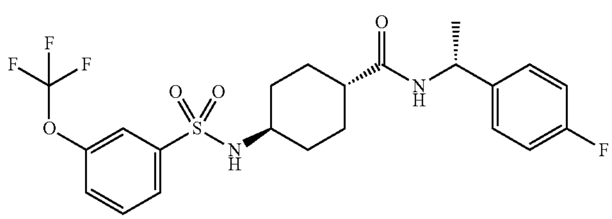 [SMILES: C[C@@H](NC(=O)[C@H]1CC[C@H](NS(=O)(=O)c2cccc(OC(F)(F)F)c2)CC1)c1ccc(F)cc1] | Example 2A | 489.1 |
| 119 | 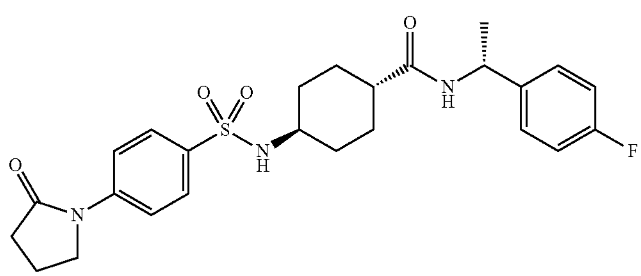 [SMILES: C[C@@H](NC(=O)[C@H]1CC[C@H](NS(=O)(=O)c2ccc(N3CCCC3=O)cc2)CC1)c1ccc(F)cc1] | Example 2A | 488.2 |
| 120 | 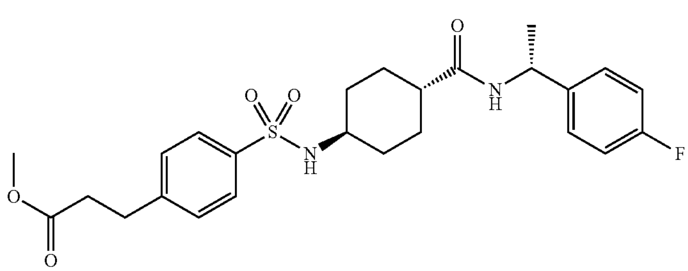 [SMILES: COC(=O)CCc1ccc(S(=O)(=O)N[C@H]2CC[C@H](C(=O)N[C@H](C)c3ccc(F)cc3)CC2)cc1] | Example 2A | 491.2 |

-continued

| Example | Structure | Method of | MS |
|---|---|---|---|
| 121 | 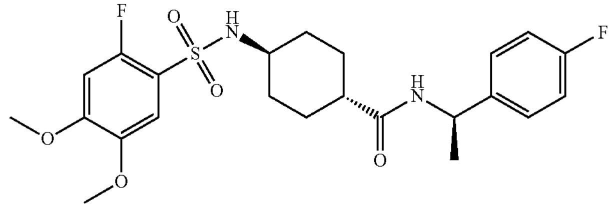 [SMILES: COc1cc(F)c(S(=O)(=O)N[C@H]2CC[C@H](C(=O)N[C@H](C)c3ccc(F)cc3)CC2)cc1OC] | Example 2A | 483.1 |
| 122 | 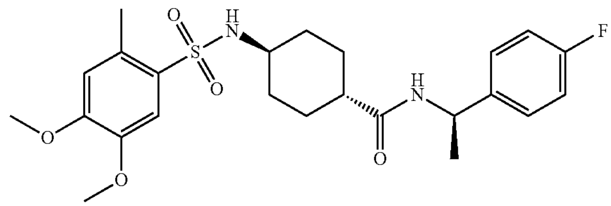 [SMILES: COc1cc(C)c(S(=O)(=O)N[C@H]2CC[C@H](C(=O)N[C@H](C)c3ccc(F)cc3)CC2)cc1OC] | Example 2A | 479.1 |
| 123 | 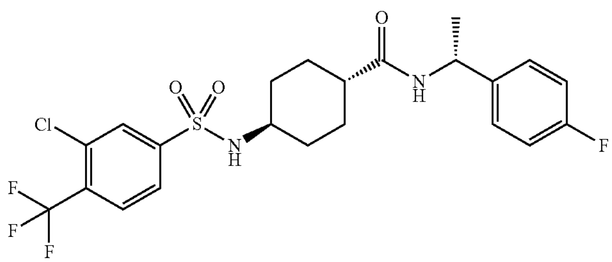 [SMILES: C[C@@H](NC(=O)[C@H]1CC[C@H](NS(=O)(=O)c2ccc(C(F)(F)F)c(Cl)c2)CC1)c1ccc(F)cc1] | Example 2A | 507.0 |
| 124 | 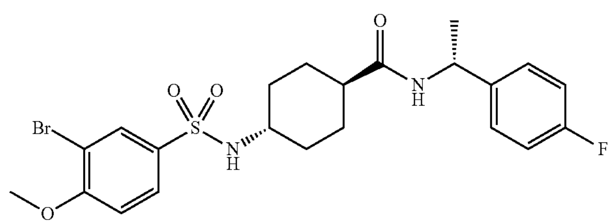 [SMILES: COc1ccc(S(=O)(=O)N[C@H]2CC[C@H](C(=O)N[C@H](C)c3ccc(F)cc3)CC2)cc1Br] | Example 2A | 514.9 |
| 125 | 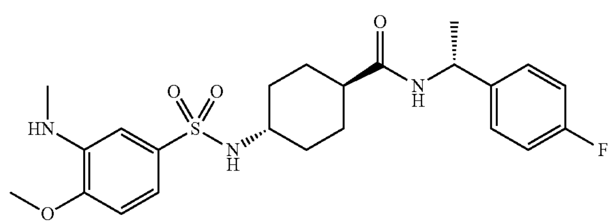 [SMILES: CNc1cc(S(=O)(=O)N[C@H]2CC[C@H](C(=O)N[C@H](C)c3ccc(F)cc3)CC2)ccc1OC] | Example 2A | 464.1 |
| 126 | 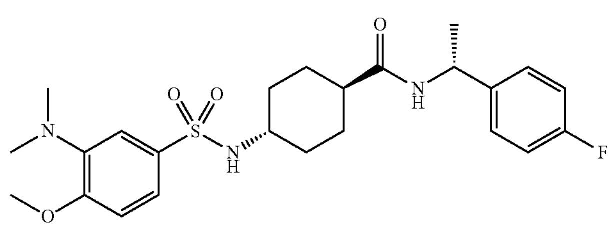 [SMILES: COc1ccc(S(=O)(=O)N[C@H]2CC[C@H](C(=O)N[C@H](C)c3ccc(F)cc3)CC2)cc1N(C)C] | Example 2A | 478.1 |
| 127 | 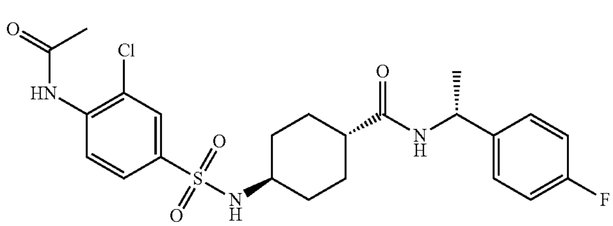 [SMILES: CC(=O)Nc1ccc(S(=O)(=O)N[C@H]2CC[C@H](C(=O)N[C@H](C)c3ccc(F)cc3)CC2)cc1Cl] | Example 2A | 496.0 |

| Example | Structure | Method of | MS |
|---|---|---|---|
| 128 | 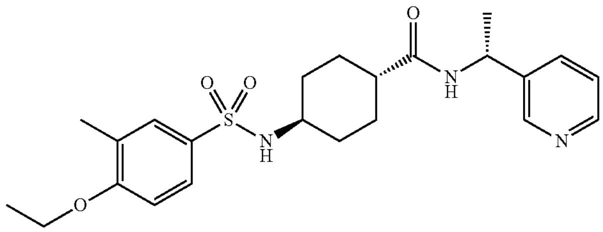 [SMILES: CCOc1ccc(S(=O)(=O)N[C@H]2CC[C@H](C(=O)N[C@H](C)c3cccnc3)CC2)cc1C] | 2A | 446.1 |
| 129 | 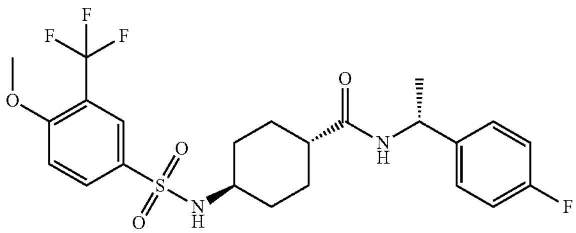 [SMILES: COc1ccc(S(=O)(=O)N[C@H]2CC[C@H](C(=O)N[C@H](C)c3ccc(F)cc3)CC2)cc1C(F)(F)F] | Example 2A | 503.0 |
| 130 | 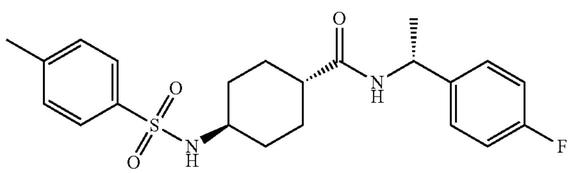 [SMILES: Cc1ccc(S(=O)(=O)N[C@H]2CC[C@H](C(=O)N[C@H](C)c3ccc(F)cc3)CC2)cc1] | Example 2A | 419.1 |
| 131 | 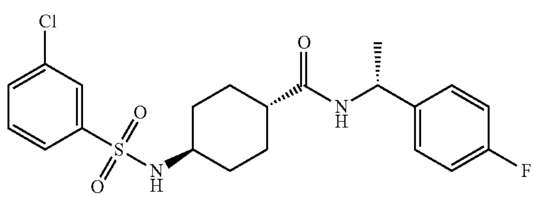 [SMILES: C[C@@H](NC(=O)[C@H]1CC[C@H](NS(=O)(=O)c2cccc(Cl)c2)CC1)c1ccc(F)cc1] | Example 2A | 439.0 |
| 132 | 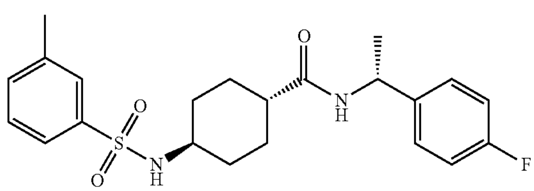 [SMILES: Cc1cccc(S(=O)(=O)N[C@H]2CC[C@H](C(=O)N[C@H](C)c3ccc(F)cc3)CC2)c1] | Example 2A | 419.1 |
| 133 | 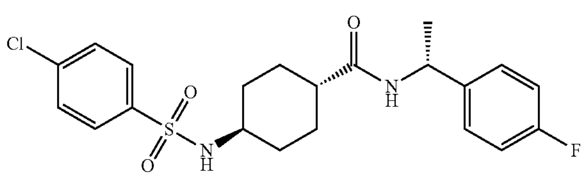 [SMILES: C[C@@H](NC(=O)[C@H]1CC[C@H](NS(=O)(=O)c2ccc(Cl)cc2)CC1)c1ccc(F)cc1] | Example 2A | 439.0 |
| 134 | 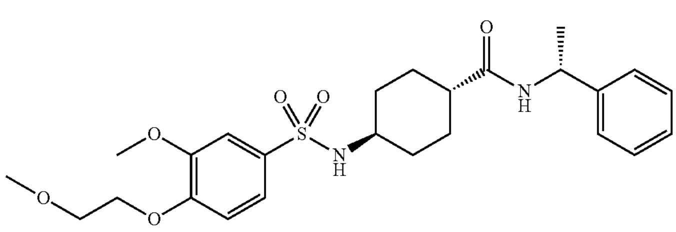 [SMILES: COCCOc1ccc(S(=O)(=O)N[C@H]2CC[C@H](C(=O)N[C@H](C)c3ccccc3)CC2)cc1OC] | Example 2A | 491.1 |

-continued

| Example | Structure | Method of | MS |
|---|---|---|---|
| 135 | 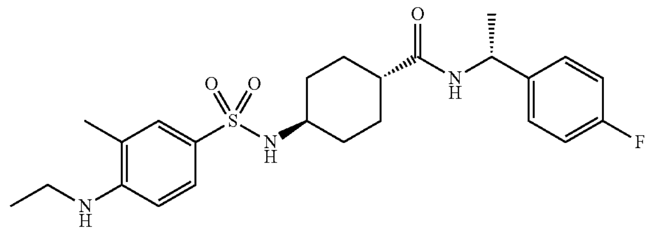 [SMILES: CCNc1ccc(S(=O)(=O)N[C@H]2CC[C@H](C(=O)N[C@H](C)c3ccc(F)cc3)CC2)cc1C] | Example 2A | 462.2 |
| 136 | 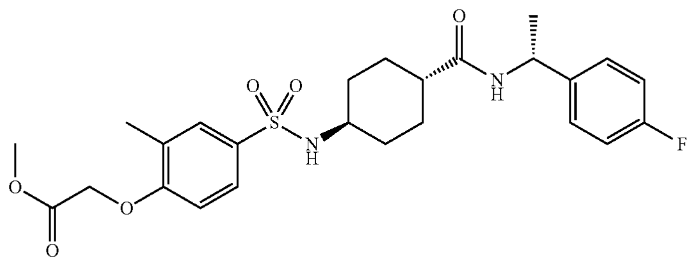 [SMILES: COC(=O)COc1ccc(S(=O)(=O)N[C@H]2CC[C@H](C(=O)N[C@H](C)c3ccc(F)cc3)CC2)cc1C] | Example 2A | 507.1 |
| 137 | 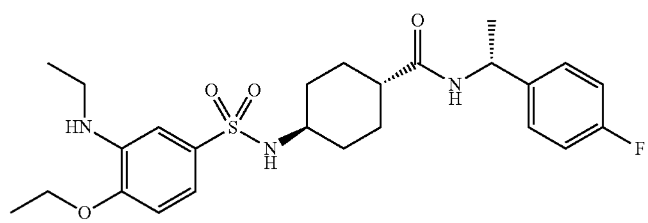 [SMILES: CCNc1cc(S(=O)(=O)N[C@H]2CC[C@H](C(=O)N[C@H](C)c3ccc(F)cc3)CC2)ccc1OCC] | Example 2A | 492.1 |
| 138 | 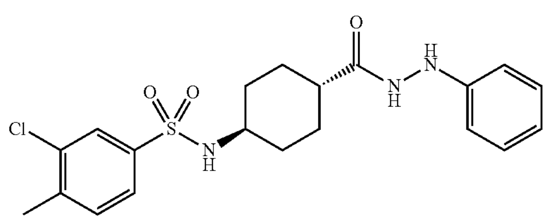 [SMILES: Cc1ccc(S(=O)(=O)N[C@H]2CC[C@H](C(=O)NNc3ccccc3)CC2)cc1Cl] | Example 1 | 422.1 |
| 139 | 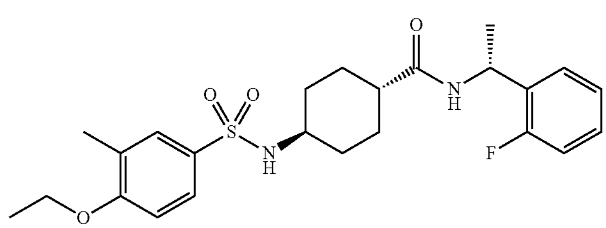 [SMILES: CCOc1ccc(S(=O)(=O)N[C@H]2CC[C@H](C(=O)N[C@H](C)c3ccccc3F)CC2)cc1C] | Example 1 | 463.3 |
| 140 | 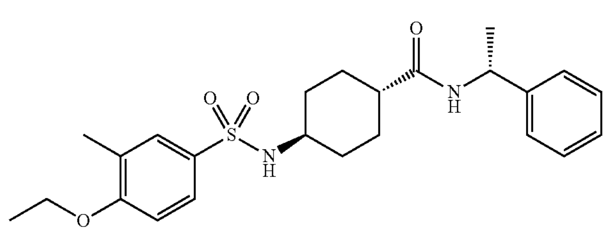 [SMILES: CCOc1ccc(S(=O)(=O)N[C@H]2CC[C@H](C(=O)N[C@H](C)c3ccccc3)CC2)cc1C] | Example 2A | 445.3 |

-continued

| Example | Structure | Method of | MS |
|---|---|---|---|
| 141 | 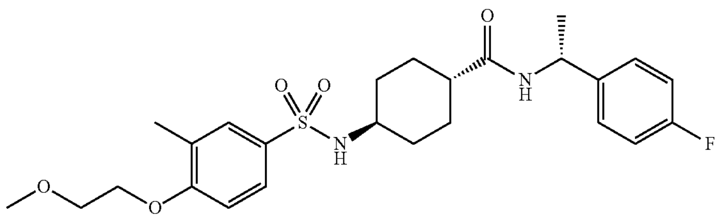 [SMILES: COCCOc1ccc(S(=O)(=O)N[C@H]2CC[C@H](C(=O)N[C@H](C)c3ccc(F)cc3)CC2)cc1C] | Example 2A | 475.3 |
| 142 | 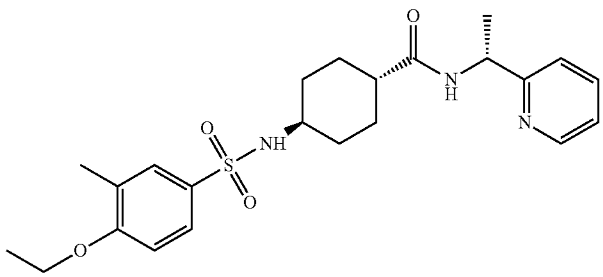 [SMILES: CCOc1ccc(S(=O)(=O)N[C@H]2CC[C@H](C(=O)N[C@H](C)c3ccccn3)CC2)cc1C] | Example 2A | — |
| 143 | 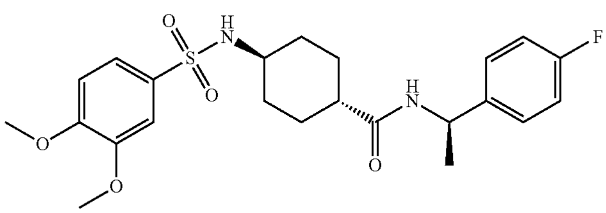 [SMILES: COc1ccc(S(=O)(=O)N[C@H]2CC[C@H](C(=O)N[C@H](C)c3ccc(F)cc3)CC2)cc1OC] | Example 2A | 465.0 |
| 144 | 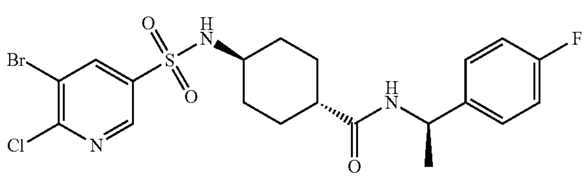 [SMILES: C[C@@H](NC(=O)[C@H]1CC[C@H](NS(=O)(=O)c2cnc(Cl)c(Br)c2)CC1)c1ccc(F)cc1] | Example 2A | 520.0 |
| 145 | 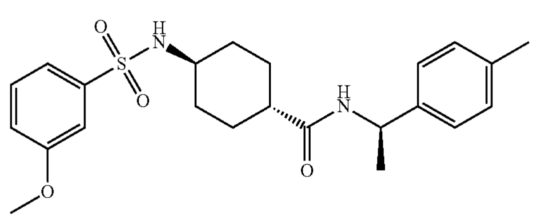 [SMILES: COc1cccc(S(=O)(=O)N[C@H]2CC[C@H](C(=O)N[C@H](C)c3ccc(C)cc3)CC2)c1] | Example 2A | 435.0 |
| 146 | 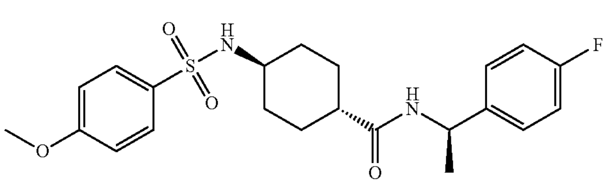 [SMILES: COc1ccc(S(=O)(=O)N[C@H]2CC[C@H](C(=O)N[C@H](C)c3ccc(F)cc3)CC2)cc1] | Example 2A | 435.0 |

-continued

| Example | Structure | Method of | MS |
|---|---|---|---|
| 147 | 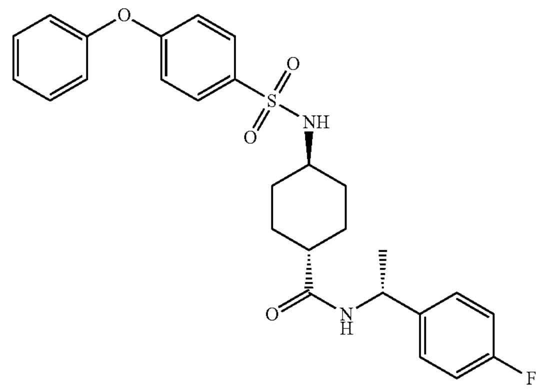 [SMILES: C[C@@H](NC(=O)[C@H]1CC[C@H](NS(=O)(=O)c2ccc(Oc3ccccc3)cc2)CC1)c1ccc(F)cc1] | Example 2A | 492.0 |
| 148 | 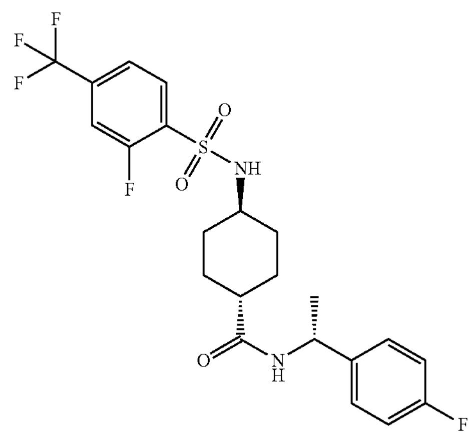 [SMILES: C[C@@H](NC(=O)[C@H]1CC[C@H](NS(=O)(=O)c2ccc(C(F)(F)F)cc2F)CC1)c1ccc(F)cc1] | Example 2A | 491.0 |
| 149 | 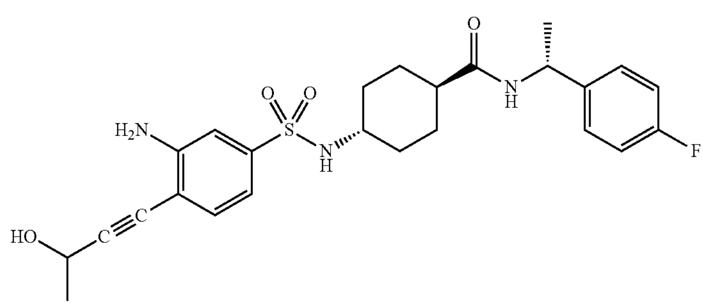 [SMILES: CC(O)C#Cc1ccc(S(=O)(=O)N[C@H]2CC[C@H](C(=O)N[C@H](C)c3ccc(F)cc3)CC2)cc1N] | Example 2A | — |
| 150 | 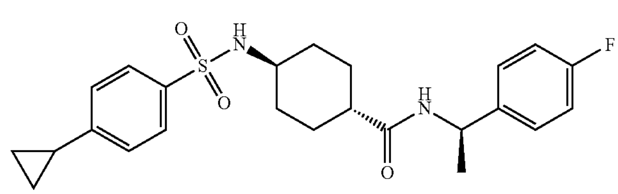 [SMILES: C[C@@H](NC(=O)[C@H]1CC[C@H](NS(=O)(=O)c2ccc(C3CC3)cc2)CC1)c1ccc(F)cc1] | Example 2A | 445.0 |
| 151 | 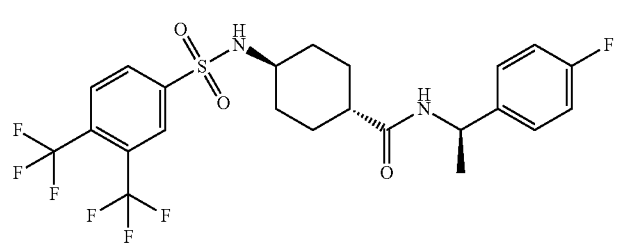 [SMILES: C[C@@H](NC(=O)[C@H]1CC[C@H](NS(=O)(=O)c2ccc(C(F)(F)F)c(C(F)(F)F)c2)CC1)c1ccc(F)cc1] | Example 2A | 541.0 |

| Example | Structure | Method of | MS |
|---|---|---|---|
| 152 | 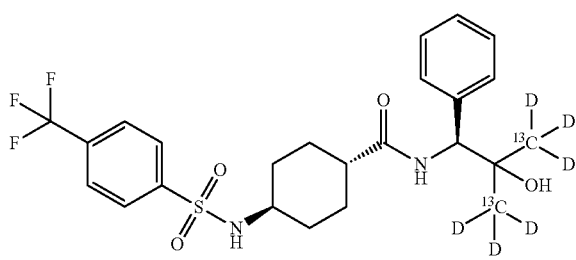 [SMILES: [2H][13C]([2H])([2H])C(O)([C@@H](NC(=O)[C@H]1CC[C@H](NS(=O)(=O)c2ccc(C(F)(F)F)cc2)CC1)c1ccccc1)[13C]([2H])([2H])[2H]] | Example 1 | 507.0 |
| 153 | 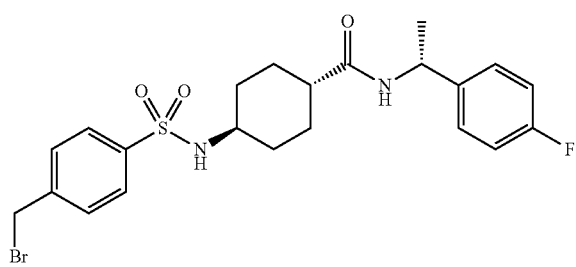 [SMILES: C[C@@H](NC(=O)[C@H]1CC[C@H](NS(=O)(=O)c2ccc(CBr)cc2)CC1)c1ccc(F)cc1] | Example 2A | 497.1 |
| 154 | 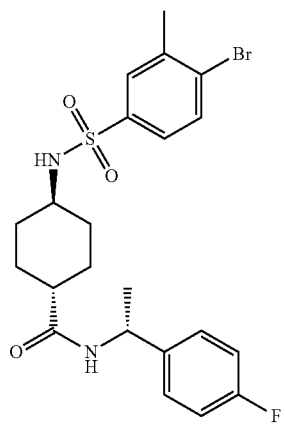 [SMILES: Cc1cc(S(=O)(=O)N[C@H]2CC[C@H](C(=O)N[C@H](C)c3ccc(F)cc3)CC2)ccc1Br] | Example 2A | [M + H] = 498.9 |
| 155 | 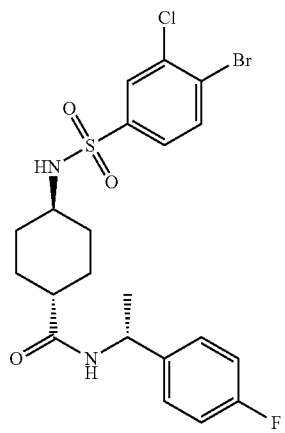 [SMILES: C[C@@H](NC(=O)[C@H]1CC[C@H](NS(=O)(=O)c2ccc(Br)c(Cl)c2)CC1)c1ccc(F)cc1] | Example 2A | [M + H] = 518.9 |

-continued

| Example | Structure | Method of | MS |
|---|---|---|---|
| 156 | 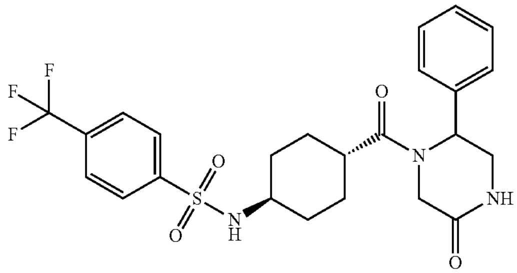 [SMILES: O=C1CN(C(=O)[C@H]2CC[C@H](NS(=O)(=O)c3ccc(C(F)(F)F)cc3)CC2)C(c2ccccc2)CN1] | Example 1 | 510.0 |
| 157 | 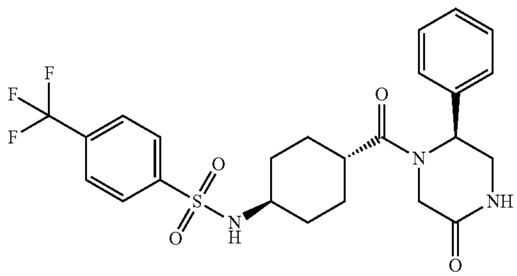 [SMILES: O=C1CN(C(=O)[C@H]2CC[C@H](NS(=O)(=O)c3ccc(C(F)(F)F)cc3)CC2)[C@@H](c2ccccc2)CN1] | Example 1 | 510.0 |
| 158 | 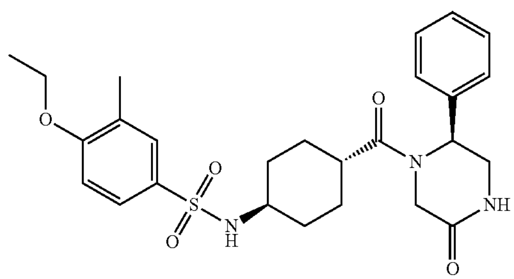 [SMILES: CCOc1ccc(S(=O)(=O)N[C@H]2CC[C@H](C(=O)N3CC(=O)NC[C@@H]3c3ccccc3)CC2)cc1C] | Example 1 | 500.0 |
| 159 | 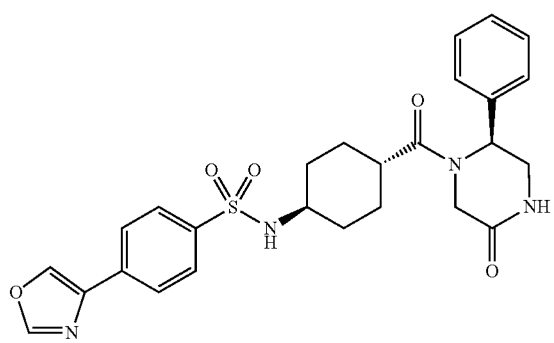 [SMILES: O=C1CN(C(=O)[C@H]2CC[C@H](NS(=O)(=O)c3ccc(-c4cocn4)cc3)CC2)[C@@H](c2ccccc2)CN1] | Example 1 | 509.3 |
| 160 | 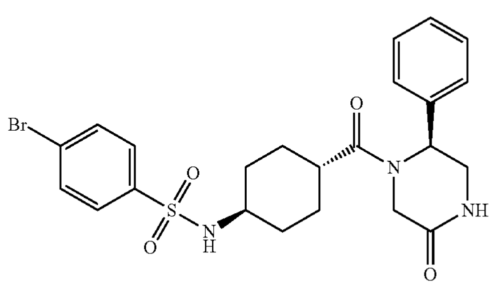 [SMILES: O=C1CN(C(=O)[C@H]2CC[C@H](NS(=O)(=O)c3ccc(Br)cc3)CC2)[C@@H](c2ccccc2)CN1] | Example 1 | 522.0 |

| Example | Structure | Method of | MS |
|---|---|---|---|
| 161 | 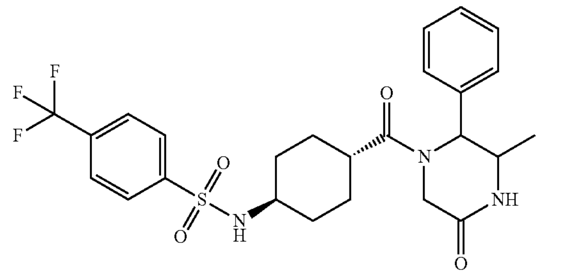 [SMILES: CC1NC(=O)CN(C(=O)[C@H]2CC[C@H](NS(=O)(=O)c3ccc(C(F)(F)F)cc3)CC2)C1c1ccccc1] | Example 1 | 524.0 |
| 162 | 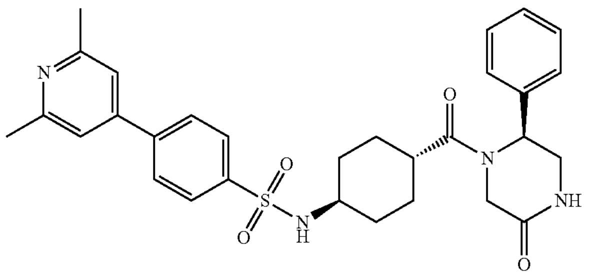 [SMILES: Cc1cc(-c2ccc(S(=O)(=O)N[C@H]3CC[C@H](C(=O)N4CC(=O)NC[C@@H]4c4ccccc4)CC3)cc2)cc(C)n1] | Example 1 | 547.0 |
| 163 | 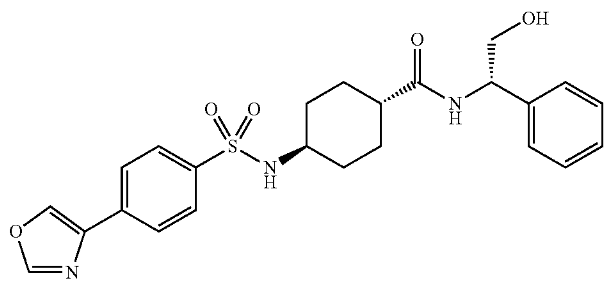 [SMILES: O=C(N[C@H](CO)c1ccccc1)[C@H]1CC[C@H](NS(=O)(=O)c2ccc(-c3cocn3)cc2)CC1] | Example 1 | 470.3 |
| 164 | 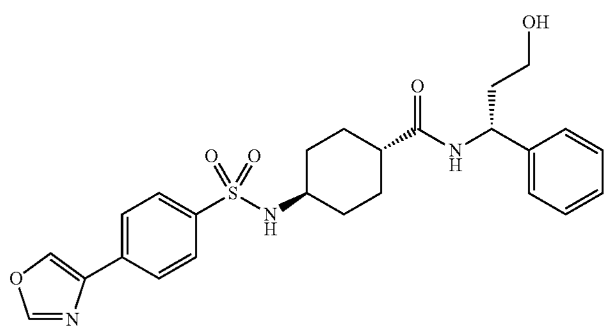 [SMILES: O=C(N[C@H](CCO)c1ccccc1)[C@H]1CC[C@H](NS(=O)(=O)c2ccc(-c3cocn3)cc2)CC1] | Example 1 | 484.2 |
| 165 | 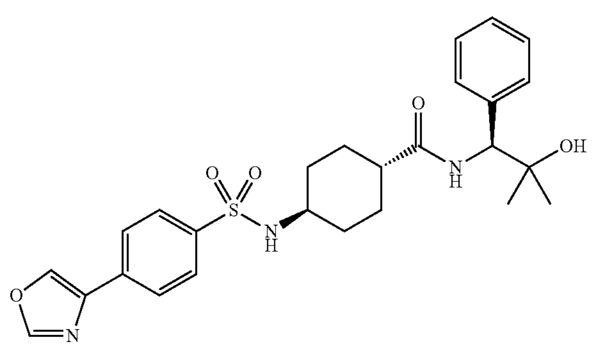 [SMILES: CC(C)(O)[C@@H](NC(=O)[C@H]1CC[C@H](NS(=O)(=O)c2ccc(-c3cocn3)cc2)CC1)c1ccccc1] | Example 1 | 498.3 |

-continued

| Example | Structure | Method of | MS |
|---|---|---|---|
| 166 | 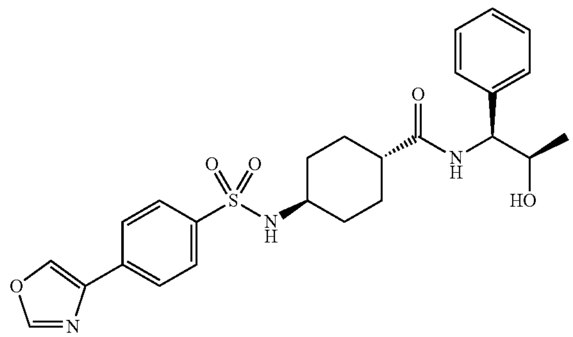 [SMILES: C[C@@H](O)[C@@H](NC(=O)[C@H]1CC[C@H](NS(=O)(=O)c2ccc(-c3cocn3)cc2)CC1)c1ccccc1] | Example 1 | 484.0 |
| 167 | 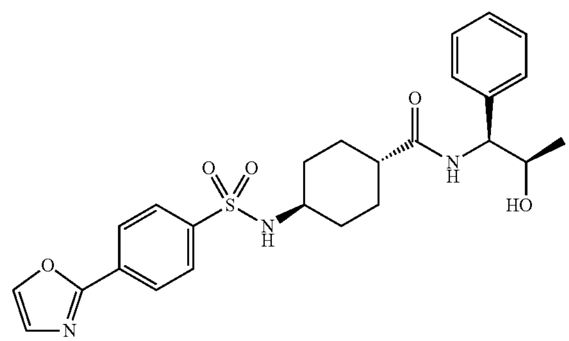 [SMILES: C[C@@H](O)[C@@H](NC(=O)[C@H]1CC[C@H](NS(=O)(=O)c2ccc(-c3ncco3)cc2)CC1)c1ccccc1] | Example 1 | 484.0 |
| 168 | 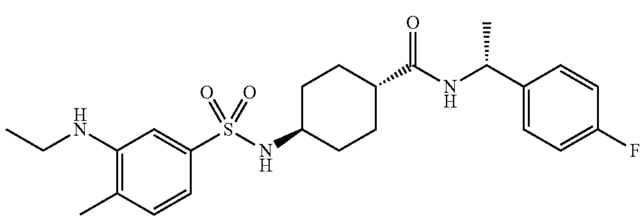 [SMILES: CCNc1cc(S(=O)(=O)N[C@H]2CC[C@H](C(=O)N[C@H](C)c3ccc(F)cc3)CC2)ccc1C] | Example 1 | 482.0 |
| 169 | 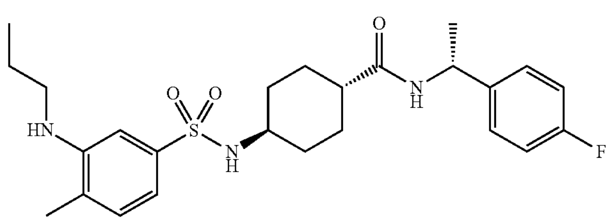 [SMILES: CCCNc1cc(S(=O)(=O)N[C@H]2CC[C@H](C(=O)N[C@H](C)c3ccc(F)cc3)CC2)ccc1C] | Example 1 | 476.1 |
| 170 | 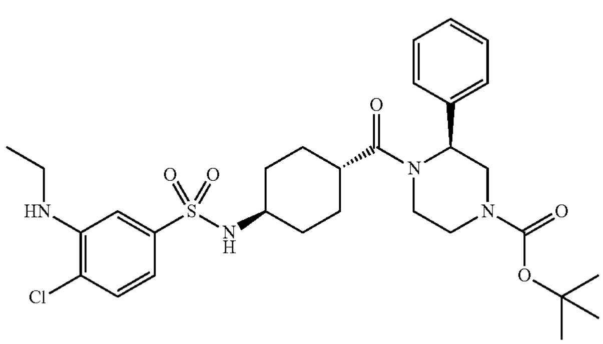 [SMILES: CCNc1cc(S(=O)(=O)N[C@H]2CC[C@H](C(=O)N3CCN(C(=O)OC(C)(C)C)C[C@@H]3c3ccccc3)CC2)ccc1Cl] | Example 1 | — |

Example 171

(1r,4S)—N-((1S,2R)-2-Hydroxy-1-phenylpropyl)-4-(4-(trifluoromethyl)phenylsulfonamido)cyclohexancarboxamide

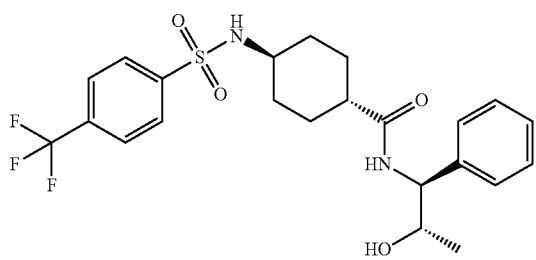 [SMILES: C[C@H](O)[C@@H](NC(=O)[C@H]1CC[C@H](NS(=O)(=O)c2ccc(C(F)(F)F)cc2)CC1)c1ccccc1]

(1r,4r)-4-(4-(Trifluoromethyl)phenylsulfonamido)-cyclohexancarboxylic acid (Intermediate 58, 5 g, 14 mmol) was suspended in DCM (150 ml), to which 2M oxalyl chloride solution (10.67 ml, 21 mmol) and 2 drops DMF were added. The reaction mixture was heated at 35° C. for 1 hr. The initial white, foamy suspension became a clear, light yellow solution (about 30-45 min). The reaction mixture was then cooled and concentrated to a light yellow waxy solid. This material was taken up in 30-40 ml DCM and added dropwise to a solution of the hydrochloride salt of (1S,2R)-1-amino-1-phenylpropan-2-ol (Intermediate 55, 2.67 g, 14 mmol) and DIPEA (7.36 g, 9.94 ml, 56 mmol) in 150 ml DCM at 0° C. Upon complete addition, the ice bath was removed and the reaction stirred 1 hr at room temperature. The reaction mixture was then concentrated and residue treated with ethyl acetate, then washed with 1M HCl (aq), then sat NaHCO$_3$ (aq), and brine. The combined organics were dried over MgSO$_4$, filtered and concentrated to afford a gummy solid. This material was purified via flash chromatography eluting with neat ethyl acetate to afford a white foam. This material was triturated with ether and filtered to afford a white powder (3.82 g, 50% yield).

$^1$H NMR (400 MHz, DMSO-d$_6$) δ ppm 0.97 (d, J=6.32 Hz, 3H) 1.09-1.31 (m, 4H) 1.54-1.70 (m, 4H) 2.09 (ddd, J=11.62, 8.46, 3.16 Hz, 1H) 2.95 (td, J=7.26, 3.66 Hz, 1H) 3.75 (d, J=6.06 Hz, 1H) 4.60 (d, J=5.56 Hz, 2H) 7.18 (td, J=5.49, 3.16 Hz, 1H) 7.23-7.28 (m, 4H) 7.94 (d, J=7.33 Hz, 1H) 7.96-8.04 (m, 5H)

M+H=485.3

Example 172

(R)-3-Phenyl-3-((1r,4R)-4-(4-(trifluoromethyl)phenylsulfonamido)cyclohexanecarboxamido)propanoic acid

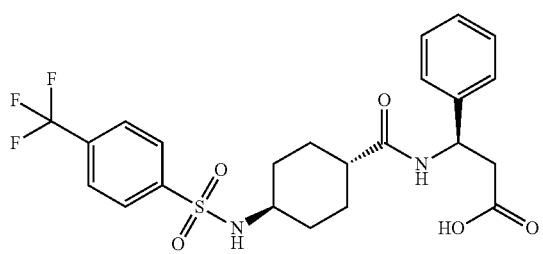 [SMILES: O=C(O)C[C@@H](NC(=O)[C@H]1CC[C@H](NS(=O)(=O)c2ccc(C(F)(F)F)cc2)CC1)c1ccccc1]

The title compound was prepared by treating Example 76 with aqueous NaOH using a method analogous to the method used to prepare Intermediate 58. MS 499.0.

Example 173

(S)-2,2-dimethyl-3-phenyl-3-((1r,4S)-4-(4-(trifluoromethyl)phenylsulfonamido)cyclohexanecarboxamido)propanoic acid

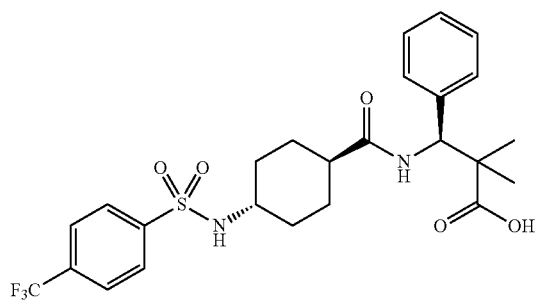 [SMILES: CC(C)(C(=O)O)[C@@H](NC(=O)[C@H]1CC[C@H](NS(=O)(=O)c2ccc(C(F)(F)F)cc2)CC1)c1ccccc1]

The title compound was prepared by treating Example 84 with aqueous using a method analogous to the method used to prepare Intermediate 58. MS MH+ 527.2

Example 174

(1r,4S)—N—((S)-3-Hydroxy-2,2-dimethyl-1-phenylpropyl)-4-(4-(trifluoromethyl)phenylsulfonamido)cyclohexanecarboxamide

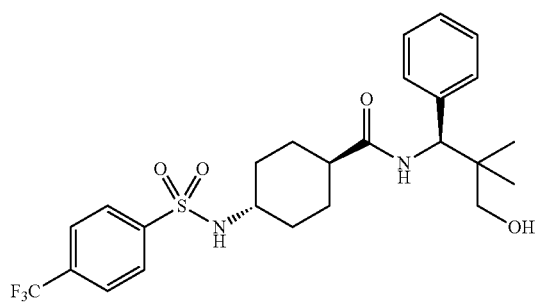 [SMILES: CC(C)(CO)[C@@H](NC(=O)[C@H]1CC[C@H](NS(=O)(=O)c2ccc(C(F)(F)F)cc2)CC1)c1ccccc1]

The title compound was prepared by reducing Example 173 with LiAlH$_4$.

Examples 175 and 176 in the table below were prepared by stirring the indicated starting material with concentrated HBr in acetic acid and then evaporate to dryness.

| Example | Structure | S.M. | MS MH+ |
|---|---|---|---|
| 175 | 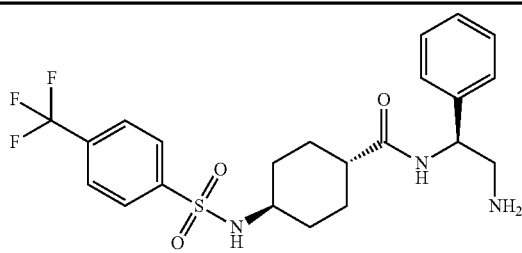 | Example 68 | 470.0 |
| 176 | 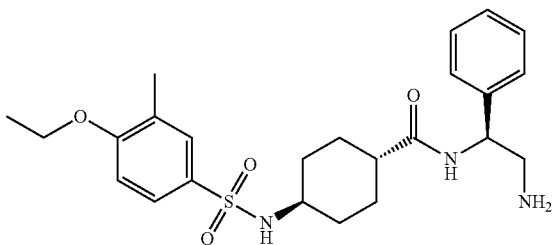 [SMILES: CCOc1ccc(S(=O)(=O)N[C@H]2CC[C@H](C(=O)N[C@H](CN)c3ccccc3)CC2)cc1C] | Example 69 | 460.0 |

Example 177

4-Chloro-3-ethylamino-N-[trans-4-((S)-2-phenyl-piperazine-1-carbonyl)cyclohexyl]benzenesulfonamide

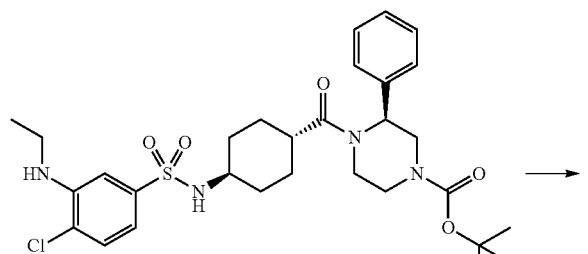

→

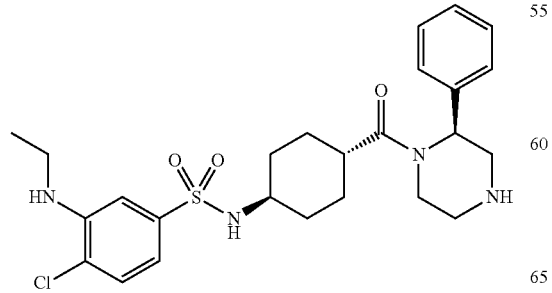

(S)-tert-Butyl 4-(trans-4-(4-chloro-3-(ethylamino)phenyl-sulfonamido)cyclo-hexanecarbonyl)-3-phenylpiperazine-1-carboxylate (Example 1, 77 mg, 0.127 mmol) was stirred in 20% v/v TFA/DCM overnight. The reaction was dilutee with DCM and water and the pH was adjusted to 13 with 1N NaOH. The layers were separated, and the organic layer was concentrated and chromatographed on reverse phase Phenomenex Gemini Axia C18 30×100 mm column using a gradient of 15-100% AcCN in water containing 5 mM ammonium hydroxide. The product was lyophilized to yield the title compound (31.5 mg, 0.62 mmol). MS MH+ 505.4.

The compounds in the Table below were prepared by a method analogous to the Boc deprotection as described in Example 177 from the appropriate Boc protected starting material.

| Example | Structure | MS |
|---------|-----------|-----|
| 178 | 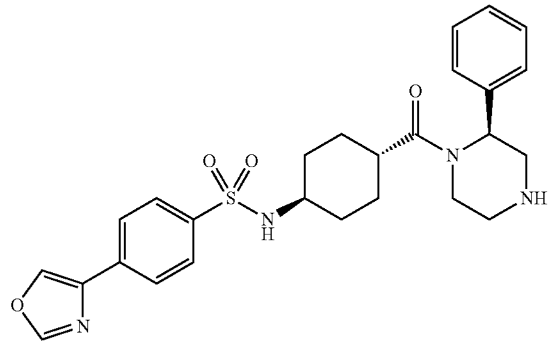 [SMILES: O=C([C@H]1CC[C@H](NS(=O)(=O)c2ccc(-c3cocn3)cc2)CC1)N1CCNC[C@@H]1c1ccccc1] | 495.2 |
| 179 | 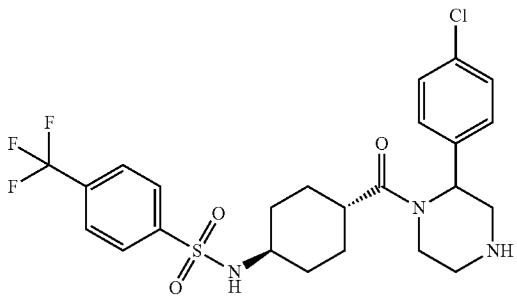 [SMILES: O=C([C@H]1CC[C@H](NS(=O)(=O)c2ccc(C(F)(F)F)cc2)CC1)N1CCNCC1c1ccc(Cl)cc1] | 530.0 |
| 180 | 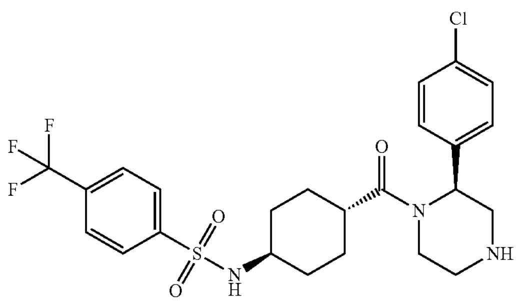 [SMILES: O=C([C@H]1CC[C@H](NS(=O)(=O)c2ccc(C(F)(F)F)cc2)CC1)N1CCNC[C@@H]1c1ccc(Cl)cc1] | 530.0 |
| 181 | 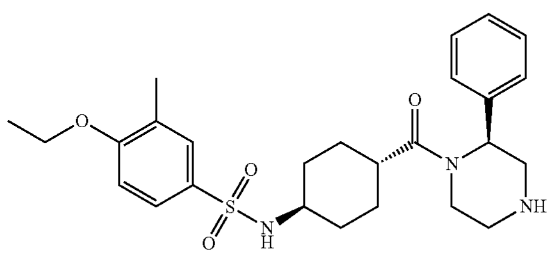 [SMILES: CCOc1ccc(S(=O)(=O)N[C@H]2CC[C@H](C(=O)N3CCNC[C@@H]3c3ccccc3)CC2)cc1C] | 486.0 |
| 182 | 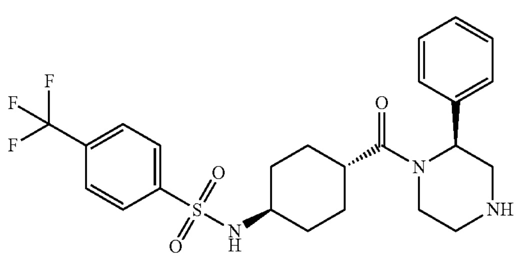 [SMILES: O=C([C@H]1CC[C@H](NS(=O)(=O)c2ccc(C(F)(F)F)cc2)CC1)N1CCNC[C@@H]1c1ccccc1] | 496.0 |

-continued

| Example | Structure | MS |
|---|---|---|
| 183 | 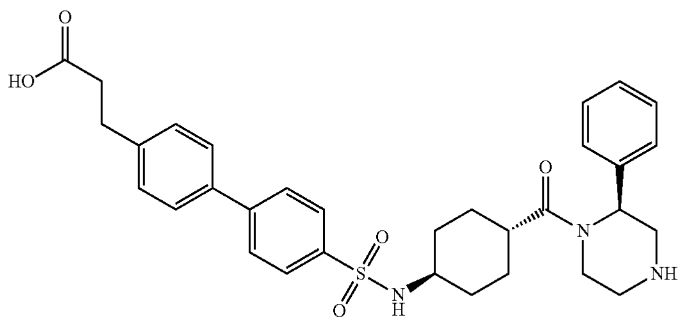 [SMILES: O=C(O)CCc1ccc(-c2ccc(S(=O)(=O)N[C@H]3CC[C@H](C(=O)N4CCNC[C@@H]4c4ccccc4)CC3)cc2)cc1] | 576.0 |
| 184 | 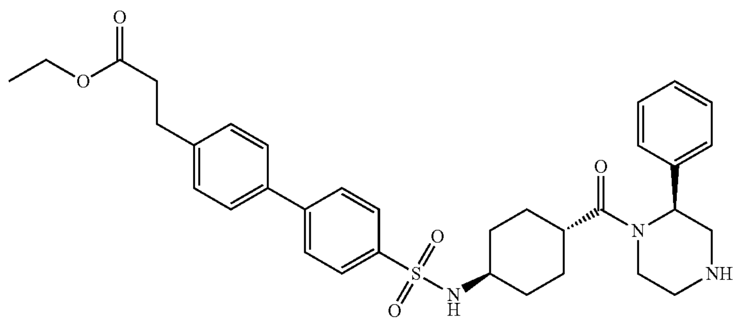 [SMILES: CCOC(=O)CCc1ccc(-c2ccc(S(=O)(=O)N[C@H]3CC[C@H](C(=O)N4CCNC[C@@H]4c4ccccc4)CC3)cc2)cc1] | 605.0 |
| 185 | 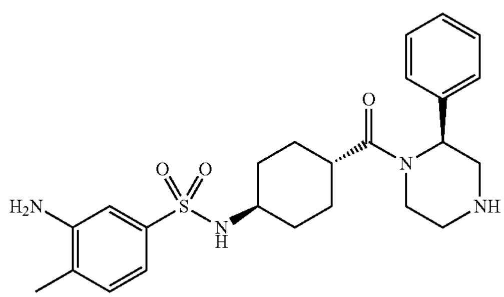 [SMILES: Cc1ccc(S(=O)(=O)N[C@H]2CC[C@H](C(=O)N3CCNC[C@@H]3c3ccccc3)CC2)cc1N] | 457.2 |
| 186 | 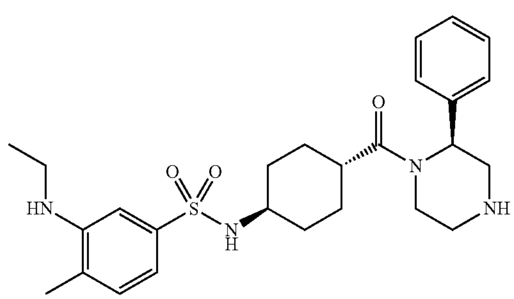 [SMILES: CCCNc1cc(S(=O)(=O)N[C@H]2CC[C@H](C(=O)N3CCNC[C@@H]3c3ccccc3)CC2)ccc1C] | 485.4 |
| 187 | 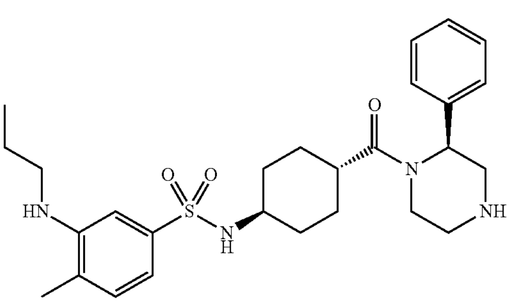 | 499.4 |

-continued

| Example | Structure | MS |
|---|---|---|
| 188 | 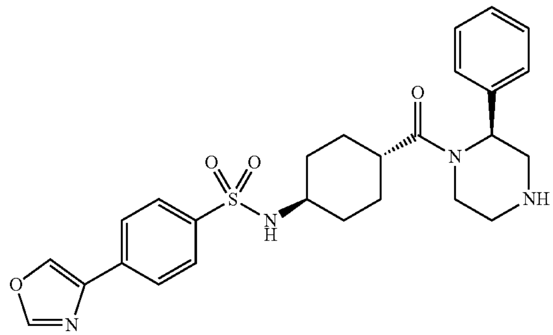 [SMILES: O=C([C@H]1CC[C@H](NS(=O)(=O)c2ccc(-c3cocn3)cc2)CC1)N1CCNC[C@@H]1c1ccccc1] | 495.2 |
| 189 | 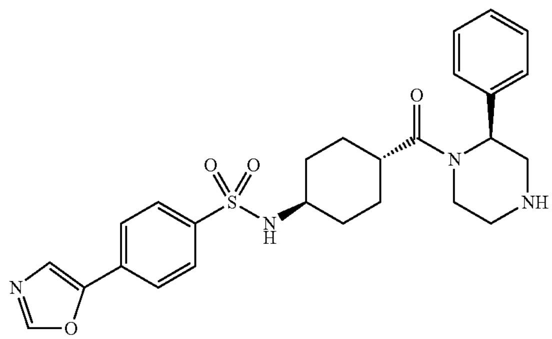 | 495.2 |
| 190 | 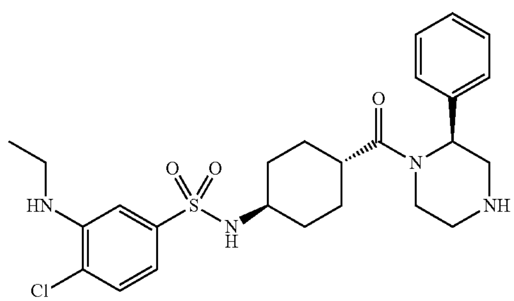 [SMILES: CCNc1cc(S(=O)(=O)N[C@H]2CC[C@H](C(=O)N3CCNC[C@@H]3c3ccccc3)CC2)ccc1Cl] | 505.4 |
| 191 | 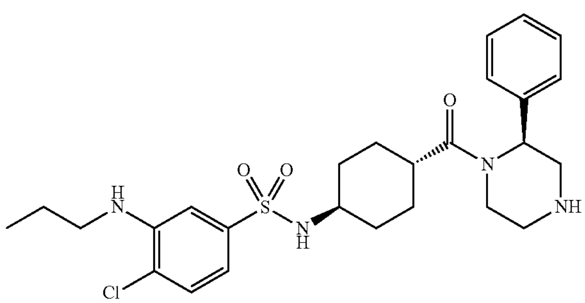 [SMILES: CCCNc1cc(S(=O)(=O)N[C@H]2CC[C@H](C(=O)N3CCNC[C@@H]3c3ccccc3)CC2)ccc1Cl] | 519.4 |
| 192 | 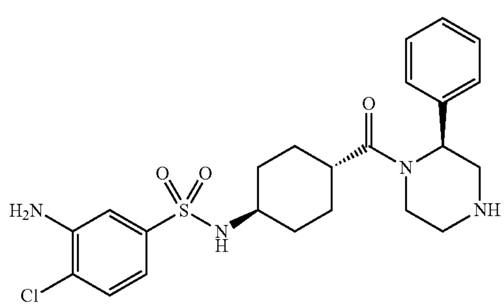 [SMILES: Nc1cc(S(=O)(=O)N[C@H]2CC[C@H](C(=O)N3CCNC[C@@H]3c3ccccc3)CC2)ccc1Cl] | 477.1 |

| Example | Structure | MS |
|---|---|---|
| 193 | 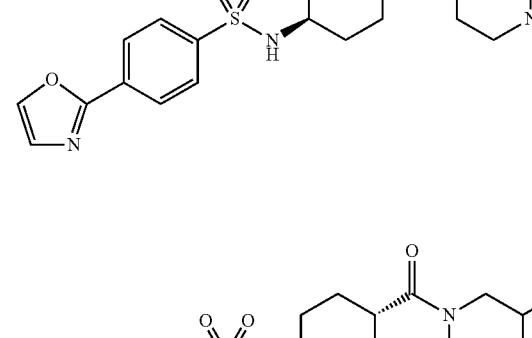 | 495.0 |
| 194 | 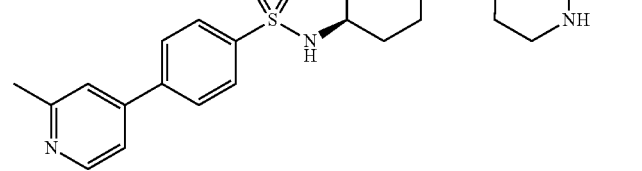 | 511.4 |
| 195 | 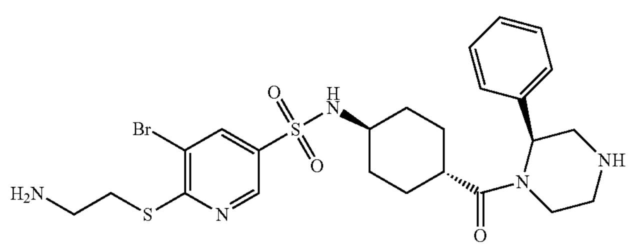 [SMILES: NCCSc1ncc(S(=O)(=O)N[C@H]2CC[C@H](C(=O)N3CCNC[C@@H]3c3ccccc3)CC2)cc1Br] | — |
| 196 | 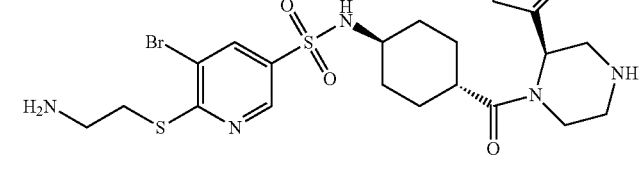 | 548.0 |
| 197 | 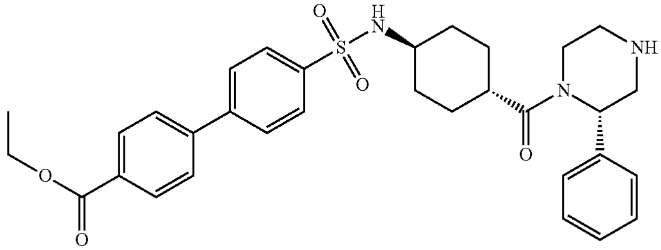 [SMILES: CCOC(=O)c1ccc(-c2ccc(S(=O)(=O)N[C@H]3CC[C@H](C(=O)N4CCNC[C@@H]4c4ccccc4)CC3)cc2)cc1] | 576.0 |

-continued

| Example | Structure | MS |
|---|---|---|
| 198 | 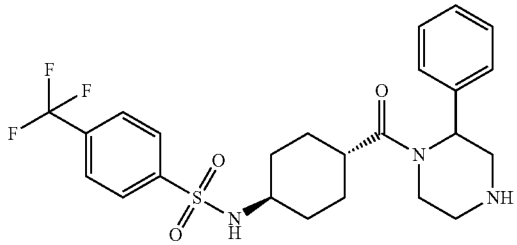 [SMILES: O=C([C@H]1CC[C@H](NS(=O)(=O)c2ccc(C(F)(F)F)cc2)CC1)N1CCNCC1c1ccccc1] | 496.0 |
| 199 | 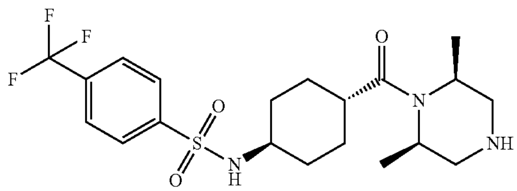 [SMILES: C[C@@H]1CNC[C@H](C)N1C(=O)[C@H]1CC[C@H](NS(=O)(=O)c2ccc(C(F)(F)F)cc2)CC1] | 448.2 |
| 200 | 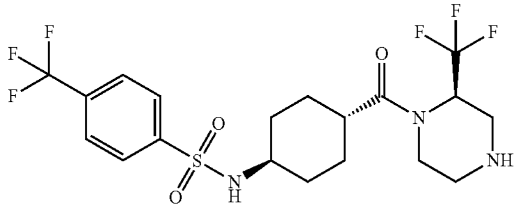 [SMILES: O=C([C@H]1CC[C@H](NS(=O)(=O)c2ccc(C(F)(F)F)cc2)CC1)N1CCNC[C@@H]1C(F)(F)F] | 488.1 |

Example 201

N-(trans-4-((S)-2-oxo-4-phenyloxazolidine-3-carbonyl)cyclohexyl)-4-(trifluoromethyl)benzenesulfonamide

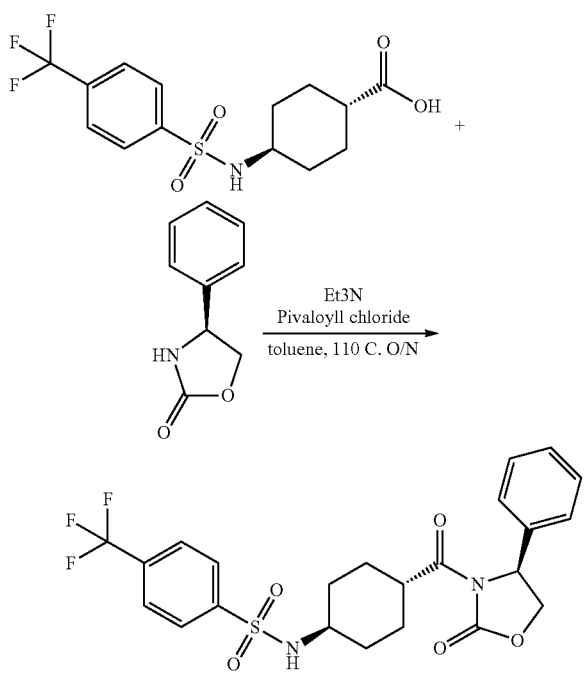

To a mixture of trans-4-(4-(trifluoromethyl)phenylsulfonamido)cyclohexanecarboxylic acid (Intermediate 18, 110 mg, 0.313 mmol,), (S)-4-phenyloxazolidin-2-one (25.5 mg, 0.157 mmol) in toluene (2 ml) was added triethylamine (0.087 ml, 0.626 mmol). The mixture was heated to 80° C. to obtain a solution. Pivaloyl chloride (0.039 ml, 0.313 mmol) in toluene (1 ml) was added to the reaction mixture, and it was heated to 110° C. with stirring for 18 hr. The reaction mixture was then diluted with 1M HCl and extracted with DCM. The DCM layer was dried (MgSO$_4$), then filtered and concentrated in vacuo to a tanned solid. The crude material was purified via normal phase chromatography on biotage SP1, using 25+M column and a calculated gradient from 50% EtOAc in heptane, to yield the title compound as a white solid (8 mg, 10%). MS MH$^+$ 497.2

Example 202

N-trans-4-((S)-4-Isopropyl-2-oxooxazolidine-3-carbonyl)cyclohexyl-4-(trifluoromethyl)benzenesulfonamide The title compound was prepared by a method analogous to the method used to prepare Example 138 using trans-4-(4-(trifluoromethyl)phenylsulfonamido)cyclohexanecarboxylic acid (Intermediate 18) and (S)-4-isopropyloxazolidin-2-one as the starting material. MS MH$^+$463.1

Example 203

Trans-4-(4-aminophenylsulfonamido)-N—((R)-1-(4-fluorophenyl)ethylcyclohexanecarboxamide

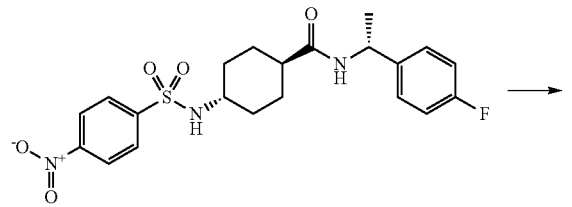

Trans-4-(4-nitro-benzenesulfonylamino)-cyclohexanecarboxylic acid [(R)-1-(4-fluoro-phenyl)-ethyl]-amide (Example 113, 0.3 g, 0.667 mmol) was suspended in EtOH (15 ml), to which ammonium formate (0.253 g, 4.0 mmol) and then Pd/C (0.15 g) were added. The reaction mixture was heated under reflux for 2 hours, at which point LC-MS showed one peak corresponding to desired product. The reaction mixture was filtered through celite and the filtrate was concentrated to afford the title compound as a white solid (0.249 g-89% yield).

The compounds in the Table below were prepared by a method analogous to the method used to prepare Example 203 using the starting materials indicated.

| Example | Structure | S.M. | MS MH+ |
|---|---|---|---|
| 204 | 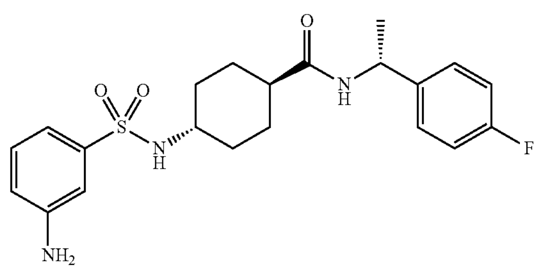 [SMILES: C[C@@H](NC(=O)[C@H]1CC[C@H](NS(=O)(=O)c2cccc(N)c2)CC1)c1ccc(F)cc1] | Example 74 | — |
| 205 | 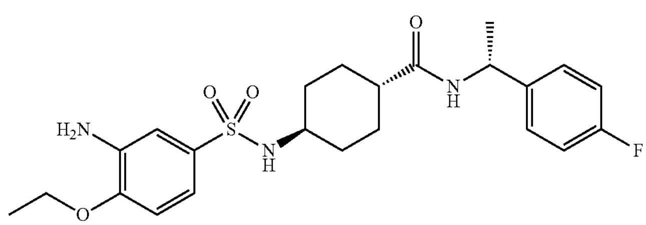 [SMILES: CCOc1ccc(S(=O)(=O)N[C@H]2CC[C@H](C(=O)N[C@H](C)c3ccc(F)cc3)CC2)cc1N] | Example 225 | 464.1 |
| 206 | 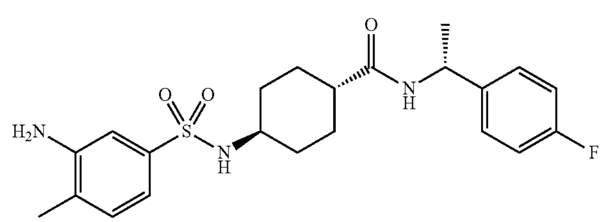 [SMILES: Cc1ccc(S(=O)(=O)N[C@H]2CC[C@H](C(=O)N[C@H](C)c3ccc(F)cc3)CC2)cc1N] | Example 108 | 434.1 |
| 207 | 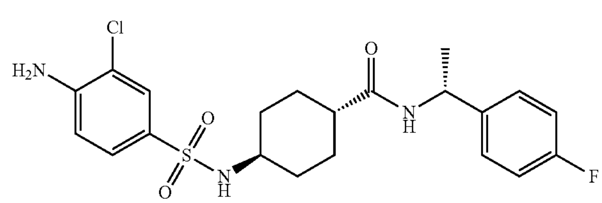 [SMILES: C[C@@H](NC(=O)[C@H]1CC[C@H](NS(=O)(=O)c2ccc(N)c(Cl)c2)CC1)c1ccc(F)cc1] | Example 106 | — |

| Example | Structure | S.M. | MS MH+ |
|---|---|---|---|
| 208 | 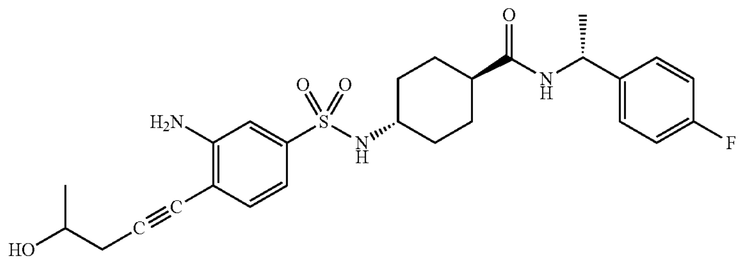 [SMILES: CC(O)CC#Cc1ccc(S(=O)(=O)N[C@H]2CC[C@H](C(=O)N[C@H](C)c3ccc(F)cc3)CC2)cc1N] | Example 79 | — |
| 209 | 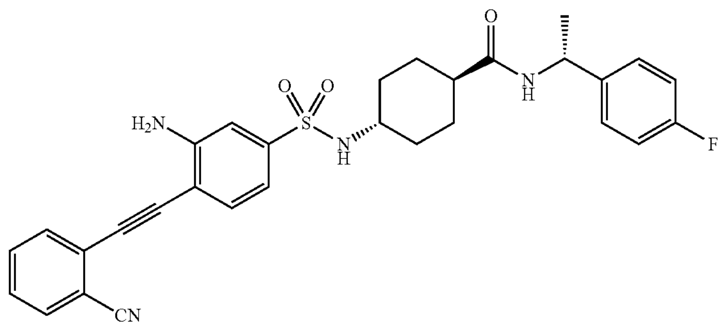 | Example 78 | — |
| 210 | 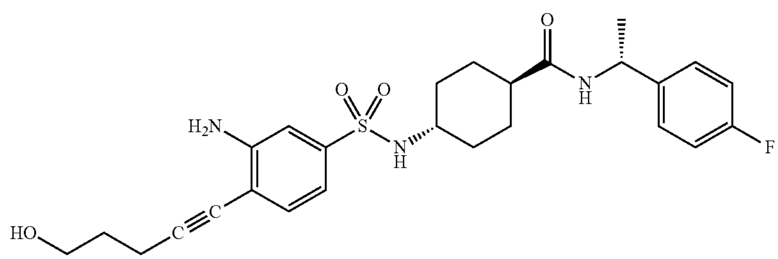 [SMILES: C[C@@H](NC(=O)[C@H]1CC[C@H](NS(=O)(=O)c2ccc(C#CCCCO)c(N)c2)CC1)c1ccc(F)cc1] | Example 81 | — |

Example 211

Methyl trans-5-(N-(trans-4-((R)-1-(4-fluorophenyl)ethylcarbamoyl)cyclohexyl)sulfamoyl)-2-methylphenylcarbamate

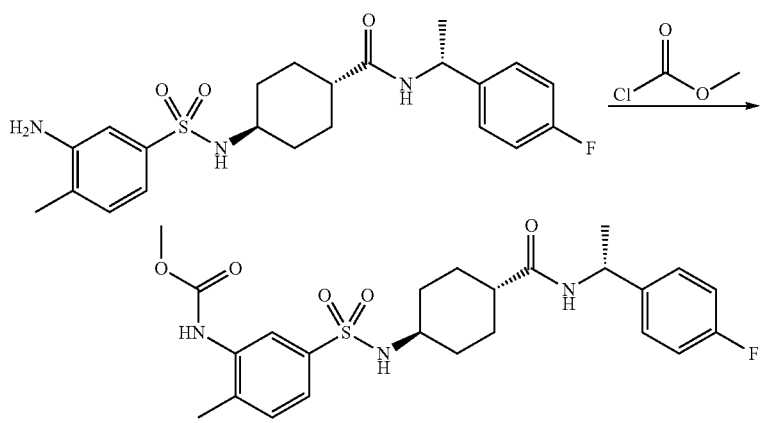

Methyl chloroformate (13.08 mg, 0.138 mmol) was added to 0° C. solution of trans-4-(3-amino-4-methyl-benzenesulfonylamino)-cyclohexanecarboxylic acid [(R)-1-(4-fluoro-phenyl)-ethyl]-amide (Example 206, 50 mg, 0.115 mmol) and pyridine (12.13 μl, 0.150 mmol) in DCM. The reaction was stirred for five minutes then the cooling bath was removed and the reaction was allowed to stir at room temperature 16 hours. The reaction was concentrated to a residue which was diluted with ethyl acetate. The ethyl acetate solution was washed successively with 1N HCl, saturated sodium bicarbonate, and brine then the organic layer was dried over sodium sulfate, filtered and concentrated to yield the title compound (27 mg). MS MH+ 492.1

Examples 212 and 213 were prepared using standard amide forming conditions from the starting materials indicated.

| Ex. | Structure | S.M. | MS |
|---|---|---|---|
| 212 | 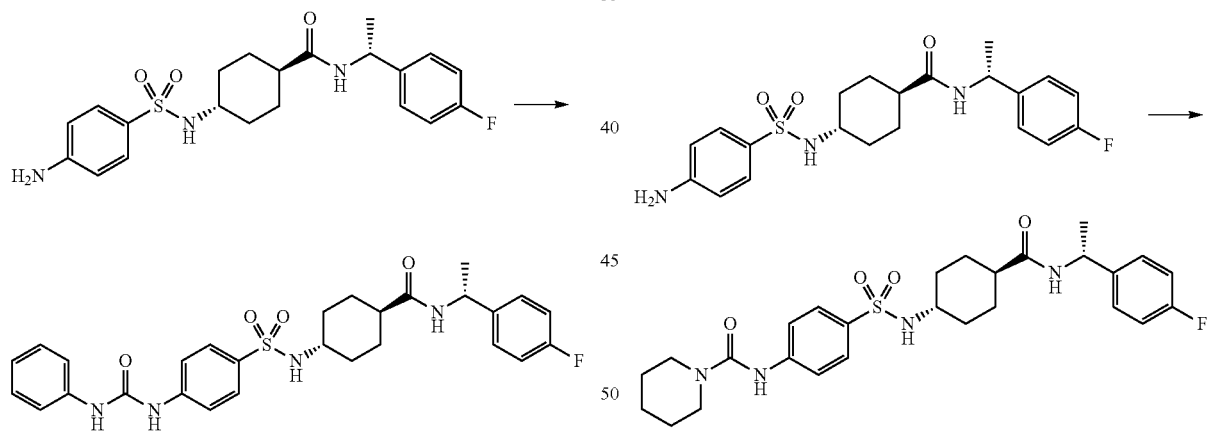 | Example 205 | 462.3 |
| 213 | 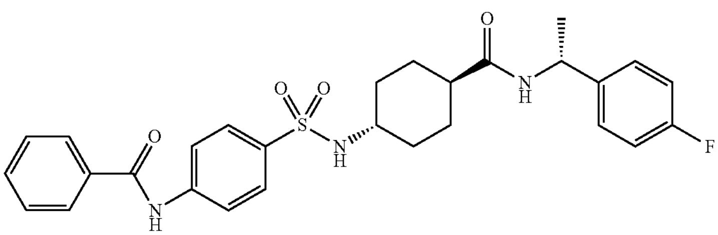 [SMILES: C[C@@H](NC(=O)[C@H]1CC[C@H](NS(=O)(=O)c2ccc(NC(=O)c3ccccc3)cc2)CC1)c1ccc(F)cc1] | Example 205 | 524.4 |

Example 214

Trans-N—((R)-1-(4-fluorophenyl)ethyl)-4-(4-phenylureido)phenylsulfonamido)cyclohexanecarboxamide Trans-4-(4-aminophenylsulfonamido)-N—((R)-1-(4-fluorophenyl)ethylcyclohexane-carboxamide (Example 203, 0.045 g, 0.107 mmol) was dissolved in DCM (5 ml), to which DIPEA (0.037 ml, 0.215 mmol) and then phenyl isocyanate (0.011 ml, 0.107 mmol) were added. The reaction mixture was stirred at room temperature for 1 hour, after which LC-MS showed one major peak corresponding to desired product. The reaction mixture was concentrated and the residue was purified via Biotage automated flash column chromatography (12M, eluting with 10-100% EtOAc/Hept). Relevant fractions were pooled and concentrated to afford the title compound as a tan solid (0.01266 g—15% yield). MS MH+ 539.4

Example 215

N-(4-(N-(Trans-4-((R)-1-(4-fluorophenyl)ethylcarbamoyl)cyclo-hexyl)sulfamoyl)phenyl)piperidine-1-carboxamide Triphosgene (0.011 g, 0.0357 mmol) was dissolved in dioxane (5 ml), to which a solution of trans-4-(4-aminophenylsulfonamido)-N—((R)-1-(4-fluorophenyl)ethylcyclohexane-carboxamide (Example 203, 0.05 g, 0.119 mmol) and DIPEA (0.041 ml, 0.238 mmol) in dioxane (5 ml) was added. The reaction mixture was stirred at room temperature for 5 mins, after which piperidine (0.012 ml, 0.119 mmol) was added, and the mixture was heated under reflux overnight. LC-MS indicated one major peak corresponding to desired product, and the reaction mixture was concentrated to a residue. The residue was purified via prep HPLC (10-80-100% ACN/water/0.1% TFA) and relevant fractions were frozen and lyophilized to afford the title compound as a white powder (0.00475 g—10% yield). MS MH+531.2

The following urea derivatives were prepared by a method analogous to the method used to prepare Example 214 or 215 using the starting material indicated.

| Example | Structure | S.M. | MS |
|---|---|---|---|
| 216 | 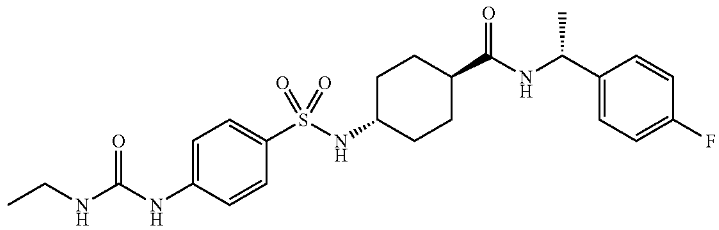 [SMILES: CCNC(=O)Nc1ccc(S(=O)(=O)N[C@H]2CC[C@H](C(=O)N[C@H](C)c3ccc(F)cc3)CC2)cc1] | Example 204 & ethyl isocyanate | 491.1 |
| 217 | 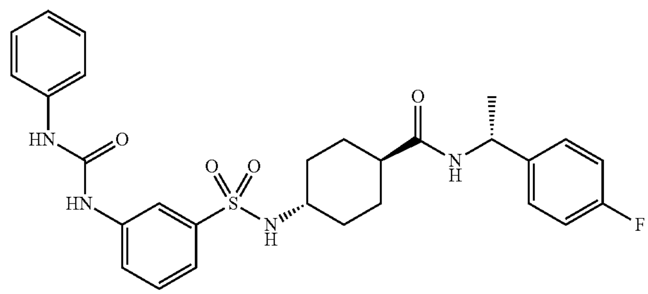 [SMILES: C[C@@H](NC(=O)[C@H]1CC[C@H](NS(=O)(=O)c2cccc(NC(=O)Nc3ccccc3)c2)CC1)c1ccc(F)cc1] | Example 205 & phenyl isocyanate | 539.2 |
| 218 | 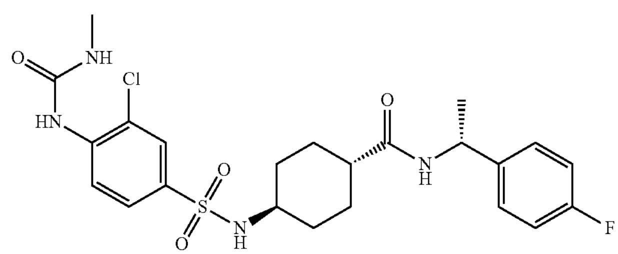 [SMILES: CNC(=O)Nc1ccc(S(=O)(=O)N[C@H]2CC[C@H](C(=O)N[C@H](C)c3ccc(F)cc3)CC2)cc1Cl] | Example 207 & methyl isocyanate | 478.1 |
| 219 | 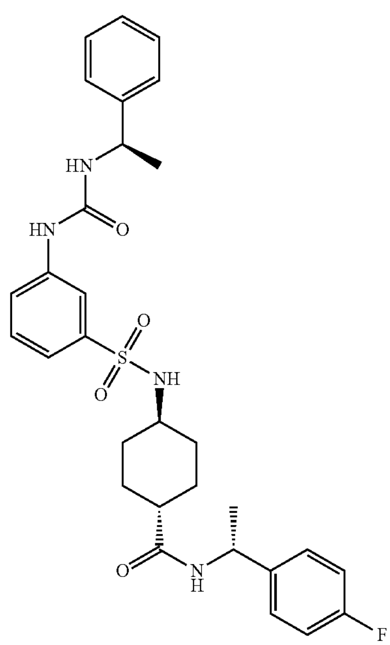 [SMILES: C[C@@H](NC(=O)Nc1cccc(S(=O)(=O)N[C@H]2CC[C@H](C(=O)N[C@H](C)c3ccc(F)cc3)CC2)c1)c1ccccc1] | Example 205, phosgene & (R)-1-phenyl-ethanamine | 567.0 |

Example 220

Trans-4-(4-Cyclopentyloxy-3-methoxy-benzene-sulfonylamino)-cyclohexanecarboxylic acid [(R)-1-(4-fluoro-phenyl)-ethyl]-amide

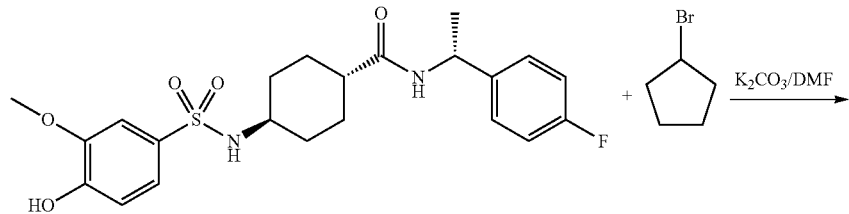

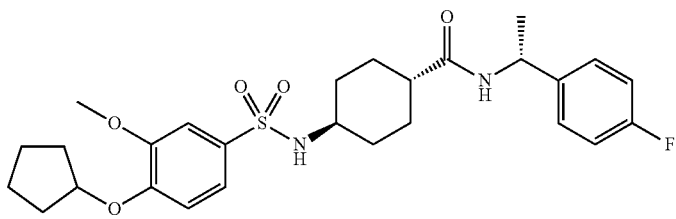

Cyclopentylbromide (10.45 mg, 0.07 mmol) was added to solution of trans-4-(4-hydroxy-3-methoxy-benzenesulfonylamino)-cyclohexanecarboxylic acid [(R)-1-(4-fluoro-phenyl)-ethyl]-amide (Example 2, 31.6 mg, 0.07 mmol) and potassium carbonate (19.4 mg, 0.14 mmol) in dimethylformamide (700 ul). The reaction was heated 50° C. for 16 h, cooled to room temperature, diluted with ethyl acetate and rinsed with 1:1 water:brine. The organic layer was concentrated and purified by reverse-phase chromatography followed by lyophilization to yield title compound (18 mg, 0.035 mmol). MS MH$^+$ 519.1

Example 221

Trans-N—((R)-1-(4-Fluorophenyl)ethyl)-4-(4-isopropoxy-3-methoxyphenylsulfonamido)cyclohexanecarboxamide

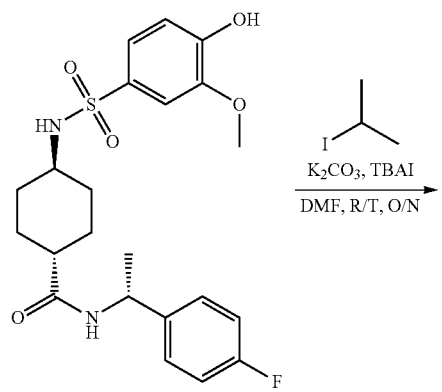

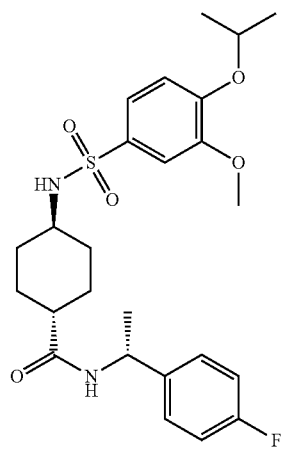

Trans-N—((R)-1-(4-Fluorophenyl)ethyl)-4-(4-hydroxy-3-methoxyphenylsulfonamido)cyclohexanecarboxamide (Example 2, 14 mg, 0.031 mmol), 2-iodopropane (4 ul, 0.037 mmol), $K_2CO_3$ (21 mg, 0.155 mmol) and tetrabutylammonium iodide (TBAI, 3 mg, cat) were dissolved in DMF (0.5 ml) and the reaction was stirred at room temperature for 15 hr under nitrogen. LCMS indicated that the reaction was complete, and the crude material was purified via reverse phase chromatography on prep-HPLC (150 mm, C8 luna, 15-20 min run, 10%-100% MeCN in water containing 0.1% TFA). Fractions containing the product were lyophilized to yield the title compound as a white solid (6.4 mg, 42%). MS MH$^+$ 493.1

Example 222

Trans-N—((R)-1-(4-fluorophenyl)ethyl)-4-(4-(methoxymethyl)phenyl-sulfonamido)cyclohexanecarboxamide

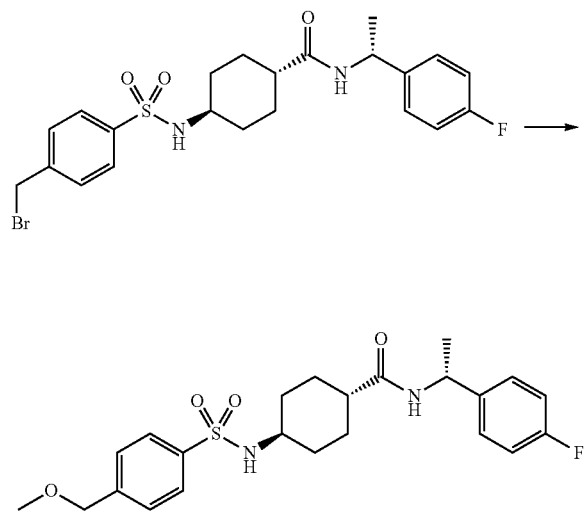

Trans-N—((R)-1-(4-fluorophenyl)ethyl)-4-(4-(methoxymethyl)phenyl-sulfonamido)cyclohexanecarboxamide was prepared from trans-N—((R)-1-(4-fluorophenyl)ethyl)-4-(4-(bromomethyl)phenylsulfonamido)cyclohexanecarboxamide (Example 153) using the method disclosed in Synthetic Communications 1993, 23(6), 749-756, B. Ortiz, et al. MS MH+ 449.2

Example 223

Trans-4-(5-Bromo-6-methoxy-pyridine-3-sulfonylamino)-cyclohexanecarboxylic acid [(R)-1-(4-fluoro-phenyl)-ethyl]-amide

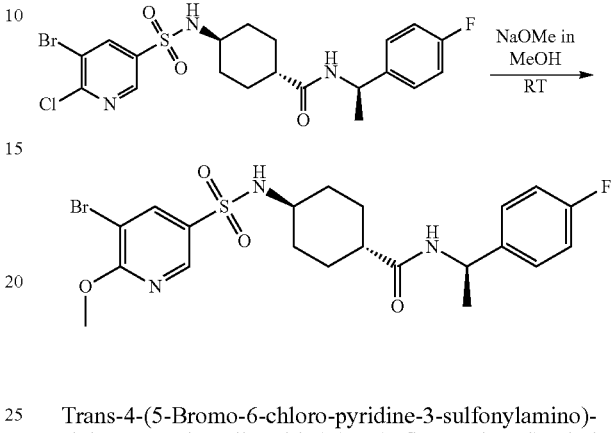

Trans-4-(5-Bromo-6-chloro-pyridine-3-sulfonylamino)-cyclohexanecarboxylic acid [(R)-1-(4-fluoro-phenyl)-ethyl]-amide (Example 144, 484 mg, 0.933 mmol) was dissolved in a solution of NaOMe in MeOH (0.5M, 28 ml, 13.99 mmol). The reaction mixture was stirred overnight at room temperature. LCMS indicated that the reaction was complete and it was concentrated in vacuo then taken up in EtOAc and purified via column chromatography using a biotage SP1, 40+M column, with 50% EtOAc in heptane as calculated gradient to yield the title compound as a white solid (313 mg, 65%). [M+H]=516.0

The compounds in the table below were prepared by a method analogous to the method of preparing Example 223 using the starting materials indicated.

| Example | Structure | S.M. | MS MH+ |
|---|---|---|---|
| 224 | 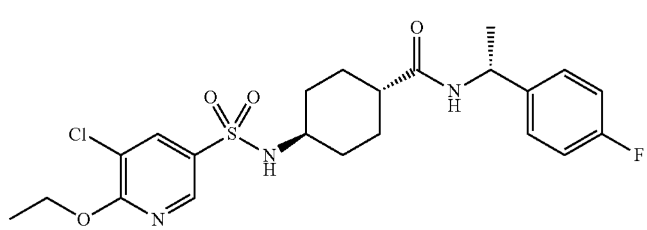 [SMILES: CCOc1ncc(S(=O)(=O)N[C@H]2CC[C@H](C(=O)N[C@H](C)c3ccc(F)cc3)CC2)cc1Cl] | Example 105 & NaOEt | 484.0 |
| 225 | 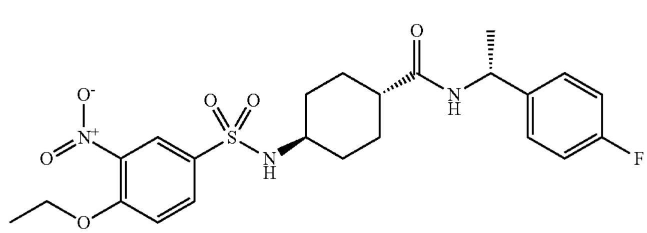 [SMILES: CCOc1ccc(S(=O)(=O)N[C@H]2CC[C@H](C(=O)N[C@H](C)c3ccc(F)cc3)CC2)cc1[N+](=O)[O-]] | Example 106 & NaOEt | 494.1 |

Examples 226 and 227 were prepared using a method analogous to the method used to prepare Example 235 using the starting materials indicated.

| Example | Structure | S.M. | MS MH+ |
|---|---|---|---|
| 226 | 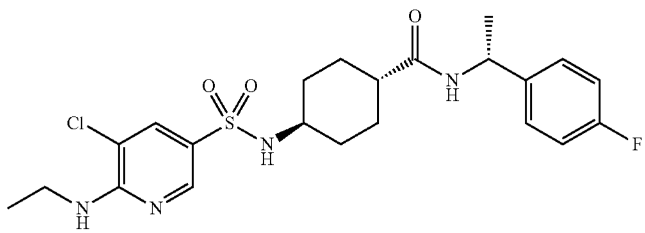 [SMILES: CCNc1ncc(S(=O)(=O)N[C@H]2CC[C@H](C(=O)N[C@H](C)c3ccc(F)cc3)CC2)cc1Cl] | Example 105 & ethylamine | 483.0 |
| 227 | 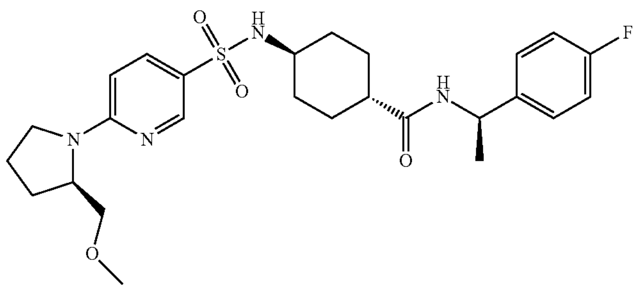 [SMILES: COC[C@H]1CCCN1c1ccc(S(=O)(=O)N[C@H]2CC[C@H](C(=O)N[C@H](C)c3ccc(F)cc3)CC2)cn1] | Example 114 & 2-methoxy-methyl-pyrrolidine | — |

Example 228 was prepared by displacment of a fluorine group of Example 109 by 3-hydroxy-oxetane.

| Example | Structure | S.M. | MS MH+ |
|---|---|---|---|
| 228 | 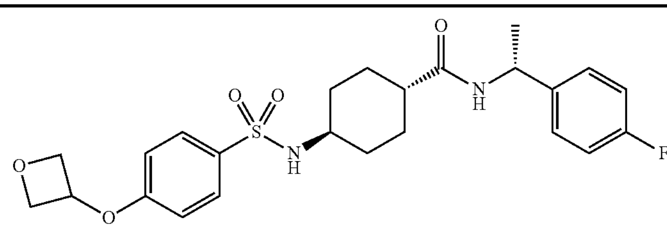 | Example 109 | 477.1 |

Example 229 was prepared by a Buchwald coupling reaction using the starting material indicated.

| Example | Structure | S.M. | MS MH+ |
|---|---|---|---|
| 229 | 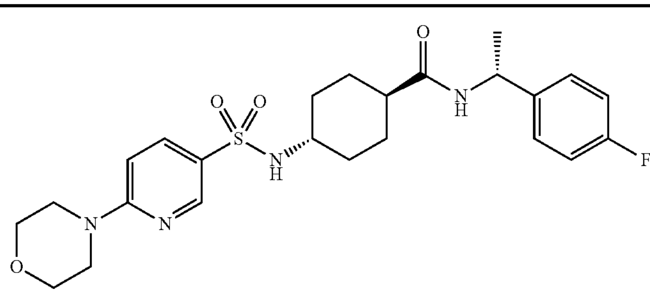 | Example 114 | 491.2 |

Example 230

(1r,4R)-4-(5,6-Divinylpyridine-3-sulfonamido)-N—((R)-1-(4-fluorophenyl)ethyl)cyclohexanecarboxamide

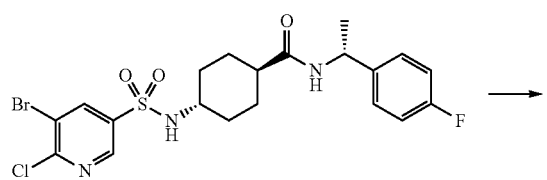

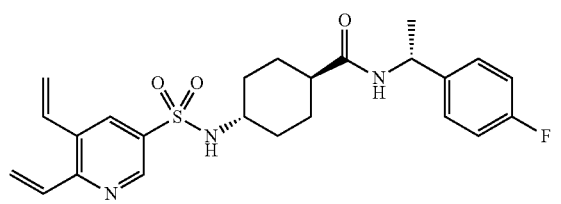

(1r,4R)-4-(5-bromo-6-chloropyridine-3-sulfonamido)-N—((R)-1-(4-fluorophenyl)ethyl)cyclohexanecarboxamide (Example 144, 0.5 g, 0.967 mmol), Pd(dppf)Cl$_2$ (0.071 g, 0.0967 mmol), Cs$_2$CO$_3$ (1.26 g, 3.87 mmol) and potassium vinyl trifluoroborate (0.194 g, 1.45 mmol) were dissolved in DME (8 ml) and water (4 ml). The reaction mixture was heated at 130° C. for 10 minutes in the microwave. LC-MS showed a number of peaks, one of which corresponded to desired product. The reaction mixture was filtered and filtrate was concentrated and dried under high vacuum overnight. The resulting brown solid was purified via flash column chromatography, eluting with 50-100% EtOAc/Heptane. Relevant fractions were pooled and concentrated to afford a peach foam (0.074 g).

Example 231

(1r,4R)-4-(5,6-diethylpyridine-3-sulfonamido)-N—((R)-1-(4-fluorophenyl)ethyl)cyclohexamecarboxamide

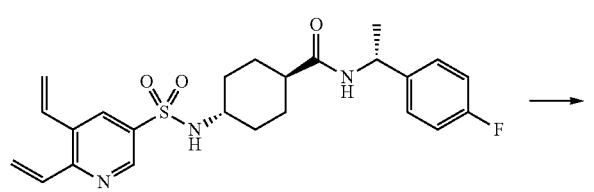

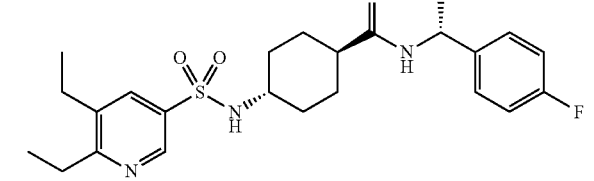

(1r,4R)-4-(5,6-Divinylpyridine-3-sulfonamido)-N—((R)-1-(4-fluorophenyl)ethyl)cyclohexanecarboxamide (Example 230, 74 mg, 0.162 mmol) was dissolved in EtOH (15 ml) and flushed with N$_2$. Palladium on carbon (50 mg, 0.047 mmol) was added and reaction mixture was flushed with N$_2$ once more. The reaction mixture was then placed under a balloon of H$_2$ and stirred vigorously for 45 mins. LC-MS showed one major peak corresponding to desired product, therefore the reaction mixture was filtered through a syringe filter and the filtrate was concentrated to afford a yellow oil. The oil was purified via reverse phase HPLC, eluting with 10-100% MeCN/0.1% TFA over 20 mins. The relevant fractions were frozen and lyophilized to give 44 mg (47.3% yield). MS MH+ 462.1

Example 232

(1r,4R)-4-(4-(cyclopropylethynyl)phenylsulfonamido)-N—((R)-1-(4-fluorophenyl)ethyl)cyclohexanecarboxamide (1r,4R-4-(4-bromophenylsulfonamido)-N—((R)-1-(4-fluorophenyl)ethyl)cyclohexanecarboxamide (Example 115, 100 mg, 0.207 mmol), Pd(PPh$_3$)$_2$Cl$_2$ (14.52 mg, 0.021 mmol) and CuI (5.91 mg, 0.031 mmol) were added to a microwave vial, to which a solution of cyclopropyl acetylene (16.41 mg, 0.248 mmol) in 2 methyl THF (3 ml) was added. Diisopropylamine (2 ml, 14.03 mmol) was then added and reaction mixture was heated at 90° C. for 10 min in microwave. LC-MS showed that the majority of the mixture was still starting material, but there was a small product peak also. Therefore, the reaction mixture was heated at 90° C. for a further 30 mins. LC-MS showed no further change, therefore the reaction mixture was filtered and filtrate was concentrated to afford a deep brown oil. This material was adsorbed onto silica and purified via Biotage automated flash column chromatography 12M, eluting with 10-100% EtOAc/Heptane. Relevant fractions were pooled and concentrated to afford a tan solid, which was dried under high vacuum. LC-MS of this material showed it to be a mixture of the starting material and the product, therefore material was re-purified via reverse phase HPLC, eluting with 40-75-100% MeCN/0.1% TFA over 20 mins (C8 Luna 150 mm). Relevant fractions were frozen and freeze dried to give 8.88 mg (9% yield) of the desired product. MS MH+ 469.1

Example 233

Trans-4-(5-(dimethylamino)-6-methoxypyridine-3-sulfonamido)-N—((R)-1-(4-fluorophenyl)ethyl)cyclohexanecarboxamide

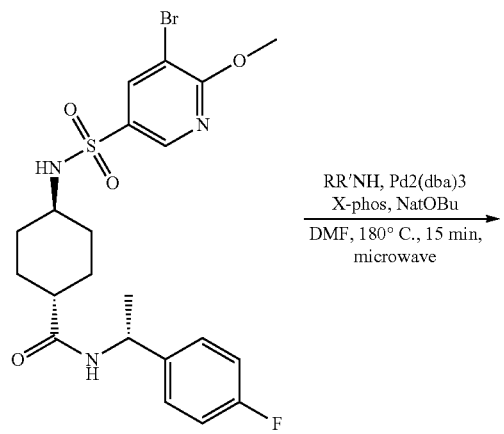

Trans-4-(5-Bromo-6-methoxy-pyridine-3-sulfonylamino)-cyclohexanecarboxylic acid [(R)-1-(4-fluoro-phenyl)-ethyl]-amide (Example 223, 65 mg, 0.126 mmol), dimethylamine in THF (2M, 630 ul, 1.26 mmol), Pd$_2$(dba)$_3$ (12 mg, 0.013 mmol), X-phos (6 mg, 0.013 mmol), sodium tert-butoxide (61 mg, 0.63 mmol) were dissolved in DMF (2 ml). The reaction mixture was microwaved at 180° C. for 15 min., after which LCMS indicated the reaction was complete. The mixture was diluted with H$_2$O and extracted with EtOAc (×3). The combined organic layers were concentrated in vacuo to a yellow oil which was purified via column chromatography using a biotage SP1, 25+M column, with 80% EtOAc in heptane as an isocratic gradient. Product containing fractions were concentrated in vacuo and repurified via reverse phase chromatography on prep-HPLC (150 mm, C8 luna, 15-20 min run, 10%-100% MeCN in water containing 0.1% TFA). Product containing fractions were collected and lyophilized to yield the title compound as a white solid (25.3 mg, 28%). MS MH$^+$ 479.1

The compound in the Table below was prepared by a method analogous to the method used to prepare Example 233 from the starting materials indicated.

| Example | Structure | S.M. | MS MH+ |
|---|---|---|---|
| 234 | 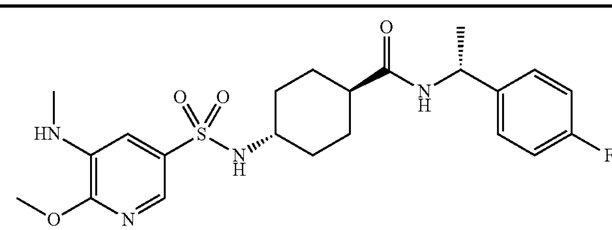 | Example 223 | 465.2 |

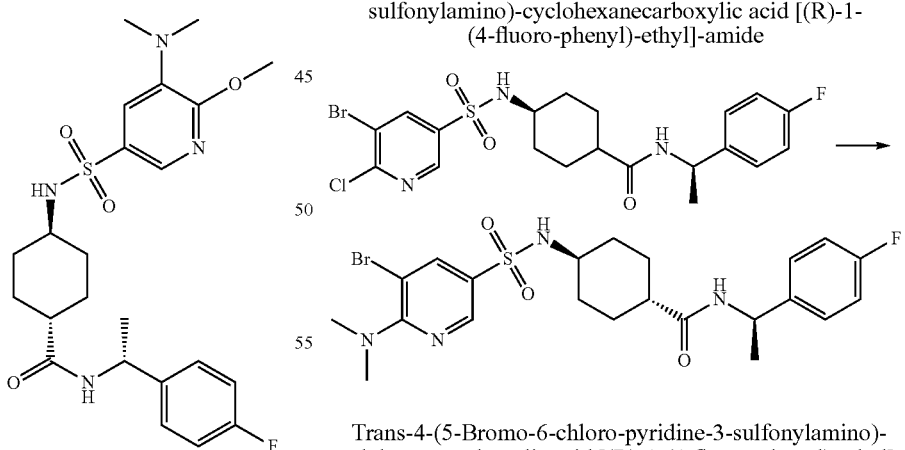

Example 235

Trans-4-(5-Bromo-6-(dimethylamino)-pyridine-3-sulfonylamino)-cyclohexanecarboxylic acid [(R)-1-(4-fluoro-phenyl)-ethyl]-amide Trans-4-(5-Bromo-6-chloro-pyridine-3-sulfonylamino)-cyclohexanecarboxylic acid [(R)-1-(4-fluoro-phenyl)-ethyl]-amide (Example 241, 300 mg, 0.580 mmol) was dissolved in NMP (3 ml). DIPEA (202 ul, 1.16 mmol) was added followed by dimethylamine in THF (2M, 0.87 ml, 1.74 mmol). The reaction mixture was microwaved at 160° C. for 15 min., after which LCMS indicated that the reaction was complete. The mixture was diluted with EtOAc and washed H$_2$O. The organic layer was concentrated in vacuo and purified via column chromatography using a biotage SP1, 12+M column, with 50% EtOAc in heptane as calculated gradient to yield the title compound as a white solid (258 mg, 84%). MS MH+ 529.9

The compound in the Table below was prepared by a method analogous to the method used to prepare Example 235 from the starting materials indicated.

| Example | Structure | S.M. | MS MH+ |
|---|---|---|---|
| 235 | 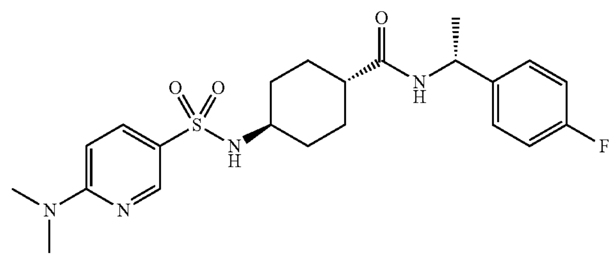 [SMILES: C[C@@H](NC(=O)[C@H]1CC[C@H](NS(=O)(=O)c2ccc(N(C)C)nc2)CC1)c1ccc(F)cc1] | Example 114 | 449.1 |

Example 237

Trans-4-(4-(5-methyl-pyridin-3-yl)-benzenesulfonylamino)-cyclohexanecarboxylic acid [(R)-1-(4-fluoro-phenyl)-ethyl]-amide Trans-4-(4-Bromo-benzenesulfonylamino)-cyclohexanecarboxylic acid [(R)-1-(4-fluoro-phenyl)-ethyl]-amide (Example 115, 100 mg, 0.206 mmol), Pd(dppf)Cl$_2$.DCM (34 mg, 0.04 mmol), 2M Na$_2$CO$_3$ (1 ml, 2.06 mmol) and 5-methyl-3-pyridine boronic acid (51 mg, 0.37 mmol) were dissolved in DMF (1-2 ml) under N$_2$. The reaction mixture was microwaved at 160° C. for 20 min., after which LCMS indicated that the reaction was complete. The mixture was diluted with EtOAc and washed with H$_2$O (×2). The organic layer was concentrated in vacuo, and the crude material purified via column chromatography using a biotage SP1 25+S column with a gradient of 80-100% EtOAc in heptane. Product fractions combined and concentrated to give the title compound as a white solid (44 mg, 43%). MS MH$^+$ 496.1

Example 238

Trans-4-(4-(3-methyl-pyridin-4-yl)-3-methyl-benzenesulfonylamino)-cyclohexanecarboxylic acid [(R)-1-(4-fluoro-phenyl)-ethyl]-amide

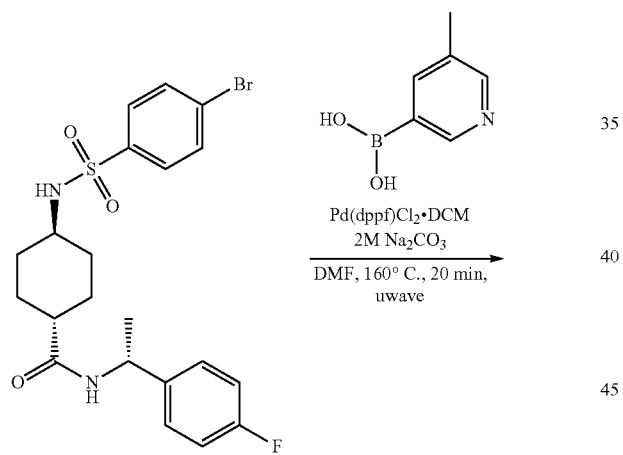

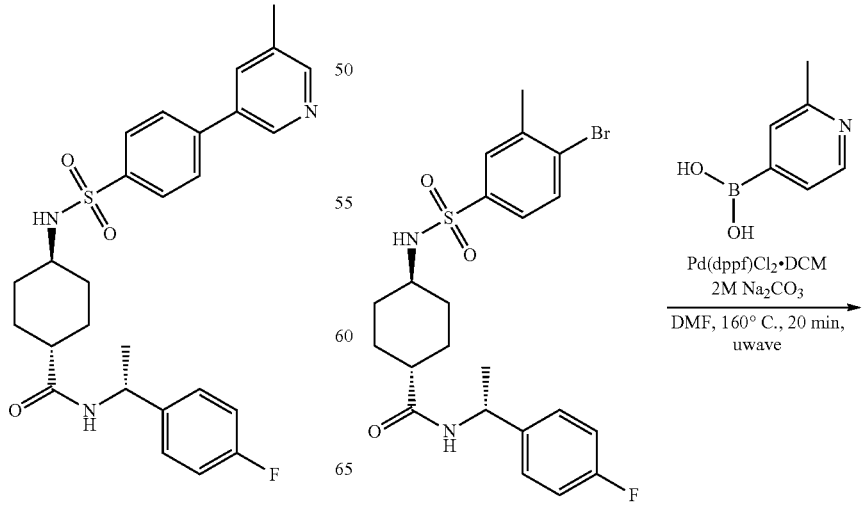

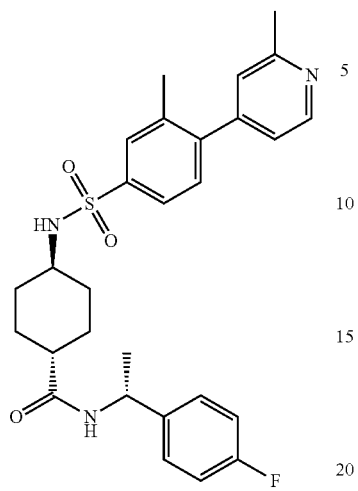

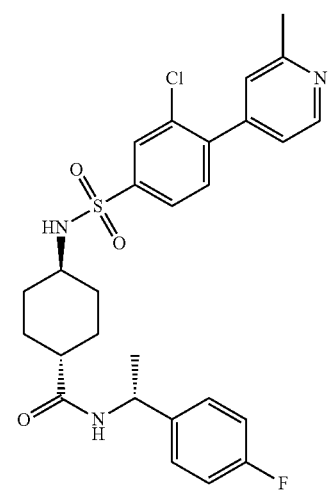

Trans-4-(4-Bromo-3-methyl-benzenesulfonylamino)-cyclohexanecarboxylic acid [(R)-1-(4-fluoro-phenyl)-ethyl]-amide (Example 154, 100 mg, 0.201 mmol), Pd(dppf)Cl$_2$·DCM (33 mg, 0.04 mmol), 2M Na$_2$CO$_3$ (1 ml, 2.01 mmol) and 2-methyl-4-pyridine boronic acid (41 mg, 0.302 mmol) were dissolved in DMF (1 ml) under N$_2$. The reaction mixture was microwaved at 160° C. for 20 min., after which LCMS indicated that the reaction was complete. The mixture was diluted with EtOAc and washed with H$_2$O (×2). The organic layer was concentrated in vacuo, and the crude material was purified via column chromatography using a biotage SP1 25+S column with a gradient 100% EtOAc. Product fractions combined and concentrated to give the title compound as a white solid (31 mg, 30%). MS MH$^+$ 510.1

Example 239

Trans-4-(4-(3-methyl-pyridin-4-yl)-3-chloro-benzenesulfonylamino)-cyclohexanecarboxylic acid [(R)-1-(4-fluoro-phenyl)-ethyl]-amide Trans-4-(4-Bromo-3-chloro-benzenesulfonylamino)-cyclohexanecarboxylic acid [(R)-1-(4-fluoro-phenyl)-ethyl]-amide (Example 155, 100 mg, 0.193 mmol), Pd tetrakis (45 mg, 0.039 mmol), Na$_2$CO$_3$ (52 mg, 4.83 mmol) and 2-methyl-4-pyridine boronic acid (34 mg, 0.251 mmol) was dissolved in EtOH (4 ml) and toluene (4 ml) under N$_2$ and the mixture was refluxed overnight. LCMS indicated that the reaction was complete, and it was concentrated in vacuo. then taken up in EtOAc and washed with H$_2$O (×2). The organic layer was concentrated in vacuo, and the crude material was purified via column chromatography using a biotage SP1 25+S column with a gradient 80%-100% EtOAc in heptane. Product fractions were combined and repurified on prep-HPLC (150 mm, C8 luna, 15-20 min run, 10%-100% MeCN in water containing 0.1% TFA), then lyophilized to yield the title compound as a white solid (27 mg, 22%). MS MH$^+$ 530.1

Example 240

Trans-4-(6-(pyrazol-1-yl)-pyridine-3-sulfonylamino)-cyclohexanecarboxylic acid [(R)-1-(4-fluoro-phenyl)-ethyl]-amide

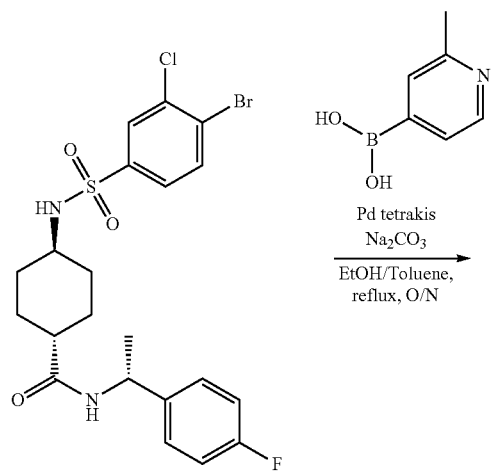

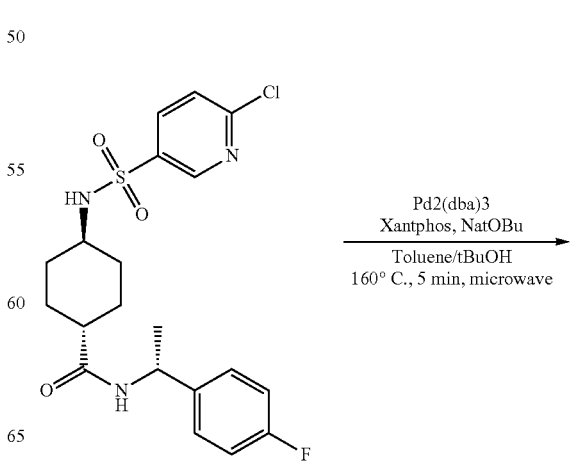

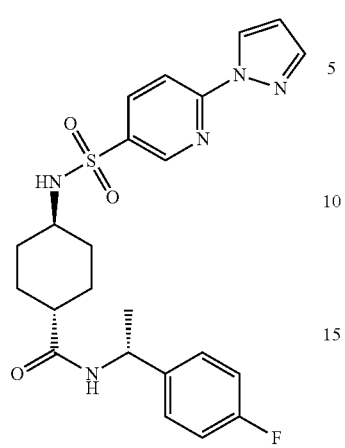

Trans-4-(6-Chloro-pyridine-3-sulfonylamino)-cyclohexanecarboxylic acid [(R)-1-(4-fluoro-phenyl)-ethyl]-amide (Example 114, 100 mg, 0.225 mmol), pyrazole (70 mg, 0.91 mmol), Pd$_2$(dba)$_3$ (25 mg, 0.025 mmol), Xantphos (20 mg, 0.05 mmol), sodium tert-butoxide (108 mg, 1.125 mmol) were dissolved in toluene (1 ml) and tert-butanol (3 ml). The reaction mixture was microwaved at 160° C. for 5 min., after which LCMS indicated that the reaction was complete. The reaction was diluted with DCM and MeCN and filtered through a syringe, the concentrated in vacuo to a yellow oil. The crude material was purified via reverse phase chromatography and lyophilized to yield the title compound as a white solid (15 mg, 14%). [M+H]=472.08

Example 241

Trans-4-(4-(imidazol-1-yl)-benzenesulfonylamino)-cyclohexanecarboxylic acid [(R)-1-(4-fluoro-phenyl)-ethyl]-amide

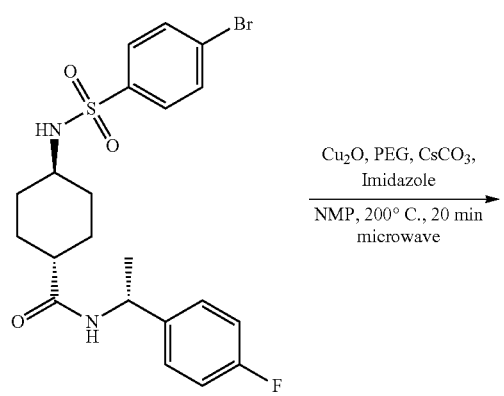

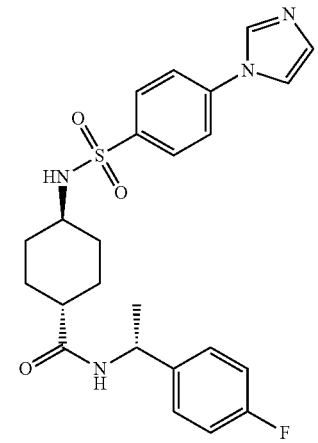

Trans-4-(4-Bromo-benzenesulfonylamino)-cyclohexanecarboxylic acid [(R)-1-(4-fluoro-phenyl)-ethyl]-amide (Example 115, 80 mg, 0.166 mmol), imidazole (14 mg, 0.199 mmol), polyethylene glycol (30 mg), Cs$_2$CO$_3$ (76 mg, 0.232 mmol), and Copper II oxide (2 mg, 0.01 mmol) were weighed into a microwave vial. The vial was flushed with N$_2$, NMP was added and the reaction mixture was microwaved at 200° C. After 20 min. the reaction mixture was diluted with EtOAc (50 ml) and filtered through celite. The filtrate was concentrated in vacuo and the residue was passed through a 25+S biotage column with an isocratic gradient of 10% MeOH in EtOAc. Product fractions combined and concentrated. The crude product was repurified via reverse phase chromatography on prep-HPLC (150 mm, C8 luna, 15-20 min run, 10%-100% MeCN in water containing 0.1% TFA) and the fractions containing the product were lyophilized to yield the title compound as a white solid (6.3 mg). MS MH$^+$ 471.1

Example 242

Trans-4-(4-(imidazol-2-yl)-benzenesulfonylamino)-cyclohexanecarboxylic acid [(R)-1-(4-fluoro-phenyl)-ethyl]-amide

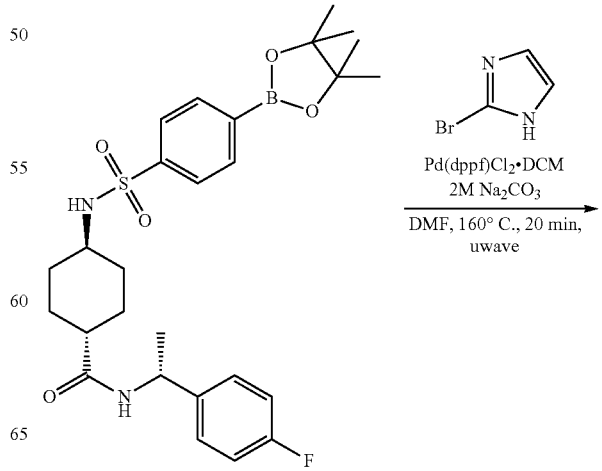

-continued

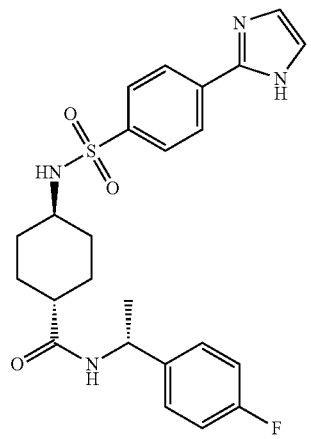

Trans-N—((R)-1-(4-fluorophenyl)ethyl)-4-(4,4,5,5-tetramethyl-1,3,2-dioxaborolan-2-yl)phenylsulfonamido)cyclohexanecaboxamide (Intermediate 64, 0.206 mmol), Pd(dppf)Cl$_2$.DCM (19 mg, 0.023 mmol), 2M Na$_2$CO$_3$ (0.57 ml, 1.14 mmol) and 2-bromo-imidazole (17 mg, 0.114 mmol) dissolved in DMF (2 ml) under N$_2$, and the mixture was microwaved at 160° C. for 20 min., after which LCMS indicated that the reaction was complete. The mixture was diluted with DCM and MeOH and filtered through a syringe filter. The filtrate was then passed through a 40+S biotage column with an isocratic gradient of 10% MeOH in EtOAc and the product fractions were combined and concentrated. Crude product was repurified via reverse phase chromatography on prep-HPLC (150 mm, C8 luna, 15-20 min run, 10%-100% MeCN in water containing 0.1% TFA) and the product containing fractions were lyophilized to yield the title compound as a white solid (4.2 mg, 3%). MS MH$^+$ 471.1

The compounds in the Table below were prepared using a method analogous to the Suzuki coupling reactions shown in Examples 237 through 242.

| Ex. | Structure | LCMS |
|---|---|---|
| 243 | 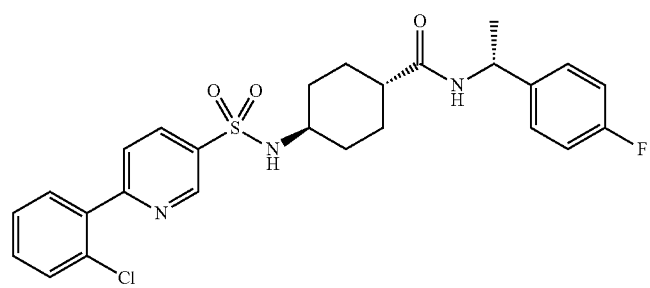 [SMILES: C[C@@H](NC(=O)[C@H]1CC[C@H](NS(=O)(=O)c2ccc(-c3ccccc3Cl)nc2)CC1)c1ccc(F)cc1] | 516.1 |
| 244 | 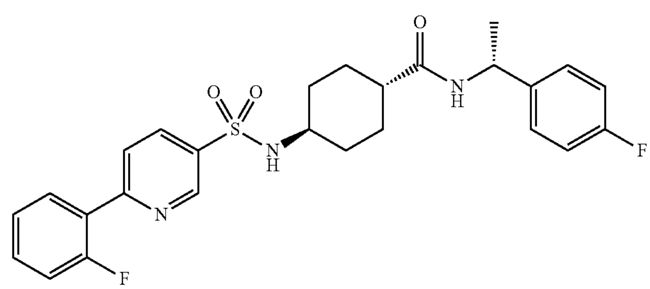 [SMILES: C[C@@H](NC(=O)[C@H]1CC[C@H](NS(=O)(=O)c2ccc(-c3ccccc3F)nc2)CC1)c1ccc(F)cc1] | 500.0 |
| 245 | 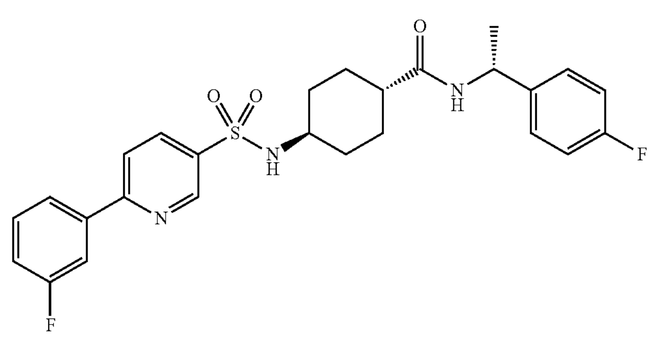 [SMILES: C[C@@H](NC(=O)[C@H]1CC[C@H](NS(=O)(=O)c2ccc(-c3cccc(F)c3)nc2)CC1)c1ccc(F)cc1] | 500.0 |

-continued

| Ex. | Structure | LCMS |
|---|---|---|
| 246 | 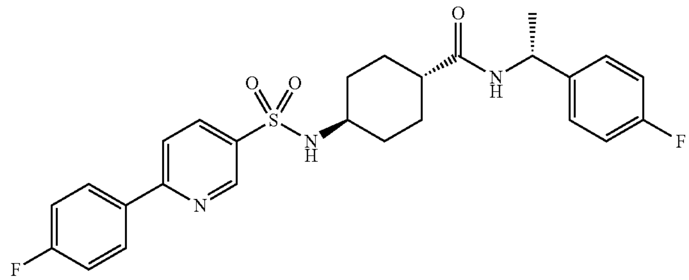 [SMILES: C[C@@H](NC(=O)[C@H]1CC[C@H](NS(=O)(=O)c2ccc(-c3ccc(F)cc3)nc2)CC1)c1ccc(F)cc1] | 500.2 |
| 247 | 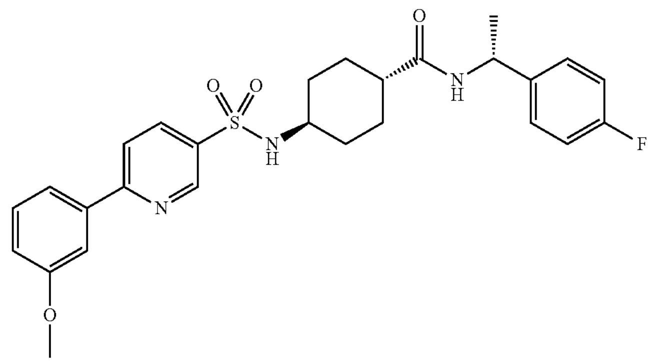 [SMILES: COc1cccc(-c2ccc(S(=O)(=O)N[C@H]3CC[C@H](C(=O)N[C@H](C)c4ccc(F)cc4)CC3)cn2)c1] | 512.2 |
| 248 | 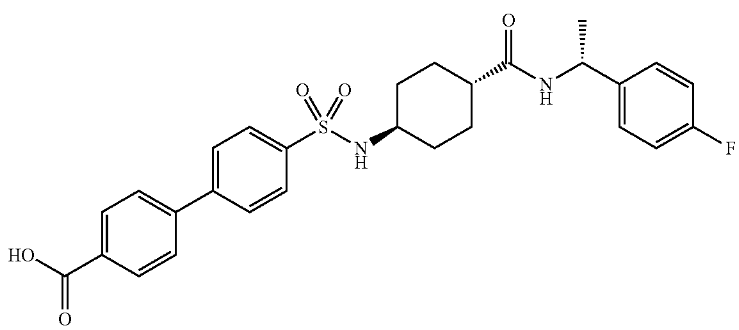 [SMILES: C[C@@H](NC(=O)[C@H]1CC[C@H](NS(=O)(=O)c2ccc(-c3ccc(C(=O)O)cc3)cc2)CC1)c1ccc(F)cc1] | 525.0 |
| 249 | 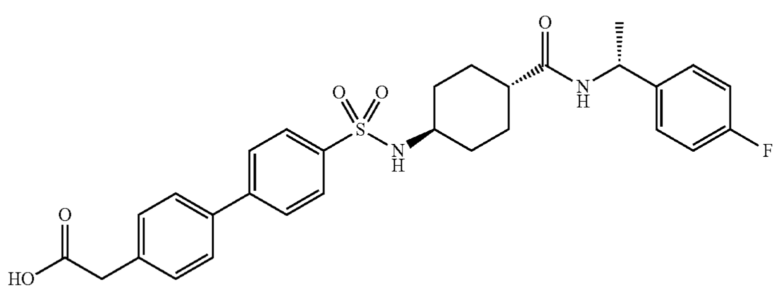 [SMILES: C[C@@H](NC(=O)[C@H]1CC[C@H](NS(=O)(=O)c2ccc(-c3ccc(CC(=O)O)cc3)cc2)CC1)c1ccc(F)cc1] | 539.2 |
| 250 | 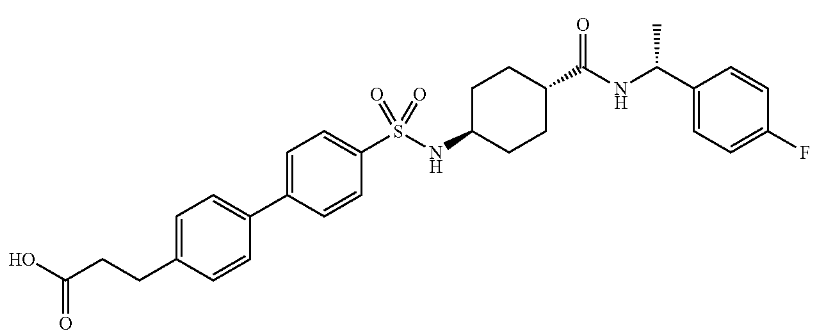 [SMILES: C[C@@H](NC(=O)[C@H]1CC[C@H](NS(=O)(=O)c2ccc(-c3ccc(CCC(=O)O)cc3)cc2)CC1)c1ccc(F)cc1] | 553.2 |

-continued

| Ex. | Structure | LCMS |
|---|---|---|
| 251 | 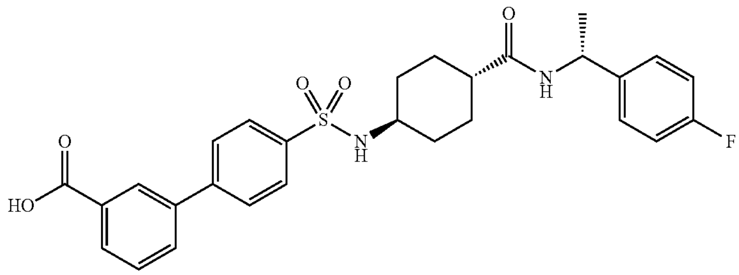 [SMILES: C[C@@H](NC(=O)[C@H]1CC[C@H](NS(=O)(=O)c2ccc(-c3cccc(C(=O)O)c3)cc2)CC1)c1ccc(F)cc1] | 525.0 |
| 252 | 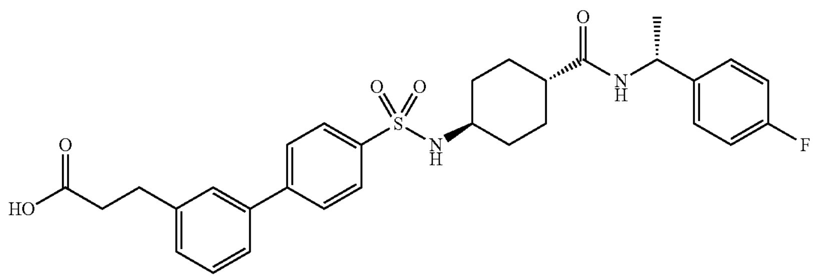 [SMILES: C[C@@H](NC(=O)[C@H]1CC[C@H](NS(=O)(=O)c2ccc(-c3cccc(CCC(=O)O)c3)cc2)CC1)c1ccc(F)cc1] | 553.0 |
| 253 | 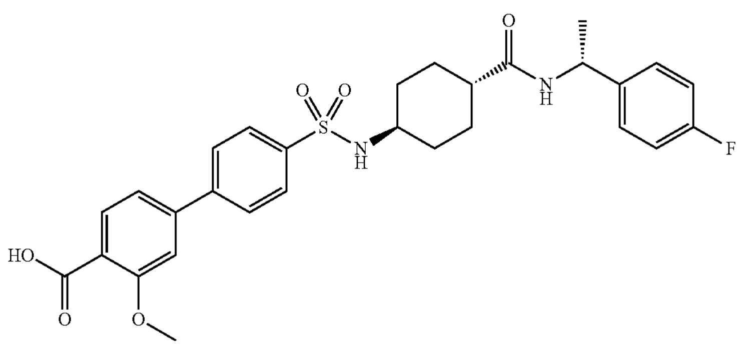 [SMILES: COc1cc(-c2ccc(S(=O)(=O)N[C@H]3CC[C@H](C(=O)N[C@H](C)c4ccc(F)cc4)CC3)cc2)ccc1C(=O)O] | 555.2 |
| 254 | 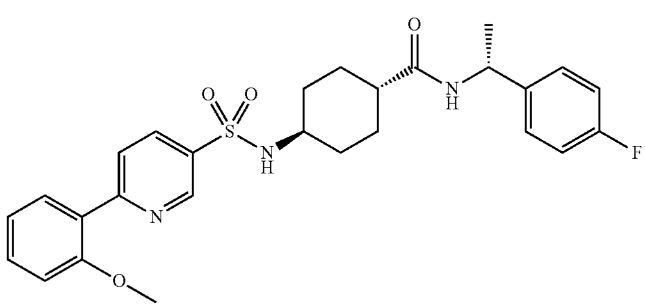 [SMILES: COc1ccccc1-c1ccc(S(=O)(=O)N[C@H]2CC[C@H](C(=O)N[C@H](C)c3ccc(F)cc3)CC2)cn1] | 512.2 |
| 255 | 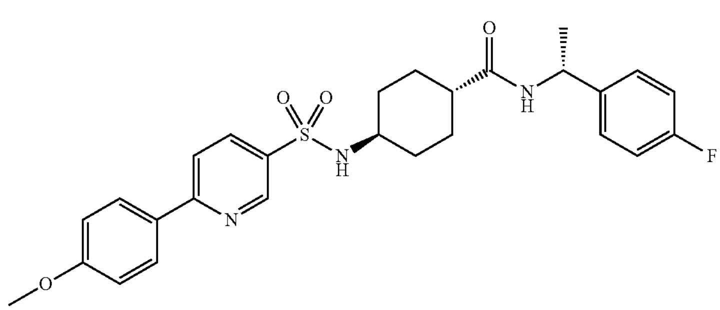 [SMILES: COc1ccc(-c2ccc(S(=O)(=O)N[C@H]3CC[C@H](C(=O)N[C@H](C)c4ccc(F)cc4)CC3)cn2)cc1] | — |

| Ex. | Structure | LCMS |
|---|---|---|
| 256 | 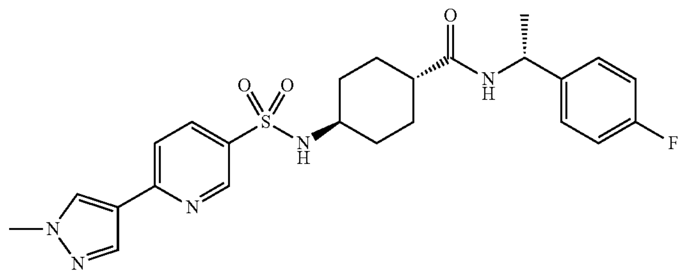 [SMILES: C[C@@H](NC(=O)[C@H]1CC[C@H](NS(=O)(=O)c2ccc(-c3cnn(C)c3)nc2)CC1)c1ccc(F)cc1] | 486.0 |
| 257 | 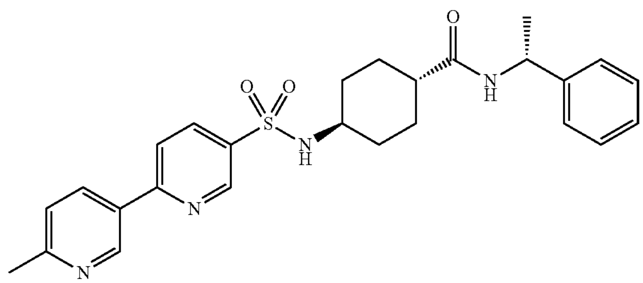 [SMILES: Cc1ccc(-c2ccc(S(=O)(=O)N[C@H]3CC[C@H](C(=O)N[C@H](C)c4ccccc4)CC3)cn2)cn1] | 479.0 |
| 258 | 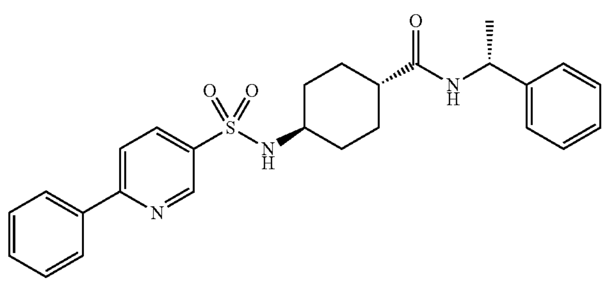 [SMILES: C[C@@H](NC(=O)[C@H]1CC[C@H](NS(=O)(=O)c2ccc(-c3ccccc3)nc2)CC1)c1ccccc1] | 464.0 |
| 259 | 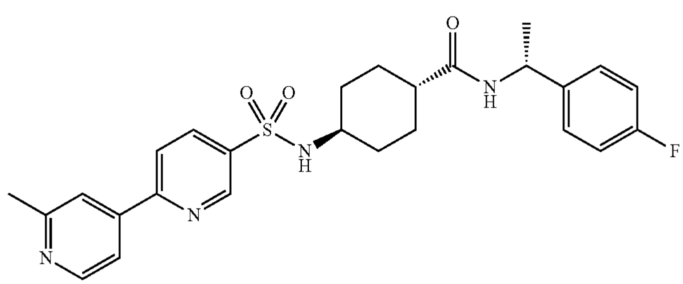 | 479.0 |
| 260 | 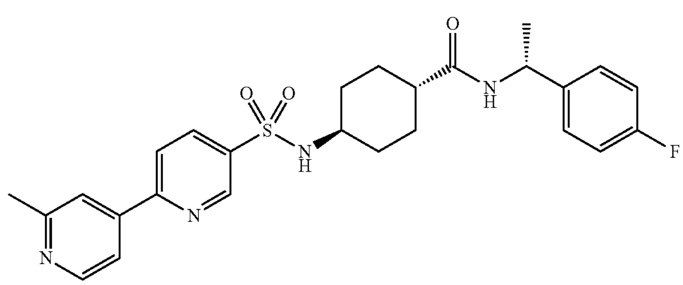 [SMILES: Cc1cc(-c2ccc(S(=O)(=O)N[C@H]3CC[C@H](C(=O)N[C@H](C)c4ccc(F)cc4)CC3)cn2)ccn1] | 497.0 |

| Ex. | Structure | LCMS |
|---|---|---|
| 261 | 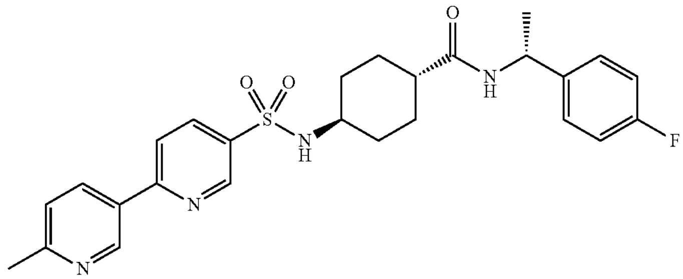 [SMILES: Cc1ccc(-c2ccc(S(=O)(=O)N[C@H]3CC[C@H](C(=O)N[C@H](C)c4ccc(F)cc4)CC3)cn2)cn1] | 497.0 |
| 262 | 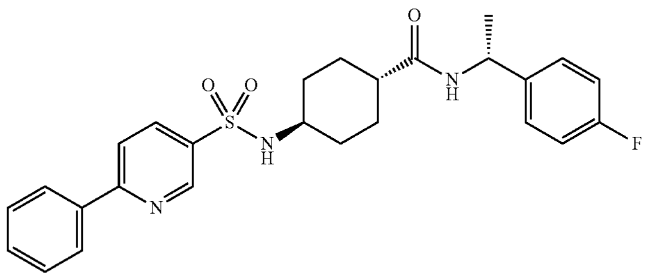 [SMILES: C[C@@H](NC(=O)[C@H]1CC[C@H](NS(=O)(=O)c2ccc(-c3ccccc3)nc2)CC1)c1ccc(F)cc1] | 482.0 |
| 263 | 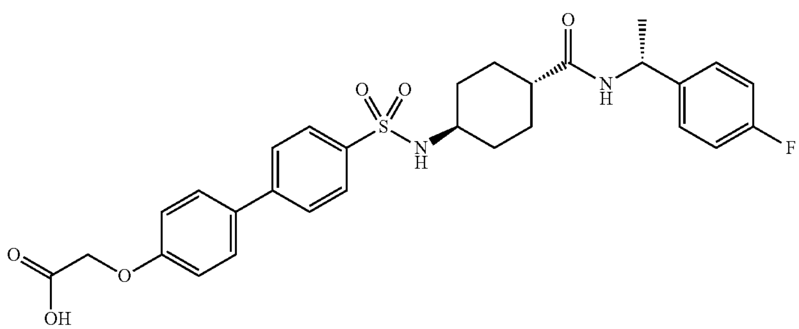 [SMILES: C[C@@H](NC(=O)[C@H]1CC[C@H](NS(=O)(=O)c2ccc(-c3ccc(OCC(=O)O)cc3)cc2)CC1)c1ccc(F)cc1] | 555.0 |
| 264 | 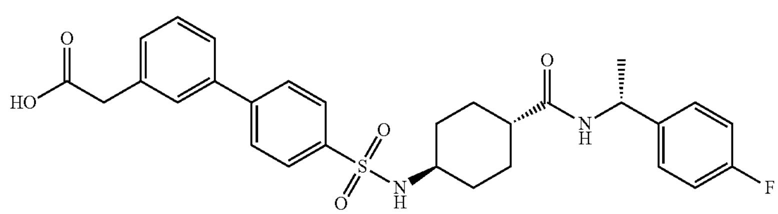 [SMILES: C[C@@H](NC(=O)[C@H]1CC[C@H](NS(=O)(=O)c2ccc(-c3cccc(CC(=O)O)c3)cc2)CC1)c1ccc(F)cc1] | 578.0 |
| 265 | 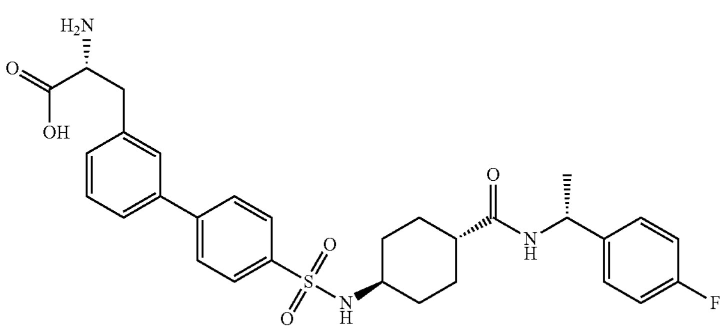 [SMILES: C[C@@H](NC(=O)[C@H]1CC[C@H](NS(=O)(=O)c2ccc(-c3cccc(C[C@@H](N)C(=O)O)c3)cc2)CC1)c1ccc(F)cc1] | 567.0 |

| Ex. | Structure | LCMS |
|---|---|---|
| 266 | 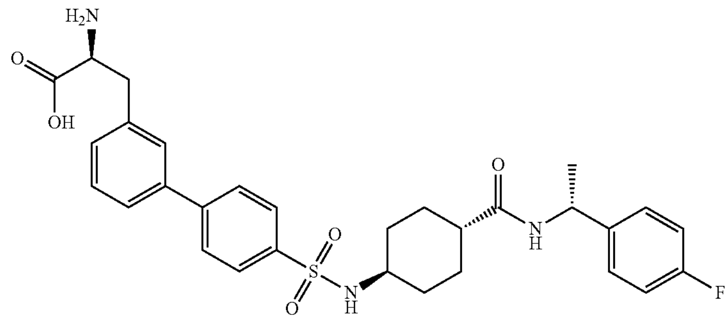 [SMILES: C[C@@H](NC(=O)[C@H]1CC[C@H](NS(=O)(=O)c2ccc(-c3cccc(C[C@H](N)C(=O)O)c3)cc2)CC1)c1ccc(F)cc1] | 568.0 |
| 267 | 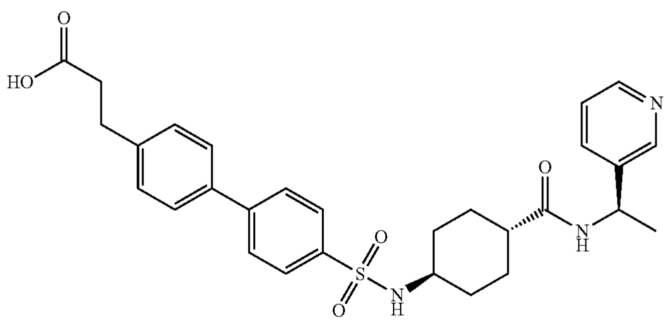 [SMILES: C[C@@H](NC(=O)[C@H]1CC[C@H](NS(=O)(=O)c2ccc(-c3ccc(CCC(=O)O)cc3)cc2)CC1)c1cccnc1] | 536.0 |
| 268 | 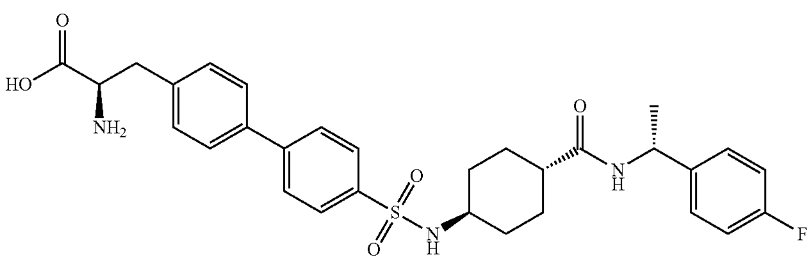 [SMILES: C[C@@H](NC(=O)[C@H]1CC[C@H](NS(=O)(=O)c2ccc(-c3ccc(C[C@@H](N)C(=O)O)cc3)cc2)CC1)c1ccc(F)cc1] | 568.0 |
| 269 | 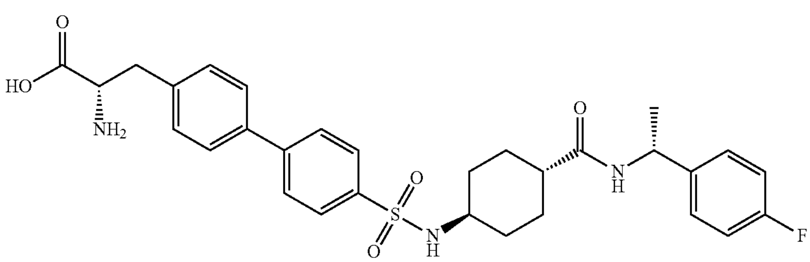 [SMILES: C[C@@H](NC(=O)[C@H]1CC[C@H](NS(=O)(=O)c2ccc(-c3ccc(C[C@H](N)C(=O)O)cc3)cc2)CC1)c1ccc(F)cc1] | 568.0 |
| 270 | 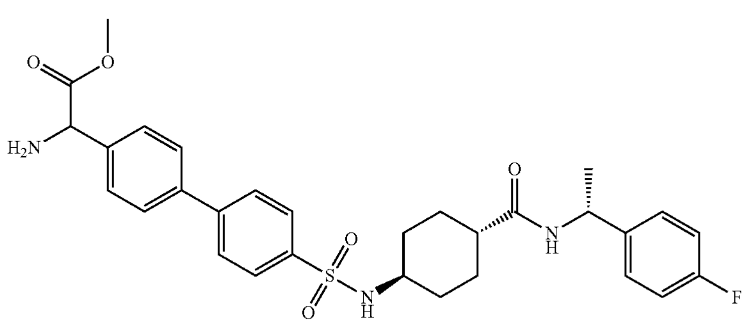 [SMILES: COC(=O)C(N)c1ccc(-c2ccc(S(=O)(=O)N[C@H]3CC[C@H](C(=O)N[C@H](C)c4ccc(F)cc4)CC3)cc2)cc1] | 568.0 |

-continued

| Ex. | Structure | LCMS |
|---|---|---|
| 271 | 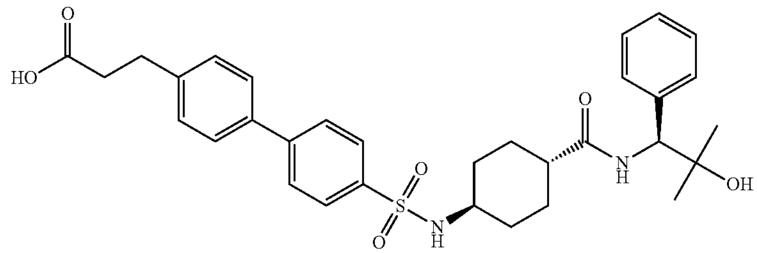 [SMILES: CC(C)(O)[C@@H](NC(=O)[C@H]1CC[C@H](NS(=O)(=O)c2ccc(-c3ccc(CCC(=O)O)cc3)cc2)CC1)c1ccccc1] | 579.0 |
| 272 | 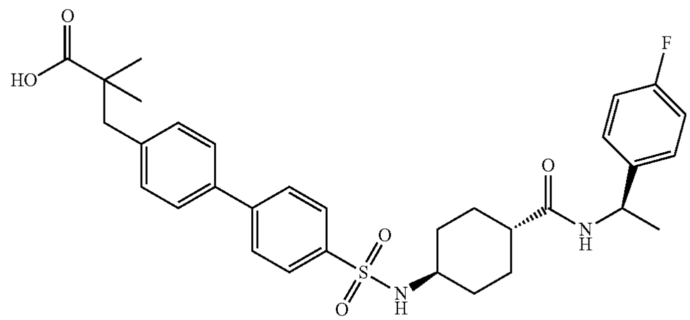 [SMILES: C[C@@H](NC(=O)[C@H]1CC[C@H](NS(=O)(=O)c2ccc(-c3ccc(CC(C)(C)C(=O)O)cc3)cc2)CC1)c1ccc(F)cc1] | 581.0 |
| 273 | 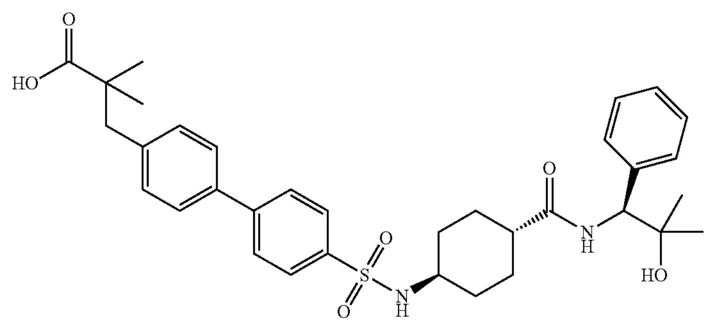 [SMILES: CC(C)(Cc1ccc(-c2ccc(S(=O)(=O)N[C@H]3CC[C@H](C(=O)N[C@@H](c4ccccc4)C(C)(C)O)CC3)cc2)cc1)C(=O)O] | 607.0 |
| 274 | 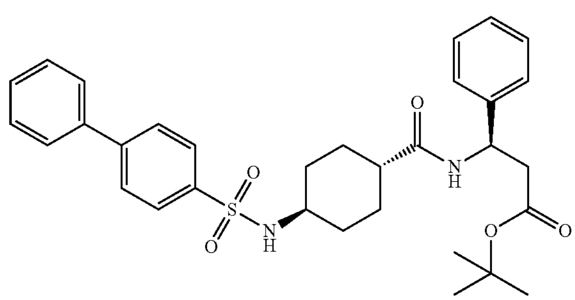 [SMILES: CC(C)(C)OC(=O)C[C@@H](NC(=O)[C@H]1CC[C@H](NS(=O)(=O)c2ccc(-c3ccccc3)cc2)CC1)c1ccccc1] | 563.0 |
| 275 | 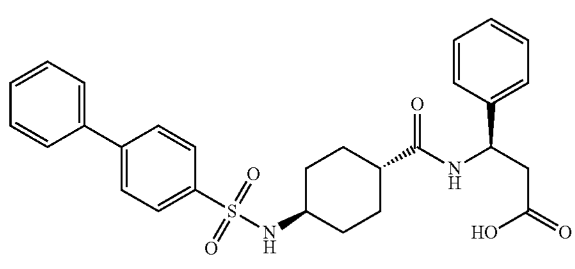 [SMILES: O=C(O)C[C@@H](NC(=O)[C@H]1CC[C@H](NS(=O)(=O)c2ccc(-c3ccccc3)cc2)CC1)c1ccccc1] | 505.0 |

-continued

| Ex. | Structure | LCMS |
|---|---|---|
| 276 | 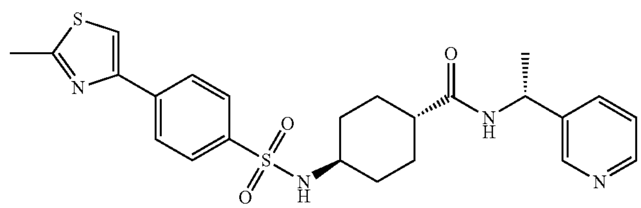 [SMILES: Cc1nc(-c2ccc(S(=O)(=O)N[C@H]3CC[C@H](C(=O)N[C@H](C)c4cccnc4)CC3)cc2)cs1] | 485.1 |
| 277 | 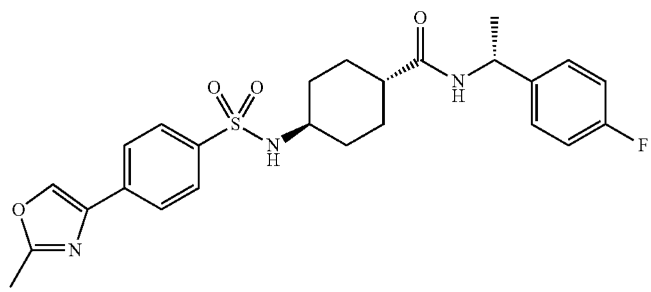 [SMILES: Cc1nc(-c2ccc(S(=O)(=O)N[C@H]3CC[C@H](C(=O)N[C@H](C)c4ccc(F)cc4)CC3)cc2)co1] | 486.1 |
| 278 | 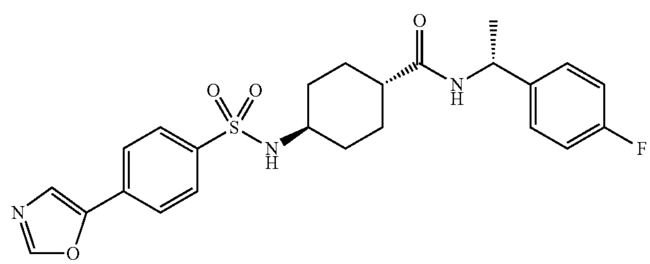 [SMILES: C[C@@H](NC(=O)[C@H]1CC[C@H](NS(=O)(=O)c2ccc(-c3cnco3)cc2)CC1)c1ccc(F)cc1] | 472.2 |
| 279 | 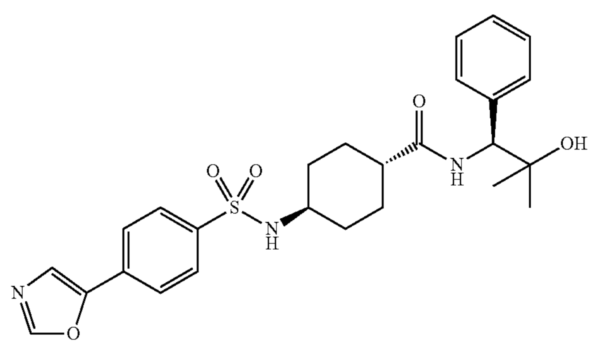 [SMILES: CC(C)(O)[C@@H](NC(=O)[C@H]1CC[C@H](NS(=O)(=O)c2ccc(-c3cnco3)cc2)CC1)c1ccccc1] | 498.3 |
| 280 | 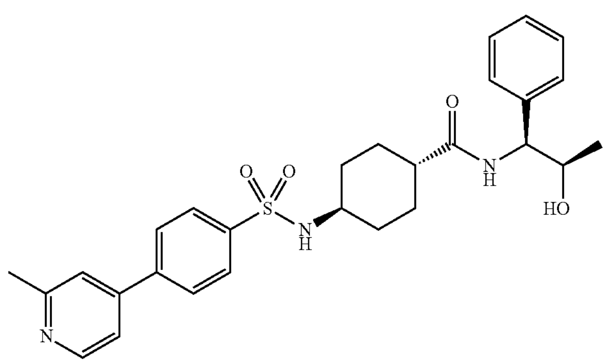 [SMILES: Cc1cc(-c2ccc(S(=O)(=O)N[C@H]3CC[C@H](C(=O)N[C@@H](c4ccccc4)[C@@H](C)O)CC3)cc2)ccn1] | 508.0 |

| Ex. | Structure | LCMS |
|---|---|---|
| 281 | 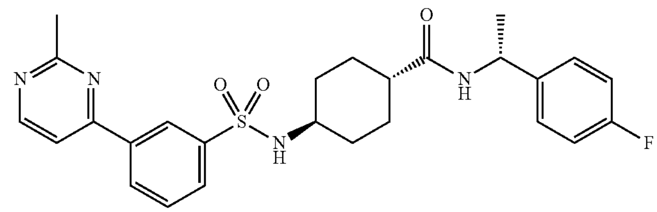 [SMILES: Cc1nccc(-c2cccc(S(=O)(=O)N[C@H]3CC[C@H](C(=O)N[C@H](C)c4ccc(F)cc4)CC3)c2)n1] | 497.2 |
| 282 | 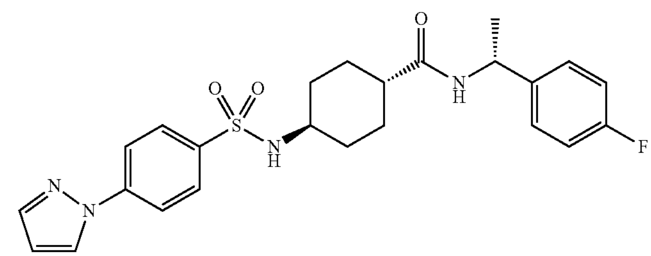 [SMILES: C[C@@H](NC(=O)[C@H]1CC[C@H](NS(=O)(=O)c2ccc(-n3cccn3)cc2)CC1)c1ccc(F)cc1] | 471.1 |
| 283 | 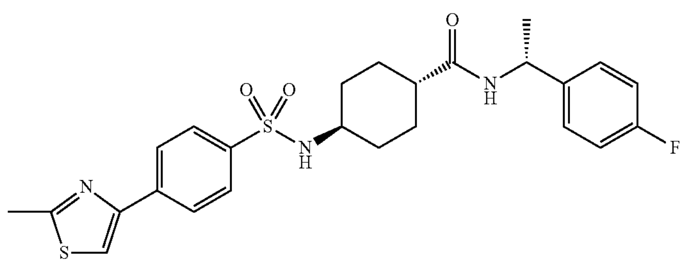 [SMILES: Cc1nc(-c2ccc(S(=O)(=O)N[C@H]3CC[C@H](C(=O)N[C@H](C)c4ccc(F)cc4)CC3)cc2)cs1] | 502.1 |
| 284 | 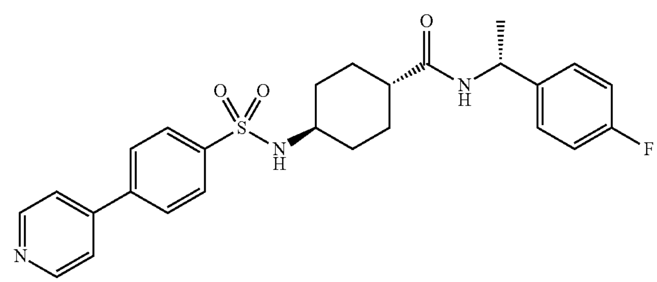 [SMILES: C[C@@H](NC(=O)[C@H]1CC[C@H](NS(=O)(=O)c2ccc(-c3ccncc3)cc2)CC1)c1ccc(F)cc1] | 482.1 |
| 285 | 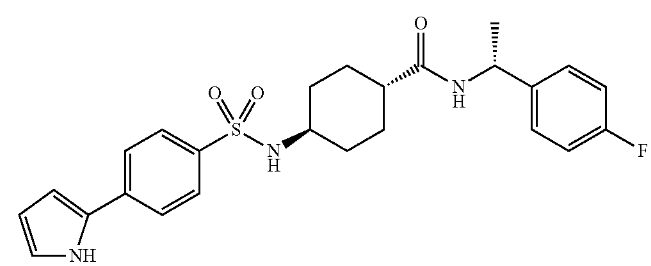 [SMILES: C[C@@H](NC(=O)[C@H]1CC[C@H](NS(=O)(=O)c2ccc(-c3ccc[nH]3)cc2)CC1)c1ccc(F)cc1] | 470.1 |
| 286 | 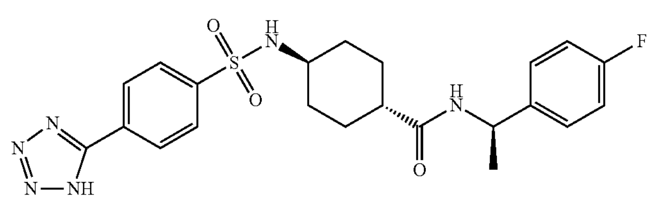 [SMILES: C[C@@H](NC(=O)[C@H]1CC[C@H](NS(=O)(=O)c2ccc(-c3nnn[nH]3)cc2)CC1)c1ccc(F)cc1] | 473.1 |

| Ex. | Structure | LCMS |
|---|---|---|
| 287 | 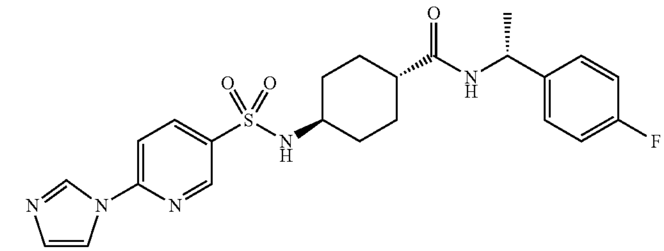 [SMILES: C[C@@H](NC(=O)[C@H]1CC[C@H](NS(=O)(=O)c2ccc(-n3ccnc3)nc2)CC1)c1ccc(F)cc1] | 472.1 |
| 288 | 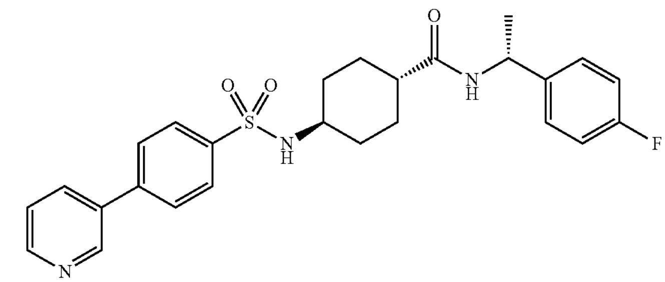 [SMILES: C[C@@H](NC(=O)[C@H]1CC[C@H](NS(=O)(=O)c2ccc(-c3cccnc3)cc2)CC1)c1ccc(F)cc1] | 482.2 |
| 289 | 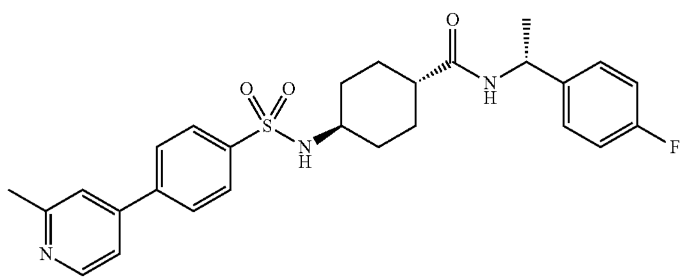 [SMILES: Cc1cc(-c2ccc(S(=O)(=O)N[C@H]3CC[C@H](C(=O)N[C@H](C)c4ccc(F)cc4)CC3)cc2)ccn1] | 496.1 |
| 290 | 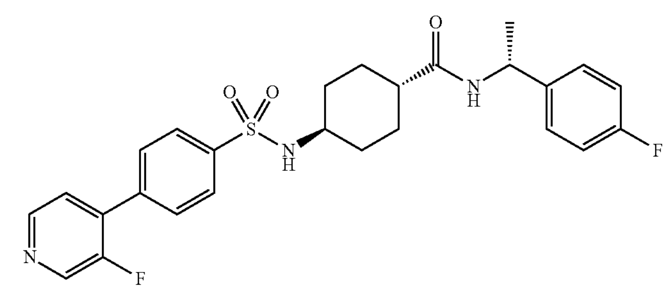 [SMILES: C[C@@H](NC(=O)[C@H]1CC[C@H](NS(=O)(=O)c2ccc(-c3ccncc3F)cc2)CC1)c1ccc(F)cc1] | 500.2 |
| 291 | 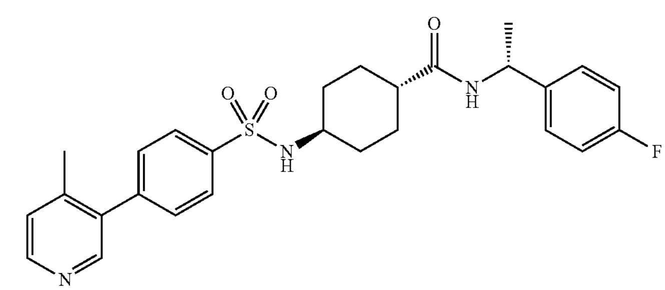 [SMILES: Cc1ccncc1-c1ccc(S(=O)(=O)N[C@H]2CC[C@H](C(=O)N[C@H](C)c3ccc(F)cc3)CC2)cc1] | 496.1 |

-continued

| Ex. | Structure | LCMS |
|---|---|---|
| 292 | 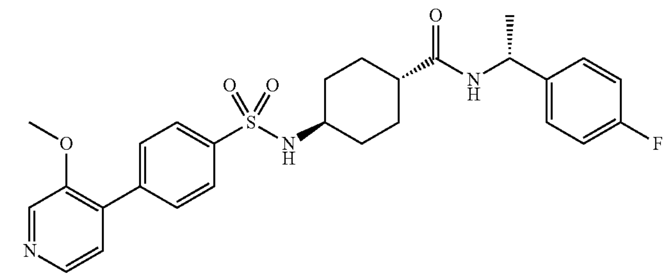 [SMILES: COc1cnccc1-c1ccc(S(=O)(=O)N[C@H]2CC[C@H](C(=O)N[C@H](C)c3ccc(F)cc3)CC2)cc1] | 512.1 |
| 293 | 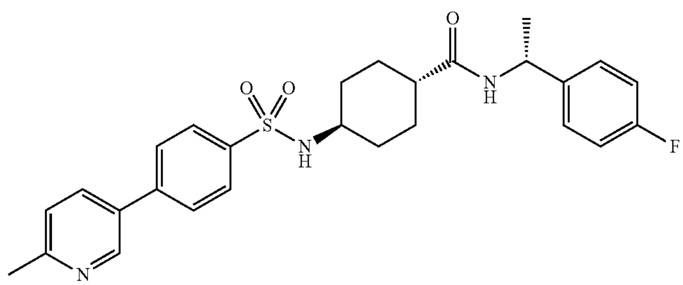 [SMILES: Cc1ccc(-c2ccc(S(=O)(=O)N[C@H]3CC[C@H](C(=O)N[C@H](C)c4ccc(F)cc4)CC3)cc2)cn1] | 496.1 |
| 294 | 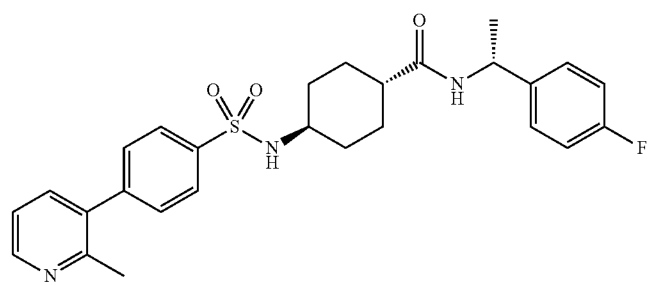 [SMILES: Cc1ncccc1-c1ccc(S(=O)(=O)N[C@H]2CC[C@H](C(=O)N[C@H](C)c3ccc(F)cc3)CC2)cc1] | 496.2 |
| 295 | 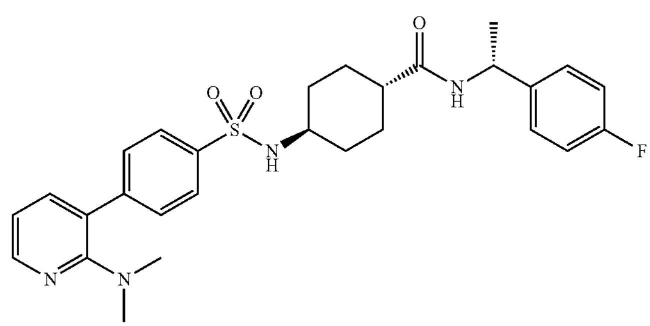 [SMILES: C[C@@H](NC(=O)[C@H]1CC[C@H](NS(=O)(=O)c2ccc(-c3cccnc3N(C)C)cc2)CC1)c1ccc(F)cc1] | 525.1 |
| 296 | 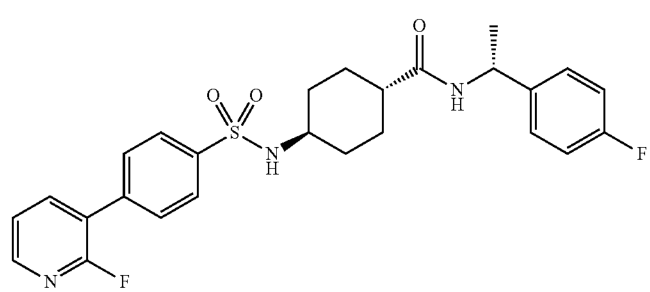 [SMILES: C[C@@H](NC(=O)[C@H]1CC[C@H](NS(=O)(=O)c2ccc(-c3cccnc3F)cc2)CC1)c1ccc(F)cc1] | 500.1 |

| Ex. | Structure | LCMS |
|---|---|---|
| 297 | 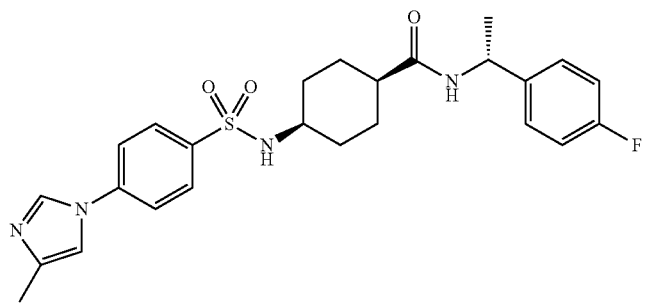 [SMILES: Cc1cn(-c2ccc(S(=O)(=O)N[C@H]3CC[C@@H](C(=O)N[C@H](C)c4ccc(F)cc4)CC3)cc2)cn1] | 485.1 |
| 298 | 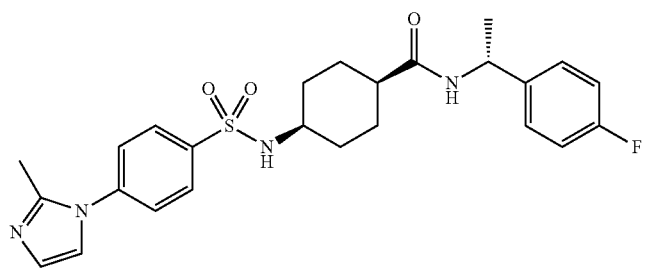 [SMILES: Cc1nccn1-c1ccc(S(=O)(=O)N[C@H]2CC[C@@H](C(=O)N[C@H](C)c3ccc(F)cc3)CC2)cc1] | 485.2 |
| 299 | 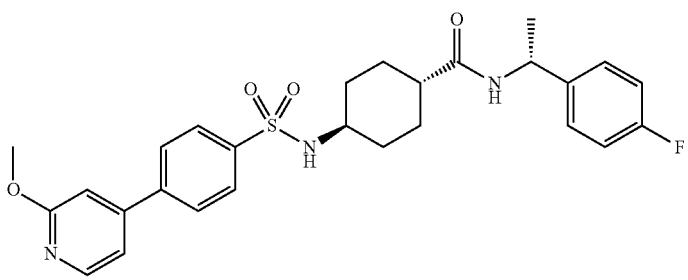 [SMILES: COc1cc(-c2ccc(S(=O)(=O)N[C@H]3CC[C@H](C(=O)N[C@H](C)c4ccc(F)cc4)CC3)cc2)ccn1] | 512.1 |
| 300 | 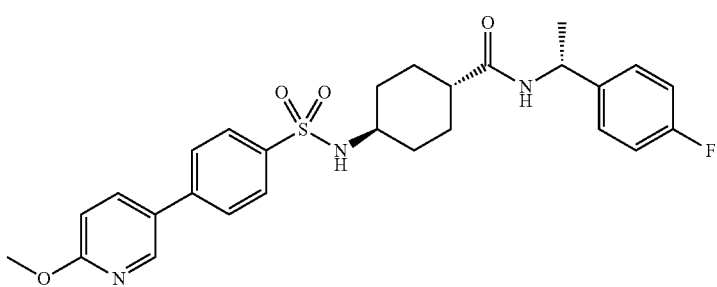 [SMILES: COc1ccc(-c2ccc(S(=O)(=O)N[C@H]3CC[C@H](C(=O)N[C@H](C)c4ccc(F)cc4)CC3)cc2)cn1] | 512.1 |
| 301 | 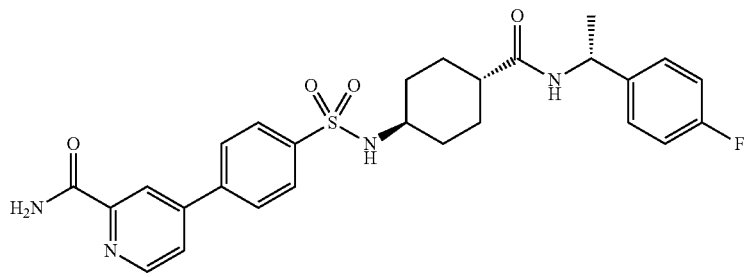 [SMILES: C[C@@H](NC(=O)[C@H]1CC[C@H](NS(=O)(=O)c2ccc(-c3ccnc(C(N)=O)c3)cc2)CC1)c1ccc(F)cc1] | 525.1 |

| Ex. | Structure | LCMS |
|---|---|---|
| 302 | 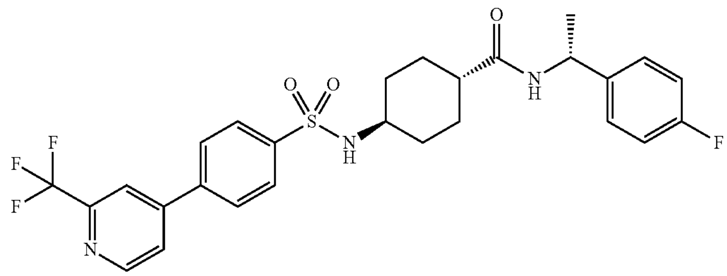 [SMILES: C[C@@H](NC(=O)[C@H]1CC[C@H](NS(=O)(=O)c2ccc(-c3ccnc(C(F)(F)F)c3)cc2)CC1)c1ccc(F)cc1] | 550.1 |
| 303 | 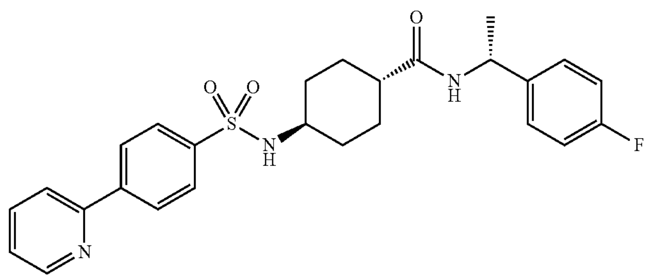 [SMILES: C[C@@H](NC(=O)[C@H]1CC[C@H](NS(=O)(=O)c2ccc(-c3ccccn3)cc2)CC1)c1ccc(F)cc1] | 482.1 |
| 304 | 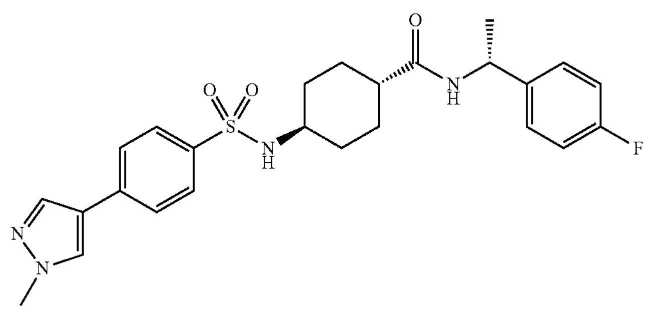 [SMILES: C[C@@H](NC(=O)[C@H]1CC[C@H](NS(=O)(=O)c2ccc(-c3cnn(C)c3)cc2)CC1)c1ccc(F)cc1] | 485.2 |
| 305 | 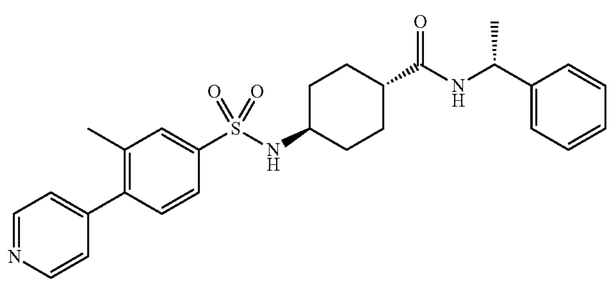 [SMILES: Cc1cc(S(=O)(=O)N[C@H]2CC[C@H](C(=O)N[C@H](C)c3ccccc3)CC2)ccc1-c1ccncc1] | 478.1 |
| 306 | 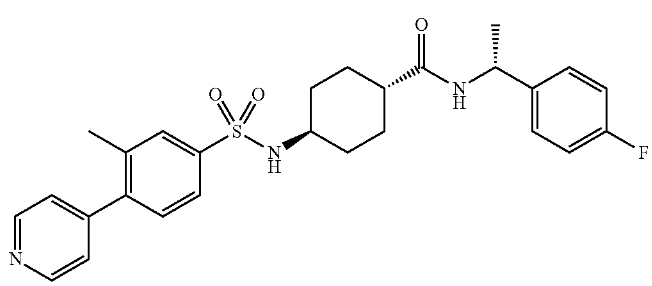 [SMILES: Cc1cc(S(=O)(=O)N[C@H]2CC[C@H](C(=O)N[C@H](C)c3ccc(F)cc3)CC2)ccc1-c1ccncc1] | 496.1 |

| Ex. | Structure | LCMS |
|---|---|---|
| 307 | 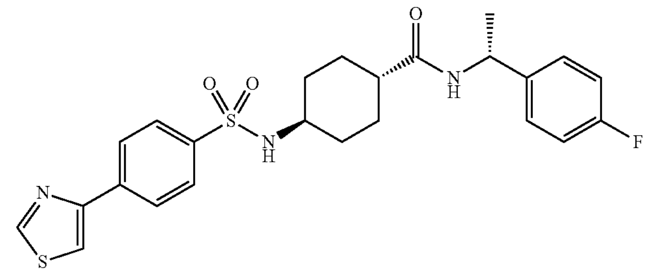 [SMILES: C[C@@H](NC(=O)[C@H]1CC[C@H](NS(=O)(=O)c2ccc(-c3cscn3)cc2)CC1)c1ccc(F)cc1] | 488.2 |
| 308 | 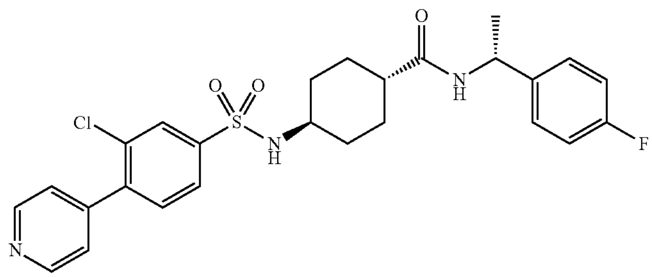 [SMILES: C[C@@H](NC(=O)[C@H]1CC[C@H](NS(=O)(=O)c2ccc(-c3ccncc3)c(Cl)c2)CC1)c1ccc(F)cc1] | 516.0 |
| 309 | 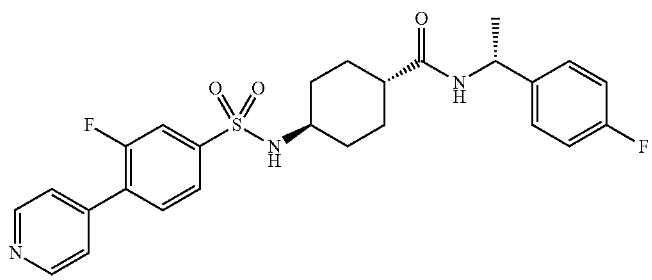 | 500.1 |
| 310 | 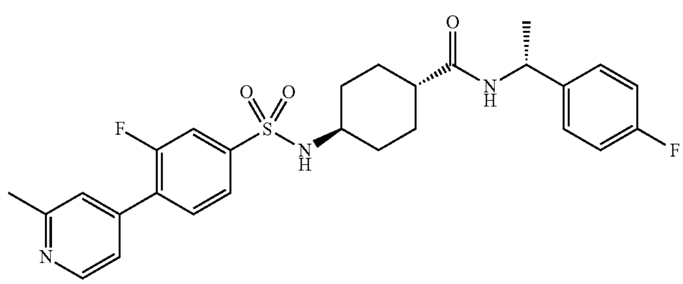 [SMILES: Cc1cc(-c2ccc(S(=O)(=O)N[C@H]3CC[C@H](C(=O)N[C@H](C)c4ccc(F)cc4)CC3)cc2F)ccn1] | 514.1 |
| 311 | 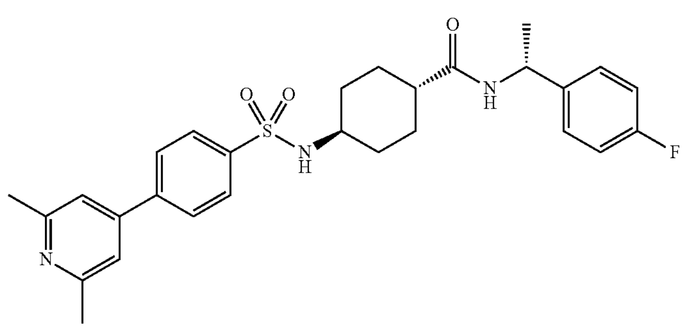 [SMILES: Cc1cc(-c2ccc(S(=O)(=O)N[C@H]3CC[C@H](C(=O)N[C@H](C)c4ccc(F)cc4)CC3)cc2)cc(C)n1] | 510.2 |

| Ex. | Structure | LCMS |
|---|---|---|
| 312 | 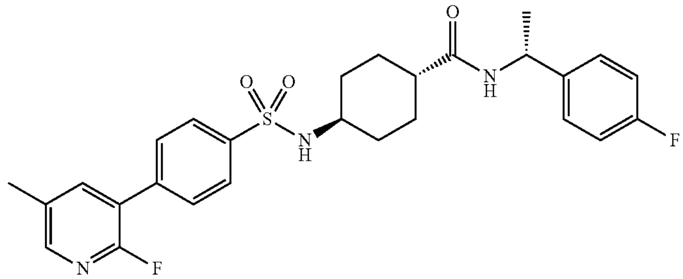 [SMILES: Cc1cnc(F)c(-c2ccc(S(=O)(=O)N[C@H]3CC[C@H](C(=O)N[C@H](C)c4ccc(F)cc4)CC3)cc2)c1] | 514.1 |
| 313 | 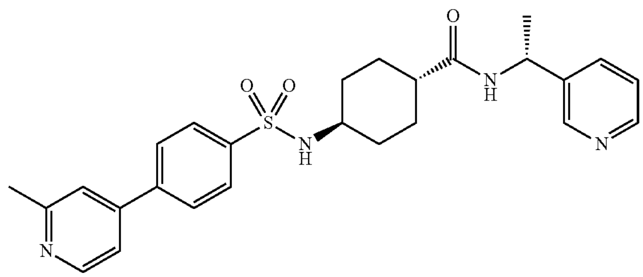 [SMILES: Cc1cc(-c2ccc(S(=O)(=O)N[C@H]3CC[C@H](C(=O)N[C@H](C)c4cccnc4)CC3)cc2)ccn1] | 479.2 |
| 314 | 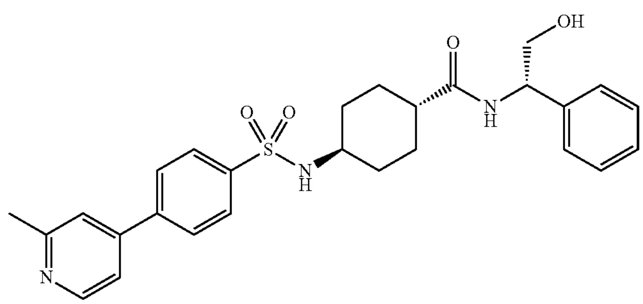 [SMILES: Cc1cc(-c2ccc(S(=O)(=O)N[C@H]3CC[C@H](C(=O)N[C@H](CO)c4ccccc4)CC3)cc2)ccn1] | 494.0 |
| 315 | 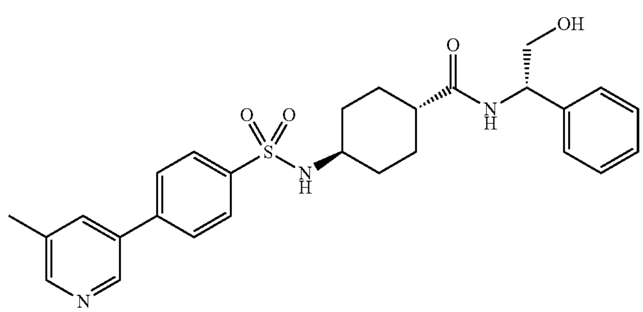 [SMILES: Cc1cncc(-c2ccc(S(=O)(=O)N[C@H]3CC[C@H](C(=O)N[C@H](CO)c4ccccc4)CC3)cc2)c1] | 494.0 |
| 316 | 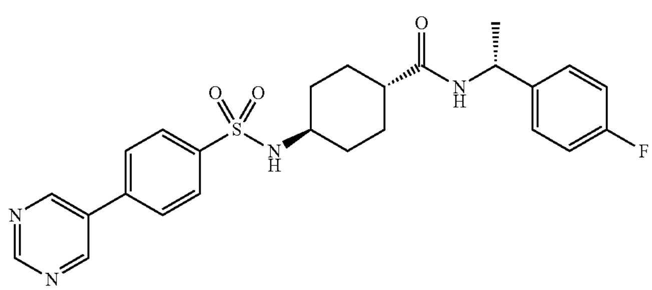 [SMILES: C[C@@H](NC(=O)[C@H]1CC[C@H](NS(=O)(=O)c2ccc(-c3cncnc3)cc2)CC1)c1ccc(F)cc1] | 483.2 |

| Ex. | Structure | LCMS |
|---|---|---|
| 317 | 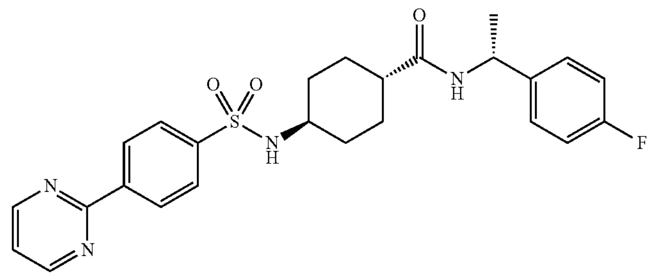 [SMILES: C[C@@H](NC(=O)[C@H]1CC[C@H](NS(=O)(=O)c2ccc(-c3ncccn3)cc2)CC1)c1ccc(F)cc1] | 483.2 |
| 318 | 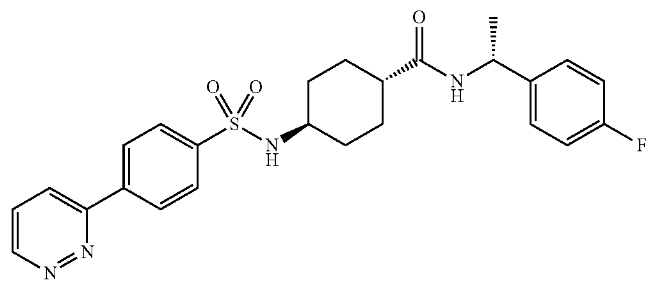 | 483.2 |
| 319 | 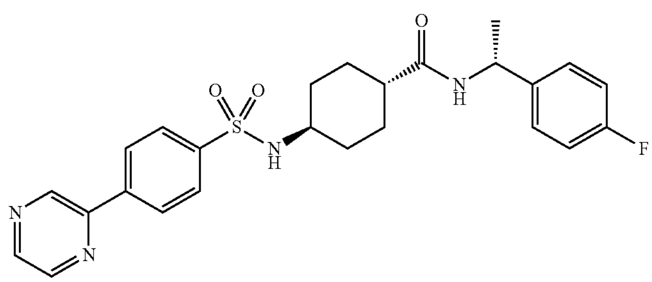 [SMILES: C[C@@H](NC(=O)[C@H]1CC[C@H](NS(=O)(=O)c2ccc(-c3cnccn3)cc2)CC1)c1ccc(F)cc1] | 483.3 |
| 320 | 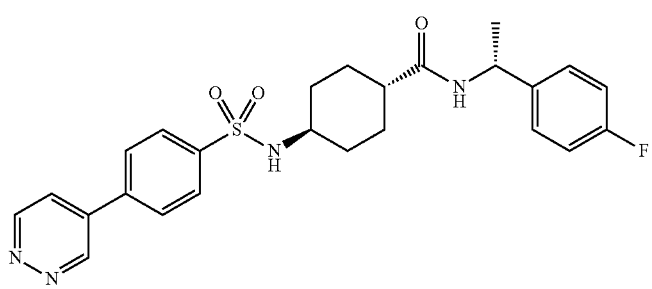 [SMILES: C[C@@H](NC(=O)[C@H]1CC[C@H](NS(=O)(=O)c2ccc(-c3ccnnc3)cc2)CC1)c1ccc(F)cc1] | 483.2 |
| 321 | 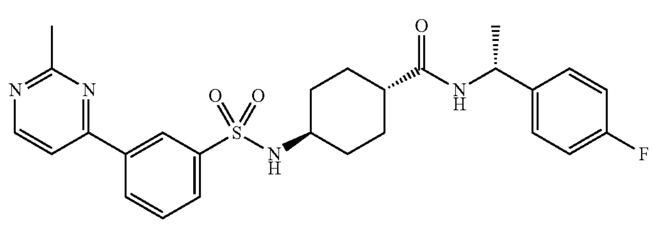 [SMILES: Cc1nccc(-c2cccc(S(=O)(=O)N[C@H]3CC[C@H](C(=O)N[C@H](C)c4ccc(F)cc4)CC3)c2)n1] | 497.2 |

-continued

| Ex. | Structure | LCMS |
|---|---|---|
| 322 | 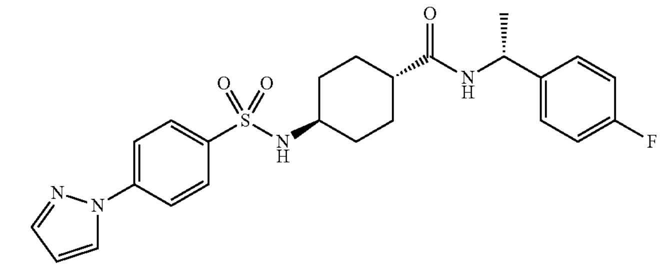 [SMILES: C[C@@H](NC(=O)[C@H]1CC[C@H](NS(=O)(=O)c2ccc(-n3cccn3)cc2)CC1)c1ccc(F)cc1] | 471.1 |
| 323 | 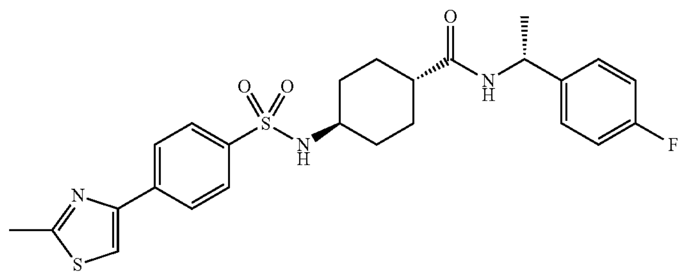 [SMILES: Cc1nc(-c2ccc(S(=O)(=O)N[C@H]3CC[C@H](C(=O)N[C@H](C)c4ccc(F)cc4)CC3)cc2)cs1] | 502.1 |
| 324 | 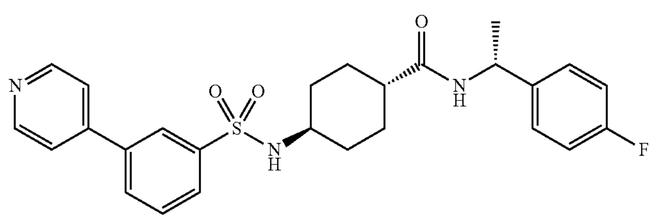 [SMILES: C[C@@H](NC(=O)[C@H]1CC[C@H](NS(=O)(=O)c2cccc(-c3ccncc3)c2)CC1)c1ccc(F)cc1] | 482.1 |
| 325 | 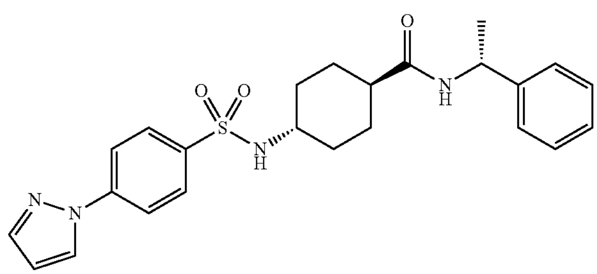 [SMILES: C[C@@H](NC(=O)[C@H]1CC[C@H](NS(=O)(=O)c2ccc(-n3cccn3)cc2)CC1)c1ccccc1] | 553.1 |
| 326 | 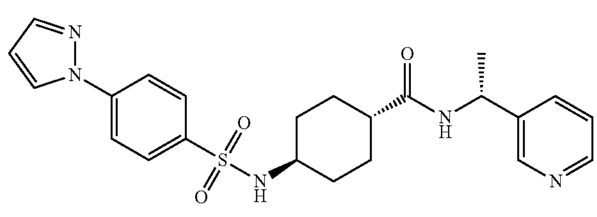 [SMILES: C[C@@H](NC(=O)[C@H]1CC[C@H](NS(=O)(=O)c2ccc(-n3cccn3)cc2)CC1)c1cccnc1] | 454.2 |
| 327 | 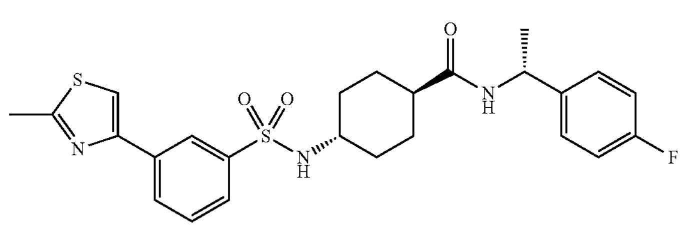 [SMILES: Cc1nc(-c2cccc(S(=O)(=O)N[C@H]3CC[C@H](C(=O)N[C@H](C)c4ccc(F)cc4)CC3)c2)cs1] | 502.0 |

| Ex. | Structure | LCMS |
|---|---|---|
| 328 | 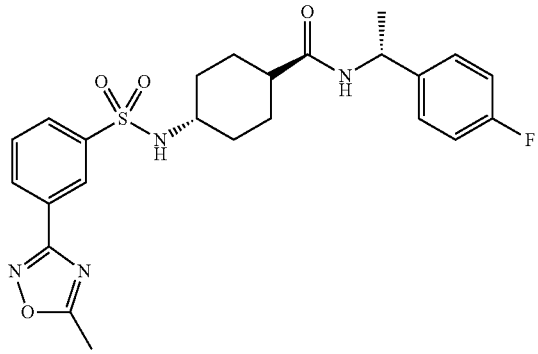 | 487.0 |
| 329 | 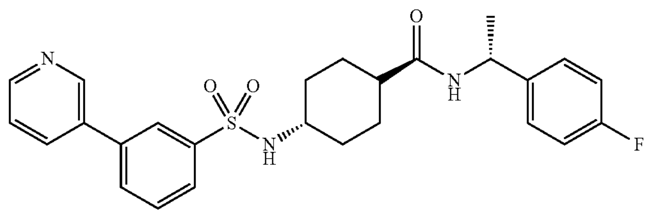 | 482.2 |
| 330 | 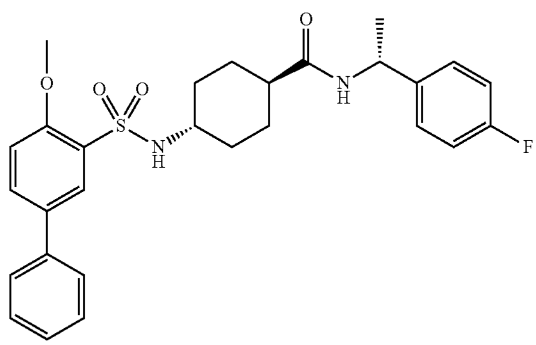 [SMILES: COc1ccc(-c2ccccc2)cc1S(=O)(=O)N[C@H]1CC[C@H](C(=O)N[C@H](C)c2ccc(F)cc2)CC1] | 511.2 |
| 331 | 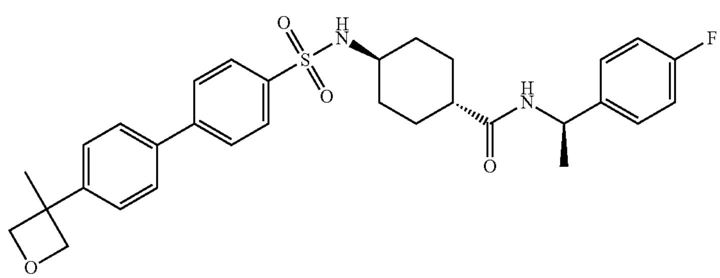 [SMILES: C[C@@H](NC(=O)[C@H]1CC[C@H](NS(=O)(=O)c2ccc(-c3ccc(C4(C)COC4)cc3)cc2)CC1)c1ccc(F)cc1] | 551.0 |
| 332 | 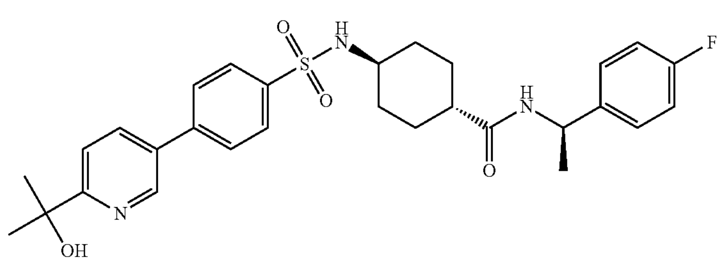 [SMILES: C[C@@H](NC(=O)[C@H]1CC[C@H](NS(=O)(=O)c2ccc(-c3ccc(C(C)(C)O)nc3)cc2)CC1)c1ccc(F)cc1] | 540.0 |

| Ex. | Structure | LCMS |
|---|---|---|
| 333 | 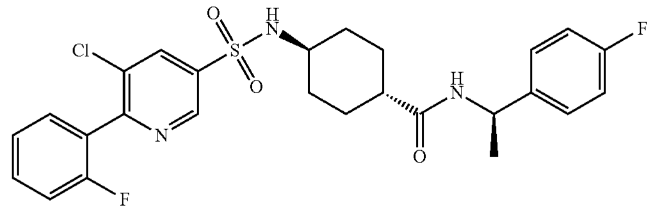 [SMILES: C[C@@H](NC(=O)[C@H]1CC[C@H](NS(=O)(=O)c2cnc(-c3ccccc3F)c(Cl)c2)CC1)c1ccc(F)cc1] | 534.0 |
| 334 | 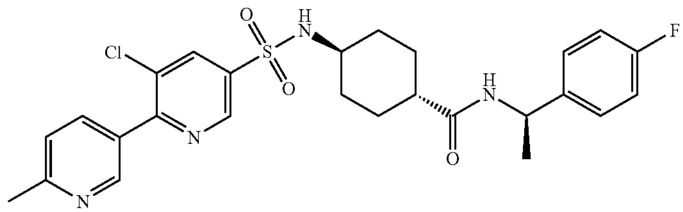 [SMILES: Cc1ccc(-c2ncc(S(=O)(=O)N[C@H]3CC[C@H](C(=O)N[C@H](C)c4ccc(F)cc4)CC3)cc2Cl)cn1] | 531.0 |
| 335 | 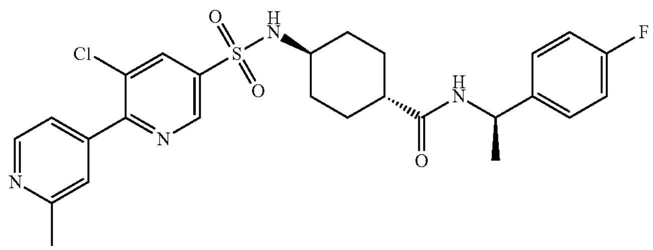 [SMILES: Cc1cc(-c2ncc(S(=O)(=O)N[C@H]3CC[C@H](C(=O)N[C@H](C)c4ccc(F)cc4)CC3)cc2Cl)ccn1] | 531.0 |
| 336 | 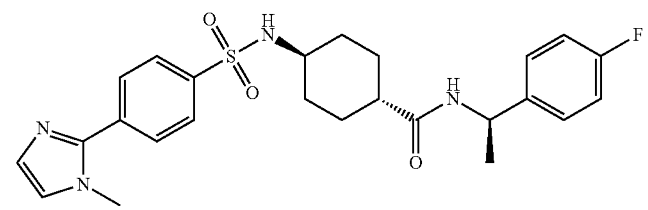 [SMILES: C[C@@H](NC(=O)[C@H]1CC[C@H](NS(=O)(=O)c2ccc(-c3nccn3C)cc2)CC1)c1ccc(F)cc1] | 485.0 |
| 337 | 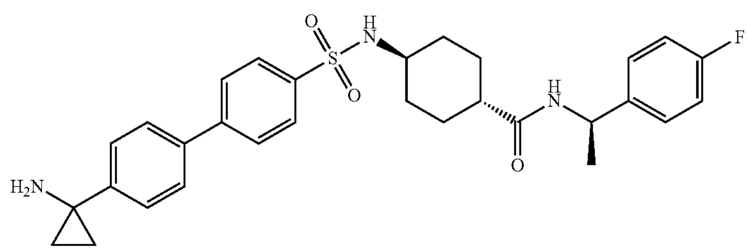 [SMILES: C[C@@H](NC(=O)[C@H]1CC[C@H](NS(=O)(=O)c2ccc(-c3ccc(C4(N)CC4)cc3)cc2)CC1)c1ccc(F)cc1] | 537.0 |
| 338 | 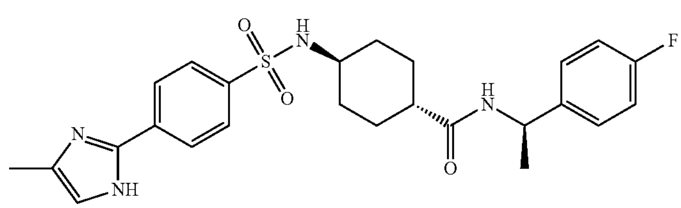 [SMILES: Cc1c[nH]c(-c2ccc(S(=O)(=O)N[C@H]3CC[C@H](C(=O)N[C@H](C)c4ccc(F)cc4)CC3)cc2)n1] | 485.0 |
| 339 | 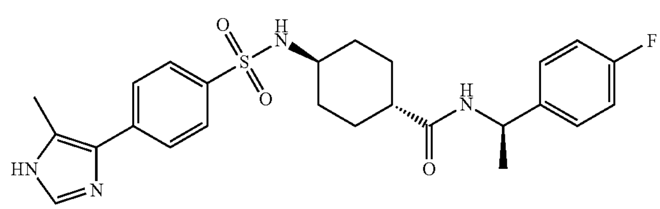 [SMILES: Cc1[nH]cnc1-c1ccc(S(=O)(=O)N[C@H]2CC[C@H](C(=O)N[C@H](C)c3ccc(F)cc3)CC2)cc1] | 485.0 |

| Ex. | Structure | LCMS |
|---|---|---|
| 340 | 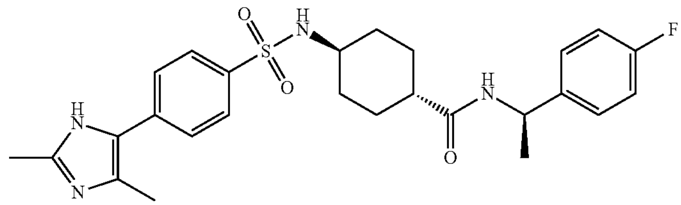 [SMILES: Cc1nc(C)c(-c2ccc(S(=O)(=O)N[C@H]3CC[C@H](C(=O)N[C@H](C)c4ccc(F)cc4)CC3)cc2)[nH]1] | 499.0 |
| 341 | 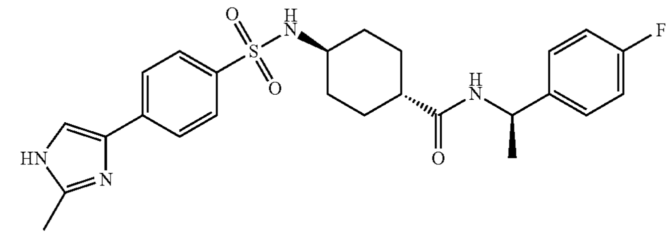 [SMILES: Cc1nc(-c2ccc(S(=O)(=O)N[C@H]3CC[C@H](C(=O)N[C@H](C)c4ccc(F)cc4)CC3)cc2)c[nH]1] | 485.0 |
| 342 | 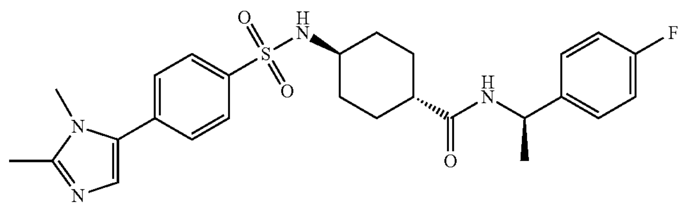 [SMILES: Cc1ncc(-c2ccc(S(=O)(=O)N[C@H]3CC[C@H](C(=O)N[C@H](C)c4ccc(F)cc4)CC3)cc2)n1C] | 499.0 |
| 343 | 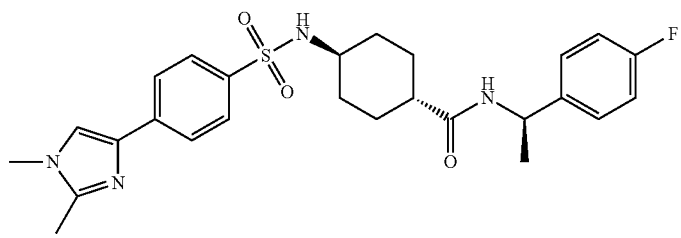 [SMILES: Cc1nc(-c2ccc(S(=O)(=O)N[C@H]3CC[C@H](C(=O)N[C@H](C)c4ccc(F)cc4)CC3)cc2)cn1C] | 499.0 |
| 344 | 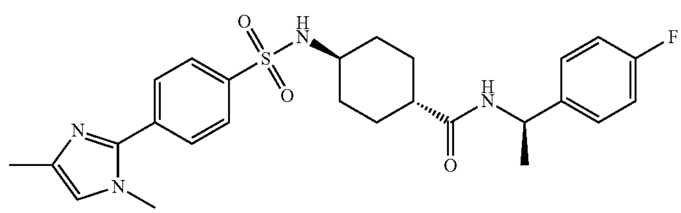 [SMILES: Cc1cn(C)c(-c2ccc(S(=O)(=O)N[C@H]3CC[C@H](C(=O)N[C@H](C)c4ccc(F)cc4)CC3)cc2)n1] | 499.0 |
| 345 | 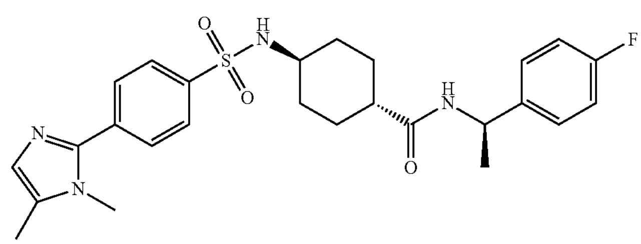 [SMILES: Cc1cnc(-c2ccc(S(=O)(=O)N[C@H]3CC[C@H](C(=O)N[C@H](C)c4ccc(F)cc4)CC3)cc2)n1C] | 499.0 |
| 346 | 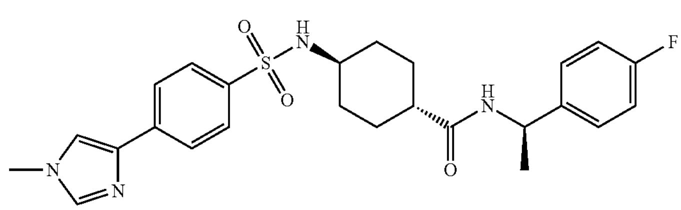 [SMILES: C[C@@H](NC(=O)[C@H]1CC[C@H](NS(=O)(=O)c2ccc(-c3cn(C)cn3)cc2)CC1)c1ccc(F)cc1] | 485.0 |

| Ex. | Structure | LCMS |
|---|---|---|
| 347 | 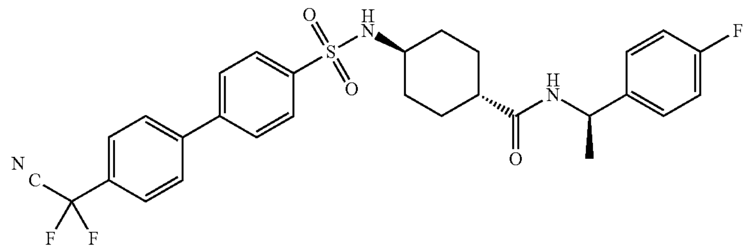 | 556.0 |
| 348 | 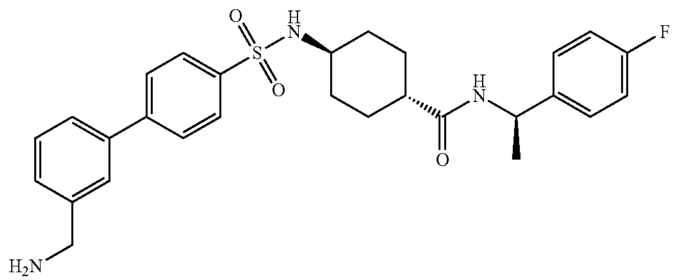 [SMILES: C[C@@H](NC(=O)[C@H]1CC[C@H](NS(=O)(=O)c2ccc(-c3cccc(CN)c3)cc2)CC1)c1ccc(F)cc1] | 510.0 |
| 349 | 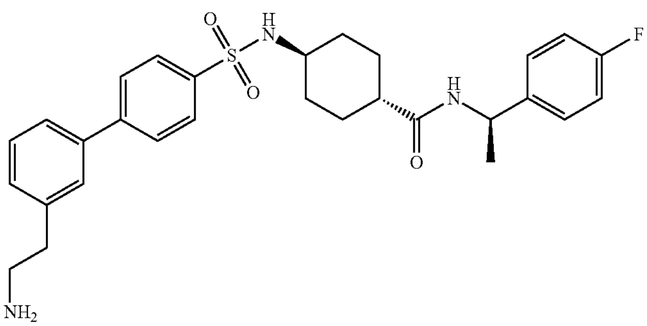 [SMILES: C[C@@H](NC(=O)[C@H]1CC[C@H](NS(=O)(=O)c2ccc(-c3cccc(CCN)c3)cc2)CC1)c1ccc(F)cc1] | 524.0 |
| 350 | 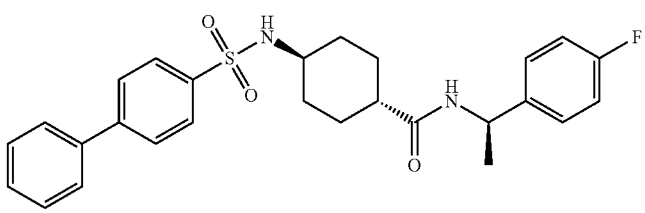 [SMILES: C[C@@H](NC(=O)[C@H]1CC[C@H](NS(=O)(=O)c2ccc(-c3ccccc3)cc2)CC1)c1ccc(F)cc1] | 481.0 |
| 351 | 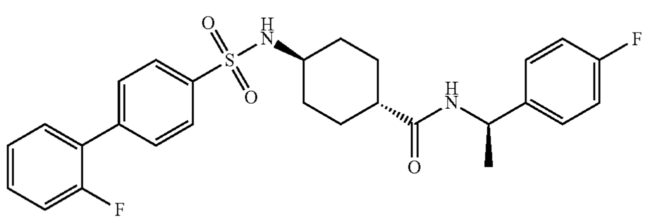 [SMILES: C[C@@H](NC(=O)[C@H]1CC[C@H](NS(=O)(=O)c2ccc(-c3ccccc3F)cc2)CC1)c1ccc(F)cc1] | 499.0 |
| 352 | 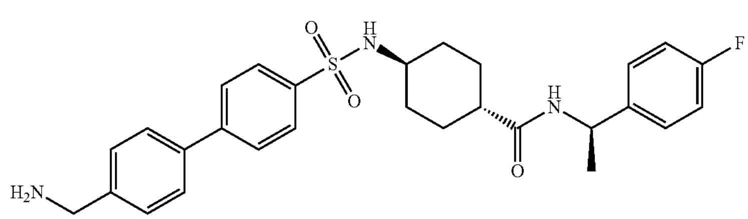 [SMILES: C[C@@H](NC(=O)[C@H]1CC[C@H](NS(=O)(=O)c2ccc(-c3ccc(CN)cc3)cc2)CC1)c1ccc(F)cc1] | 510.0 |

| Ex. | Structure | LCMS |
|---|---|---|
| 353 | 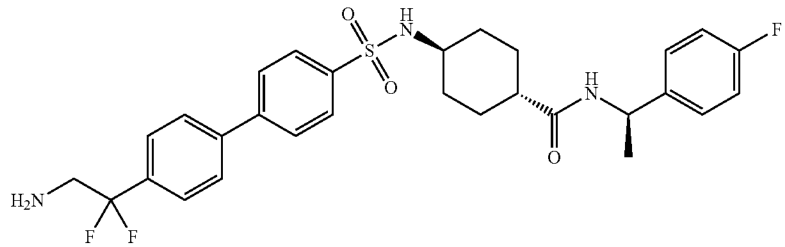 [SMILES: C[C@@H](NC(=O)[C@H]1CC[C@H](NS(=O)(=O)c2ccc(-c3ccc(C(F)(F)CN)cc3)cc2)CC1)c1ccc(F)cc1] | 560.0 |
| 354 | 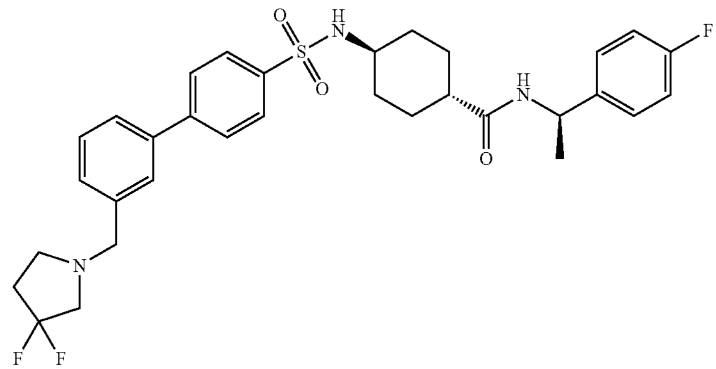 [SMILES: C[C@@H](NC(=O)[C@H]1CC[C@H](NS(=O)(=O)c2ccc(-c3cccc(CN4CCC(F)(F)C4)c3)cc2)CC1)c1ccc(F)cc1] | 600.0 |
| 355 | 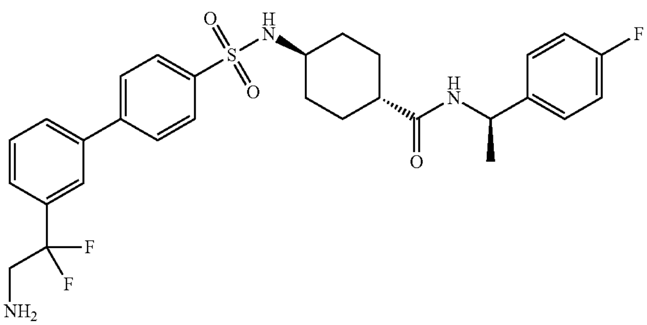 [SMILES: C[C@@H](NC(=O)[C@H]1CC[C@H](NS(=O)(=O)c2ccc(-c3cccc(C(F)(F)CN)c3)cc2)CC1)c1ccc(F)cc1] | 560.0 |
| 356 | 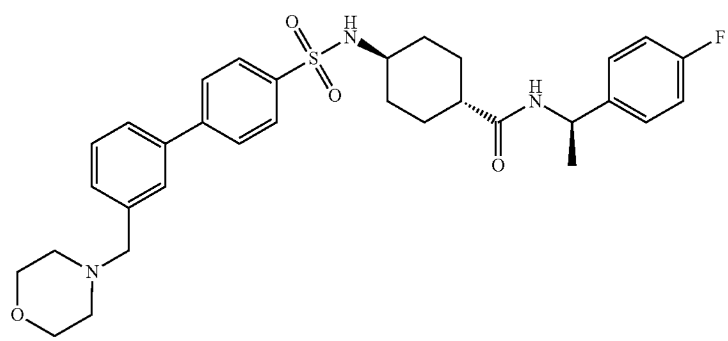 [SMILES: C[C@@H](NC(=O)[C@H]1CC[C@H](NS(=O)(=O)c2ccc(-c3cccc(CN4CCOCC4)c3)cc2)CC1)c1ccc(F)cc1] | 580.0 |
| 357 | 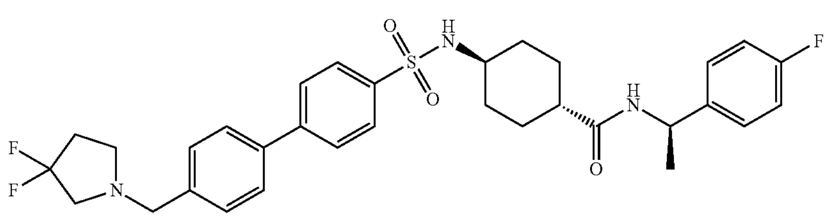 | 600.0 |

| Ex. | Structure | LCMS |
|---|---|---|
| 358 | 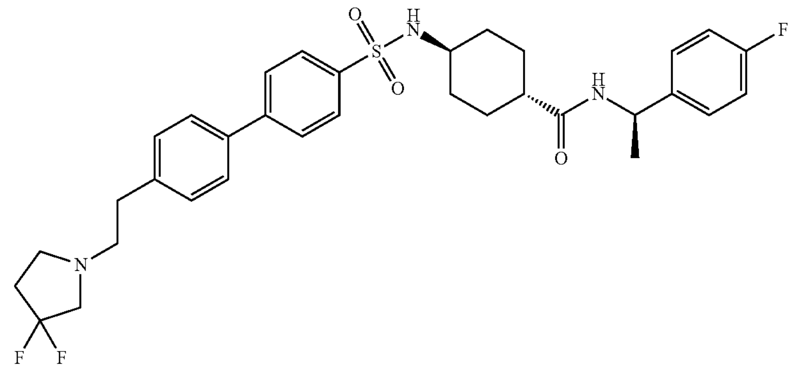 [SMILES: C[C@@H](NC(=O)[C@H]1CC[C@H](NS(=O)(=O)c2ccc(-c3ccc(CCN4CCC(F)(F)C4)cc3)cc2)CC1)c1ccc(F)cc1] | 614.0 |
| 359 | 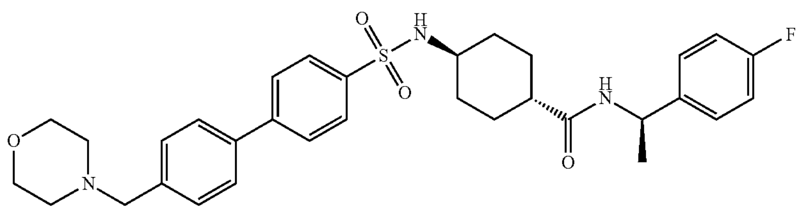 [SMILES: C[C@@H](NC(=O)[C@H]1CC[C@H](NS(=O)(=O)c2ccc(-c3ccc(CN4CCOCC4)cc3)cc2)CC1)c1ccc(F)cc1] | 580.0 |
| 360 | 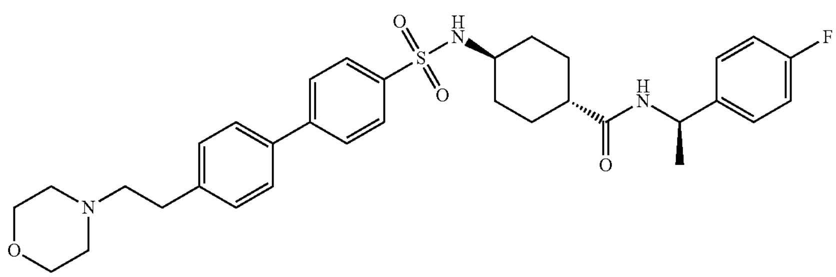 [SMILES: C[C@@H](NC(=O)[C@H]1CC[C@H](NS(=O)(=O)c2ccc(-c3ccc(CCN4CCOCC4)cc3)cc2)CC1)c1ccc(F)cc1] | 595.0 |
| 361 | 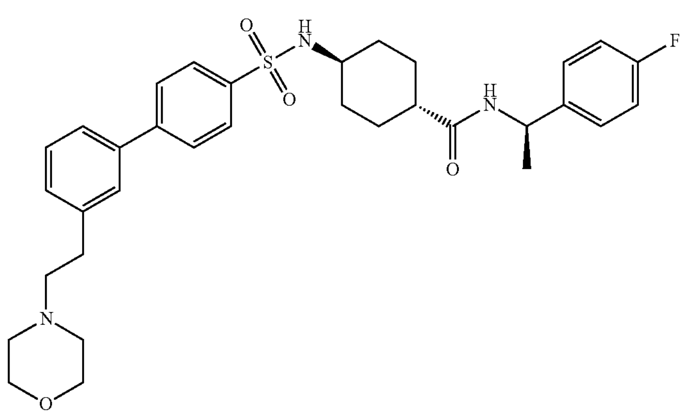 [SMILES: C[C@@H](NC(=O)[C@H]1CC[C@H](NS(=O)(=O)c2ccc(-c3cccc(CCN4CCOCC4)c3)cc2)CC1)c1ccc(F)cc1] | 595.0 |

-continued
| Ex. | Structure | LCMS |
|---|---|---|
| 362 | 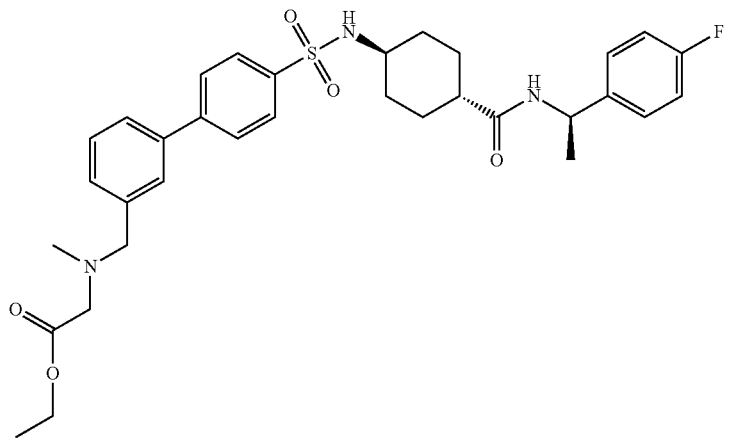 [SMILES: CCOC(=O)CN(C)Cc1cccc(-c2ccc(S(=O)(=O)N[C@H]3CC[C@H](C(=O)N[C@H](C)c4ccc(F)cc4)CC3)cc2)c1] | 611.0 |
| 363 | 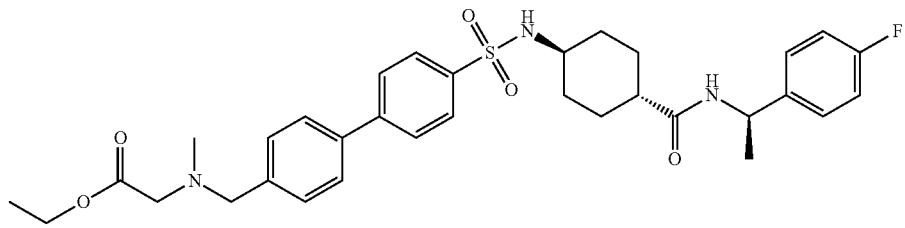 [SMILES: CCOC(=O)CN(C)Cc1ccc(-c2ccc(S(=O)(=O)N[C@H]3CC[C@H](C(=O)N[C@H](C)c4ccc(F)cc4)CC3)cc2)cc1] | 611.0 |
| 364 | 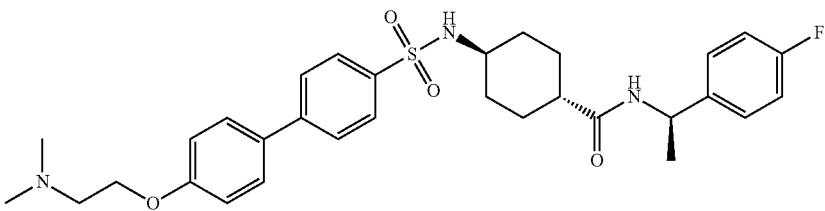 [SMILES: C[C@@H](NC(=O)[C@H]1CC[C@H](NS(=O)(=O)c2ccc(-c3ccc(OCCN(C)C)cc3)cc2)CC1)c1ccc(F)cc1] | 568.0 |
| 365 | 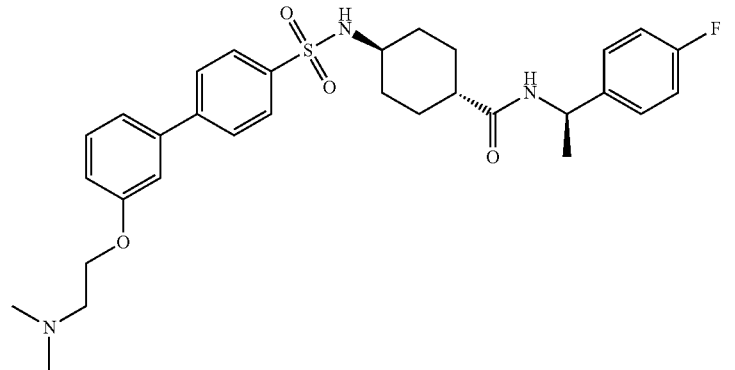 [SMILES: C[C@@H](NC(=O)[C@H]1CC[C@H](NS(=O)(=O)c2ccc(-c3cccc(OCCN(C)C)c3)cc2)CC1)c1ccc(F)cc1] | 569.0 |

| Ex. | Structure | LCMS |
|---|---|---|
| 366 | 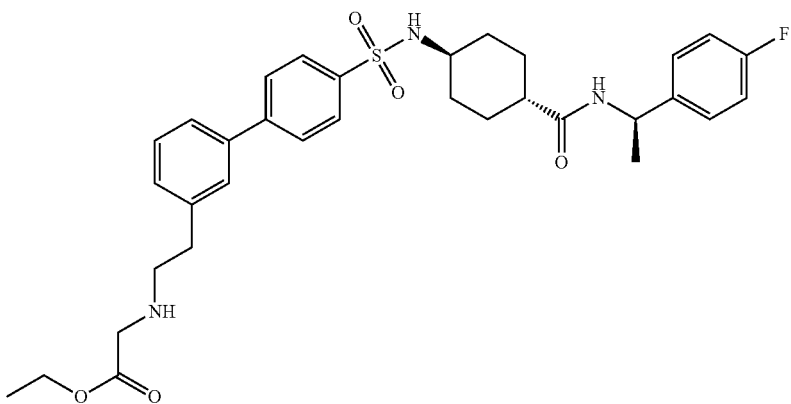 [SMILES: CCOC(=O)CNCCc1cccc(-c2ccc(S(=O)(=O)N[C@H]3CC[C@H](C(=O)N[C@H](C)c4ccc(F)cc4)CC3)cc2)c1] | 610.0 |
| 367 | 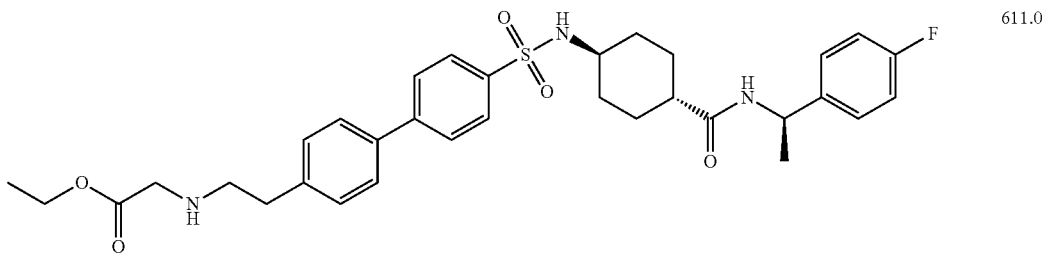 | 611.0 |
| 368 | 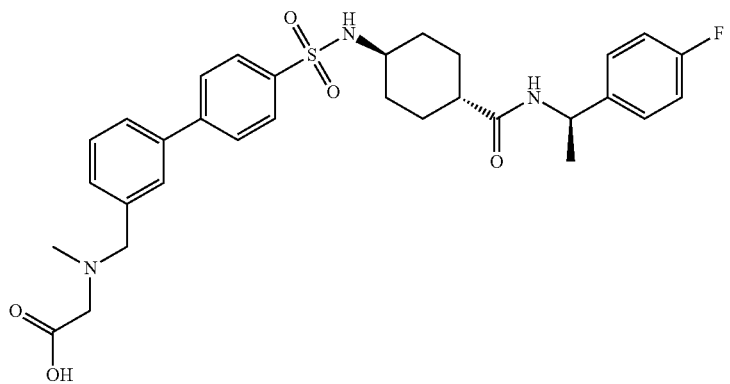 [SMILES: C[C@@H](NC(=O)[C@H]1CC[C@H](NS(=O)(=O)c2ccc(-c3cccc(CN(C)CC(=O)O)c3)cc2)CC1)c1ccc(F)cc1] | 582.0 |
| 369 | 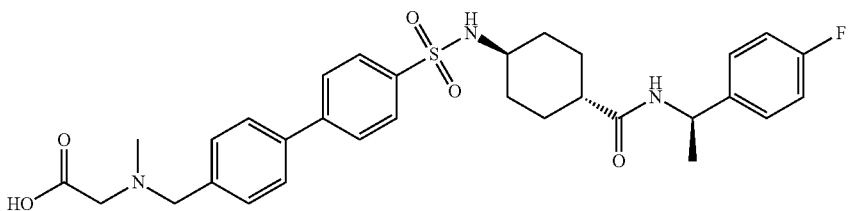 [SMILES: C[C@@H](NC(=O)[C@H]1CC[C@H](NS(=O)(=O)c2ccc(-c3ccc(CN(C)CC(=O)O)cc3)cc2)CC1)c1ccc(F)cc1] | 582.0 |
| 370 | 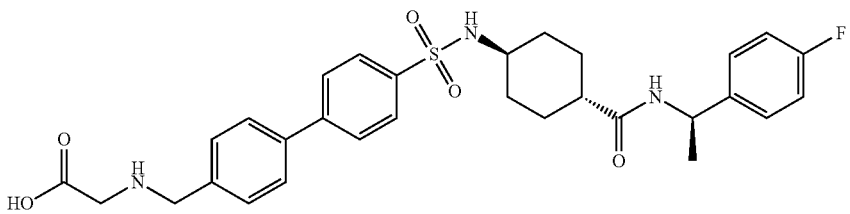 [SMILES: C[C@@H](NC(=O)[C@H]1CC[C@H](NS(=O)(=O)c2ccc(-c3ccc(CNCC(=O)O)cc3)cc2)CC1)c1ccc(F)cc1] | 568.0 |

| Ex. | Structure | LCMS |
|---|---|---|
| 371 | 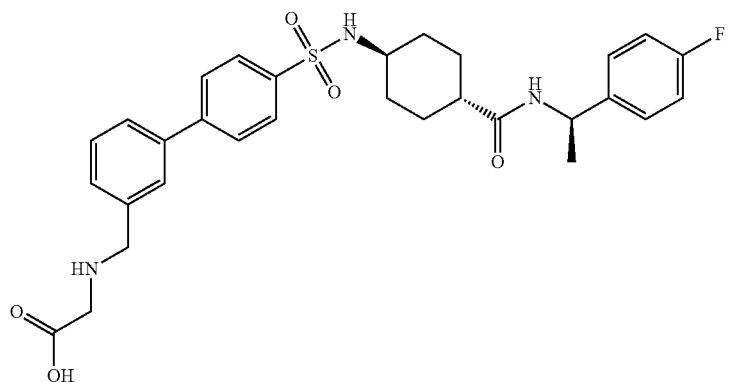 [SMILES: C[C@@H](NC(=O)[C@H]1CC[C@H](NS(=O)(=O)c2ccc(-c3cccc(CNCC(=O)O)c3)cc2)CC1)c1ccc(F)cc1] | 568.0 |
| 372 | 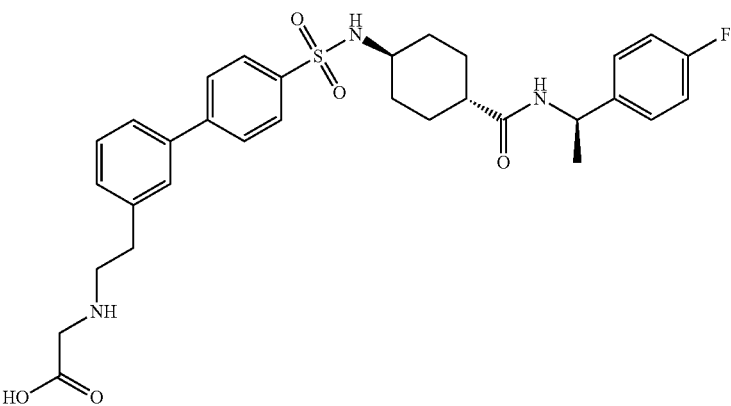 [SMILES: C[C@@H](NC(=O)[C@H]1CC[C@H](NS(=O)(=O)c2ccc(-c3cccc(CCNCC(=O)O)c3)cc2)CC1)c1ccc(F)cc1] | 582.0 |
| 373 | 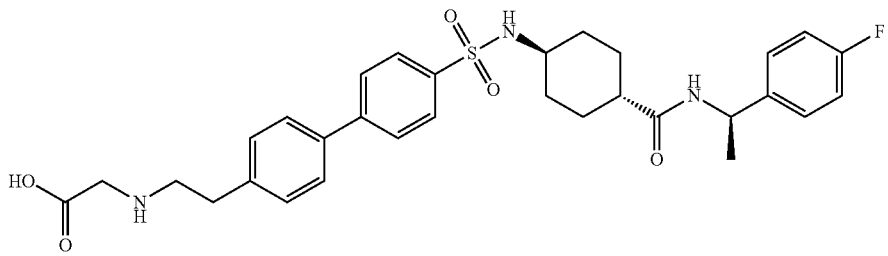 [SMILES: C[C@@H](NC(=O)[C@H]1CC[C@H](NS(=O)(=O)c2ccc(-c3ccc(CCNCC(=O)O)cc3)cc2)CC1)c1ccc(F)cc1] | 583.0 |
| 374 | 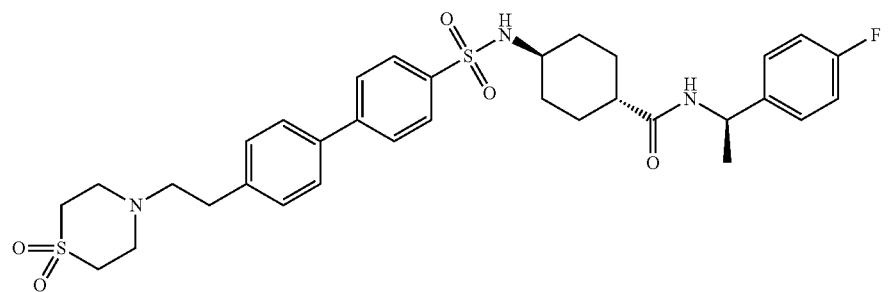 [SMILES: C[C@@H](NC(=O)[C@H]1CC[C@H](NS(=O)(=O)c2ccc(-c3ccc(CCN4CCS(=O)(=O)CC4)cc3)cc2)CC1)c1ccc(F)cc1] | 642.0 |

-continued

| Ex. | Structure | LCMS |
|---|---|---|
| 375 | 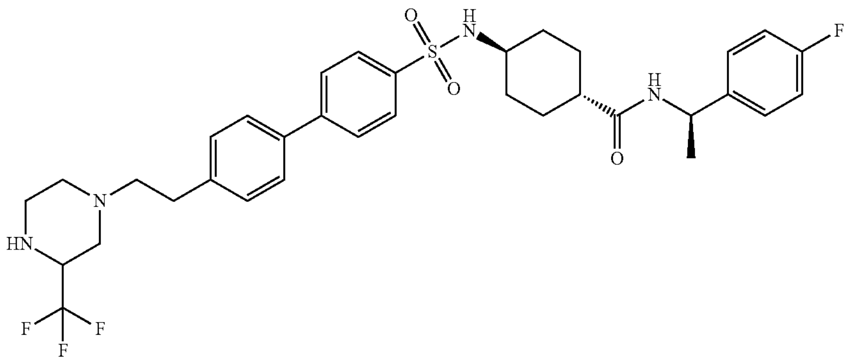 [SMILES: C[C@@H](NC(=O)[C@H]1CC[C@H](NS(=O)(=O)c2ccc(-c3ccc(CCN4CCNC(C(F)(F)F)C4)cc3)cc2)CC1)c1ccc(F)cc1] | 662.0 |
| 376 | 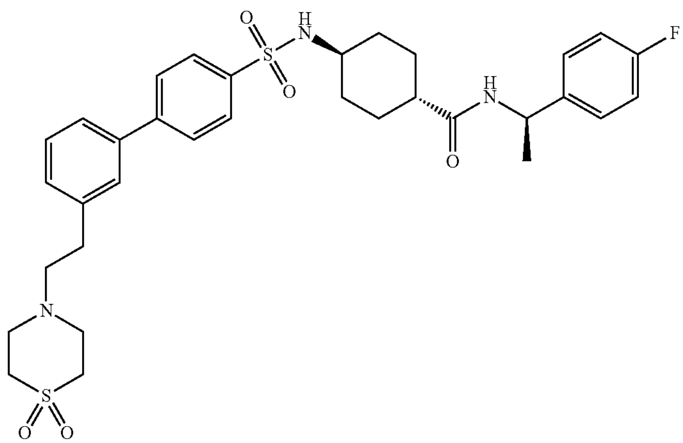 [SMILES: C[C@@H](NC(=O)[C@H]1CC[C@H](NS(=O)(=O)c2ccc(-c3cccc(CCN4CCS(=O)(=O)CC4)c3)cc2)CC1)c1ccc(F)cc1] | 642.0 |
| 377 | 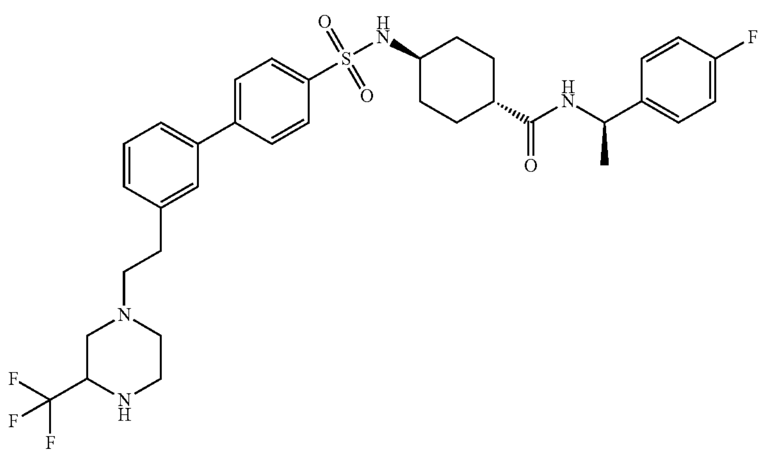 [SMILES: C[C@@H](NC(=O)[C@H]1CC[C@H](NS(=O)(=O)c2ccc(-c3cccc(CCN4CCNC(C(F)(F)F)C4)c3)cc2)CC1)c1ccc(F)cc1] | 662.0 |
| 378 | 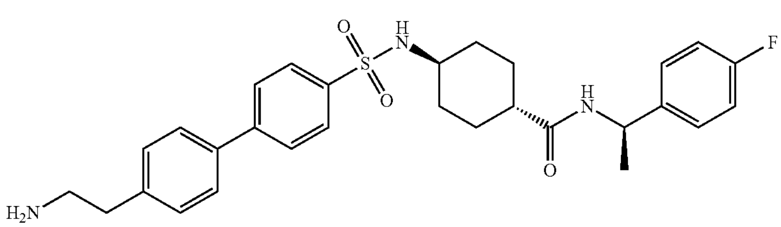 [SMILES: C[C@@H](NC(=O)[C@H]1CC[C@H](NS(=O)(=O)c2ccc(-c3ccc(CCN)cc3)cc2)CC1)c1ccc(F)cc1] | 524.0 |

-continued
| Ex. | Structure | LCMS |
|---|---|---|
| 379 | 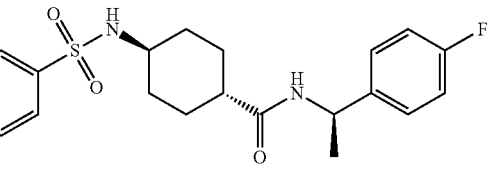 | 596.0 |
| 380 | 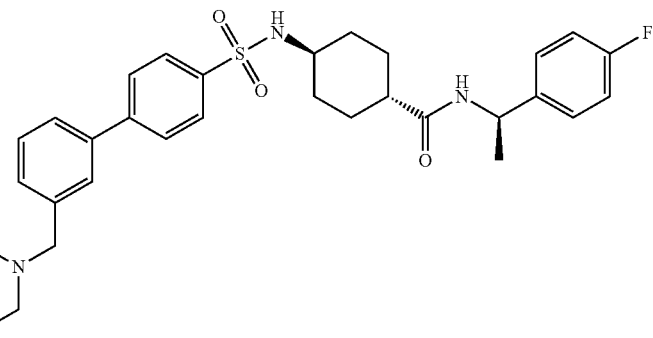 | 629.0 |
| 381 | 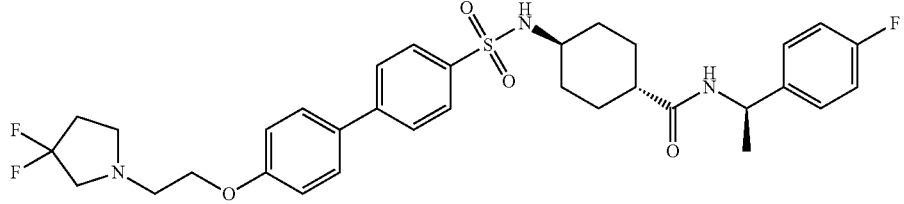 [SMILES: C[C@@H](NC(=O)[C@H]1CC[C@H](NS(=O)(=O)c2ccc(-c3ccc(OCCN4CCC(F)(F)C4)cc3)cc2)CC1)c1ccc(F)cc1] | 630.0 |
| 382 | 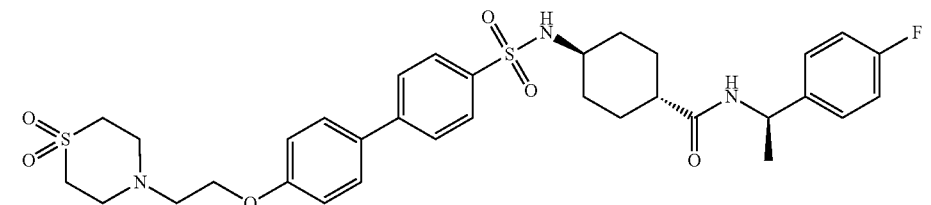 | 658.0 |
| 383 | 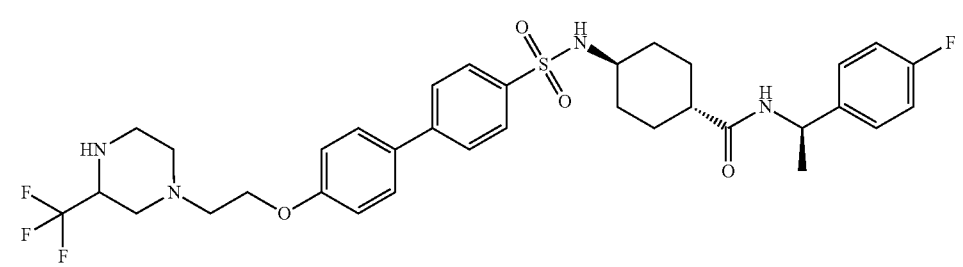 [SMILES: C[C@@H](NC(=O)[C@H]1CC[C@H](NS(=O)(=O)c2ccc(-c3ccc(OCCN4CCNC(C(F)(F)F)C4)cc3)cc2)CC1)c1ccc(F)cc1] | 678.0 |
| 384 | 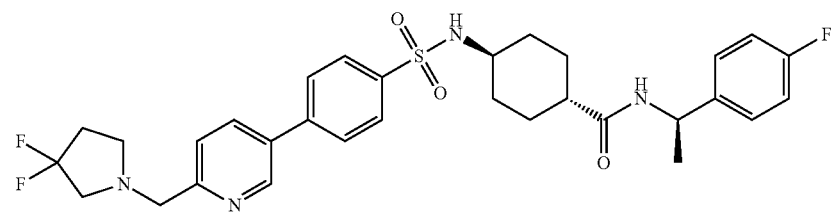 [SMILES: C[C@@H](NC(=O)[C@H]1CC[C@H](NS(=O)(=O)c2ccc(-c3ccc(CN4CCC(F)(F)C4)nc3)cc2)CC1)c1ccc(F)cc1] | 601.0 |

| Ex. | Structure | LCMS |
|---|---|---|
| 385 | 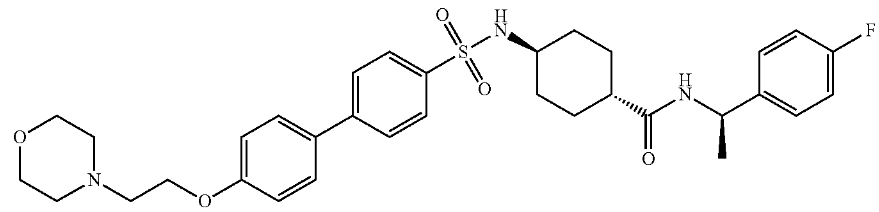 [SMILES: C[C@@H](NC(=O)[C@H]1CC[C@H](NS(=O)(=O)c2ccc(-c3ccc(OCCN4CCOCC4)cc3)cc2)CC1)c1ccc(F)cc1] | 611.0 |
| 386 | 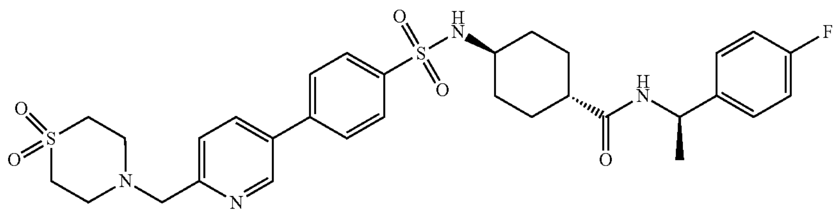 [SMILES: C[C@@H](NC(=O)[C@H]1CC[C@H](NS(=O)(=O)c2ccc(-c3ccc(CN4CCS(=O)(=O)CC4)nc3)cc2)CC1)c1ccc(F)cc1] | 629.0 |
| 387 | 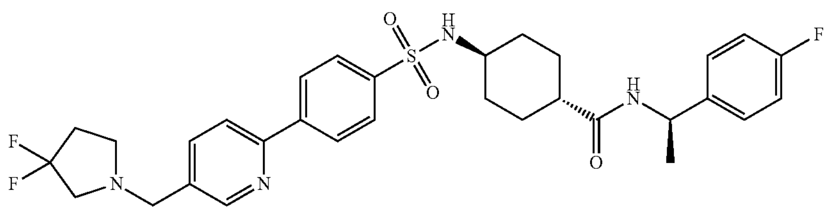 [SMILES: C[C@@H](NC(=O)[C@H]1CC[C@H](NS(=O)(=O)c2ccc(-c3ccc(CN4CCC(F)(F)C4)cn3)cc2)CC1)c1ccc(F)cc1] | 601.0 |
| 388 | 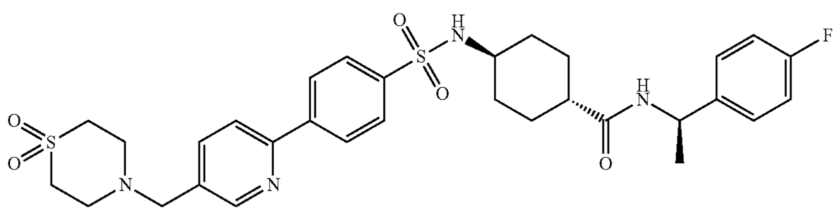 [SMILES: C[C@@H](NC(=O)[C@H]1CC[C@H](NS(=O)(=O)c2ccc(-c3ccc(CN4CCS(=O)(=O)CC4)cn3)cc2)CC1)c1ccc(F)cc1] | 629.0 |
| 389 | 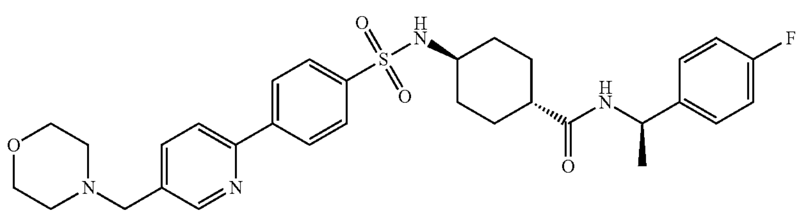 [SMILES: C[C@@H](NC(=O)[C@H]1CC[C@H](NS(=O)(=O)c2ccc(-c3ccc(CN4CCOCC4)cn3)cc2)CC1)c1ccc(F)cc1] | 581.0 |
| 390 | 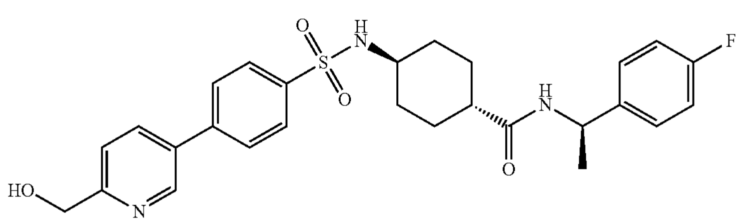 [SMILES: C[C@@H](NC(=O)[C@H]1CC[C@H](NS(=O)(=O)c2ccc(-c3ccc(CO)nc3)cc2)CC1)c1ccc(F)cc1] | 512.0 |
| 391 | 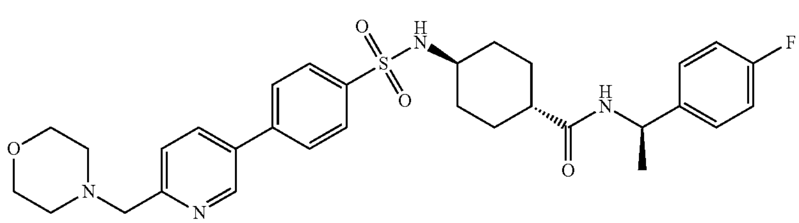 [SMILES: C[C@@H](NC(=O)[C@H]1CC[C@H](NS(=O)(=O)c2ccc(-c3ccc(CN4CCOCC4)nc3)cc2)CC1)c1ccc(F)cc1] | 581.0 |

| Ex. | Structure | LCMS |
|---|---|---|
| 392 | 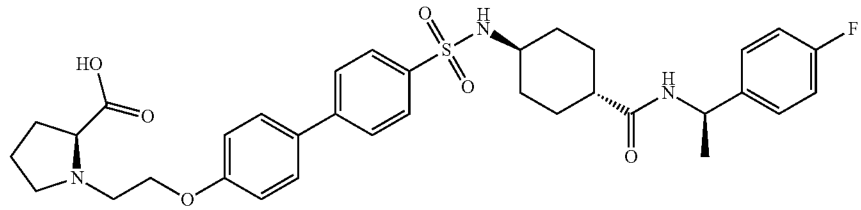 [SMILES: C[C@@H](NC(=O)[C@H]1CC[C@H](NS(=O)(=O)c2ccc(-c3ccc(OCCN4CCC[C@H]4C(=O)O)cc3)cc2)CC1)c1ccc(F)cc1] | 639.0 |
| 393 | 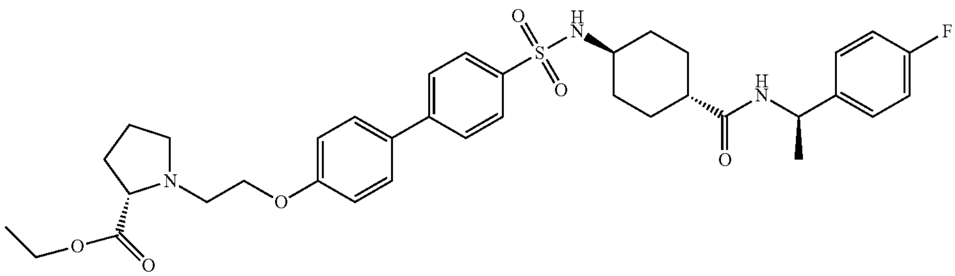 [SMILES: CCOC(=O)[C@@H]1CCCN1CCOc1ccc(-c2ccc(S(=O)(=O)N[C@H]3CC[C@H](C(=O)N[C@H](C)c4ccc(F)cc4)CC3)cc2)cc1] | 667.0 |
| 394 | 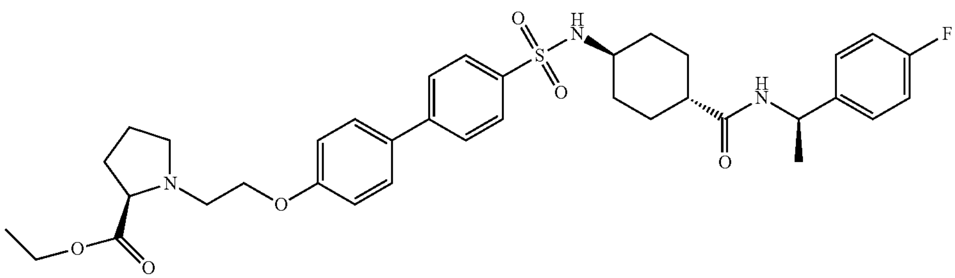 [SMILES: CCOC(=O)[C@H]1CCCN1CCOc1ccc(-c2ccc(S(=O)(=O)N[C@H]3CC[C@H](C(=O)N[C@H](C)c4ccc(F)cc4)CC3)cc2)cc1] | 667.0 |
| 395 | 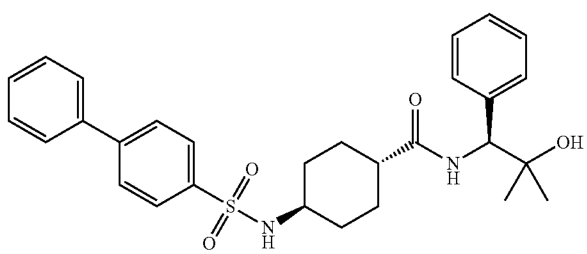 [SMILES: CC(C)(O)[C@@H](NC(=O)[C@H]1CC[C@H](NS(=O)(=O)c2ccc(-c3ccccc3)cc2)CC1)c1ccccc1] | 507.0 |
| 396 | 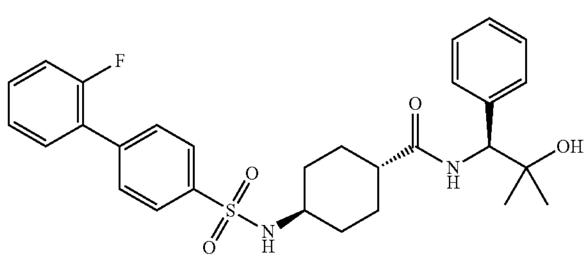 [SMILES: CC(C)(O)[C@@H](NC(=O)[C@H]1CC[C@H](NS(=O)(=O)c2ccc(-c3ccccc3F)cc2)CC1)c1ccccc1] | 525.0 |
| 397 | 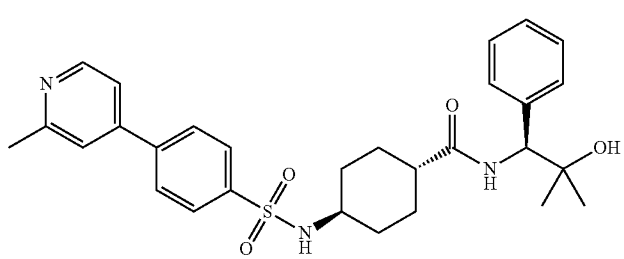 [SMILES: Cc1cc(-c2ccc(S(=O)(=O)N[C@H]3CC[C@H](C(=O)N[C@@H](c4ccccc4)C(C)(C)O)CC3)cc2)ccn1] | 522.0 |

-continued

| Ex. | Structure | LCMS |
|---|---|---|
| 398 | 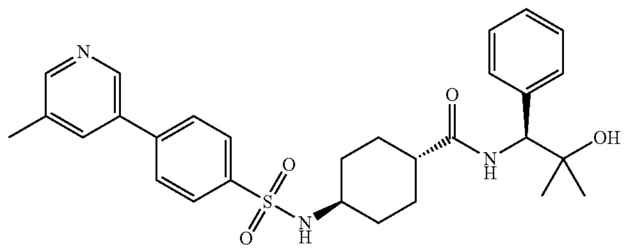 [SMILES: Cc1cncc(-c2ccc(S(=O)(=O)N[C@H]3CC[C@H](C(=O)N[C@@H](c4ccccc4)C(C)(C)O)CC3)cc2)c1] | 522.0 |
| 399 | 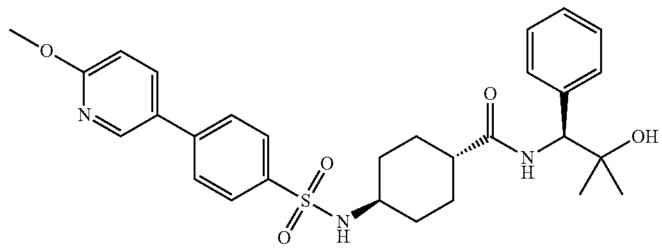 [SMILES: COc1ccc(-c2ccc(S(=O)(=O)N[C@H]3CC[C@H](C(=O)N[C@@H](c4ccccc4)C(C)(C)O)CC3)cc2)cn1] | 538.0 |
| 400 | 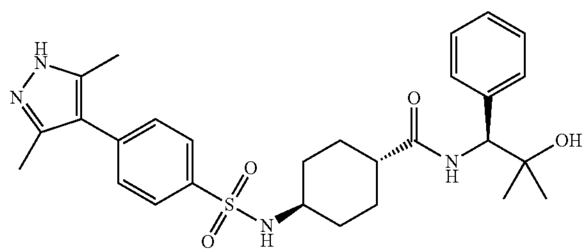 [SMILES: Cc1n[nH]c(C)c1-c1ccc(S(=O)(=O)N[C@H]2CC[C@H](C(=O)N[C@@H](c3ccccc3)C(C)(C)O)CC2)cc1] | 525.0 |
| 401 | 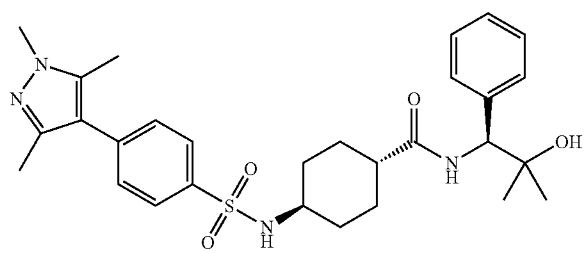 [SMILES: Cc1nn(C)c(C)c1-c1ccc(S(=O)(=O)N[C@H]2CC[C@H](C(=O)N[C@@H](c3ccccc3)C(C)(C)O)CC2)cc1] | 539.0 |
| 402 | 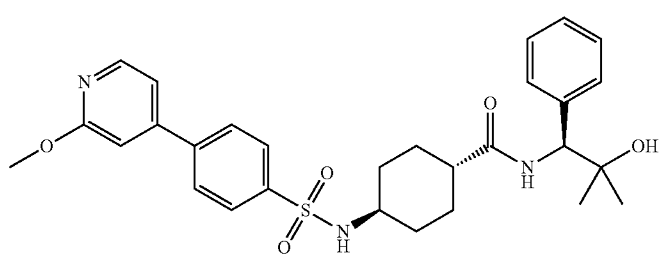 [SMILES: COc1cc(-c2ccc(S(=O)(=O)N[C@H]3CC[C@H](C(=O)N[C@@H](c4ccccc4)C(C)(C)O)CC3)cc2)ccn1] | 538.0 |
| 403 | 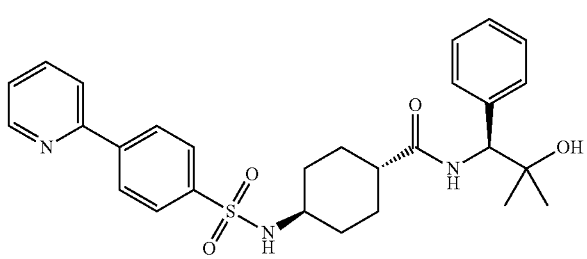 [SMILES: CC(C)(O)[C@@H](NC(=O)[C@H]1CC[C@H](NS(=O)(=O)c2ccc(-c3ccccn3)cc2)CC1)c1ccccc1] | 508.0 |

| Ex. | Structure | LCMS |
|---|---|---|
| 404 | 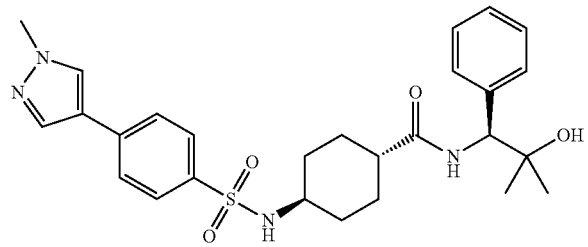 [SMILES: Cn1cc(-c2ccc(S(=O)(=O)N[C@H]3CC[C@H](C(=O)N[C@@H](c4ccccc4)C(C)(C)O)CC3)cc2)cn1] | 511.0 |
| 405 | 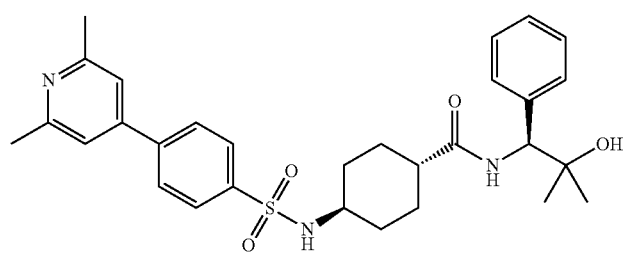 [SMILES: Cc1cc(-c2ccc(S(=O)(=O)N[C@H]3CC[C@H](C(=O)N[C@@H](c4ccccc4)C(C)(C)O)CC3)cc2)cc(C)n1] | 536.0 |
| 406 | 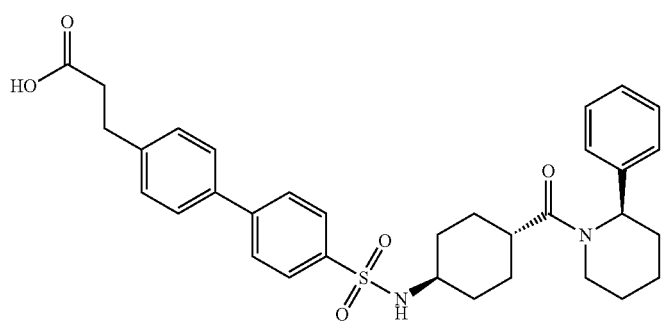 [SMILES: O=C(O)CCc1ccc(-c2ccc(S(=O)(=O)N[C@H]3CC[C@H](C(=O)N4CCCC[C@@H]4c4ccccc4)CC3)cc2)cc1] | 577.4 |
| 407 | 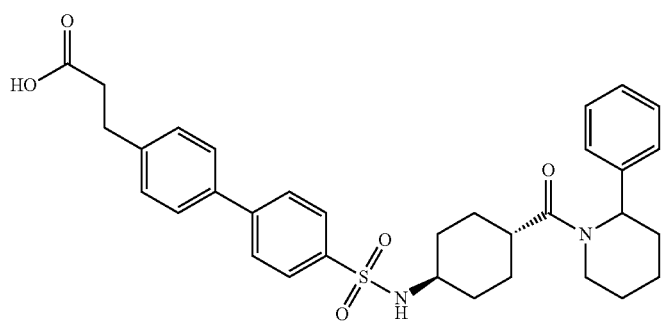 [SMILES: O=C(O)CCc1ccc(-c2ccc(S(=O)(=O)N[C@H]3CC[C@H](C(=O)N4CCCCC4c4ccccc4)CC3)cc2)cc1] | 576.0 |
| 408 | 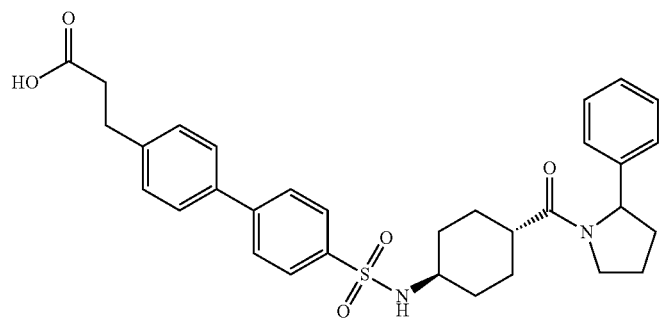 [SMILES: O=C(O)CCc1ccc(-c2ccc(S(=O)(=O)N[C@H]3CC[C@H](C(=O)N4CCCC4c4ccccc4)CC3)cc2)cc1] | 562.0 |

| Ex. | Structure | LCMS |
|---|---|---|
| 409 | 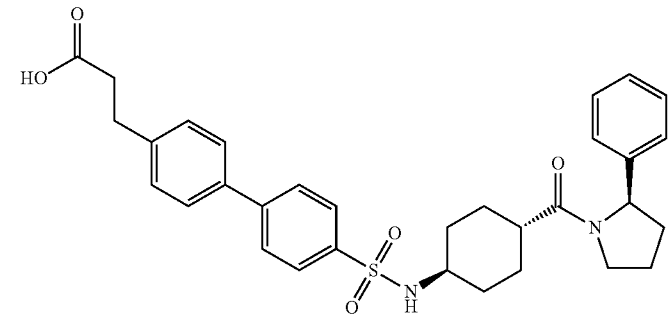 [SMILES: O=C(O)CCc1ccc(-c2ccc(S(=O)(=O)N[C@H]3CC[C@H](C(=O)N4CCC[C@@H]4c4ccccc4)CC3)cc2)cc1] | 561.0 |
| 410 | 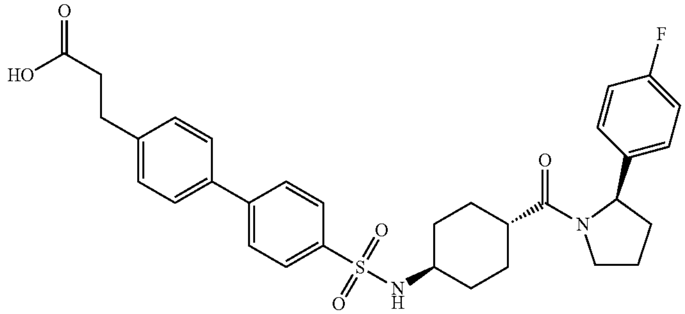 [SMILES: O=C(O)CCc1ccc(-c2ccc(S(=O)(=O)N[C@H]3CC[C@H](C(=O)N4CCC[C@@H]4c4ccc(F)cc4)CC3)cc2)cc1] | 579.0 |
| 411 | 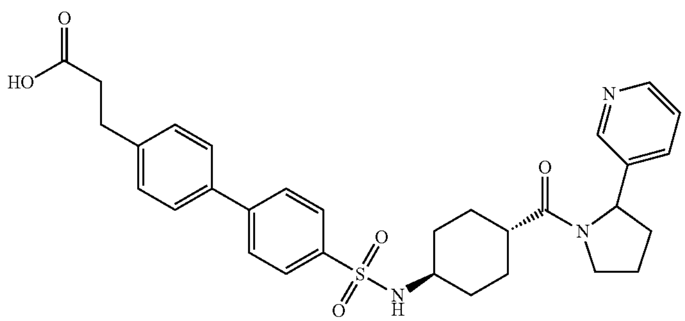 [SMILES: O=C(O)CCc1ccc(-c2ccc(S(=O)(=O)N[C@H]3CC[C@H](C(=O)N4CCCC4c4cccnc4)CC3)cc2)cc1] | 562.0 |
| 412 | 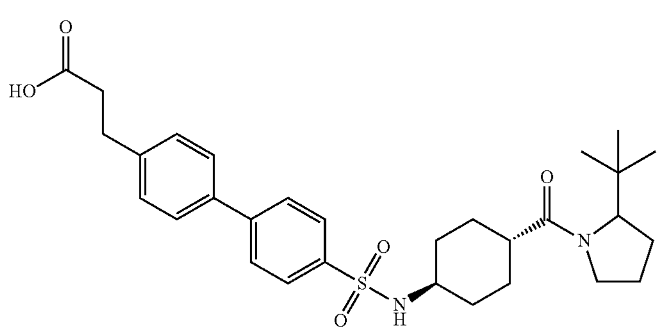 [SMILES: CC(C)(C)C1CCCN1C(=O)[C@H]1CC[C@H](NS(=O)(=O)c2ccc(-c3ccc(CCC(=O)O)cc3)cc2)CC1] | 542.0 |

US 8,394,858 B2

281                    282

-continued

| Ex. | Structure | LCMS |
|---|---|---|
| 413 | 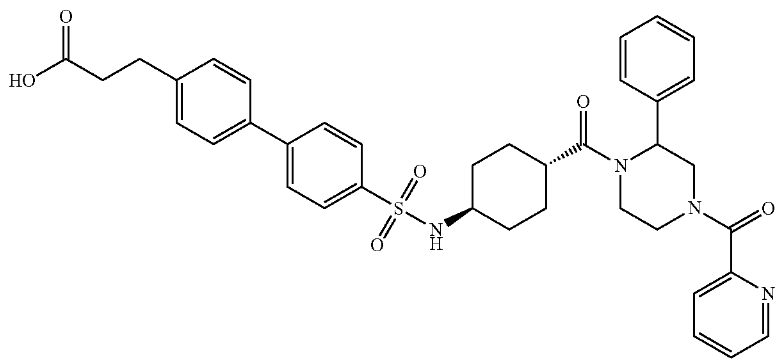 [SMILES: O=C(O)CCc1ccc(-c2ccc(S(=O)(=O)N[C@H]3CC[C@H](C(=O)N4CCN(C(=O)c5ccccn5)CC4c4ccccc4)CC3)cc2)cc1] | 682.0 |
| 414 | 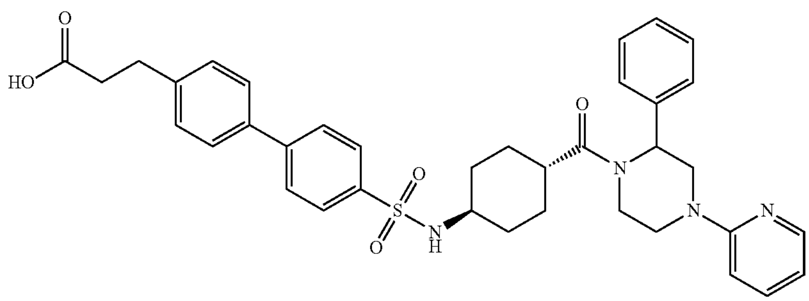 [SMILES: O=C(O)CCc1ccc(-c2ccc(S(=O)(=O)N[C@H]3CC[C@H](C(=O)N4CCN(c5ccccn5)CC4c4ccccc4)CC3)cc2)cc1] | 654.0 |
| 415 | 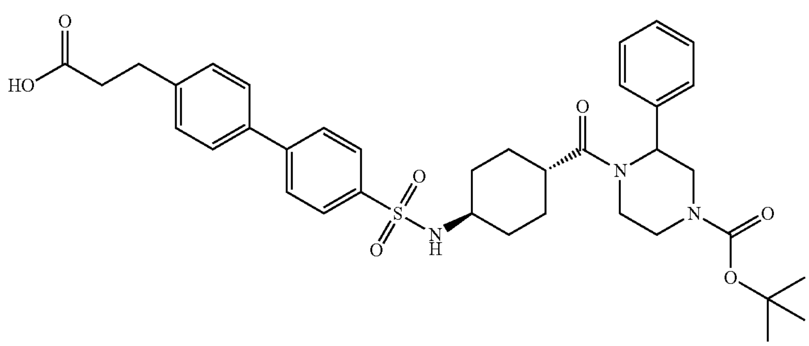 [SMILES: CC(C)(C)OC(=O)N1CCN(C(=O)[C@H]2CC[C@H](NS(=O)(=O)c3ccc(-c4ccc(CCC(=O)O)cc4)cc3)CC2)C(c2ccccc2)C1] | 674.6 (M − H) |
| 416 | 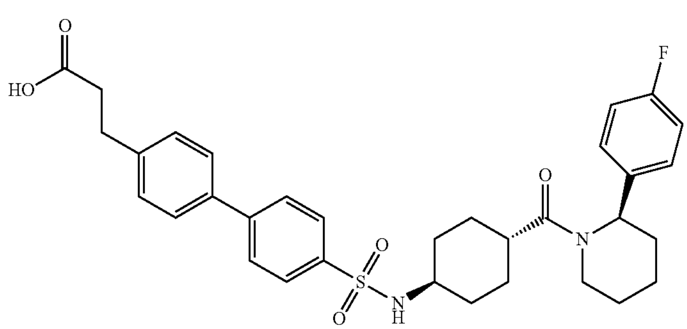 [SMILES: O=C(O)CCc1ccc(-c2ccc(S(=O)(=O)N[C@H]3CC[C@H](C(=O)N4CCCC[C@@H]4c4ccc(F)cc4)CC3)cc2)cc1] | 594.0 |

| Ex. | Structure | LCMS |
|---|---|---|
| 417 | 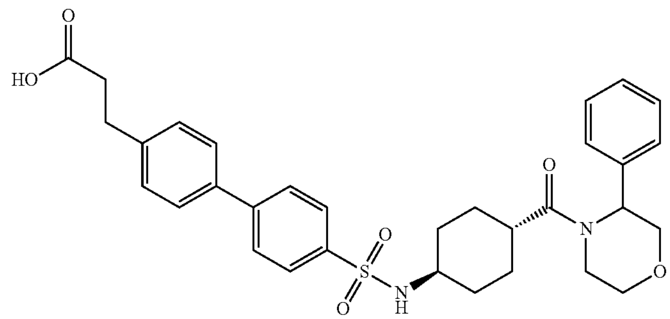 [SMILES: O=C(O)CCc1ccc(-c2ccc(S(=O)(=O)N[C@H]3CC[C@H](C(=O)N4CCOCC4c4ccccc4)CC3)cc2)cc1] | 577.0 |
| 418 | 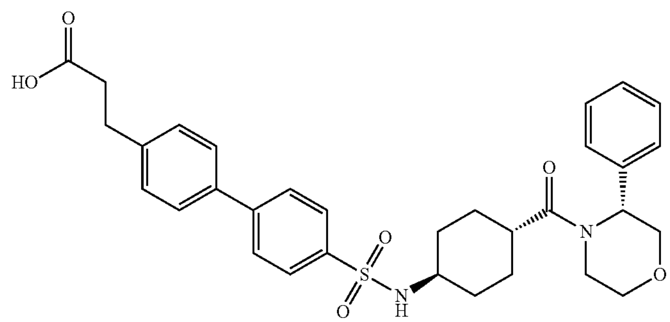 | 577.0 |
| 419 | 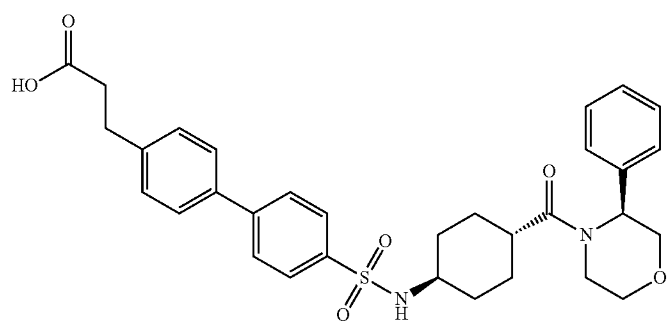 [SMILES: O=C(O)CCc1ccc(-c2ccc(S(=O)(=O)N[C@H]3CC[C@H](C(=O)N4CCOC[C@@H]4c4ccccc4)CC3)cc2)cc1] | 577.0 |
| 420 | 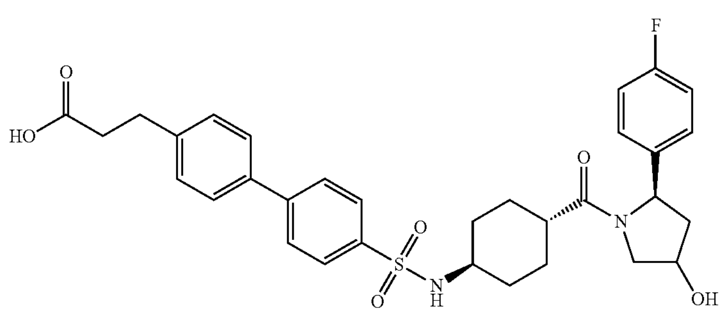 [SMILES: O=C(O)CCc1ccc(-c2ccc(S(=O)(=O)N[C@H]3CC[C@H](C(=O)N4CC(O)C[C@@H]4c4ccc(F)cc4)CC3)cc2)cc1] | 595.0 |
| 421 | 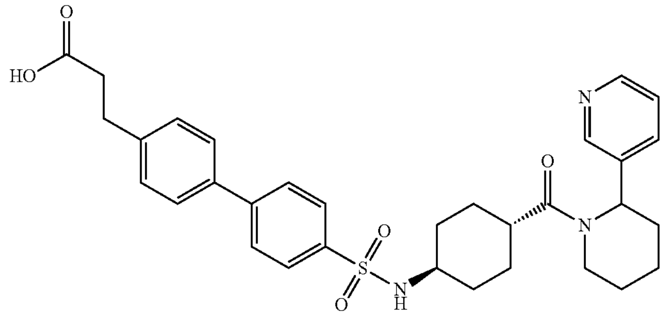 [SMILES: O=C(O)CCc1ccc(-c2ccc(S(=O)(=O)N[C@H]3CC[C@H](C(=O)N4CCCCC4c4cccnc4)CC3)cc2)cc1] | 577.0 |

| Ex. | Structure | LCMS |
|---|---|---|
| 422 | 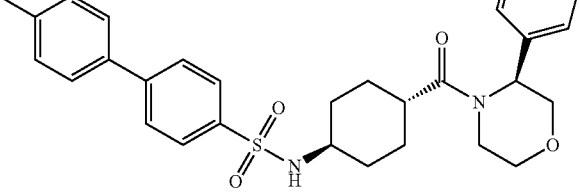 | 605.0 |
| 423 | 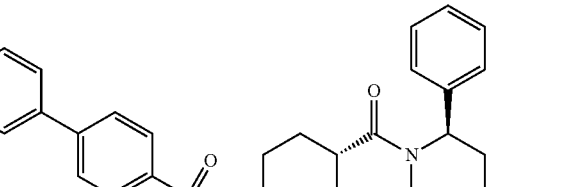 | 646 (M − H) |
| 424 | 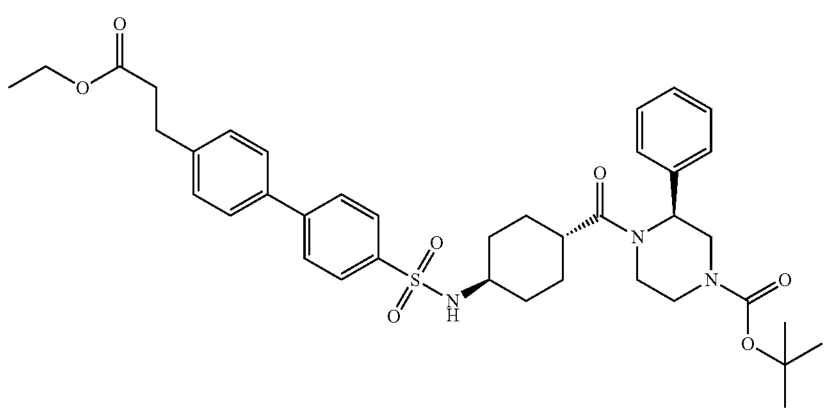 [SMILES: CCOC(=O)CCc1ccc(-c2ccc(S(=O)(=O)N[C@H]3CC[C@H](C(=O)N4CCN(C(=O)OC(C)(C)C)C[C@@H]4c4ccccc4)CC3)cc2)cc1] | 704.3 |
| 425 | 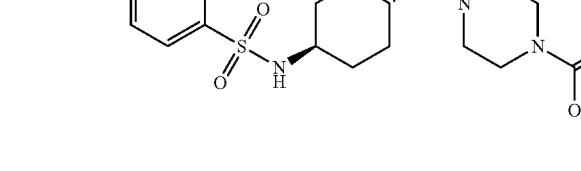 | — |

| Ex. | Structure | LCMS |
|---|---|---|
| 426 | 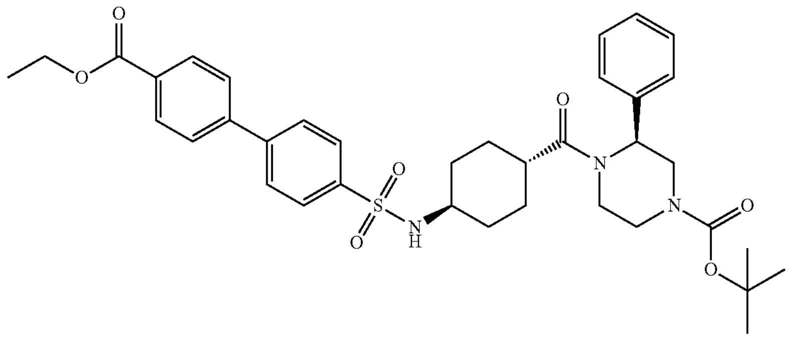 [SMILES: CCOC(=O)c1ccc(-c2ccc(S(=O)(=O)N[C@H]3CC[C@H](C(=O)N4CCN(C(=O)OC(C)(C)C)C[C@@H]4c4ccccc4)CC3)cc2)cc1] | 676.3 |
| 427 | 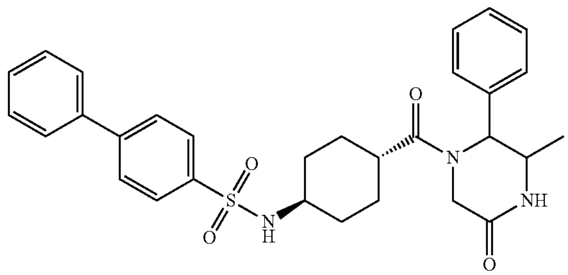 [SMILES: CC1NC(=O)CN(C(=O)[C@H]2CC[C@H](NS(=O)(=O)c3ccc(-c4ccccc4)cc3)CC2)C1c1ccccc1] | 532.0 |
| 428 | 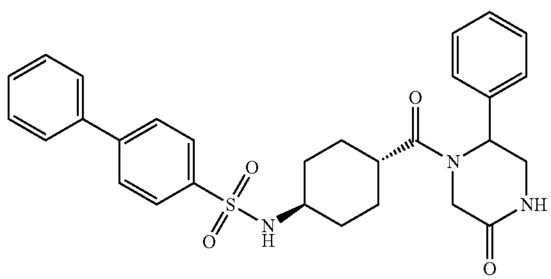 [SMILES: O=C1CN(C(=O)[C@H]2CC[C@H](NS(=O)(=O)c3ccc(-c4ccccc4)cc3)CC2)C(c2ccccc2)CN1] | 518.0 |
| 429 | 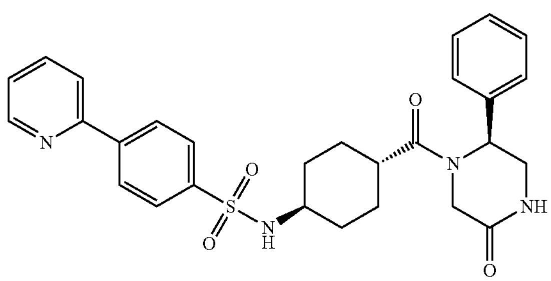 [SMILES: O=C1CN(C(=O)[C@H]2CC[C@H](NS(=O)(=O)c3ccc(-c4ccccn4)cc3)CC2)[C@@H](c2ccccc2)CN1] | 519.0 |
| 430 | 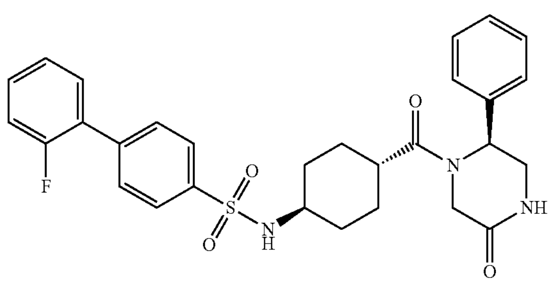 [SMILES: O=C1CN(C(=O)[C@H]2CC[C@H](NS(=O)(=O)c3ccc(-c4ccccc4F)cc3)CC2)[C@@H](c2ccccc2)CN1] | 536.0 |

| Ex. | Structure | LCMS |
|---|---|---|
| 431 | 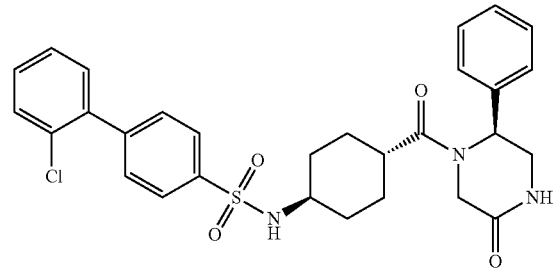 [SMILES: O=C1CN(C(=O)[C@H]2CC[C@H](NS(=O)(=O)c3ccc(-c4ccccc4Cl)cc3)CC2)[C@@H](c2ccccc2)CN1] | 552.0 |
| 432 | 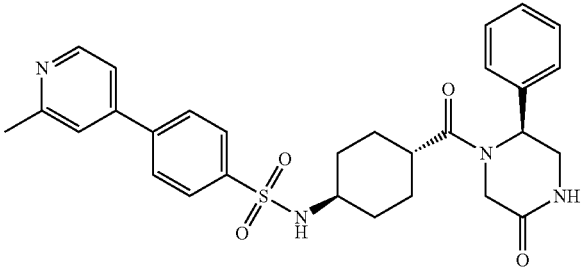 [SMILES: Cc1cc(-c2ccc(S(=O)(=O)N[C@H]3CC[C@H](C(=O)N4CC(=O)NC[C@@H]4c4ccccc4)CC3)cc2)ccn1] | 533.0 |
| 433 | 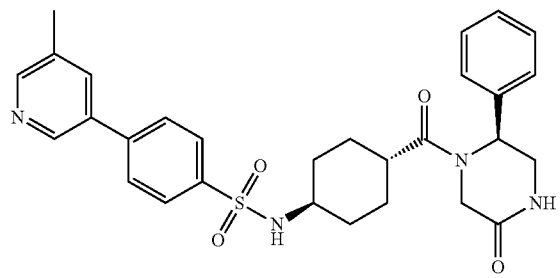 [SMILES: Cc1cncc(-c2ccc(S(=O)(=O)N[C@H]3CC[C@H](C(=O)N4CC(=O)NC[C@@H]4c4ccccc4)CC3)cc2)c1] | 533.0 |
| 434 | 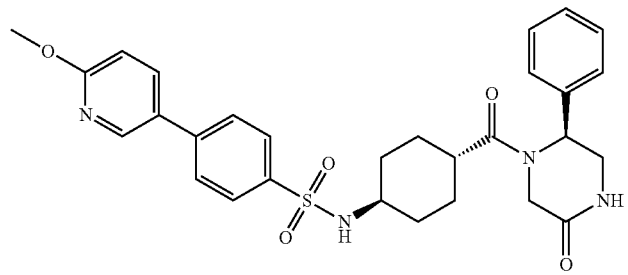 [SMILES: COc1ccc(-c2ccc(S(=O)(=O)N[C@H]3CC[C@H](C(=O)N4CC(=O)NC[C@@H]4c4ccccc4)CC3)cc2)cn1] | 549.0 |
| 435 | 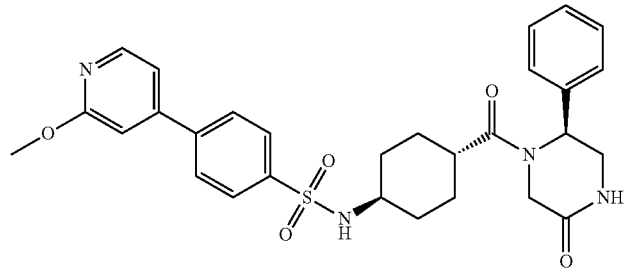 [SMILES: COc1cc(-c2ccc(S(=O)(=O)N[C@H]3CC[C@H](C(=O)N4CC(=O)NC[C@@H]4c4ccccc4)CC3)cc2)ccn1] | 549.0 |

-continued

| Ex. | Structure | LCMS |
|---|---|---|
| 436 | 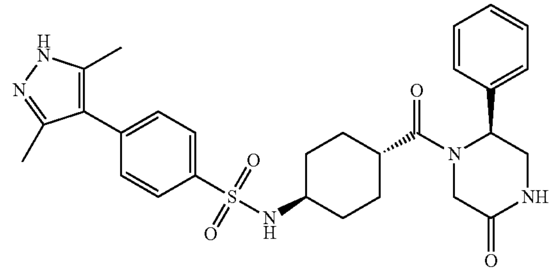 [SMILES: Cc1n[nH]c(C)c1-c1ccc(S(=O)(=O)N[C@H]2CC[C@H](C(=O)N3CC(=O)NC[C@@H]3c3ccccc3)CC2)cc1] | 536.0 |
| 437 | 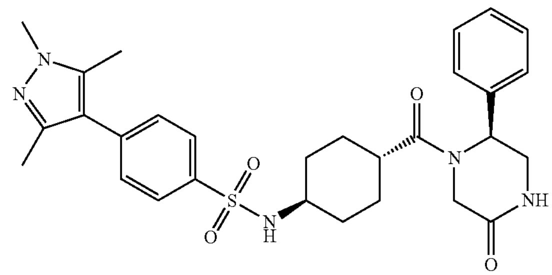 [SMILES: Cc1nn(C)c(C)c1-c1ccc(S(=O)(=O)N[C@H]2CC[C@H](C(=O)N3CC(=O)NC[C@@H]3c3ccccc3)CC2)cc1] | 550.0 |
| 438 | 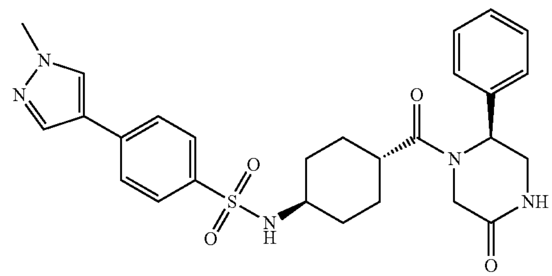 [SMILES: Cn1cc(-c2ccc(S(=O)(=O)N[C@H]3CC[C@H](C(=O)N4CC(=O)NC[C@@H]4c4ccccc4)CC3)cc2)cn1] | 522.0 |
| 439 | 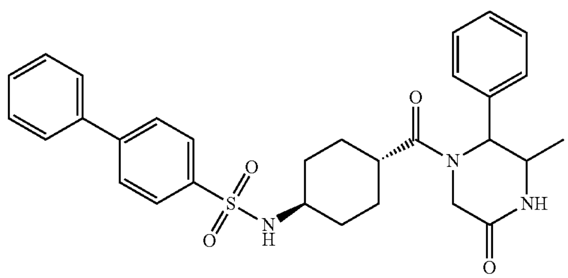 [SMILES: CC1NC(=O)CN(C(=O)[C@H]2CC[C@H](NS(=O)(=O)c3ccc(-c4ccccc4)cc3)CC2)C1c1ccccc1] | 532.0 |

Example 440

Trans-4-[4-(2-Bromo-acetyl)-benzenesulfonylamino]-cyclohexanecarboxylic acid [(R)-1-(4-fluoro-phenyl)-ethyl]-amide

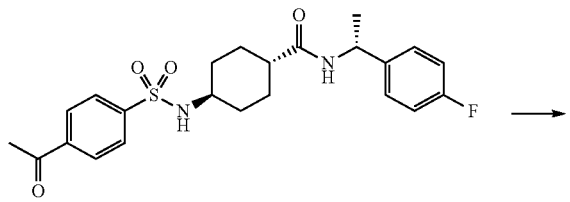

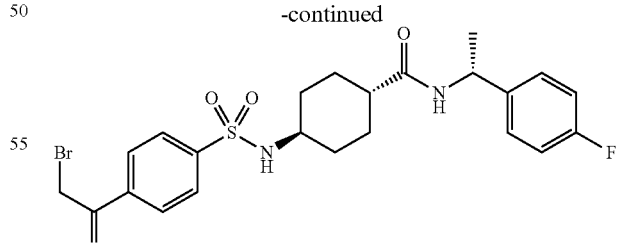

Tetrabutylammonium-tribromide (216 mg, 0.447 mmol) was added to solution of trans-4-(4-acetyl-benzenesulfonylamino)-cyclohexanecarboxylic acid [(R)-1-(4-fluoro-phenyl)-ethyl]-amide (Example 104, 194 mg, 0.434 mmol) in DCM/MeOH (2/1, 1.45 ml) at room temperature. The reaction was stirred 16-40 hours, then concentrated and partitioned between ethyl acetate and saturated sodium bicarbonate. The organic layer was dried over magnesium sulfate and concentrated to crude product which was chromatographed on a Biotage 40S column using ethyl acetate/heptane as the eluent to give the title compound (122 mg, 0.232 mmol).

Example 441

Trans-4-(4-Oxazol-4-yl-benzenesulfonylamino)-cyclohexanecarboxylic acid [(R)-1-(4-fluoro-phenyl)-ethyl]-amide

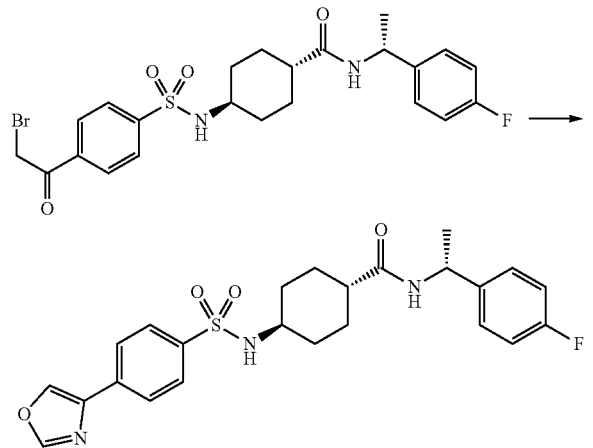

A slurry of trans-4-[4-(2-bromo-acetyl)-benzenesulfonylamino]-cyclohexanecarboxylic acid [(R)-1-(4-fluoro-phenyl)-ethyl]-amide (Example 440, 45 mg, 0.086 mmol) in formamide (57.9 mg, 1.285 mmol) was prepared and immersed in 130° C. oil for 90 minutes. The reaction was cooled to room temperature and the residue was diluted in 10% water in acetonitrile and chromatographed under basic reverse phase conditions on Phenomenex Gemini Axia C18 30×100 mm 15-100% over 12 minutes; tr 7.05 minutes. Product containing fractions were lyophilized overnight to yield the title compound (16 mg, 0.034 mmol).

Example 442

4-(4-(N-(trans-4-((R)-1-(4-fluorophenyl)ethylcarbamoyl)cyclo-hexyl)sulfamoyl)phenyl)pyridine 1-oxide

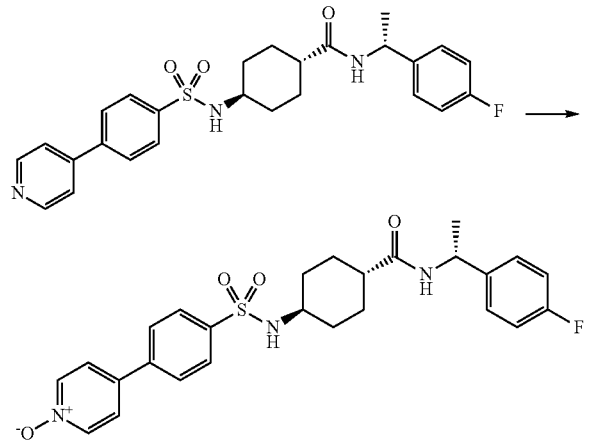

Magnesium monoperoxyphthalate hexahydrate (66.8 mg, 0.135 mmol) was suspended in MeOH (0.5 ml) and cooled to 0° C. Trans-4-(4-pyridin-4-yl-benzenesulfonylamino)-cyclohexanecarboxylic acid [(R)-1-(4-fluoro-phenyl)-ethyl]-amide (Example 284, 50 mg, 0.097 mmol) in DCM (0.5 ml) was added dropwise and the reaction mixture was left to stir overnight at 23° C. LCMS indicated that the reaction was complete, and the mixture was concentrated in vacuo to a residue which was purified by reverse phase chromatography on prep-HPLC (150 mm, C8 luna, 15-20 min run, 10%-100% MeCN in water containing 0.1% TFA). Product containing fractions were lyophilized to yield the title compound (10 mg, 21%). MS MH+ 498.1

Example 443

(1s,4S)—N—((R)-1-(4-fluorophenyl)ethyl)-1-hydroxy-4-(4-(trifluoromethyl)phenylsulfonamido)cyclohexanecarboxamide

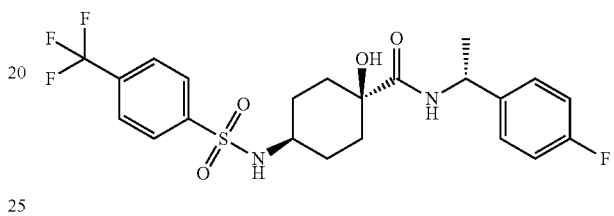

tert-Butyl (1S,4s)-4-((R)-1-(-4-fluorophenyl)ethylcarbamoyl)-4-hydroxycyclohexyl(4-(trifluoromethyl)phenylsulfonyl)cabamate (Intermediate 90, 4 mg) was deprotected using standard TFA in dichloromethane conditions (see Example 177) to afford the title compound (2.4 mg). MS MH+ 488.9

Example 444

1-Hydroxy-4-(4-(oxazol-4-yl)phenylsulfonamido)-N-(1-phenylethyl)cyclohexanecarboxamide

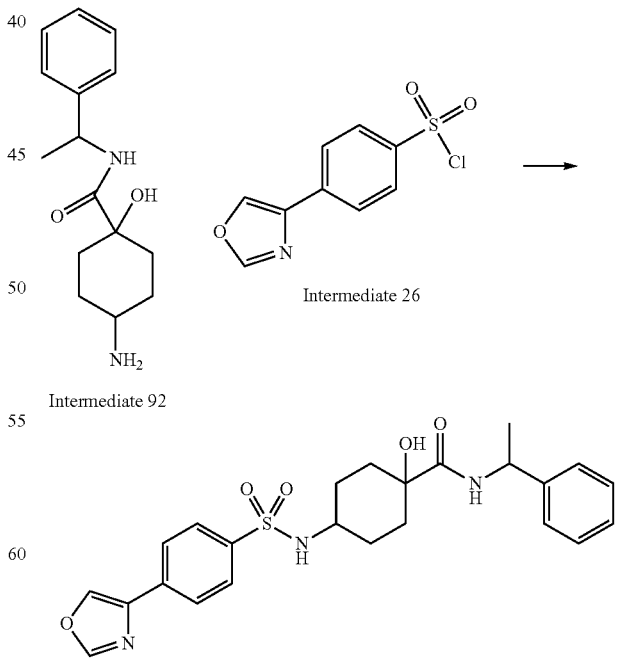

Example 444

4-Oxazol-4-yl-benzenesulfonyl chloride (Intermediate 26, 71.5 mg) was added to solution of 4-amino-1-hydroxy-N-(1-phenylethyl)cyclohexanecarboxamide (Intermediate 92, 70 mg) and diisopropylethylamine (0.103 ml) in dichloromethane (2.7 ml). After 16 hours the reaction was diluted with dichloromethane, rinse once using 1N hydrochloric acid followed by once using saturated aqueous sodium bicarbonate. The organics were dried over sodium sulfate, filtered and concentrate to 126 mg crude solid. The title compound was isolated by preparative basic reverse-phase chromatography to yield two isomeric samples of 1-hydroxy-4-(4-(oxazol-4-yl)phenylsulfonamido)-N-(1-phenylethyl)cyclohexanecarboxamide. Yield 4.5 mg.

Basic reverse-phase analytical chromatography using Waters Xbridge C18 100×4.6 mm 40-75% methanol in water containing 5 mM ammonium hydroxide over 8 minutes indicated >97% purity.

LCMS M+H=470.0

The compound in the following Table was prepared by a method analogous to the method used to prepare Example 444 using the starting materials indicated.

Example 447

(1s,4S)-1-Amino-N—((R)-1-(4-fluorophenyl)ethyl)-4-(4-(oxazol-4-yl)phenylsulfonamido)cyclohexanecarboxamide

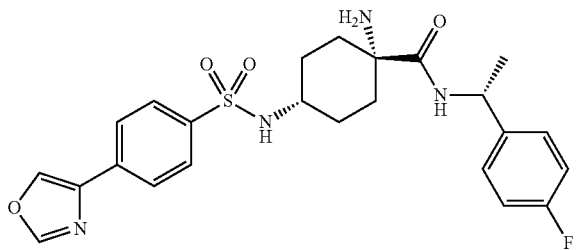

(1s,4S)-1-Amino-N—((R)-1-(4-fluorophenyl)ethyl)-4-(4-(oxazol-4-yl)phenylsulfonamido)cyclohexanecarboxamide

| Example | Structure | S.M. | MS |
|---|---|---|---|
| 445 | 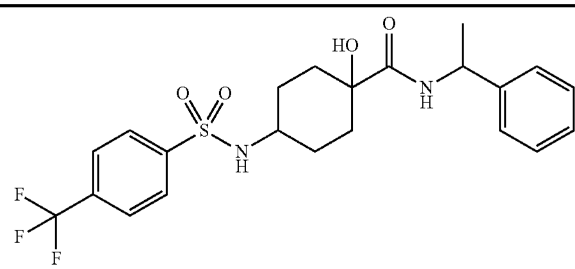 | Intermediate 92 & 4-trifluoromethyl-benzensulfonyl chloride | 470.9 |

Example 446

(1s,4S)-1-Amino-N—((R)-1-(4-fluorophenyl)ethyl)-4-(4-(trifluoromethyl)phenylsulfonamido)cyclohexanecarboxamide

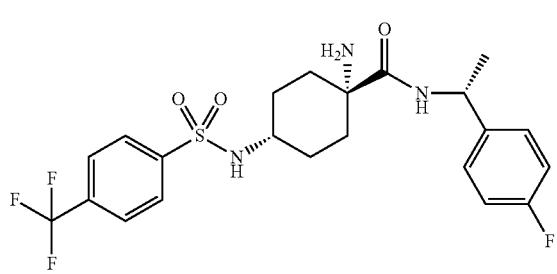 [SMILES: C[C@@H](NC(=O)[C@]1(N)CC[C@@H](NS(=O)(=O)c2ccc(C(F)(F)F)cc2)CC1)c1ccc(F)cc1]

(1s,4S)-1-Amino-N—((R)-1-(4-fluorophenyl)ethyl)-4-(4-(trifluoromethyl)phenylsulfonamido)cyclohexanecarboxamide was prepared from Intermediate 96 using the Boc-deprotection method described in Example 177. MS MH+ 488.3 was prepared from Intermediate 97 using the Boc-deprotection method described in Example 177. MS MH+ 487.3

Example 448

(1r,4S)—N—((S)-2-Hydroxy-2-methyl-1-phenylpropyl)-1-methyl-4-(4-(trifluoromethyl)phenylsulfonamido)cyclohexanecarboxamide

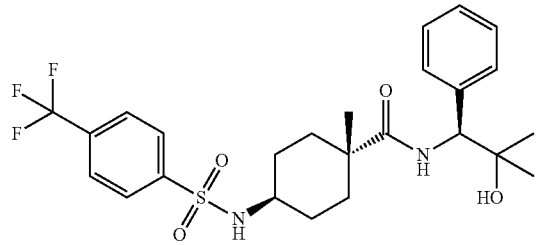 [SMILES: CC(C)(O)[C@@H](NC(=O)[C@]1(C)CC[C@@H](NS(=O)(=O)c2ccc(C(F)(F)F)cc2)CC1)c1ccccc1]

(1r,4r)-1-Methyl-4-(4-(trifluoromethyl)phenylsulfonamido)cyclohexancarboxylic acid (Intermediate 71, 603 mg, 1.650 mmol) was suspended in DCM (10 ml), to which oxalyl chloride (2M solution in DCM) (0.825 ml, 1.650 mmol) and then 1 drop of DMF were added. The reaction mixture was stirred at room temperature for approximately 15 mins. The reaction mixture was then concentrated to afford a yellow solid, which was dried under high vacuum. This material was then redissolved in DCM (10 ml), to which a solution of (S)-1-amino-2-methyl-1-phenylpropan-2-ol (Intermediate 49, 359 mg, 1.650 mmol) and DIPEA (0.865 ml, 4.95 mmol) in DCM (10 ml) was added. The reaction mixture was stirred at room temperature for 1 h, then concentrated and the residue was purified via flash column chromatography, eluting with 10-100% EtOAc/Hept. Relevant fractions were pooled and concentrated to afford a white foam, which was dried under high vacuum overnight. This material was then triturated with hexane and filtered to afford a white powder (419 mg-50% yield).

$^1$H NMR (400 MHz, DMSO-d$_6$) δ ppm 0.91 (s, 3H) 1.05 (s, 3H) 1.11 (s, 3H) 1.33 (d, J=9.98 Hz, 2H) 1.41 (br. s., 2H) 1.50 (br. s., 2H) 1.62 (t, J=9.47 Hz, 2H) 3.09 (d, J=0.76 Hz, 1H) 4.61 (s, 1H) 4.66 (d, J=8.84 Hz, 1H) 7.15-7.30 (m, 6H) 7.94 (d, J=7.20 Hz, 1H) 7.96-8.05 (m, 4H)

M+H=513.3

The compounds in the table below were prepared by a method analogous to the method used to prepare Example 448 using the appropriate starting materials.

| Example | Structure | S.M. | MS |
|---------|-----------|------|-----|
| 449 | 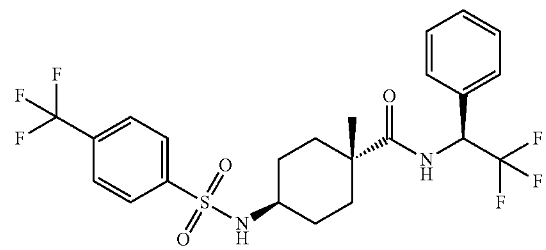 [SMILES: C[C@]1(C(=O)N[C@@H](c2ccccc2)C(F)(F)F)CC[C@H](NS(=O)(=O)c2ccc(C(F)(F)F)cc2)CC1] | Intermed. 71 & (S)-2,2,2-trifluoro-1-phenyl-ethanamine | 523.0 |
| 450 | 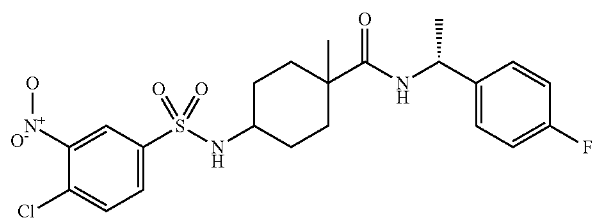 | Intermed. 134 & (R)-1-(4-fluoro-phenyl)ethanamine | — |
| 451 | 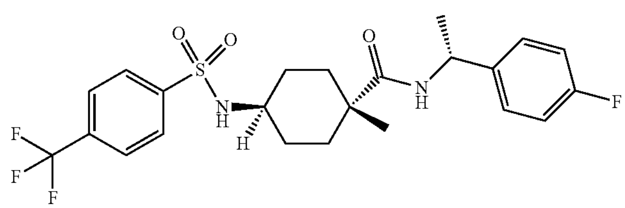 [SMILES: C[C@@H](NC(=O)[C@]1(C)CC[C@@H](NS(=O)(=O)c2ccc(C(F)(F)F)cc2)CC1)c1ccc(F)cc1] | Intermed. 71 & (R)-1-(4-fluoro-phenyl)ethanamine | 487.1 |
| 452 | 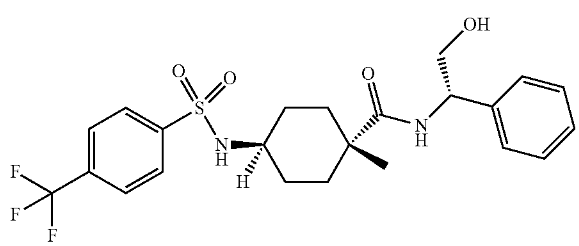 [SMILES: C[C@]1(C(=O)N[C@H](CO)c2ccccc2)CC[C@H](NS(=O)(=O)c2ccc(C(F)(F)F)cc2)CC1] | Intermed. 71 & (S)-2-amino-2-phenylethanol | 486.0 |
| 453 | 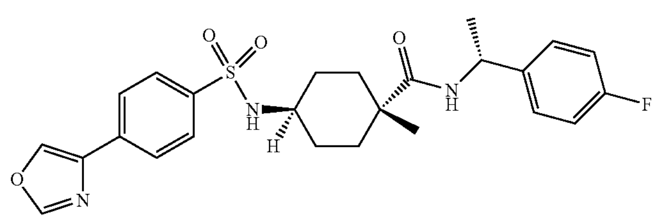 [SMILES: C[C@@H](NC(=O)[C@]1(C)CC[C@@H](NS(=O)(=O)c2ccc(-c3cocn3)cc2)CC1)c1ccc(F)cc1] | Intermed. 135 & (R)-1-(4-fluoro-phenyl)ethanamine | 484.0 |

| Example | Structure | S.M. | MS |
|---|---|---|---|
| 454 | 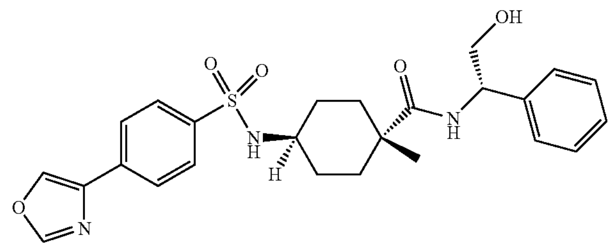 [SMILES: C[C@]1(C(=O)N[C@H](CO)c2ccccc2)CC[C@H](NS(=O)(=O)c2ccc(-c3cocn3)cc2)CC1] | Intermed. 135 & (S)-2-amino-2-phenylethanol | 484.0 |
| 455 | 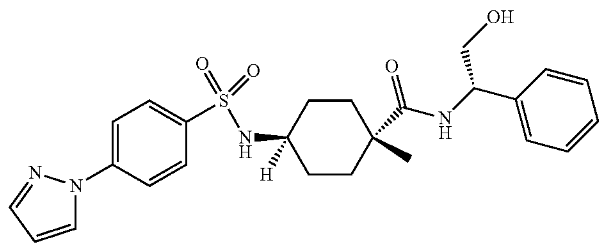 [SMILES: C[C@]1(C(=O)N[C@H](CO)c2ccccc2)CC[C@H](NS(=O)(=O)c2ccc(-n3cccn3)cc2)CC1] | Intermed. 135 & (S)-2-amino-2-phenylethanol | 483.4 |

The compounds in the table below can be prepared by a method analogous to the method used to prepare Example 448 using the appropriate starting materials.

| Example | Structure | S.M. | MS |
|---|---|---|---|
| 456 | 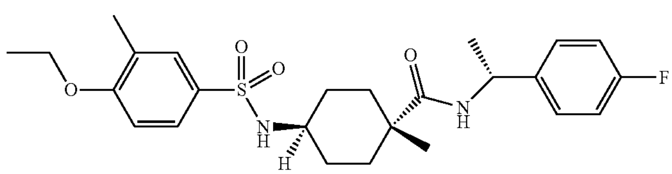 [SMILES: CCOc1ccc(S(=O)(=O)N[C@H]2CC[C@](C)(C(=O)N[C@H](C)c3ccc(F)cc3)CC2)cc1C] | Intermed. 137 & (R)-1-(4-fluorophenyl)ethanamine | 477.3 |
| 457 | 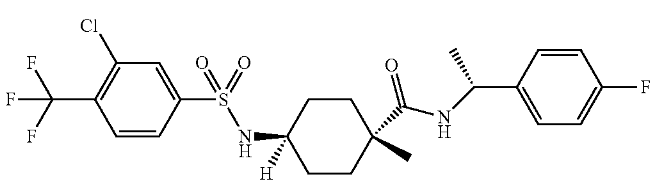 [SMILES: C[C@@H](NC(=O)[C@]1(C)CC[C@@H](NS(=O)(=O)c2ccc(C(F)(F)F)c(Cl)c2)CC1)c1ccc(F)cc1] | Intermed. 138 & (R)-1-(4-fluorophenyl)ethanamine | 521.1 |
| 458 | 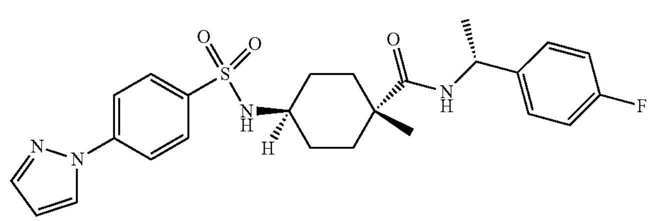 [SMILES: C[C@@H](NC(=O)[C@]1(C)CC[C@@H](NS(=O)(=O)c2ccc(-n3cccn3)cc2)CC1)c1ccc(F)cc1] | Intermed. 139 & (R)-1-(4-fluorophenyl)ethanamine | 485.2 |

Example 459

(1r,4S)-1cyano-N—((S)-2-hydroxy-2-methyl-1-phenylpropyl)-N-methyl-4-(4-(trifluoromethyl)phenylsulfonamido)cyclohexanecarboxamide

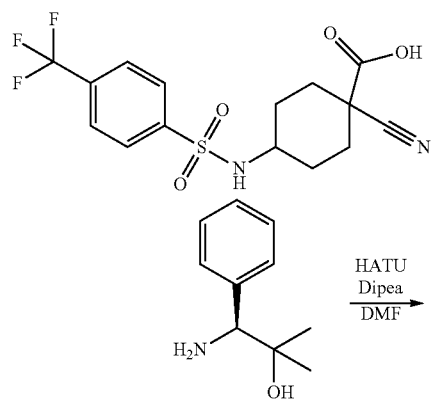

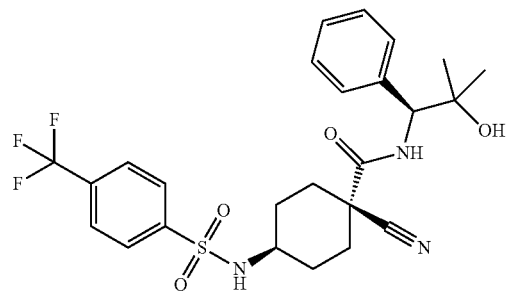

1-Cyano-4-(4-trifluoromethyl-benzenesulfonylamino)-cyclohexanecarboxylic acid ((S)-2-hydroxy-2-methyl-1-phenyl-propyl)-amide was prepared according to the method in Example 1 using Intermediate 142 as the starting material. MS MH– 522.0

Examples 460 and 461 where prepared by a method analogous to the method used to prepare Example 1 using the starting material indicated.

| Example | Structure | S.M. | MS |
|---|---|---|---|
| 460 | 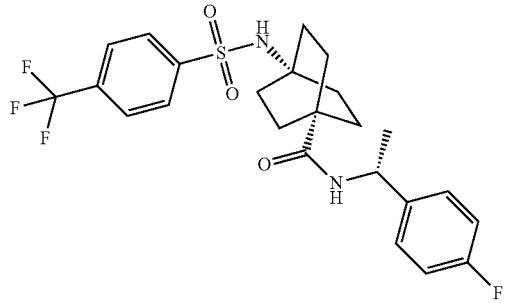 [SMILES: C[C@@H](NC(=O)[C@]12CC[C@@](NS(=O)(=O)c3ccc(C(F)(F)F)cc3)(CC1)CC2)c1ccc(F)cc1] | Intermed. 144 | 499.1 |
| 461 | 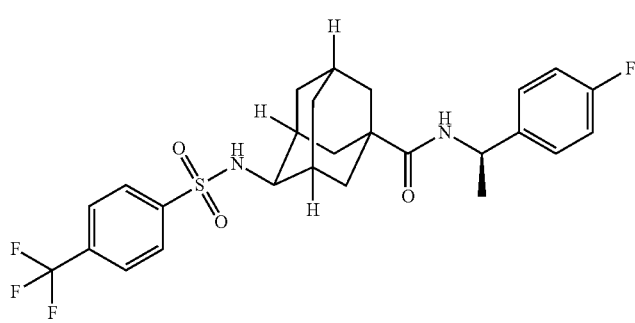 [SMILES: C[C@@H](NC(=O)C12CC3CC(C1)C(NS(=O)(=O)c1ccc(C(F)(F)F)cc1)C(C3)C2)c1ccc(F)cc1] | Intermed. 146 | 525.0 |

Example 462 in the table below was prepared from Intermediate 139 and (R)-1-(4-fluorophenyl)ethanamine using a method analogous to the method used to prepare Example 1.

| Example | Structure | S.M. | MS |
|---|---|---|---|
| 462 | 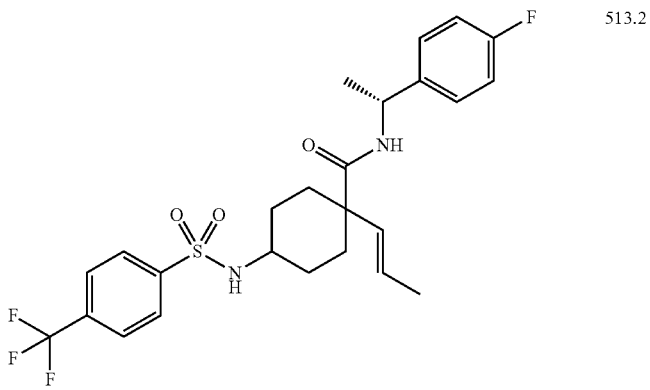 | | 513.2 |

Example 463

(R)—N-(1-oxo-2-(1-phenylethyl)-2-azaspiro[4.5]decan-8-yl)-4-(1H-pyrazol-1-yl)benzenesulfonamide

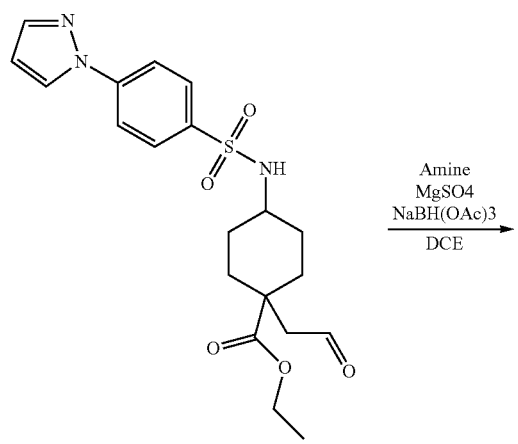

Amine
MgSO4
NaBH(OAc)3
———————→
DCE

-continued

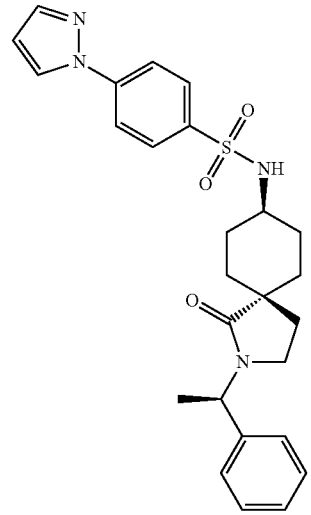

1-(2-oxo-ethyl)-4-(4-pyrazol-1-yl-benzenesulfonylamino)-cyclohexanecarboxylic acid ethyl ester (Intermediate 114, 40 mg, 0.095 mmol) and (R)-1-phenylethanamine (0.036 ml, 0.286 mmol) were dissolved in DCE (2 ml). MgSO$_4$ was added (20-30 mg) followed by NaBH(OAc)$_3$ (60.6 mg, 0.286 mmol). The reaction mixture was stirred overnight at room tempereature, then further DCE was added, and the reaction mixture was heated at 50° C. overnight. The reaction mixture was concentrated in vacuo, and the crude material taken up in DCM, and washed with water (×2). The organic layer was concentrated in vacuo, and the resultan crude oil was purified via normal phase chromatography using biotage SP1, with 25+S column, using a calculated gradient from TLC of 50% EtOAc in heptane to yield the title compound as a white solid (29 mg, 64%) as a mixture of 95% "trans" (as shown above): 5% "cis". MS MH+ 479.1

The Examples in the following Table were prepared by a method analogous to the method used to prepare Example 463 using the starting materials indicated.

| Example | Structure | S.M. | MS MH+ |
|---|---|---|---|
| 464 | 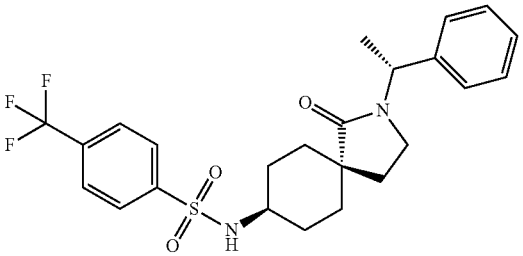 [SMILES: C[C@H](c1ccccc1)N1CC[C@]2(CC[C@@H](NS(=O)(=O)c3ccc(C(F)(F)F)cc3)CC2)C1=O] | Intermediate 115 and (R)-1-phenyl-ethanamine | 481.1 |
| 465 | 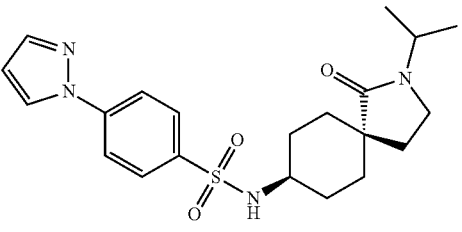 [SMILES: CC(C)N1CC[C@]2(CC[C@@H](NS(=O)(=O)c3ccc(-n4cccn4)cc3)CC2)C1=O] | Intermediate 114 and isopropyl amine | 417.1 |

The Example in the following Table can be prepared by a method analogous to the method used to prepare Example 463 using the starting materials indicated.

| Example | Structure | S.M. | MS MH+ |
|---|---|---|---|
| 466 | 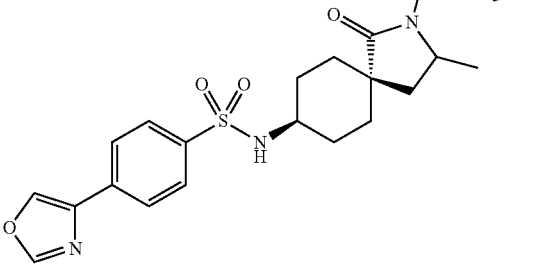 | Intermediate 113 and (R)-1-phenyl-ethanamine | 494.2 |

Example 467

N-((5r,8r)-3-cyclohexyl-4-oxo-2,3-diazaspiro[4.5]dec-1-en-8-yl)-4-(trifluoromethyl)Benzenesulfonamide

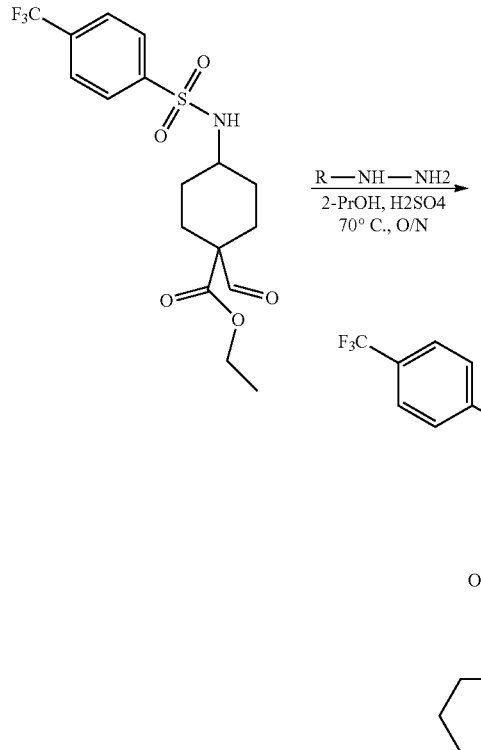

1-Formyl-4-(4-trifluoromethyl-benzenesulfonylamino)-cyclohexanecarboxylic acid ethyl ester (Intermediate 120, 100 mg, 0.245 mmol) and cyclohexyl hydrazine (111 mg, 0.736 mmol) were dissolved in 2-propanol (2 ml) and concentrated $H_2SO_4$ (2.000 ml). The mixture was stirred for 18 hr at 70° C., and the product observed by LCMS. The reaction mixture was basified with NaOH (1M), and extracted with DCM (×2). The DCM layers were combined and concentrated in vacuo to a tanned solid which was purified via normal phase chromatography on biotage SP1, 25+M column, using 50% EtOAc in heptane calculated gradient to yield the title compound as a white solid (12 mg, 11%) which was a 9:1 mixture of diastereoisomers. [M+H]=458.2

The Examples in the following Table was prepared by a method analogous to the method used to prepare Example 467 using the starting materials indicated.

| Example | Structure | S.M. | MS MH+ |
|---|---|---|---|
| 468 | 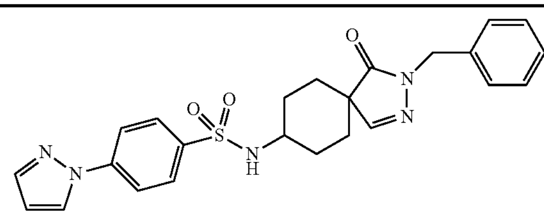 | Intermediate 121 and benzyl hydrazine | 464.0 |
| 469 | 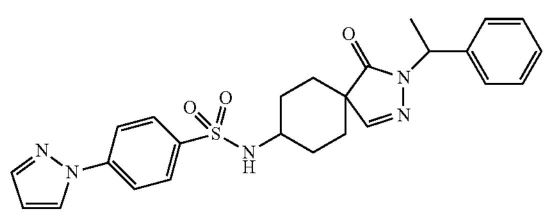 [SMILES: CC(c1ccccc1)N1N=CC2(CCC(NS(=O)(=O)c3ccc(-n4cccn4)cc3)CC2)C1=O] | Intermediate 121 and 1-phenyl-ethyl hydrazine | 478.2 |
| 470 | 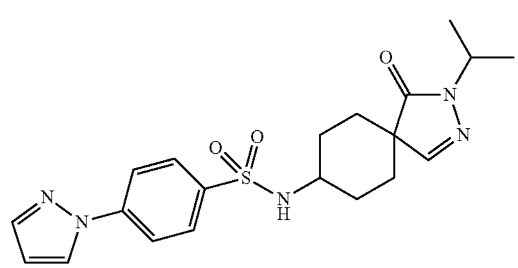 [SMILES: CC(C)N1N=CC2(CCC(NS(=O)(=O)c3ccc(-n4cccn4)cc3)CC2)C1=O] | Intermediate 121 and isopropyl hydrazine | 416.3 |

Example 471

4-Ethoxy-3-methyl-N-(2-methyl-4-oxo-1,3-diazaspiro[4.5]dec-1-en-8-yl)benzenesulfonamide

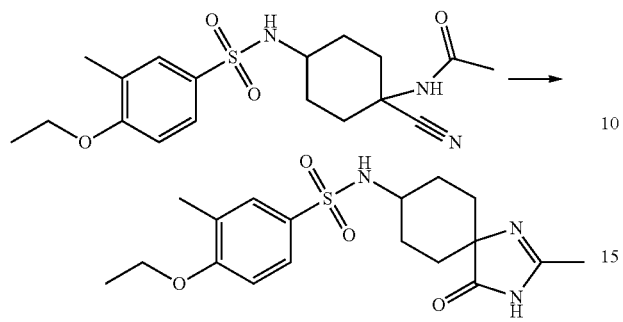

5N Sodium hydroxide (320 ul, 1.59 mmol) followed by 50% aqueous hydrogen peroxide (157 ul, 2.55 mmol) were added to solution of N-(1-cyano-4-(4-ethoxy-3-methylphenylsulfonamido)cyclohexyl)acetamide (Intermediate 126, 242 mg, 0.638 mmol) in ethanol (6.4 ml). The reaction was heated to 80° C. for three hours. LCMS indicated approximately 3:1 product:starting material by co-injection. The reaction was diluted with water and extract with four volumes ethyl acetate. The combined organics were dried over sodium sulfate, filtered and concentrate to 226 mg crude. TLC (10% methanol in ethyl acetate): Rf starting material 0.66; major spot Rf=0.25. The crude was chromatographed on Biotage 12M eluting 0-100% ethyl acetate in (10% methanol in ethyl acetate) to give the product as an off-white solid (117 mg, 0.308 mmol). LCMS [M+H]=380.2.

Example 472

4-Ethoxy-3-methyl-N-(4-oxo-1,3-diazaspiro[4.5]dec-1-en-8-yl)benzenesulfonamide

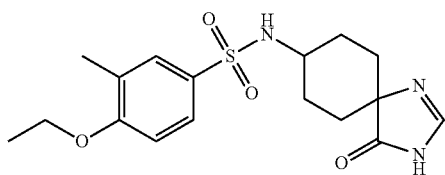 [SMILES: CCOc1ccc(S(=O)(=O)NC2CCC3(CC2)N=CNC3=O)cc1C]

Example 472 was prepared from Intermediate 128 by a method analogous to the method used to prepare Example 471.

Example 473

N-(2-Methyl-4-oxo-1,3-diazaspiro[4.5]dec-1-en-8-yl)-4-(trifluoromethyl)benzenesulfonamide

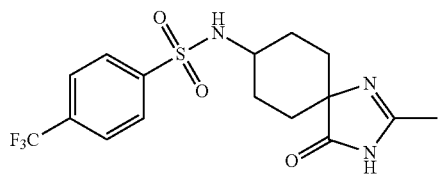 [SMILES: CC1=NC2(CCC(NS(=O)(=O)c3ccc(C(F)(F)F)cc3)CC2)C(=O)N1]

Example 473 was prepared from Intermediate 127 by a method analogous to the method used to prepare Example 471.

Example 474

4-Ethoxy-3-methyl-N-(2-methyl-4-oxo-3-(1-phenylethyl)-1,3-diazaspiro[4.5]dec-1-en-8-yl)benzenesulfonamide

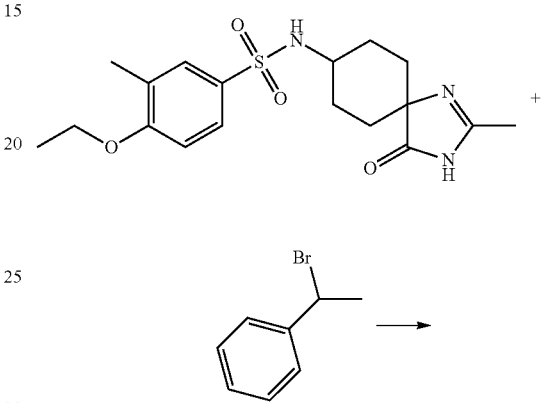

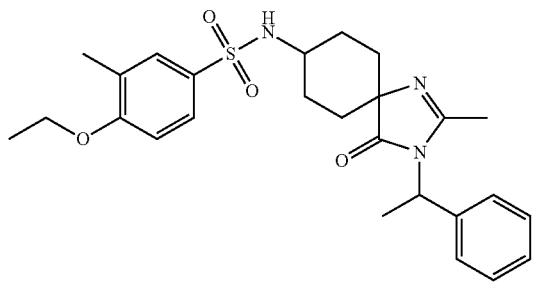

Sodium hydride (4.74 mg, 0.119 mmol) was added at room temperature to 4-ethoxy-3-methyl-N-(2-methyl-4-oxo-1,3-diazaspiro[4.5]dec-1-en-8-yl)benzenesulfonamide (Example 471, 30 mg, 0.079 mmol) in DMF (988 µl). The reaction was stirred five minutes then a solution of (1-bromoethyl)benzene (16.18 µl, 0.119 mmol) in 200 ul DMF was added and the reaction stirred overnight at room temperature. After 16 hours, LCMS and HPLC indicated approximately 4:1 product:smarting material. The reaction was diluted with saturated sodium bicarbonate and extracted with multiple volumes ethyl acetate. The combined organics were rinsed 1× brine and dried over sodium sulfate. TLC (ethyl acetate) gave a product Rf 0.38 and starting material on the baseline. The crude was chromatographed on Biotage 12S by manual step gradient 7-100% EtOAc/heptane to yield the product as an off-white solid (21 mg). LCMS [M+H]=484.2.

The examples in the table below were prepared by a method analogous to the method used to prepare Example 473 using the starting materials indicated

| Example | Structure | S.M. |
|---|---|---|
| 475 | 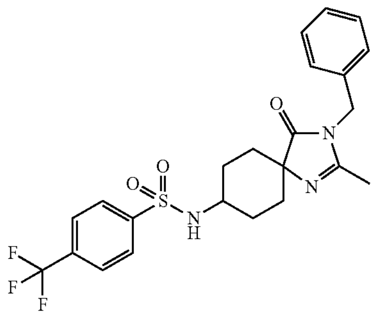 [SMILES: CC1=NC2(CCC(NS(=O)(=O)c3ccc(C(F)(F)F)cc3)CC2)C(=O)N1Cc1ccccc1] | Example 473 & benzyl bromide |
| 476 | | Example 472 & benzyl bromide |
Prodrug
Examples 477 through 490 are examples of prodrugs of the invention.
Example 477
Potassium 4-oxo-4-((S)-2-phenyl-2-((1r,4S)-4-(4-(trifluoromethyl)phenylsulfonamido)cyclohexanecarboxamido)ethoxy)butanoate
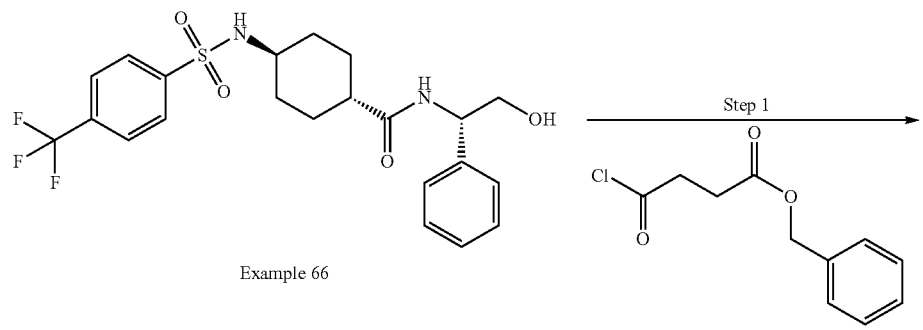
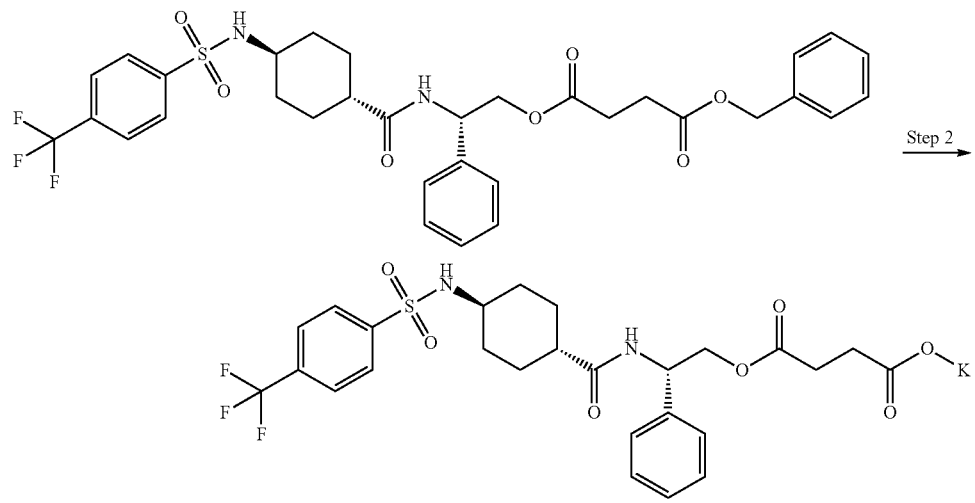
Example 477

Step 1:

Benzyl 4-chloro-4-oxobutanoate (48.2 mg, 0.213 mmol) was dissolved in DCM (5 ml), to which a suspension of (1r,4S)—N—((S)-2-hydroxy-1-phenylethyl)-4-(4-(trifluoromethyl)phenylsulfonamido)cyclohexanecarboxamide (Example 66, 100 mg, 0.213 mmol) and DIPEA (74.2 μl, 0.425 mmol) in DCM (5 ml) was added. The resulting suspension was stirred at room temperature for 1 h. LC-MS at this point showed one major peak corresponding to the starting material, therefore 2 ml acetonitrile were added, upon which all material went into solution. The reaction mixture was stirred at room temperature over the weekend and was then concentrated and the residue was purified via Biotage automated flash column chromatography 12M, eluting with 10-100% EtOAc/Hept. Relevant fractions were pooled and concentrated to afford benzyl (S)-2-phenyl-2-((1r,4S)-4-(4-(trifluoromethyl)phenylsulfonamido)cyclohexanecarboxamido)ethyl succinate as a white sticky solid, which was dried under high vacuum. Mass of dry material=24 mg (17% yield).

M+H=661.1

$^1$H NMR (400 MHz, DMSO-$d_6$) δ ppm 1.11-1.33 (m, 6H) 1.66 (d, J=9.09 Hz, 4H) 2.06 (td, J=11.75, 3.28 Hz, 1H) 2.53-2.61 (m, 3H) 2.96 (td, J=7.45, 3.54 Hz, 1H) 4.02-4.18 (m, 2H) 5.02-5.10 (m, 3H) 7.23-7.39 (m, 10H) 7.94 (s, 1H) 7.95-8.04 (m, 4H) 8.23 (d, J=8.59 Hz, 1H)

Step 2:

Benzyl (S)-2-phenyl-2-((1r,4S)-4-(4-(trifluoromethyl)phenylsulfonamido)cyclohexanecarboxamido)ethyl succinate (24 mg, 0.036 mmol) was dissolved in MeOH (10 ml) and flushed with $N_2$. Pd/C (10 mg, 0.094 mmol) was then added and the reaction mixture was flushed with $N_2$ once more, then placed under a balloon of $H_2$ and stirred vigorously for 30 mins. The reaction mixture was then filtered through a syringe filter and filtrate was concentrated to afford a clear sticky solid. This material (16 mg, 0.028 mmol) was then suspended in water (2 ml), to which KOH (0.1M solution) (0.280 ml, 0.028 mmol) was added. The mixture was sonicated for 5 mins, after which it was frozen and lyopholyzed to afford potassium 4-oxo-4-((S)-2-phenyl-2-((1r,4S)-4-(4-(trifluoromethyl)phenylsulfonamido)cyclohexanecarboxamido)ethoxy)butanoate as a fluffy solid-12.37 mg (72% yield).

$^1$H NMR (400 MHz, DMSO-$d_6$) δ ppm 1.10-1.31 (m, 2H) 1.20 (dd, J=16.55, 10.23 Hz, 2H) 1.59 (br. s., 1H) 1.62 (d, J=2.53 Hz, 3H) 2.06 (td, J=6.25, 3.16 Hz, 2H) 2.15-2.29 (m, 3H) 2.93 (d, J=3.54 Hz, 1H) 3.83 (dd, J=10.99, 4.67 Hz, 1H) 4.52 (dd, J=10.99, 3.92 Hz, 1H) 5.06 (dt, J=8.59, 4.29 Hz, 1H) 7.22 (d, J=7.33 Hz, 1H) 7.28 (t, J=7.45 Hz, 2H) 7.33-7.39 (m, 2H) 7.90-8.04 (m, 5H) 9.05 (d, J=8.84 Hz, 1H)

M+H=571.0

HPLC (Luna 10-100) RT=8.928 mins

Example 478

(S)-2-Phenyl-2-((1r,4S)-4-(4-(trifluoromethyl)phenylsulfonamido)cyclohexanecarboxamido)ethyl dihydrogen phosphate (as a di-potasium salt)

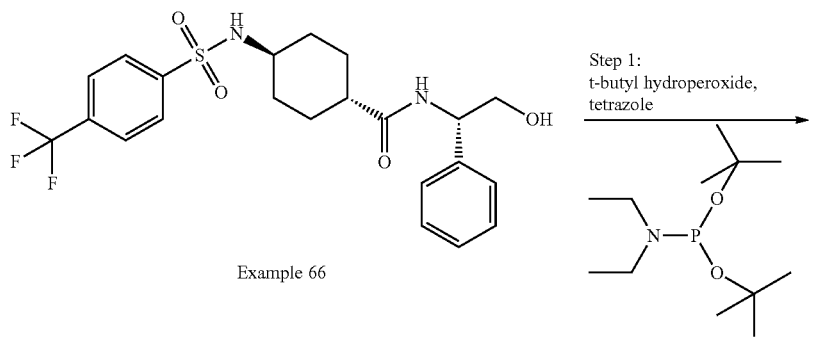

Example 66

Step 1:
t-butyl hydroperoxide, tetrazole

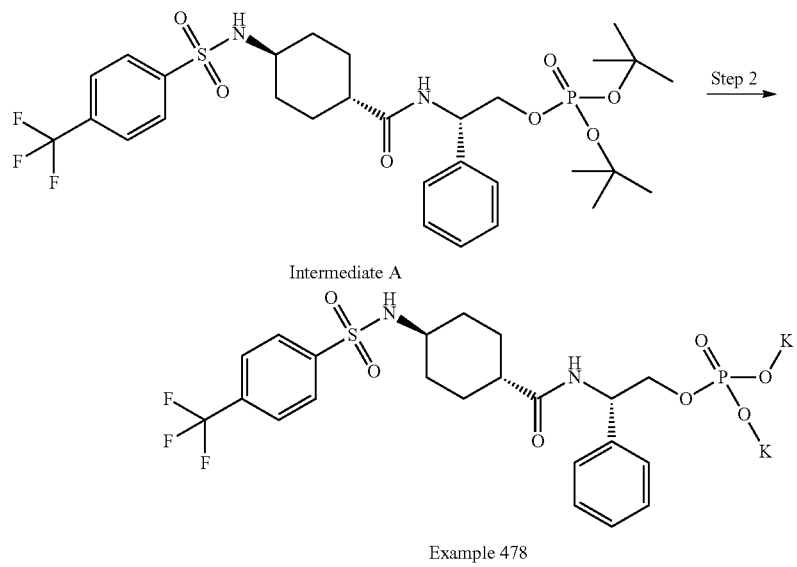

Intermediate A

Step 2

Example 478

The title compound was prepared as described in Miller, Christa et al. *Water-Soluble Phosphate Prodrugs of* 1-*Propargyl*-8-*strylxanthine Derivatives, A-Selective Adenosine Receptor Antagonists. Journal of Medicinal Chemistry.* 43(3): 440-448, 2000.

Intermediate A: Di-tert-butyl (S)-2-phenyl-2-((1r, 4S)-4-(4-(trifluoromethyl)phenylsulfonamido)cyclohexanecarboxamido)ethyl phosphate M+H=663.4
¹H NMR (400 MHz, DMSO-d₆) δ ppm 1.09-1.27 (m, 4H) 1.33 (d, J=9.85 Hz, 18H) 1.36 (d, J=2.27 Hz, 1H) 1.65 (d, J=8.84 Hz, 3H) 2.07 (td, J=11.68, 2.91 Hz, 1H) 2.97 (td, J=7.26, 3.66 Hz, 1H) 3.92 (qd, J=6.65, 3.79 Hz, 2H) 5.03 (d, J=8.08 Hz, 1H) 7.22-7.35 (m, 5H) 7.94 (d, J=7.33 Hz, 1H) 7.96-8.04 (m, 4H) 8.26 (d, J=8.34 Hz, 1H)

Example 478

(S)-2-phenyl-2-((1r,4S)-4-(4-(trifluoromethyl)phenylsulfonamido)cyclohexanecarboxamido)ethyl dihydrogen phosphate (as a di potassium salt)

M+H=551.1
¹H NMR (400 MHz, DEUTERIUM OXIDE) δ ppm 1.11-1.33 (m, 6H) 1.65 (s, 1H) 1.67 (d, J=3.79 Hz, 1H) 1.75 (br. s., 2H) 2.23 (t, J=3.28 Hz, 1H) 2.78 (d, J=4.04 Hz, 1H) 3.81 (ddd, J=10.93, 7.26, 6.32 Hz, 1H) 3.92 (ddd, J=10.80, 5.24, 4.93 Hz, 1H) 7.24-7.37 (m, 6H) 7.79 (d, J=8.34 Hz, 2H) 7.90 (d, J=8.34 Hz, 2H)
HPLC (Luna 10-100) RT=7.68 mins Example 479

(S)—((S)-2-phenyl-2-((1r,4S)-4-(4-(trifluoromethyl) phenylsulfonamido) cyclohexanecarboxamido)ethyl) 2-amino-3-methylbutanoate hydrochloride

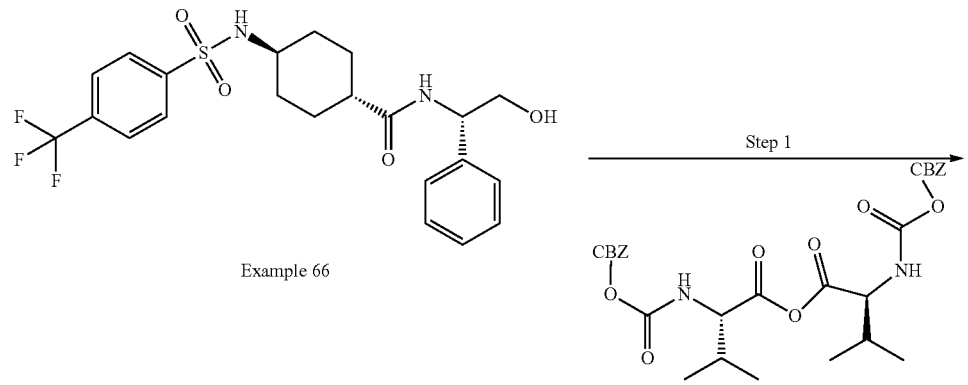

Example 66     Step 1

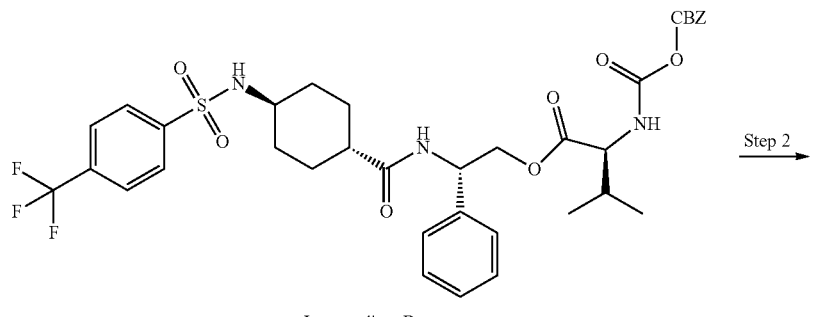

Intermediate B     Step 2

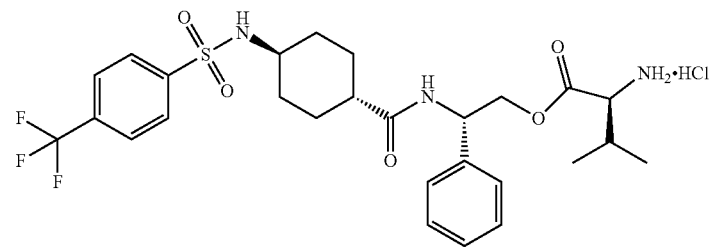

Example 479

Step 1: Intermediate B (1r,4S)—N—((S)-2-hydroxy-1-phenylethyl)-4-(4-(trifluoromethyl)phenylsulfonamido)cyclohexanecarboxamide (Example 66, 250 mg, 0.531 mmol) was suspended in THF (5 ml), to which a solution of (S)-2-(benzyloxycarbonylamino)-3-methylbutanoic anhydride (515 mg, 1.063 mmol, prepared as described in *Molecules* (2008) 13: 348-359) in THF (5 ml) and then DMAP (0.649 mg, 5.31 μmol) were added. The reaction mixture was stirred at room temperature overnight, then concentrated and the residue was purified via Biotage automated flash column chromatography (40 g isco column), eluting with 10-100% EtOAc/Hept. Relevant fractions were pooled and concentrated to afford (S)—((S)-2-phenyl-2-((1r,4S)-4-(4-(trifluoromethyl)phenylsulfonamido)cyclohexanecarboxamido)ethyl) 2-(benzyloxycarbonylamino)-3-methylbutanoate as a white solid –311 mg (83% yield).

M+H=704.5

$^1$H NMR (400 MHz, DMSO-d$_6$) δ ppm 0.77 (dd, J=12.25, 6.95 Hz, 5H) 0.88 (t, J=7.07 Hz, 1H) 1.09-1.31 (m, 4H) 1.36 (br. s., 1H) 1.64 (d, J=10.86 Hz, 4H) 1.94 (dq, J=13.26, 6.61 Hz, 1H) 2.05 (t, J=13.14 Hz, 1H) 2.92 (br. s., 1H) 2.96 (dd, J=11.24, 3.66 Hz, 1H) 3.93 (dd, J=8.34, 6.06 Hz, 1H) 4.13 (d, J=4.80 Hz, 1H) 4.98-5.06 (m, 1H) 5.02 (d, J=4.04 Hz, 1H) 5.11 (td, J=8.08, 5.05 Hz, 1H) 7.22-7.39 (m, 10H) 7.62 (d, J=8.34 Hz, 1H) 7.93-8.04 (m, 4H) 8.25 (d, J=8.59 Hz, 1H)

Step 2: ((1r,4S)-4-(4-(Trifluoromethyl)phenylsulfonamido)cyclohexanecarboxamido)ethyl) 2-(benzyloxycarbonylamino)-3-methylbutanoate (Intermediate B, 311 mg, 0.442 mmol) was suspended in EtOAc (20 ml) and flushed with N$_2$. Pd/C (100 mg, 0.940 mmol) was then added slowly and reaction mixture was flushed with N$_2$ once more, then stirred vigorously under a balloon of H$_2$ for 2 h. The reaction mixture was then filtered through a syringe filter and filtrate was concentrated to afford an off white solid. This material was adsorbed onto silica and purified via Biotage automated flash column chromatography (40 g isco column), eluting with 50-100% EtOAc/Heptane and then 0-20% MeOH/EtOAc. Relevant fractions were pooled and concentrated to afford a white solid –151 mg. This material was then dissolved in THF (10 ml), to which HCl (2M in ether) (5 ml, 10.00 mmol) was added. No precipitation occurred, therefore the mixture was concentrated and the residue was dried under high vacuum for 30 mins. This material was then dissolved in water/ACN, frozen and lypholized to afford (S)—((S)-2-phenyl-2-((1r,4S)-4-(4-(trifluoromethyl)phenylsulfonamido)cyclohexanecarboxamido)ethyl) 2-amino-3-methylbutanoate hydrochloride as a white fluffy solid –120 mg (45% yield).

$^1$H NMR (400 MHz, DMSO-d$_6$) δ ppm 0.86 (t, J=7.07 Hz, 6H) 1.11-1.35 (m, 4H) 1.66 (d, J=10.61 Hz, 4H) 2.05 (dd, J=13.89, 2.53 Hz, 1H) 1.99-2.07 (m, 1H) 2.08 (d, J=1.77 Hz, 1H) 2.96 (d, J=7.33 Hz, 1H) 4.37 (dd, J=10.99, 8.46 Hz, 1H) 5.16 (td, J=8.46, 5.05 Hz, 1H) 7.25-7.37 (m, 5H) 7.96 (s, 1H) 7.97-8.05 (m, 2H) 7.98 (d, J=8.34 Hz, 2H) 8.29 (br. s., 1H) 8.34 (s, 1H) 8.31 (d, J=9.09 Hz, 2H)

M+H=570.3

HPLC (Luna) RT=8.053 mins

Prodrugs in Examples 480-488 were prepared by a method analogous to the method used to prepare Example 479 using the appropriate CBZ protected amino acid.

Example 480

(S)—((S)-2-phenyl-2-((1r,4S)-4-(4-(trifluoromethyl)phenylsulfonamido) cyclohexanecarboxamido)ethyl) 2-methylamino-3-methylbutanoate hydrochloride

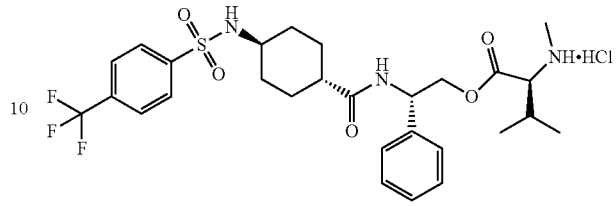

M+H=584.3

$^1$H NMR (400 MHz, DMSO-d$_6$) δ ppm 0.90 (dd, J=18.57, 6.95 Hz, 6H) 1.12-1.36 (m, 5H) 1.66 (d, J=11.62 Hz, 4H) 2.06-2.24 (m, 2H) 2.94 (br. s., 1H) 2.97 (dd, J=10.74, 3.41 Hz, 1H) 3.89 (br. s., 1H) 4.28-4.39 (m, 2H) 5.21 (td, J=8.34, 5.05 Hz, 1H) 7.25-7.41 (m, 5H) 7.96-8.05 (m, 5H) 8.45 (d, J=8.84 Hz, 1H) 9.15 (br. s., 2H)

HPLC (Luna 10-100) RT=8.021 mins

Example 481

(S)—((S)-2-phenyl-2-((1r,4S)-4-(4-(trifluoromethyl) phenylsulfonamido) cyclohexanecarboxamido)ethyl) 2-amino-propanoate hydrochloride

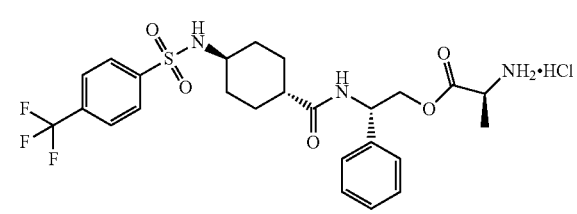

M+H=542.3

$^1$H NMR (400 MHz, DMSO-d$_6$) δ ppm 1.11-1.35 (m, 3H) 1.28 (d, J=7.07 Hz, 4H) 1.59-1.73 (m, 4H) 1.99-2.14 (m, 1H) 2.96 (br. s., 1H) 4.03 (q, J=7.16 Hz, 1H) 4.23 (d, J=5.05 Hz, 1H) 4.34 (dd, J=11.12, 7.83 Hz, 1H) 5.15 (td, J=8.15, 4.93 Hz, 1H) 7.23-7.37 (m, 4H) 7.23-7.37 (m, J=8.78, 4.33, 4.33, 4.04 Hz, 1H) 7.93-8.05 (m, 2H) 8.01 (d, J=9.85 Hz, 3H) 8.33 (d, J=8.59 Hz, 3H)

HPLC (Luna 10-100) RT=7.712 mins

Example 482

(S)—((S)-2-phenyl-2-((1r,4S)-4-(4-(trifluoromethyl) phenylsulfonamido) cyclohexanecarboxamido)ethyl) 2-amino-4-methylpentanoate hydrochloride

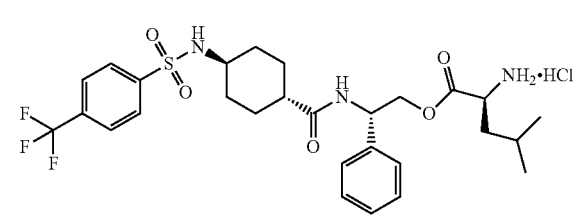

M+H=584.3

¹H NMR (400 MHz, DMSO-d₆) δ ppm 0.76 (dd, J=6.57, 5.31 Hz, 3H) 0.88 (dd, J=11.87, 6.57 Hz, 3H) 0.81-0.91 (m, 2H) 1.10-1.33 (m, 5H) 1.54-1.73 (m, 4H) 1.99-2.13 (m, 1H) 2.96 (br. s., 1H) 3.21 (dd, J=8.59, 5.81 Hz, 1H) 4.02-4.18 (m, 2H) 5.10 (td, J=8.40, 5.18 Hz, 1H) 7.22-7.35 (m, 5H) 7.94 (br. s., 1H) 7.95-8.04 (m, 4H) 8.20 (br. s., 2H) 8.25 (d, J=8.59 Hz, 1H)

HPLC (Luna 10-100) RT=8.235 mins

Example 483

(S)-2-phenyl-2-((1r,4S)-4-(4-(trifluoromethyl)phenylsulfonamido) cyclohexanecarboxamido)ethyl) 2-amino-2-methylproanoate hydrochloride

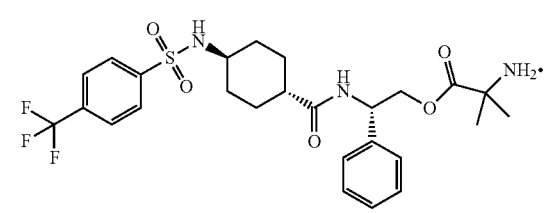

M+H=556.3

¹H NMR (400 MHz, DMSO-d₆) δ ppm 1.11-1.26 (m, 3H) 1.35 (d, J=1.52 Hz, 6H) 1.27-1.37 (m, 1H) 1.66 (t, J=12.38 Hz, 4H) 2.11 (t, J=11.87 Hz, 1H) 2.97 (dd, J=10.99, 3.66 Hz, 1H) 4.24-4.34 (m, 2H) 5.20 (s, 1H) 7.24-7.31 (m, 1H) 7.34 (d, J=4.55 Hz, 3H) 7.31-7.36 (m, 1H) 7.96-8.05 (m, 5H) 8.40 (d, J=8.84 Hz, 1H) 8.47 (br. s., 2H)

HPLC (Luna 10-100) RT=7.787 mins

Example 484

(S)—((S)-2-phenyl-2-((1r,4S)-4-(4-(trifluoromethyl) phenylsulfonamido) cyclohexanecarboxamido)ethyl) 2-amino-3-(4-hydroxyphenyl)propanoate hydrochloride

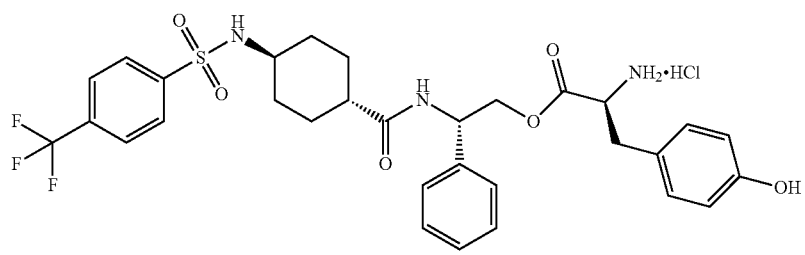

M+H=634.4

¹H NMR (400 MHz, DMSO-d₆) δ ppm 1.15 (br. s., 4H) 1.64 (br. s., 4H) 2.09 (br. s., 1H) 2.87 (dd, J=9.22, 6.44 Hz, 2H) 2.97 (m, 1H) 4.15 (br. s., 1H) 4.25 (dd, J=5.81, 3.28 Hz, 2H) 5.15 (d, J=8.84 Hz, 1H) 6.66 (d, J=8.34 Hz, 2H) 6.85 (d, J=8.34 Hz, 2H) 7.25-7.37 (m, 2H) 7.33 (d, J=2.02 Hz, 3H) 7.95-8.05 (m, 5H) 8.17-8.25 (br. s., 2H) 8.32 (d, J=8.59 Hz, 1H) 9.40 (s, 1H)

HPLC (Luna 10-100) RT=8.021 mins

Example 485

(S)—((S)-2-phenyl-2-((1r,4S)-4-(4-(trifluoromethyl) phenylsulfonamido) cyclohexanecarboxamido)ethyl) 2-amino-3-phenylpropanoate hydrochloride

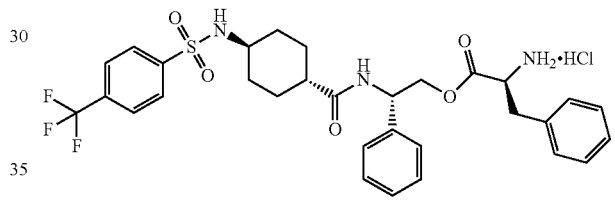

M+H=618.4

¹H NMR (400 MHz, DMSO-d₆) δ ppm 1.10-1.35 (m., 4H) 1.64 (d, J=9.85 Hz, 4H) 2.02-2.11 (m, 1H) 2.90-3.05 (m, 3H) 4.25 (d, J=6.32 Hz, 3H) 5.09-5.15 (m, 1H) 7.08 (dd, J=7.20, 1.89 Hz, 2H) 7.25-7.37 (m, 8H) 7.93-8.05 (m, 5H) 8.31 (d, J=8.84 Hz, 1H) 8.35 (br s., 2H).

HPLC (Luna 10-100) RT=8.437 mins

Example 486

(S)—((S)-2-phenyl-2-((1r,4S)-4-(4-(trifluoromethyl) phenylsulfonamido) cyclohexanecarboxamido)ethyl) ((S)-2-amino-3-methylbutanamido)-3-methylbutanoate hydrochloride

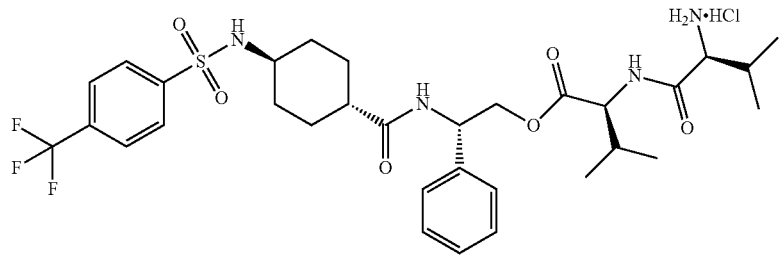

M+H=669.5
$^1$H NMR (400 MHz, DMSO-d$_6$) δ ppm 0.73-0.85 (m, 6H) 0.86-0.98 (m, 6H) 1.10-1.35 (m, 4H) 1.65 (br. s., 4H) 1.95-2.10 (m, 3H) 2.96 (br. s., 1H) 3.67-3.76 (m, 1H) 4.08-4.35 (m, 3H) 5.02-5.14 (m, 1H) 7.24-7.36 (m, 5H) 7.95-8.12 (m, 7H) 8.28 (d, J=8.59 Hz, 0.5H) 8.38 (d, J=8.34 Hz, 0.5H) 8.52 (d, J=7.83 Hz, 0.5H) 8.72 (d, J=8.08 Hz, 0.5H)
HPLC (Luna 10-100) RT=8.373 mins

Example 487

(S)—((S)-2-phenyl-2-((1r,4S)-4-(4-(trifluoromethyl) phenylsulfonamido) cyclohexanecarboxamido)ethyl) pyrrolidine-2-carboxylate hydrochloride

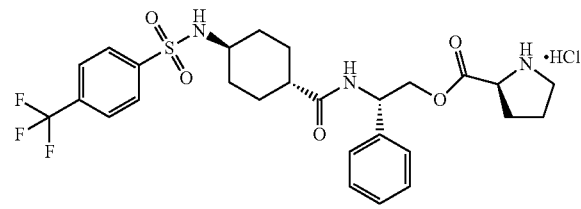 [SMILES: O=C(OC[C@@H](NC(=O)[C@H]1CC[C@H](NS(=O)(=O)c2ccc(C(F)(F)F)cc2)CC1)c1ccccc1)[C@@H]1CCCN1 ; Cl]

M+H=568.4
$^1$H NMR (400 MHz, DMSO-d$_6$) δ ppm 1.10-1.35 (m, 4H) 1.66 (m, 4H) 1.78-1.91 (m, 3H) 2.06-2.19 (m, 2H) 2.97 (d, J=7.33 Hz, 1H) 3.12-3.23 (m, 2H) 4.24-4.37 (m, 3H) 5.15 (td, J=8.02, 5.43 Hz, 1H) 7.20-7.30 (m, 1H) 7.30-7.40 (m, 4H) 7.93-8.06 (m, 6H) 8.37 (d, J=8.59 Hz, 1H)
HPLC (Luna 10-100) RT=7.819 mins

Example 488

(S)—((S)-2-phenyl-2-((1r,4S)-4-(4-(trifluoromethyl) phenylsulfonamido) cyclohexanecarboxamido)ethyl) 2-amino-3-hydroxypropanoate hydrochloride

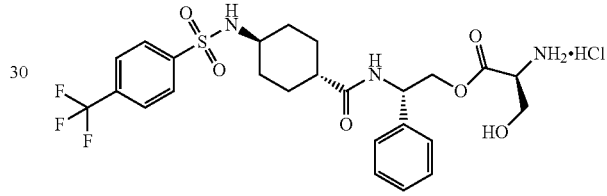

M+H=558.1
$^1$H NMR (400 MHz, DMSO-d$_6$) δ ppm 1.14-1.35 (m, 4H) 1.61-1.73 (m, 4H) 2.03-2.15 (m, 1H) 2.97 (dd, J=10.86, 3.79 Hz, 1H) 3.72 (t, J=4.17 Hz, 2H) 4.07 (br. s., 1H) 4.21-4.32 (m, 2H) 5.07-5.19 (m, 1H) 5.57 (t, J=4.93 Hz, 1H) 7.23-7.31 (m, 1H) 7.31-7.38 (m, 4H) 7.94-8.06 (m, 4H) 8.33-8.45 (m, 4H)
HPLC (Atlantis 0-95) RT=10.11 mins

Example 489

(R)-2-amino-5-oxo-5-((S)-2-phenyl-2-((1r,4S)-4-(4-(trifluoromethyl)phenylsulfonamido)cyclohexanecarboxamido)ethoxy)pentanoic acid hydrochloride

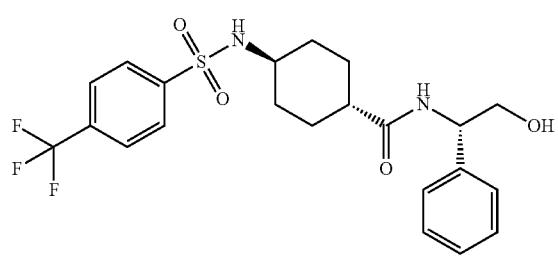

Example 66

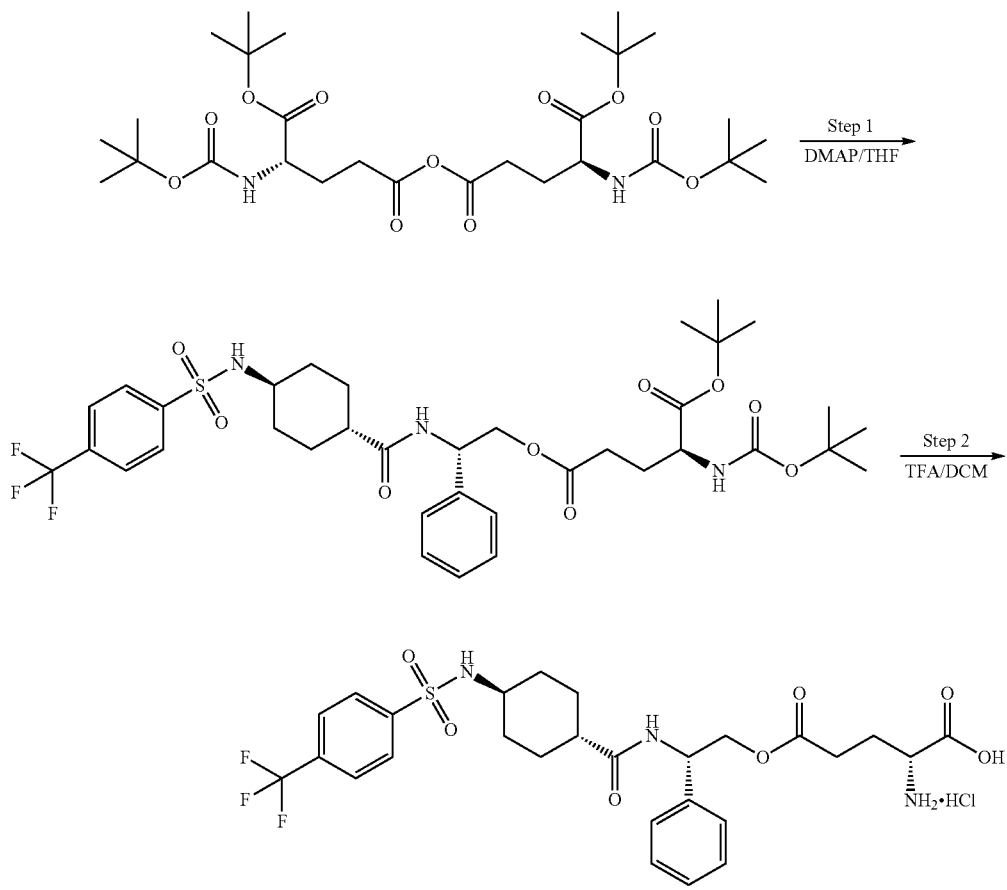

Example 489

Step 1: (1r,4S)—N—((S)-2-hydroxy-1-phenylethyl)-4-(4-(trifluoromethyl)phenylsulfonamido)cyclohexanecarboxamide (Example 66, 100 mg, 0.212 mmol) was suspended in THF (5 ml), to which a solution of (S)-5-tert-butoxy-4-(tert-butoxycarbonylamino)-5-oxopentanoic anhydride (88 mg, 0.149 mmol, prepared as described in Molecules (2008) 13: 348-359) in THF (5 ml) and then DMAP (1.708 mg, 0.014 mmol) were added. The reaction mixture was stirred at room temperature overnight, then concentrated and residue purified via Biotage automated flash column chromatography (40 g isco column), eluting with 10-100% EtOAc/Heptane. Relevant fractions were pooled and concentrated to afford (S)-1-tert-butyl 5-((S)-2-phenyl-2-((1r,4S)-4-(4-(trifluoromethyl)phenylsulfonamido)cyclohexanecarboxamido)ethyl) 2-(tert-butoxycarbonylamino)pentanedioate as a white solid—140 mg (87% yield).

M+H=756.5

$^1$H NMR (400 MHz, DMSO-$d_6$) δ ppm 1.11-1.30 (m, 6H) 1.36 (d, J=3.28 Hz, 18H) 1.59-1.76 (m, 4H) 1.85 (dd, J=8.59, 7.07 Hz, 1H) 2.21-2.40 (m, 3H) 2.89-3.02 (m, 1H) 3.80 (dd, J=7.96, 3.66 Hz, 1H) 4.00-4.10 (m, 1H) 4.03 (d, J=7.07 Hz, 1H) 5.07 (td, J=8.59, 5.05 Hz, 1H) 7.16 (d, J=7.83 Hz, 1H) 7.26 (dd, J=6.06, 2.53 Hz, 1H) 7.28-7.35 (m, 4H) 7.95 (s, 1H) 7.96-8.04 (m, 1H) 8.00 (d, J=9.60 Hz, 2H) 8.23 (d, J=8.59 Hz, 1H)

Step 2: (S)-1-tert-butyl 5-((S)-2-phenyl-2-((1r,4S)-4-(4-(trifluoromethyl)phenylsulfonamido)cyclohexanecarboxamido)ethyl) 2-(tert-butoxycarbonylamino)pentanedioate (140 mg, 0.185 mmol) was dissolved in DCM (5 ml) to which TFA (1 mL, 12.98 mmol) was added. The reaction mixture was stirred at room temperature overnight, then concentrated and the residue purified via prep HPLC using a gradient of 20-100% MeCN/water/0.1% TFA (150 mm C8Luna column). Fractions that contained product were frozen and lypholized to afford a white fluffy solid. This material was dissolved in a minimal amount of THF and 2M HCl in ether was added. The mixture was concentrated and the residue dissolved in water, frozen and lypholized to afford (R)-2-amino-5-oxo-5-((S)-2-phenyl-2-((1r,4S)-4-(4-(trifluoromethyl)phenylsulfonamido)cyclohexanecarboxamido)ethoxy) pentanoic acid hydrochloride as a white solid (35 mg-30% yield).

M+H=600.3

$^1$H NMR (400 MHz, DMSO-$d_6$) δ ppm 1.13-1.37 (m, 4H) 1.57-1.75 (m, 4H) 1.90-2.12 (m, 3H) 2.42 (dd, J=9.35, 6.32 Hz, 2H) 2.97 (d, J=7.07 Hz, 1H) 3.93 (br. s., 1H) 4.11 (d, J=8.34 Hz, 1H) 4.17 (d, J=5.05 Hz, 1H) 5.08 (td, J=8.34, 5.31 Hz, 1H) 7.23-7.36 (m, 5H) 7.96-8.05 (m, 2H) 7.98 (d, J=8.84 Hz, 3H) 8.27-8.43 (m, 3H) 13.92 (br. s., 1H)

HPLC (Luna 10-100) RT=7.701 mins

The prodrug in Example 490 was prepared by a method analogous to the method used to prepare Example 489 using the appropriate Boc protected amino acid.

Example 490

(S)-2-phenyl-2-((1r,4S)-4-(4-(trifluoromethyl)phenylsulfonamido) cyclohexanecarboxamido)ethyl) 3-aminopropanoate hydrochloride

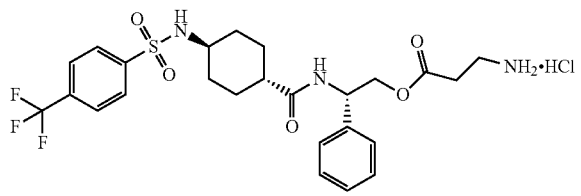

M+H=542.3

¹H NMR (400 MHz, DMSO-d₆) δ ppm 1.13-1.36 (m, 4H) 1.67 (br. s., 4H) 2.02-2.13 (m, 1H) 2.60 (t, J=7.20 Hz, 2H) 2.97 (d, J=5.56 Hz, 3H) 4.11 (dd, J=10.86, 8.34 Hz, 1H) 4.17-4.27 (m, 1H) 5.11 (td, J=8.40, 5.18 Hz, 1H) 7.24-7.37 (m, 5H) 7.80 (br. s., 2H) 7.93-8.05 (m, 5H) 8.31 (d, J=8.59 Hz, 1H)

HPLC (Luna 10-100) RT=7.659 mins

Additional NMR Data

The table below lists H¹ NMR data for specific compounds of the invention.

| Example | H¹ NMR |
|---|---|
| 72 | ¹H NMR (400 MHz, CDCl3) d ppm 1.1 (m, 2H), 1.7-2.1 (m, 5H), 3.1 (m, 3H), 4.35 (d, 1H), 5.6 (m, 1H), 5.95 (d, 1H), 7.25-7.45 (m, 5H), 7.73 (d, 2H), 7.95 (d, 2H) |
| 339 | ¹H NMR (400 MHz, d6-DMSO) d ppm 1.08-1.30 (m, 7H), 1.60-1.70 (m, 4H), 1.97-2.03 (m, 1H), 2.43 (s, 3H), 2.85-2.91 (m, 1H), 4.79-4.86 (m, 1H), 7.07-7.12 (m, 2H), 7.25-7.28 (m, 2H), 7.61 (s, 1H), 7.77-7.83 (m, 4H), 8.08-8.10 (m, 1H). |
| 359 | ¹H NMR (400 MHz, d6-DMSO) d ppm 1.15-1.31 (m, 7H), 1.61-1.73 (m, 4H), 1.99-2.05 (m, 1H), 2.86-2.97 (m, 1H), 3.10-3.19 (m, 2H), 3.63-3.69 (t, 2H), 3.96-3.99 (m, 2H), 4.41-4.42 (m, 2H), 4.79-4.86 (m, 1H), 7.08-7.12 (m, 2H), 7.25-7.29 (m, 2H), 7.65-7.66 (m, 1H), 7.73-7.75 (m, 1H), 7.88-7.94 (m, 6H), 8.11-8.13 (m, 1H), 10.09 (br, 1H). |
| 370 | ¹H NMR (400 MHz, d6-DMSO) d ppm 1.15-1.24 (m, 4H), 1.27 (d, 3H), 1.6-1.7 (m, 4H), 2.2 (m, 1H), 2.9 (m, 2H), 3.8 (m, 1H), 4.7 (m, 1H), 7.07-7.12 (m, 2H), 7.25-7.28 (m, 2H), 7.44-7.46 (m, 2H), 7.70-7.72 (m, 2H), 7.87-7.88 (m, 4H), 8.1 (d, 2H). |
| 378 | ¹H NMR (400 MHz, d6-DMSO) d ppm 1.14-1.31 (m, 7H), 1.61-1.72 (m, 4H), 1.99-2.05 (m, 1H), 2.89-2.93 (m, 3H), 3.08-3.12 (m, 2H), 4.79-4.86 (m, 1H), 7.08-7.12 (m, 2H), 7.25-7.29 (m, 2H), 7.40-7.42 (m, 2H), 7.70-7.79 (m, 6H), 7.87 (m, 4H), 8.10-8.12 (m, 1H). |
| 385 | ¹H NMR (400 MHz, d6-DMSO) d ppm 1.15-1.24 (m, 4H), 1.24-1.26 (d, 3H), 1.63-1.67 (m, 4H), 2.32-2.34 (m, 2H), 2.90 (m, 2H), 3.25 (m, 1H), 3.5 (m, 2H), 3.7 (m, 2H), 4.0 (m, 2H), 4.4 (br s, 1H), 4.83 (m, 1H), 7.08-7.16 (m, 4H), 7.25-7.28 (m, 2H), 7.68-7.69 (d, 2H), 7.75-7.77 (d, 2H), 8.10-8.12 (d, 2H), 9.85 (br s, 1H) |
| 395 | ¹H NMR (400 MHz, d6-DMSO) d ppm 0.94 (s, 3H), 1.04 (s, 3H), 1.1-1.4 (m, 4H), 1.5-1.7 (m, 4H), 2.2 (m, 1H), 2.9 (m, 1H), 4.4 (s, 1H), 4.6 (m, 1H), 7.15 (m, 1H), 7.25 (m, 2H), 7.30 (m, 2H), 7.45 (m, 2H), 7.52 (m, 2H), 7.7 (m, 1H), 7.77 (m, 2H), 7.9 (m, 2H) |
| 406 | ¹H NMR (400 MHz, CD₃OD) d ppm 1.24-1.43 (m, 2H), 1.43-1.70 (m, 4H), 1.70-1.95 (m, 4H), 2.40-2.52 (m, 2H), 2.56 (t, 2H), 2.60-2.71 (m, 2H), 4..09(d, 1H), 4.45 (d, 1H), 5.27 (br s, 1H), 5.84 (br s, 1H), 7.11-7.25 (m, 3H), 7.28-7.41 (m, 4H), 7.61 (d, 2H), 7.79 (d, 2H), 7.87-7.99 (m, 2H) |
| 410 | ¹H NMR (400 MHz, CD₃OD) d ppm 0.77-0.79 (m, 2H), 1.01-1.18 (m, 2H), 1.25-1.48 (m, 3H), 1.53 (d, 1H), 1.71-1.98 (m, 3H), 2.03-2.14 (m, 1H), 2.21-2.33 (m, 1H), 2.35-2.55 (m, 1H), 2.64 (t, 2H), 2.97 (t, 2H), 3.58-3.85 (m, 2H), 5.08 (dd, 1H), 6.98 (t, 1H), 7.05-7.16 (m, 2H), 7.19-7.22 (m, 1H), 7.36 (d, 2H), 7.60-7.65 (m, 2H), 7.78 (t, 2H), 7.85-7.92 (m, 2H) |
| 414 | ¹H NMR (400 MHz, CD₃OD) d ppm 0.83-1.75 (m, 4H), 1.75-1.95 (m, 2H), 2.06 (s, 2H), 2.28-2.80 (m, 2H), 2.99 (t, 2H), 3.15-3.24 (m, 2H), 3.51 (t, 2H), 3.64-4.15 (m, 2H), 5.31-5.77 (m, 1H), 6.61-6.75 (m, 2H), 6.75-6.85 (m, 1H), 7.18-7.47 (m, 6H), 7.50-7.68 (m, 2H), 7.68-8.00 (m, 2H), 8.02-8.17 (m, 1H) |
| 419 | ¹H NMR (400 MHz, CD₃OD) d ppm 1.24-1.39 (m, 2H), 1.39-1.58 (m, 2H), 1.68-1.85 (m, 4H), 2.51-2.55 (m, 4H), 2.94-2.98 (m, 2H), 3.07 (m, 1H), 3.47-3.56 (m, 1H), 3.67-3.77 (m, 2H), 3.84-3.88 (m, 1H), 4.43-4.46 (m, 1H), 5.55 (br s, 1H), 7.15-7.37 (m, 5H), 7.58-7.60 (m, 2H), 7.77-7.79 (m, 2H) 7.90-7.92 (m, 2H) |
| | ¹H NMR (400 MHz, CDCl₃) d ppm 1.4 (m, 4H), 1.9 (m, 4H), 2.3 (m, 1H), 2.4 (m, 1H), 3.0 (m, 2H), 3.26 (m, 2H), 3.4 (m, 1H), 3.6 (m, 1H), 3.75 (m, 1H), 4.0-4.2 (m, 1H), 4.6 (m, 1H), 4.7 (m, 1H), 5.1 (br s, 1H), 5.4 (br s, 1H), 6.0 (br s, 1H), 6.8 (br s, 1H), 7.55-7.68 (m, 7H), 7.82-7.84 (m, 2H), 7.97-7.99 (m, 2H), 8.18-8.20 (m, 2H) |

| Example | H¹ NMR |
|---|---|
| 428 | ¹H NMR (400 MHz, d6-DMSO) d ppm 0.82-1.73 (m, 8H), 2.24-2.29 (m, 1H), 2.86-2.96 (m, 1H), 3.54 (m, 2H), 3.68-3.94 (m, 1H), 4.15-4.34 (m, 1H), 5.36-5.55 (m, 1H), 7.15-7.45 (m, 6H), 7.49-7.53 (m, 2H), 7.69 (br, 1H), 7.74-7.77 (m, 2H), 7.86-7.89 (m, 4H), 8.02-8.06 (m, 1H). |

Example 528

Acetyl-CoA Carboxylase Enzyme Assay

The inhibitory effect of compounds on the acetyl-CoA carboxylase enzyme may be demonstrated using the following test procedures.

The cDNA encoding amino acids 144 to 2458 of human acetyl-CoA carboxylase 2 (ACC2, GenBank Accession # NM_001093) was cloned into the SalI and NotI sites of pFastBac1 (Invitrogen; Carlsbad, Calif.). The resulting plasmid was used to generate a recombinant ACC2 baculovirus that was amplified and titered according to the protocols in the Bac-to-Bac baculovirus expression system manual (Invitrogen). The titered virus was used to infect Sf9 cells grown in Ex-Cell 420 serum-free medium (JRH Biosciences; Lenexa, Kans.). At 48 hours post-infection, the cells were harvested and stored at −80° C. until purification. ACC2 was purified using ammonium sulfate precipitation and anion exchange chromatography.

The enzymatic assay was run as follows: 30 µL of reaction buffer (100 mM HEPES pH 7.5, 20 mM MgCl₂, 20 mM potassium citrate, 2 mM DTT) was added to a 384-well microtiter plate followed by 2 µL of the test compound (or 100% DMSO control). ACC2 protein (10 µL of a 50 nM working solution) was added to plate, which was incubated at room temperature for 15 minutes. A 30 µL addition of substrate solution (50 µM acetyl-CoA, 120 µM ATP, 2 mM KHCO₃) was used to initiate the reactions which were quenched with 6% acetic acid (40 µL). ACC catalyzed malonyl-CoA formation was detected by LC/MS/MS using a Cohesive Technologies LX Series multiplex LC/MS/MS system configured with four binary pumps (Agilent Technologies; Palo Alto, Calif.), a dual arm autosampler (Leap Technologies; Cary, N.C.), and one Quattro Micro triple quadrupole mass spectrometer (Waters, Milford, Mass.), all run by Aria Software version 1.5 (Cohesive Technologies; Franklin, Mass.). Four samples were injected (20 µL) onto four Phenosphere NEXT C18 30×2 mm 5 µm columns (Phenomenex; Torrance, Calif.), eluted by four separate pumps, running identical gradients, through a column switching manifold with the one outlet fitted to the electrospray (ESI) source. Malonyl-CoA was eluted with 5 mM ammonium acetate, pH 4.5 (Buffer A) and 100% acetonitrile (Buffer B) via a step gradient. Argon was used as the collision gas and the following species were monitored via MRM detection: malonyl-CoA (853.8>346.9), internal standard (A: [¹³C3]-malonyl-CoA, 857>350). The lower limit of detection is 0.3 uM for malonyl-CoA in this assay.

The compounds according to the invention may for example have IC₅₀ values below 1000 nM, particularly below 100 nM, most preferably below 10 nM. The Examples in the Table below were evaluated in the above described assay, the results of which are collated below.

| Example | IC50 (µM) |
|---|---|
| 1 | 0.025 |
| 72 | 0.094 |
| 171 | 0.090 |
| 339 | 0.025 |
| 359 | 0.052 |
| 370 | 0.010 |
| 378 | 0.010 |
| 385 | 0.010 |
| 395 | 0.010 |
| 406 | 0.055 |
| 410 | 0.090 |
| 414 | 0.010 |
| 419 | 0.025 |
| 428 | 0.770 |
| 448 | 0.040 |

It can be seen that the compounds of the invention are useful as inhibitors of ACC2 and therefore useful in the treatment of diseases and conditions mediated by ACC2 such as the metabolic disorders disclosed herein.

It will be understood that the invention has been described by way of example only and modifications may be made whilst remaining within the scope and spirit of the invention.

We claim:

1. A compound according to Formula (II):

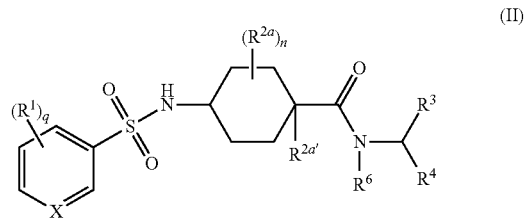

(II)

wherein

X is CH, CR¹, or N;

q is 0, 1, 2, 3, or 4;

R¹, for each occurrence, is independently selected from halo, hydroxy, nitro, $C_{1-7}$alkyl, $C_{1-7}$alkoxy, —NH—C(O)R⁹, $C_{2-7}$alkynyl, $C_{3-7}$cycloalkyl, $C_{3-7}$cycloalkoxy, $C_{1-7}$alkoxycarbonyl, $C_{1-7}$alkanoyl, $C_{1-7}$alkylamido, amino, N—$C_{1-7}$alkylamino, N,N-di-($C_{1-7}$alkyl)amino, $C_{1-7}$alkoxycarbonylamino, phenoxy, 3- to 7-membered heterocyclyl, 3- to 7-membered heterocyclyloxy, 3- to 7-membered heterocyclylamido, —NH—C(O)NHR¹⁰, and $C_{1-7}$alkylthio; wherein R¹ may be optionally substituted on one or more carbon atoms with from one to three independently selected R¹³;

R²ᵃ, for each occurrence, is independently selected from cyano, amino, hydroxy, $C_{1-4}$alkyl, and $C_{2-4}$alkenyl;

n is 0 or 1;

R²ᵃ' is hydrogen, cyano, amino, hydroxy, $C_{1-4}$alkyl, or $C_{2-4}$alkenyl;

$R^3$ is selected from the group consisting of a $C_{1-7}$ alkyl, $C_{3-8}$cycloalkyl, $C_{6-10}$aryl, a 5- to 10-membered heteroaryl, or a 3- to 10-membered heterocyclyl, wherein $R^3$ is optionally substituted on one or more carbon with one or more independently selected $R^{14}$; and wherein when $R^3$ is a heteroaryl or heterocyclyl comprising —NH—, the hydrogen of the —NH— group may be optionally replaced with a $C_{1-7}$alkyl; and wherein when $R^3$ is a heteroaryl or a heterocyclyl comprising —N=, —S— or both, the —N= may be substituted with —O⁻ and the —S— group may be substituted with one or two =O groups;

$R^4$ is hydrogen, a $C_{1-7}$alkyl, or carbamoyl, wherein the alkyl may be optionally substituted with one or more substituent which may be independently selected from the group consisting of duetero, hydroxy, amino, halo, carboxy, $C_{1-7}$alkoxy, $C_{1-7}$alkoxycarbonyl, phosphonooxy, a peptide having from 1 to 3 amino acids and $C_{1-7}$ alkanoyloxy wherein the alkanoyloxy may be optionally substituted with one or more carboxy, amino, N—$C_{1-6}$ alkylamino, N,N-di-($C_{1-6}$alkyl)amino, or amino acid sidechain;

$R^6$ is hydrogen or $C_{1-7}$ alkyl; or $R^6$ and $R^4$ may be linked to form a 3- to 7-membered heterocyclyl, wherein the heterocyclyl may be optionally substituted on one or more carbon with one or more $R^{15}$; and wherein when the heterocyclyl comprises —NH—, the hydrogen of the —NH— group may be optionally replaced with $R^{16}$; and wherein when the heterocyclyl comprises —N=, —S— or both, the —N= may be substituted with —O⁻ and the —S— group may be substituted with one or two =O groups;

$R^9$, for each occurrence, is independently selected from $C_{1-7}$alkyl, phenyl, and benzyl, wherein $R^9$ may be optionally substituted on one or more carbon atoms with from one to three independently selected $R^{13}$;

$R^{10}$, for each occurrence, is independently selected from hydrogen, $C_{1-7}$ alkyl, phenyl, and benzyl, wherein $R^{10}$ may be optionally substituted on one or more carbon atoms with from one to three independently selected $R^{13}$;

$R^{13}$, for each occurrence, is independently selected from the group consisting of halo, duetero, hydroxy, oxo, amino, $C_{1-7}$alkyl, $C_{1-7}$alkoxy, $C_{1-7}$alkoxycarbonyl, $C_{3-7}$cycloalkyl, $C_{1-7}$alkoxy$C_{1-7}$alkyl, $C_{1-7}$alkylsulfonyl, and phenyl which is optionally substituted with halo, cyano;

and $R^{14}$, for each occurrence is independently halo;

or a pharmaceutically acceptable salt thereof.

2. The compound according to claim 1, or a pharmaceutically acceptable salt thereof, wherein $R^1$, for each occurrence, is independently selected from fluoro, chloro, bromo, methyl, ethyl, isopropyl, tert-butyl, methoxy, ethoxy, isopropoxy, phenoxy, methoxymethyl, cyclopentoxy, trifluoromethyl, trifluoromethoxy, 1-hydroxy-1-methyl-ethyl, nitro, amino, N-methylamino, N,N-dimethylamino, N-(trideuteromethyl)-N-(2-hydroxyethyl)-amino, N-ethylamino, N-propylamino, n-propylamino, 2-aminoethylthio, phenylamido, 2-cyanophenyl-ethynyl, 3-hydroxy-but-1-yn-1-yl, 4-hydroxy-pent-1-yn-1-yl, 5-hydroxy-pent-1-yn-1-yl, acetyl, acetamido, carbamoyl, ethoxycarbonyl, methoxycarbonylamino, (t-butoxycarbonyl)-methoxy, 3-methyl-oxetan-3-yl, oxetan-3-yloxy, N'-methyl-ureido, N'-ethyl-ureido, N'-phenyl-ureido, N'-(1-phenyl-ethyl)-ureido, piperidine-1-carboxamido, cyclopropyl-ethynyl, 2-oxopyrrolidino, 2-methoxymethyl-pyrrolidino, 2-(methoxycarbonyl)-ethyl, 2-methoxy-ethoxy, methoxycarbonyl-methoxy, and cyclopropyl.

3. The compound according to claim 2, or a pharmaceutically acceptable salt thereof, wherein q is 1 and $R^1$ is trifluoromethyl.

4. A compound according to Formula (III):

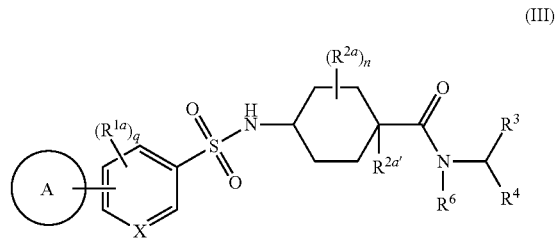

(III)

wherein ring A is a $C_{1-10}$ heteroaryl, wherein ring A may be optionally substituted with one to three independently selected $R^{17}$; and when ring A is a heterocyclyl comprising —NH—, the hydrogen of the —NH— group may be optionally replaced with a $C_{1-7}$alkyl; and wherein when ring A is a heterocyclyl comprising —N=, —S— or both, the —N=may be substituted with —O⁻ and the —S— group may be substituted with one or two =O groups;

X is CH, CR¹, or N;

q is 0 or 1;

$R^1$, for each occurrence, is independently hydroxy, nitro, halo, carboxy, formyl, $C_{1-7}$alkyl, $C_{3-8}$cycloalkyl, $C_{2-7}$alkenyl, $C_{2-7}$alkynyl, $C_{1-7}$alkoxy, $C_{3-8}$alkylthioxy, heterocyclyloxy, $C_{6-10}$aryloxy, amino, $C_{1-7}$alkylamino, di-($C_{1-7}$alkyl)amino, $C_{6-10}$aryl, 3- to 10-membered heterocyclyl, 5- to 10-membered heteroaryl, $C_{1-7}$alkanoyl, $C_{1-7}$alkoxycarbonyl, $C_{1-7}$alkanoyloxy, $C_{1-7}$alkylamido, $C_{1-7}$arylamido, heterocyclylamino, carbarnoyl, N—$C_{1-7}$ alkylcarbarnoyl, N,N-di-($C_{1-7}$alkyl)carbamoyl, $C_{1-7}$alkoxyamido, $C_{1-7}$alkylureido, and $C_{6-10}$arylureido, wherein $R^1$ is optionally substituted on one or more carbon atom with one or more independently selected $R^{13}$; and wherein when $R^1$ comprises a heterocyclyl or a heteroaryl comprising —NH—, the hydrogen of the —NH— group may be optionally replaced with a $C_{1-7}$alkyl; and wherein when $R^1$ comprises a heterocyclyl or a heteroaryl comprising —N=, —S— or both, the —N= may be substituted with —O⁻ and the —S— group may be substituted with one or two =O groups;

$R^{1a}$ is halo, $C_{1-4}$alkyl, or $C_{1-4}$alkoxy;

$R^{2a}$, for each occurrence, is independently selected from cyano, amino, hydroxy, $C_{1-4}$alkyl, and $C_{2-4}$alkenyl;

n is 0 or 1; and $R^{2a'}$ is hydrogen, cyano, amino, hydroxy, $C_{1-4}$alkyl, or $C_{2-4}$alkenyl;

$R^3$ is selected from the group consisting of a $C_{1-7}$alkyl, $C_{3-8}$cycloalkyl, $C_{6-10}$aryl, a 5- to 10-membered heteroaryl, or a 3- to 10-membered heterocyclyl, wherein $R^3$ is optionally substituted on one or more carbon atom with one or more independently selected $R^{14}$; and wherein when $R^3$ is a heteroaryl or heterocyclyl comprising —NH—, the hydrogen of the —NH— group may be optionally replaced with a $C_{1-7}$alkyl; and wherein when $R^3$ is a heteroaryl or a heterocyclyl comprising —N=, —S— or both, the —N=may be substituted with —O⁻ and the —S— group may be substituted with one or two =O groups;

R⁴ is hydrogen, a $C_{1-7}$alkyl, or carbamoyl, wherein the alkyl may be optionally substituted with one or more substituent which may be independently selected from the group consisting of duetero, hydroxy, amino, halo, carboxy, $C_{1-7}$alkoxy, $C_{1-7}$alkoxycarbonyl, phosphonooxy, a peptide having from 1 to 3 amino acids and $C_{1-7}$alkanoyloxy wherein the alkanoyloxy may be optionally substituted with one or more carboxy, amino, N—$C_{1-6}$alkylamino, N,N-di-($C_{1-6}$alkyl)amino, or amino acid sidechain;

R⁶ is hydrogen or $C_{1-7}$alkyl; or

R⁶ and R⁴ may be linked to form a 3- to 7-membered heterocyclyl, wherein the heterocyclyl may be optionally substituted on one or more carbon with one or more R¹⁵; and wherein when the heterocyclyl comprises —NH—, the hydrogen of the —NH— group may be optionally replaced with R¹⁶; and wherein when the heterocyclyl comprises —N=, —S— or both, the —N= may be substituted with —O⁻ and the —S— group may be substituted with one or two =O groups;

R¹³, for each occurrence, is independently deutero, halo, hydroxy, oxo, carboxy, $C_{1-7}$alkyl, $C_{3-9}$cycloakyl, $C_{1-7}$alkoxy, $C_{6-10}$aryl, 3- to 10-membered heterocyclyl, 5- to 10-membered heteroaryl, amino, $C_{1-7}$alkylamino, di-($C_{1-7}$alkoxycarbonyl, $C_{1-7}$alkoxycarbonyl, carbamoyl, wherein R¹³ is optionally substituted on one or more carbon atom with one or more independently selected R¹⁷; and wherein when R¹³ is a heterocyclyl or a heteroaryl comprising —NH—, the hydrogen of the —NH— group may be optionally replaced with a $C_{1-7}$alkyl; and wherein when R¹³ is a heterocyclyl or heteroaryl comprising —N=, —S— or both, the —N= may be substituted with —O⁻ and the —S— group may be substituted with one or two =O groups;

R¹⁴, for each occurrence, is independently halo;

R¹⁶, for each occurrence, is independently selected from the group consisting of $C_{1-7}$alkanoyl, $C_{6-10}$arylcarbonyl, heteroarylcarbonyl, $C_{1-7}$alkoxycarbonyl, 5- to 10-membered heteroaryl, and $C_{1-7}$alkylsulfonyl, wherein R¹⁶ may be optionally substituted with one or more substituent independently selected from the group consisting of carboxy, amino, $C_{1-7}$alkylamino, di-($C_{1-7}$alkyl)amino, and $C_{1-7}$alkoxycarbonyl; and R¹⁷, for each occurrence, is independently selected from cyano, halo, hydroxy, carboxy, $C_{1-7}$alkyl, $C_{1-7}$alkoxy, amino, $C_{1-7}$alkylamino, di-($C_{1-7}$alkyl)amino, $C_{1-7}$alkoxycarbonyl, 3- to 10-membered heterocyclyl, wherein R¹⁷ may be optionally substituted on one or more carbon atoms with one or more independently selected halo, trifluoromethyl, carboxy, or $C_{1-4}$alkyoxycarbonyl; and wherein when R¹⁷ is a heterocyclyl comprising —NH—, the hydrogen of the —NH— group may be optionally replaced with a $C_{1-7}$alkyl; and wherein when R¹⁷ is a heterocyclyl comprising —N=, —S— or both, the —N= may be substituted with —O⁻ and the —S— group may be substituted with one or two =O groups;

or a pharmaceutically acceptable salt thereof.

5. The compound according to claim 4, or a pharmaceutically acceptable salt thereof, wherein ring A is pyrazolyl, pyridinyl, oxazolyl, pyrimidinyl, thiazolyl, pyrrolyl, tetrazolyl, imidazolyl, pyridazinyl, pyrazinyl, or 1,2,4-oxadiazolyl, each of which may be optionally substituted with one to three independently selected R¹⁷; and when ring A is a heterocyclyl comprising —NH—, the hydrogen of the —NH— group may be optionally replaced with a $C_{1-7}$alkyl; and wherein when ring A is a heterocyclyl comprising —N=, —S— or both, the —N= may be substituted with —O⁻ and the —S— group may be substituted with one or two =O groups.

6. The compound according to claim 4, or a pharmaceutically acceptable salt thereof, wherein ring A is selected from:

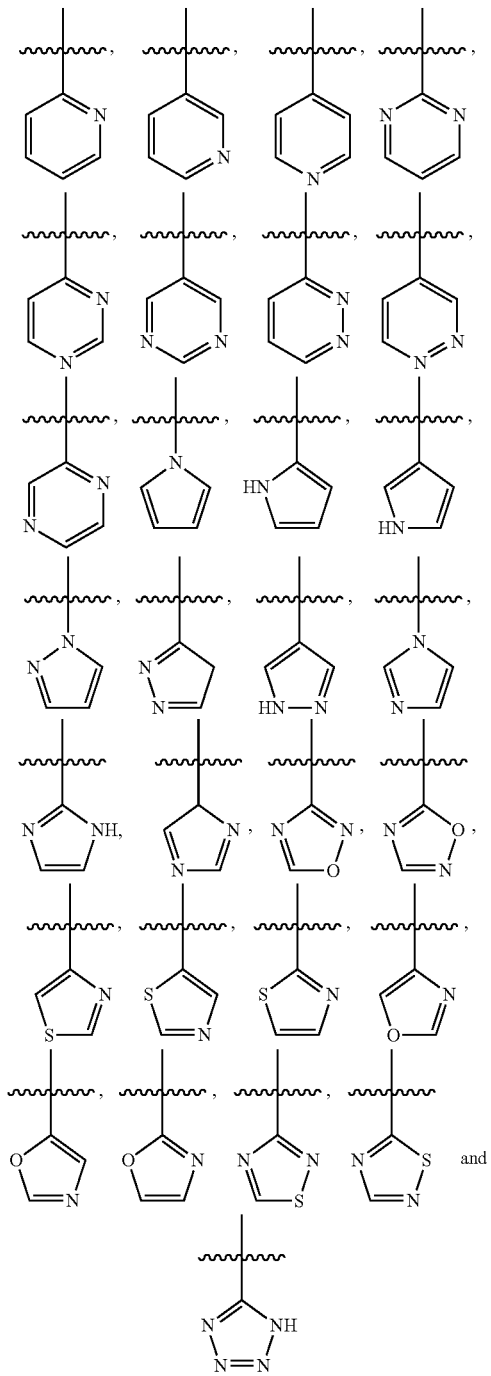

each of which may be optionally substituted with from one to three independently selected R¹⁷.

7. The compound according to claim 6, or a pharmaceutically acceptable salt thereof, wherein R¹⁷, for each occurrence, is independently selected from halo, $C_{1-4}$alkyl, $C_{1-4}$alkoxy, halo$C_{1-4}$alkyl, carboxy-(CR'R")—, $C_{1-4}$alkoxycarbony-(CR'R")$_a$—, hydroxy-(CR'R")$_a$—, cyano- (CR'R")$_a$—, —(CR'R")$_a$—NR$^{18}$R$^{19}$, carboxy-(CR'R")$_a$—O—, C$_{1-4}$alkoxycarbony-(CR'R")$_a$—O—, hydroxy-(CR'R")$_a$—O—, —O—(CR'R")$_a$—NR$^{18}$R$^{19}$, carbamoyl, N—(C$_{1-4}$alkyl)carbamoyl, N,N-di-(C$_{1-4}$alkyl)carbamoyl, oxetanyl, cyclopropyl, pyrrolidino-C$_{1-4}$alkyl, pyrrolidino-C$_{1-4}$alkoxy, morpholino-C$_{1-4}$alkyl, morpholino-C$_{1-4}$alkoxy, S,S-dioxothiomorpholino-C$_{1-4}$alkyl, piperazino-C$_{1-4}$alkyl, wherein oxetanyl, cyclopropyl, pyrrolidino, morpholino, thiomorpholino, and piperazino, for each occurrence may be optionally substituted with one to three substituents that are independently selected from amino, halo, C$_{1-4}$alkyl, trifluoromethyl, carboxy, ethoxycarbonyl, and methoxycarbonyl;

R' and R", for each occurrence, is independently hydrogen, a halo, a C$_{1-4}$alkyl or amino;

R$^{18}$ and R$^{19}$, for each occurrence, are independently selected from hydrogen, C$_{1-4}$alkyl, C$_{1-4}$alkoxycarbonylC$_{1-4}$alkyl, and carboxyC$_{1-4}$alkyl;

a is 0, 1, 2, or 3.

8. The compound according to claim 6, or a pharmaceutically acceptable salt thereof, wherein R$^{17}$, for each occurrence is independently selected from fluoro, chloro, methyl, methoxy, hydroxymethyl, carboxy, ethoxycarbonyl, carboxymethyl, 2-carboxyethyl, 2-(ethoxycarbonyl)-ethyl, 2-carboxy-2-methylpropyl, carboxymethoxy, 2-carboxy-2-amino-ethyl, amino-(methoxycarbonyl)-methyl, N,N-dimethylamino, carbamoyl, trifluoromethyl, 3-methyl-oxetan-3-yl, 1-hydroxy-1-methyl-ethyl, 1-aminocyclopropyl, cyano-difluoro-methyl, aminomethyl, 2-aminoethyl, 2-amino-1,1-difluoro-ethyl, 3,3-difluoropyrrolidinomethyl, morpholinomethyl, 2-morpholino-ethyl, 2-morpholino-ethoxy, 2-(3,3-difluoropyrrolidino)-ethyl, 2-(3,3-difluoropyrrolidino)-ethoxy, 2-(2-carboxy-pyrrolidino)-ethoxy, 2-[2-(ethoxycarbonyl)-pyrrolidino]-ethoxy, N-(ethoxycarbonylmethyl)-N-methyl-amino-methyl, 2-[N-(ethoxycarbonylmethyl)-N-methyl-amino]-ethyl, N-(carboxymethyl)-amino-methyl, N-(carboxymethyl)-N-methyl-amino-methyl, 2-[N-(carboxymethyl)-N-methyl-amino]-ethyl, 2-[N-(carboxymethyl)-amino]-ethyl, 2-(N,N-dimethylamino)-ethoxy, S,S-dioxo-thiomorpholino-methyl, 2-(S,S-dioxo-thiomorpholino)-ethyl, 2-(S,S-dioxo-thiomorpholino)-ethoxy, 2-(3-trifluoromethyl-piperazino)-ethyl, and 2-(3-trifluoromethyl-piperazino)-ethoxy.

9. The compound according to claim 1, or a pharmaceutically acceptable salt thereof, wherein R$^6$ is hydrogen and R$^4$ is an unsubstituted C$_{1-7}$alkyl.

10. The compound according to claim 1, or a pharmaceutically acceptable salt thereof, wherein R$^6$ is hydrogen and R$^4$ is a C$_{1-7}$alkyl which is substituted with a hydroxy.

11. The compound according to claim 1, or a pharmaceutically acceptable salt thereof, wherein R$^6$ is hydrogen and R$^4$ is 1-hydroxy-ethyl or 1-hydroxy-1-methyl-ethyl.

12. The compound according to claim 1, or a pharmaceutically acceptable salt thereof, wherein R$^3$ is phenyl or pyridinyl, wherein R$^3$ is optionally substituted on one or more carbon atom with one to three independently selected R$^{14}$; and wherein when R$^3$ is pyridinyl, the —N=may be substituted with —O$^-$.

13. The compound according to claim 12, or a pharmaceutically acceptable salt thereof, wherein R$^3$ is unsubstituted.

14. The compound according to claim 12, or a pharmaceutically acceptable salt thereof, wherein R$^3$ is selected from:

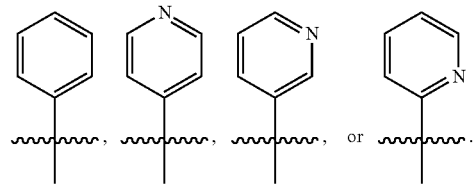

15. The compound according to claim 12, or a pharmaceutically acceptable salt thereof, wherein R$^3$ is substituted with one R$^{14}$; and R$^{14}$ is selected from the group consisting of fluoro, chloro, and bromo.

16. The compound according to claim 15, or a pharmaceutically acceptable salt thereof, wherein R$^3$ is 4-fluorophenyl.

17. The compound according to claim 1, or a pharmaceutically acceptable salt thereof, wherein X is CH.

18. The compound according to claim 1, or a pharmaceutically acceptable salt thereof, wherein X is CR$^1$.

19. The compound according to claim 1, or a pharmaceutically acceptable salt thereof, wherein the compound has the stereochemcal configuration of formula (IIA):

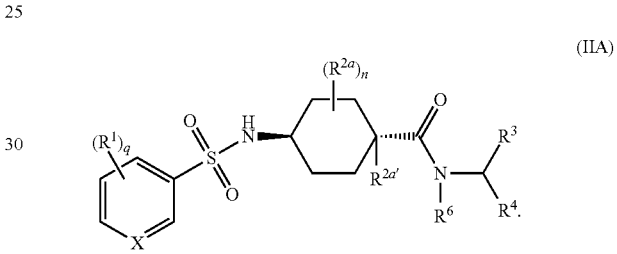

20. The compound according to claim 4, or a pharmaceutically acceptable salt thereof, wherein the compound has the stereochemcal configuration of formula (IIIA):

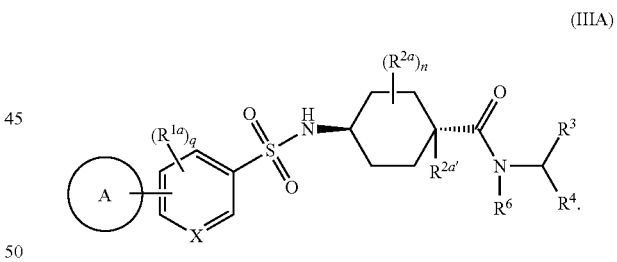

21. The compound of claim 1, wherein the compound is selected from the group consisting of:
(1r,4S)—N—((S)-2-Hydroxy-2-methyl-1-phenylpropyl)-4-(4-(trifluoromethyl)phenylsulfonamido)cyclohexanecarboxamide;
(1r,4S)—N—((S)-2,2,2-trifluoro-1-phenylethyl)-4-(4-(trifluoromethyl)phenylsulfonamido)cyclohexanecarboxamide;
(1r,4S)—N-((1S,2R)-2-Hydroxy-1-phenylpropyl)-4-(4-(trifluoromethyl)phenylsulfonamido)cyclohexancarboxamide;
(1r,4S)—N—((S)-2-Hydroxy-2-methyl-1-phenylpropyl)-1-methyl-4-(4-(trifluoromethyl)phenylsulfonamido) cyclohexanecarboxamide;
or a pharmaceutically acceptable salt thereof.

22. A pharmaceutical composition, comprising:
   a compound according to claim 1, or a pharmaceutically acceptable salt thereof; and
   a pharmaceutically acceptable excipient or carrier.

23. A method of inhibiting Acetyl CoA carboxylase activity, comprising:
   contacting a source of acetyl CoA carboxylase with a compound according to claim 1, or a pharmaceutically acceptable salt thereof.

24. A method of treating a disease or condition mediated by the inhibition of acetyl CoA carboxylase in a mammal having said disease or condition, comprising:
   administering to the mammal in need thereof a therapeutically effective amount of a compound according to claim 1, or a pharmaceutically acceptable salt thereof.

25. The method according to claim 24, wherein the disease or condition is metabolic syndrome, Syndrome X, diabetes, insulin resistance, decreased glucose tolerance, non-insulin-dependent diabetes mellitus, Type II diabetes, Type I diabetes, diabetic complications, body weight disorders, or leptin related diseases.

26. The method according to claim 24, wherein the disease or condition is insulin resistance, decreased glucose tolerance, non-insulin-dependent diabetes mellitus, Type II diabetes, or Type I diabetes.

27. The method according to claim 25, wherein the metabolic syndrome is dyslipidemia, obesity, insulin resistance, hypertension, microalbuminemia, hyperuricaemia, or hypercoagulability.

28. The method according to claim 25, wherein the bodyweight disorder is obesity, overweight, cachexia or anorexia.

29. A pharmaceutical composition, comprising a therapeutically effective amount of a compound according to claim 1, or a pharmaceutically acceptable salt thereof, in combination with a therapeutically effective amount of insulin, insulin derivative or mimetic; insulin secretagogue; insulinotropic sulfonylurea receptor ligand; PPAR ligand; insulin sensitizer; biguanide; alpha-glucosidase inhibitors; GLP-1, GLP-1 analog or mimetic; DPPIV inhibitor; HMG-CoA reductase inhibitor; squalene synthase inhibitor; FXR or LXR ligand; cholestyramine; fibrates; nicotinic acid; or aspirin.

30. The compound of claim 4, wherein the compound is selected from the group consisting of:
   (1r,4R)—N—((R)-1-(4-fluorophenyl)ethyl)-4-(4-(5-methyl-1H-imidazol-4-yl)phenylsulfonamido)cyclohexanecarboxamide;
   4-(oxazol-4-yl)-N-((1S,4r)-4-((S)-2-phenylpiperazine-1-carbonyl)cyclohexyl)benzenesulfonamide;
   (1r,4R)—N—((R)-1-(4-fluorophenyl)ethyl)-4-(4-(pyridin-4-yl)phenylsulfonamido) cyclohexanecarboxamide
   or a pharmaceutically acceptable salt thereof.

* * * * *